(12) United States Patent
Frank et al.

(10) Patent No.: US 8,592,471 B2
(45) Date of Patent: Nov. 26, 2013

(54) SUBSTITUTED PHENYLUREAS AND PHENYLAMIDES AS VANILLOID RECEPTOR LIGANDS

(75) Inventors: Robert Frank, Aachen (DE); Gregor Bahrenberg, Monschau-Konzen (DE); Thomas Christoph, Aachen (DE); Klaus Schiene, Juechen (DE); Jean De Vry, Stolberg (DE); Nils Damann, Cologne (DE); Sven Frormann, Aachen (DE); Bernhard Lesch, Aachen (DE); Jeewoo Lee, Seoul (KR); Yong-Soo Kim, Gyengnam (KR); Myeong-Seop Kim, Gangw-do (KR); Derek Saunders, Aachen (DE); Hannelore Stockhausen, Huertgenwald (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/775,235

(22) Filed: May 6, 2010

(65) Prior Publication Data

US 2010/0331381 A1 Dec. 30, 2010

Related U.S. Application Data

(60) Provisional application No. 61/176,284, filed on May 7, 2009.

(30) Foreign Application Priority Data

May 7, 2009 (EP) .................................. 09006237

(51) Int. Cl.
*A61K 31/41* (2006.01)
*C07D 231/12* (2006.01)

(52) U.S. Cl.
USPC ...... 514/383; 514/406; 548/364.1; 548/373.1

(58) Field of Classification Search
USPC .................. 514/383, 406; 548/364.1, 373.1
See application file for complete search history.

(56) References Cited

U.S. PATENT DOCUMENTS

| | | | |
|---|---|---|---|
| 2008/0021217 A1* | 1/2008 | Borchardt et al. ............ | 544/235 |
| 2009/0018134 A1 | 1/2009 | Pike et al. | |
| 2009/0156590 A1 | 6/2009 | Frank et al. | |
| 2012/0101096 A1 | 4/2012 | Hedstrom et al. | |

FOREIGN PATENT DOCUMENTS

| | | |
|---|---|---|
| EP | 1 020 447 A1 | 7/2000 |
| WO | WO 2005/004810 A2 | 1/2005 |
| WO | WO 2005/004810 A3 | 1/2005 |
| WO | WO 2008/011557 A2 | 1/2008 |
| WO | WO 2008/011557 A3 | 1/2008 |
| WO | WO 2008/059370 A2 | 5/2008 |
| WO | WO 2008/059370 A3 | 5/2008 |
| WO | WO 2008/059370 A8 | 5/2008 |
| WO | WO 2008/075064 A1 | 6/2008 |
| WO | WO 2008/125342 A2 | 10/2008 |
| WO | WO 2008/137102 A2 | 11/2008 |
| WO | WO 2008/137102 A3 | 11/2008 |
| WO | WO 2010/108187 A2 | 9/2010 |
| WO | WO 2010/108187 A3 | 9/2010 |

OTHER PUBLICATIONS

Hedstrom et al. CAS: 153: 431376, 2010.*
Borchardt et al. CAS: 148: 191965, 2008.*
Gary J. Bennett et al., A peripheral mononeuropathy in rat that produces disorders of pain sensation like those seen in man, Pain, 33, 1988, pp. 87-107.
Yung-Chi Cheng et al., Relationship Between the Inhibition Constant ($K_1$) and the Concentration of Inhibitor Which Causes 50 Per Cent Inhibition ($I_{50}$) of an Enzymatic Reaction, Biochemical Pharmacology, vol. 22, pp. 3009-3108, 1973.
Terrence J. Coderre et al., Contribution of central neuroplasticity to pathological pain: review of clinical and experimental evidence, Pain, 521993, pp. 259-285, 1993.
David Dubuisson et al., The Formalin Test A Quantitative Study of the Analgesic Effects of Morphine, Meperidine, and Brain Stem Stimulation in Rats and Cats, Pain 4, 1977, pp. 161-174.
L.C. Hendershot et al., Antagonism of the Frequency of Phenylquinone-Induced Writing in the Mouse by Weak Analgesics and Nonanalgesics, J. Pharmacol Exp Ther, Mar. 1959, pp. 237-240.
Jerry March, Aliphatic Nucleophilic Substitution, Advanced Organic Chemistry, Reactions, Mechanisms, and Structure, $4^{th}$ Edition, 1992, pp. 378-383.

* cited by examiner

*Primary Examiner* — Rei-tsang Shiao
(74) *Attorney, Agent, or Firm* — Crowell & Moring LLP

(57) ABSTRACT

The invention relates to substituted phenylureas and phenylamides, to processes for the preparation thereof, to pharmaceutical compositions containing these compounds and also to the use of these compounds for preparing pharmaceutical compositions.

11 Claims, No Drawings

SUBSTITUTED PHENYLUREAS AND PHENYLAMIDES AS VANILLOID RECEPTOR LIGANDS

This application claims priority under 35 U.S.C. §119(e) to U.S. Provisional Patent Application No. 61/176,284, filed on May 7, 2009, and also claims priority under 35 U.S.C. §119 (a) to European Application No. 09 006 237.3, filed May 7, 2009. The contents of both applications are hereby incorporated by reference in their entirety.

The invention relates to substituted phenylureas and phenylamides, to processes for the preparation thereof, to pharmaceutical compositions containing these compounds and also to the use of these compounds for preparing pharmaceutical compositions.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain, particularly preferably of neuropathic pain. This receptor is stimulated inter alia by vanilloids such as capsaicin, heat and protons and plays a central role in the formation of pain. In addition, it is important for a large number of further physiological and pathophysiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and in particular urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

It was therefore an object of the invention to provide new compounds having advantages over the prior-art compounds. The compounds should be suitable in particular as pharmacological active ingredients in pharmaceutical compositions, preferably in pharmaceutical compositions for the treatment and/or prophylaxis of disorders or diseases which are mediated, at least in some cases, by vanilloid receptors 1 (VR1/TRPV1 receptors).

This object is achieved by the subject matter of the claims.

Now, it has surprisingly been found that the substituted compounds of general formula (I), as indicated below, display outstanding affinity to the subtype 1 vanilloid receptor (VR1/TRPV1 receptor) and are therefore particularly suitable for the prophylaxis and/or treatment of disorders or diseases which are mediated, at least in some cases, by vanilloid receptors 1 (VR1/TRPV1). The substituted compounds of general formula (I), as indicated below, also have anti-inflammatory activity.

The present invention therefore relates to substituted compounds of general formula (I),

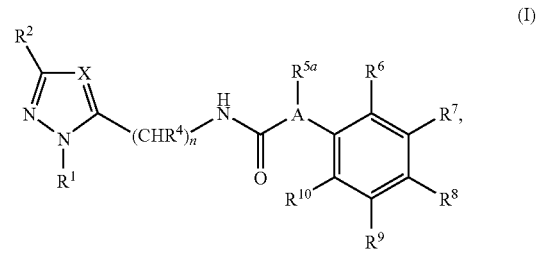

(I)

in which
X represents $CR^3$ or N,
  wherein $R^3$ represents H; $C_{1-10}$ alkyl, saturated or unsaturated, branched or unbranched, unsubstituted or mono- or polysubstituted;
A represents N or $CR^{5b}$,
n represents 0, 1, 2, 3 or 4; preferably 1, 2, 3 or 4,
$R^0$ represents $C_{1-10}$ alkyl, saturated or unsaturated, branched or unbranched, unsubstituted or mono- or polysubstituted; $C_{3-10}$ cycloalkyl or heterocyclyl, respectively saturated or unsaturated, unsubstituted or mono- or polysubstituted; aryl or heteroaryl, respectively unsubstituted or mono- or polysubstituted; $C_{3-10}$ cycloalkyl or heterocyclyl bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted;
$R^1$ represents H; $C_{1-10}$ alkyl, saturated or unsaturated, branched or unbranched, unsubstituted or mono- or polysubstituted; $C_{3-10}$ cycloalkyl$^1$ or heterocyclyl$^1$, respectively saturated or unsaturated, unsubstituted or mono- or polysubstituted; aryl or heteroaryl, respectively unsubstituted or mono- or polysubstituted; $C_{3-10}$ cycloalkyl$^1$ or heterocyclyl$^1$ bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; $C(=O)$—$R^0$; $C(=O)$—OH; $C(=O)$—$OR^0$; $C(=O)$—$NHR^0$; $C(=O)$—$N(R^0)_2$; OH; O—$R^0$; SH; S—$R^0$; $S(=O)_2$—$R^0$;

S(=O)$_2$—OR$^0$; S(=O)$_2$—NHR$^0$; S(=O)$_2$—N(R$^0$)$_2$; NH$_2$; NHR$^0$; N(R$^0$)$_2$; NH—S(=O)$_2$—R$^0$; N(R$^0$ (S(=O)$_2$—R$^0$; or SCl$_3$; preferably represents C$_{1-10}$ alkyl, saturated or unsaturated, branched or unbranched, unsubstituted or mono- or polysubstituted; C$_{3-10}$ cycloalkyl$^1$ or heterocyclyl$^1$, respectively saturated or unsaturated, unsubstituted or mono- or polysubstituted; aryl or heteroaryl, respectively unsubstituted or mono- or polysubstituted; C$_{3-10}$ cycloalkyl$^1$ or heterocyclyl$^1$ bridged via C$_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via C$_{1-8}$ alkyl, respectively unsubstituted or mono- or polysubstituted, wherein the alkyl chain can be respectively branched or unbranched, saturated or unsaturated, unsubstituted, mono- or polysubstituted; C(=O)—R$^0$; C(=O)—OH; C(=O)—OR$^0$; C(=O)—NHR$^0$; C(=O)—N(R$^0$)$_2$; OH; O—R$^0$; SH; S—R$^0$; S(=O)$_2$—R$^0$; S(=O)$_2$—OR$^0$; S(=O)$_2$—NHR$^0$; S(=O)$_2$—N(R$^0$)$_2$; NH$_2$; NHR$^0$; N(R$^0$)$_2$; NH—S(=O)$_2$—R$^0$; N(R$^0$ (S(=O)$_2$R$^0$; or SCl$_3$;

R$^2$ represents H; R$^0$; F; Cl; Br; I; CN; NO$_2$; OH; SH; CF$_3$; CF$_2$H; CFH$_2$; CF$_2$Cl; CFCl$_2$; CH$_2$CF$_3$; OCF$_3$; OCF$_2$H; OCFH$_2$; OCF$_2$Cl; OCFCl$_2$; SCF$_3$; SCF$_2$H; SCFH$_2$; SCF$_2$Cl; SCFCl$_2$; S(=O)$_2$—CF$_3$; S(=O)$_2$—CF$_2$H; S(=O)$_2$—CFH$_2$; or SF$_5$; preferably represents H; R$^0$; F; I; CN; NO$_2$; OH; SH; CF$_3$; CF$_2$H; CFH$_2$; CF$_2$Cl; CFCl$_2$; CH$_2$CF$_3$; OCF$_3$; OCF$_2$H; OCFH$_2$; OCF$_2$Cl; OCFCl$_2$; SCF$_3$; SCF$_2$H; SCFH$_2$; SCF$_2$Cl; SCFCl$_2$; S(=O)$_2$—CF$_3$; S(=O)$_2$—CF$_2$H; S(=O)$_2$—CFH$_2$; or SF$_5$;

R$^4$ represents H; F; Cl; Br; I; OH; C$_{1-10}$ alkyl, saturated or unsaturated, branched or unbranched, unsubstituted or mono- or polysubstituted;

R$^{5a}$ represents H; OH; C$_{1-10}$ alkyl, saturated or unsaturated, branched or unbranched, unsubstituted or mono- or polysubstituted;

R$^{5b}$ represents H; or R$^0$;

or R$^{5a}$ and R$^{5b}$ form together with the carbon atom connecting them a C$_{3-10}$ cycloalkyl or a heterocyclyl, respectively saturated or unsaturated, unsubstituted or mono- or polysubstituted;

R$^6$, R$^7$, R$^8$, R$^9$ and R$^{10}$ each independently of one another represent H; F; Cl; Br; I; NO$_2$; CN; CF$_3$; CF$_2$H; CFH$_2$; CF$_2$Cl; CFCl$_2$; R$^0$; C(=O)H; C(=O)R$^0$; CO$_2$H; C(=O)OR$^0$; CONH$_2$; C(=O)NHR$^0$; C(=O)N(R$^0$)$_2$; OH; OCF$_3$; OCF$_2$H; OCFH$_2$; OCF$_2$Cl; OCFCl$_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; SCF$_3$; SCF$_2$H; SCFH$_2$; SCF$_2$Cl; SCFCl$_2$; SR$^0$; S(=O)R$^0$; S(=O)$_2$R$^0$); S(=O)$_2$OH; S(=O)$_2$OR$^0$; S(=O)$_2$NH$_2$; S(=O)$_2$NHR$^0$; or S(=O)$_2$N(R)$_2$;

preferably R$^6$, R$^7$, R$^9$ and R$^{10}$ each independently of one another represent H; F; Cl; Br; I; NO$_2$; CN; CF$_3$; CF$_2$H; CFH$_2$; CF$_2$Cl; CFCl$_2$; R$^0$; C(=O)H; C(=O)R$^0$; CO$_2$H; C(=O)OR$^0$; CONH$_2$; C(=O)NHR$^0$; C(=O)N(R$^0$)$_2$; OH; OCF$_3$; OCF$_2$H; OCFH$_2$; OCF$_2$Cl; OCFCl$_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; SCF$_3$; SCF$_2$H; SCFH$_2$; SCF$_2$Cl; SCFCl$_2$; SR$^0$; S(=O)R$^0$; S(=O)$_2$R$^0$); S(=O)$_2$OH; S(=O)$_2$OR$^0$; S(=O)$_2$NH$_2$; S(=O)$_2$NHR$^0$; or S(=O)$_2$N(R)$_2$;

preferably R$^8$ represents H; F; Cl; Br; I; NO$_2$; CN; CF$_3$; CF$_2$H; CFH$_2$; CF$_2$Cl; CFCl$_2$; R$^0$; C(=O)H; C(=O)R$^0$; CO$_2$H; C(=O)OR$^0$; CONH$_2$; C(=O)NHR$^0$; C(=O)N(R$^0$)$_2$; OH; OCF$_3$; OCF$_2$H; OCFH$_2$; OCF$_2$Cl; OCFCl$_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; SCF$_3$; SCF$_2$H; SCFH$_2$; SCF$_2$Cl; SCFCl$_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$; wherein, if R$^8$ denotes R$^0$ and R$^0$ represents heteroaryl, said heteroaryl is selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl;

in which "substituted alkyl", "substituted heterocyclyl" and "substituted cycloalkyl" relate, with respect to the corresponding residues, to the substitution of one or more hydrogen atoms each independently of one another by F; Cl; Br; I; NO$_2$; CN; =O; =NH; =C(NH$_2$)$_2$; CF$_3$; CF$_2$H; CFH$_2$; CF$_2$Cl; CFCl$_2$; R$^0$; C(=O)H; C(=O)R$^0$; CO$_2$H; C(=O)OR$^0$; CONH$_2$; C(=O)NHR$^0$; C(=O)N(R$^0$)$_2$; OH; OCF$_3$; OCF$_2$H; OCFH$_2$; OCF$_2$Cl; OCFCl$_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; SCF$_3$; SCF$_2$H; SCFH$_2$; SCF$_2$Cl; SCFCl$_2$; SR$^0$; S(=O)

R⁰; S(=O)₂R⁰; S(=O)₂OH; S(=O)₂OR⁰; S(=O)₂NH₂; S(=O)₂NHR⁰; or S(=O)₂N(R)₂;

in which "substituted cycloalkyl'" and "substituted heterocyclyl¹'" relate, with respect to the corresponding residues, to the substitution of one or more hydrogen atoms each independently of one another by F; Cl; Br; I; NO₂; CN; =O; =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; SH; SCF₃; SCF₂H; SCFH₂; SCF₂Cl; SCFCl₂; SR⁰; S(=O)R⁰; S(=O)₂ R⁰; S(=O)₂OH; S(=O)₂OR⁰; S(=O)₂NH₂; S(=O)₂ NHR⁰; or S(=O)₂N(R)₂;

in which "substituted aryl" and "substituted heteroaryl" relate, with respect to the corresponding residues, to the substitution of one or more hydrogen atoms each independently of one another by F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰); NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R)₂;

preferably in which "substituted aryl" relates, with respect to the corresponding residues, to the substitution of one or more hydrogen atoms each independently of one another by F; Cl; Br; I; NO₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R)₂;

preferably in which "substituted heteroaryl" relates, with respect to the corresponding residues, to the substitution of one or more hydrogen atoms each independently of one another by F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C (=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R)₂;

in the form of the free compounds; the tautomers; the N-oxides; the racemate; the enantiomers, diastereomers, mixtures of the enantiomers or diastereomers or of an individual enantiomer or diastereomer; or in the form of the salts of physiologically compatible acids or bases; or if appropriate in the form of solvates.

The terms "alkyl" or "$C_{1-10}$ alkyl", "$C_{1-8}$ alkyl", "$C_{1-6}$ alkyl", "$C_{1-4}$ alkyl" comprise in the sense of this invention acyclic saturated or unsaturated aliphatic hydrocarbon residues, i.e. $C_{1-10}$ aliphatic residues, $C_{1-8}$ aliphatic residues, $C_{1-6}$ aliphatic residues and $C_{1-4}$ aliphatic residues, which can be respectively branched or unbranched and also unsubstituted or mono- or polysubstituted, containing 1 to 10 or 1 to 8 or 1 to 6 or 1 to 4 carbon atoms, i.e. $C_{1-10}$ alkanyls, $C_{2-10}$ alkenyls and $C_{2-10}$ alkinyls or $C_{1-8}$ alkanyls, $C_{2-8}$ alkenyls and $C_{2-8}$ alkinyls or $C_{1-6}$ alkanyls, $C_{2-6}$ alkenyls and $C_{2-6}$ alkinyls or $C_{1-4}$ alkanyls, $C_{2-4}$ alkenyls and $C_{2-4}$ alkinyls. In this case, alkenyls comprise at least one C—C double bond and alkinyls comprise at least one C—C triple bond. Preferably, alkyl is selected from the group comprising methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl, n-decyl, ethenyl (vinyl), ethinyl, propenyl (—CH₂CH=CH₂, —CH=CH—CH₃, —C(=CH₂)—CH₃), propinyl (—CH—C≡CH, —C≡O—CH₃), butenyl, butinyl, pentenyl, pentinyl, hexenyl and hexinyl, heptenyl, heptinyl, octenyl, octinyl, nonenyl, noninyl, decenyl and decinyl.

The terms "cycloalkyl" or "$C_{3-10}$ cycloalkyl" and "cycloalkyl'" or "$C_{3-10}$ cycloalkyl'" mean for the purposes of this invention cyclic aliphatic (cycloaliphatic) hydrocarbons containing 3, 4, 5, 6, 7, 8, 9 or 10 carbon atoms, i.e. $C_{3-10}$-cycloaliphatic residues, wherein the hydrocarbons can be saturated or unsaturated (but not aromatic), unsubstituted or mono- or polysubstituted. The cycloalkyl can be bound to the respective superordinate general structure via any desired and possible ring member of the cycloalkyl residue. The cycloalkyl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. The cycloalkyl residues can furthermore be singly or multiply bridged such as, for example, in the case of adamantyl, bicyclo[2.2.1]heptyl or bicyclo[2.2.2]octyl. Preferably, cycloalkyl is selected from the group comprising cyclopropyl, cyclobutyl, cyclopentyl, cyclohexyl, cycloheptyl, cyclooctyl, cyclononyl, cyclodecyl, adamantyl,

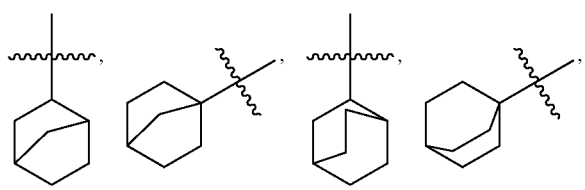

cyclopentenyl, cyclohexenyl, cycloheptenyl and cyclooctenyl.

The terms "heterocyclyl" or "heterocycloalkyl" and "heterocyclyl'" or "heterocycloalkyl'" comprise aliphatic saturated or unsaturated (but not aromatic) cycloalkyls having three to ten, i.e. 3, 4, 5, 6, 7, 8, 9 or 10, ring members, in which at least one, if appropriate also two or three carbon atoms are replaced by a heteroatom or a heteroatom group each selected independently of one another from the group consisting of O, S, S(=O)$_2$, N, NH and N($C_{1-8}$ alkyl), preferably N($CH_3$), wherein the ring members can be unsubstituted or mono- or polysubstituted. Heterocyclyls are thus heterocycloaliphatic residues. The heterocyclyl can be bound to the superordinate general structure via any desired and possible ring member of the heterocyclyl residue. The heterocyclyl residues can therefore be condensed with further saturated, (partially) unsaturated (hetero)cyclic or aromatic or heteroaromatic ring systems, i.e. with cycloalkyl, heterocyclyl, aryl or heteroaryl which can in turn be unsubstituted or mono- or polysubstituted. Heterocyclyl residues from the group comprising azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl are preferred.

The term "aryl" means in the sense of this invention aromatic hydrocarbons having up to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. Examples of condensed aryl residues are benzodioxolanyl and benzodioxanyl. Preferably, aryl is selected from the group containing phenyl, 1-naphthyl and 2-naphthyl which can be respectively unsubstituted or mono- or polysubstituted. A particularly preferred aryl is phenyl, unsubstituted or mono- or polysubstituted.

The term "heteroaryl" represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cyclic or aromatic or heteroaromatic rings, i.e. with cycloalkyl, heterocyclyl, aryl or heteroaryl which can in turn be unsubstituted or mono- or polysubstituted. It is preferable for the heteroaryl residue to be selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl or triazinyl. Furyl, pyridyl and thienyl are particularly preferred.

The terms "aryl, heteroaryl, heterocyclyl, cycloalkyl, heterocyclyl$^1$ or cycloalkyl$^1$ bridged via $C_{1-4}$ alkyl or $C_{1-8}$ alkyl" mean in the sense of the invention that $C_{1-4}$ alkyl or $C_{1-8}$ alkyl and aryl or heteroaryl or heterocyclyl or cycloalkyl or heterocyclyl$^1$ or cycloalkyl$^1$ have the above-defined meanings and the aryl or heteroaryl or heterocyclyl or cycloalkyl or heterocyclyl$^1$ or cycloalkyl$^1$ residue is bound to the respective superordinate general structure via a $C_{1-4}$ alkyl or a $C_{1-8}$ alkyl group. The alkyl chain of the alkyl group can in all cases be branched or unbranched, unsubstituted or mono- or polysubstituted. The alkyl chain of the alkyl group can furthermore be in all cases saturated or unsaturated, i.e. can be an alkylene group, i.e. a $C_{1-4}$ alkylene group or a $C_{1-8}$ alkylene group, an alkenylene group, i.e. a $C_{2-4}$ alkenylene group or a $C_{2-8}$ alkenylene group, or an alkinylene group, i.e. a $C_{2-4}$ alkinylene group or a $C_{2-8}$ alkinylene group. Preferably, $C_{1-4}$ alkyl is selected from the group comprising —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —C≡C—, —C≡C—CH$_2$—, —C≡C—CH$_2$—CH$_2$—, —C≡C—CH(CH$_3$)—, —CH$_2$—C≡C—CH$_2$— and —C≡C—C≡C— and $C_{1-8}$ alkyl is selected from the group comprising —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$—, —CH$_2$—(CH$_2$)$_4$—CH$_2$—, —CH═CH—, —CH═CH—CH$_2$—, —C(CH$_3$)═CH$_2$—, —CH═CH—CH$_2$—CH$_2$—, —CH$_2$—CH═CH—CH$_2$—, —CH═CH—CH═CH—, —C(CH$_3$)═CH—CH$_2$—, —CH═C(CH$_3$)—CH$_2$—, —C(CH$_3$)═C(CH$_3$)—, —C(CH$_2$CH$_3$)═CH—, —CH═CH—CH$_2$—CH$_2$—CH$_2$—, —CH$_2$—CH═CH—CH$_2$—CH$_2$—, —CH═CH—CH—CH$_2$—CH$_2$—, —CH═CH$_2$—CH═CH—CH$_2$—, —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

In relation to "alkyl", "heterocyclyl" and "cycloalkyl", the term "mono- or polysubstituted" refers in the sense of this invention to the single or multiple, for example double, triple or quadruple, substitution of one or more hydrogen atoms each independently of one another by substituents selected from the group of F; Cl; Br; I; NO$_2$; CN; ═O; ═NH; ═C(NH$_2$)$_2$; CF$_3$; CF$_2$H; CFH$_2$; CF$_2$Cl; CFCl$_2$; R$^0$; C(═O)H; C(═O)R$^0$; CO$_2$H; C(═O)OR$^0$; CONH$_2$; C(═O)NHR$^0$; C(═O)N(R$^0$)$_2$; OH; OCF$_3$; OCF$_2$H; OCFH$_2$; OCF$_2$Cl; OCFCl$_2$; OR$^0$; O—C(═O)—R$^0$; O—C(═O)—O—R$^0$; O—(C═O)—NH—R$^0$; O—C(═O)—N(R$^0$)$_2$; O—S(═O)$_2$—R$^0$; O—S(═O)$_2$OH; O—S(═O)$_2$OR$^0$; O—S(═O)$_2$NH$_2$; O—S(═O)$_2$NHR$^0$; O—S(═O)$_2$N(R$^0$)$_2$; NH$_2$; NH—R$^0$; N(R$^0$)$_2$; NH—C(═O)—R$^0$; NH—C(═O)—O—R$^0$; NH—C(═O)—NH$_2$; NH—C(═O)—NH—R$^0$; NH—C(═O)—N(R)$_2$; NR$^0$—C(═O)—R$^0$; NR$^0$—C(═O)—O—R$^0$; NR$^0$—C(═O)—NH$_2$; NR$^0$—C(═O)—NH—R$^0$; NR$^0$—C(═O)—N(R)$_2$; NH—S(═O)$_2$OH; NH—S(═O)$_2$R$^0$; NH—S(═O)$_2$OR$^0$; NH—S(═O)$_2$NH; NH—S(═O)$_2$NHR$^0$; NH—S(═O)$_2$N(R)$_2$; NR$^0$—S(═O)$_2$OH; NR$^0$—S(═O)$_2$R$^0$; NR$^0$—S(═O)$_2$OR$^0$; NR$^0$—S(═O)$_2$NH$_2$; NR$^0$—S(═O)$_2$NHR$^0$; NR$^0$—S(═O)$_2$N(R)$_2$; SH; SCF$_3$; SCF$_2$H; SCFH$_2$; SCF$_2$Cl; SCFCl$_2$; SR$^0$; S(═O)R$^0$; S(═O)$_2$R$^0$; S(═O)$_2$OH; S(═O)$_2$OR$^0$; S(═O)$_2$NH$_2$; S(═O)$_2$NHR$^0$; or S(═O)$_2$N(R)$_2$; wherein the term "polysubstituted residues" refers to residues of the type that are polysubstituted, for example di-, tri- or tetrasubstituted, either on different or on the same atoms, for example trisubstituted on the same C atom, as in the case of CF$_3$ or CH$_2$CF$_3$, or at various points, as in the case of CH(OH)—CH═CH—CHCl$_2$. A substituent can if appropriate for its part in turn be mono- or polysubstituted. The multiple substitution can be carried out using the same or using different substituents.

In relation to "cycloalkyl$^1$" and "heterocyclyl$^1$", the term "mono- or polysubstituted" refers in the sense of this invention to the single or multiple, for example double, triple or quadruple, substitution of one or more hydrogen atoms each independently of one another by substituents selected from the group of F; Cl; Br; I; NO$_2$; CN; ═O; ═C(NH$_2$)$_2$; CF$_3$; CF$_2$H; CFH$_2$; CF$_2$Cl; CFCl$_2$; R$^0$; C(═O)H; C(═O)R$^0$; CO$_2$H; C(═O)OR$^0$; CONH$_2$; C(═O)NHR$^0$; C(═O)N(R)$_2$; OH; OCF$_3$; OCF$_2$H; OCFH$_2$; OCF$_2$Cl; OCFCl$_2$; OR$^0$; O—C(═O)—R$^0$; O—C(═O)—O—R$^0$; O—(C═O)—NH—R$^0$; O—C(═O)—N(R)$_2$; O—S(═O)$_2$—R$^0$; O—S(═O)$_2$OH; O—S(═O)$_2$OR$^0$; O—S(═O)$_2$NH$_2$; O—S(═O)$_2$NHR$^0$; O—S(═O)$_2$N(R)$_2$; SH; SCF$_3$; SCF$_2$H; SCFH$_2$; SCF$_2$Cl; SCFCl$_2$; SR$^0$; S(═O)R$^0$; S(═O)$_2$R$^0$; S(═O)$_2$OH; S(═O)$_2$OR$^0$; S(═O)$_2$NH$_2$; S(═O)$_2$NHR$^0$; or S(═O)$_2$N(R)$_2$; wherein the term "polysubstituted residues" refers to residues of the type that are multiply, for example di-, tri- or tetrasubstituted, either on different or on the same atoms, for example trisubstituted on the same C atom, as in the case of 1,1-difluorocyclohexyl, or at various points, as in the case of 1,2-difluorocyclohexyl. A substituent can if appropriate for its part in turn be mono- or polysubstituted. The multiple substitution can be carried out using the same or using different substituents.

Preferred "alkyl", "heterocyclyl" and "cycloalkyl" substituents are selected from the group of F; Cl; Br; I; NO$_2$; CF$_3$; CN; ═O; ═NH; R$^0$; C(═O)(R$^0$ or H); C(═O)O(R$^0$ or H); C(═O)N(R$^0$ or H)$_2$; OH; OR$^0$; O—C(═O)—R$^0$; O—(C$_{1-8}$ alkyl)-OH; O—(C$_{1-8}$ alkyl)-O—C$_{1-8}$ alkyl; OCF$_3$; N(R$^0$ or H)$_2$; N(R$^0$ or H)—C(═O)—R$^0$; N(R$^0$ or H)—C(═O)—N(R$^0$ or H)$_2$; SH; SCF$_3$; SR$^0$; S(═O)$_2$R$^0$; S(═O)$_2$O(R$^0$ or H) and S(═O)$_2$—N(R$^0$ or H)$_2$.

Particularly preferred "alkyl", "heterocyclyl" and "cycloalkyl" substituents are selected from the group consisting of F; Cl; Br; I; NO$_2$; CF$_3$; CN; ═O; C$_{1-8}$ alkyl; aryl; heteroaryl; C$_{3-10}$ cycloalkyl; heterocyclyl; aryl, heteroaryl, C$_{3-10}$ cycloalkyl or heterocyclyl bridged via C$_{1-8}$ alkyl; CHO; C(═O)C$_{1-8}$ alkyl; C(═O)aryl; C(═O)heteroaryl; CO$_2$H; C(═O)O—C$_{1-8}$ alkyl; C(═O)O-aryl; C(═O)O-heteroaryl; CONH$_2$; C(═O)NH—C$_{1-8}$ alkyl; C(═O)N(C$_{1-8}$ alkyl)$_2$; C(═O)NH-aryl; C(═O)N(aryl)$_2$; C(═O)NH-heteroaryl; C(═O)N(heteroaryl)$_2$; C(═O)N(C$_{1-8}$ alkyl)(aryl); C(═O)N(C$_{1-8}$ alkyl)(heteroaryl); C(═O)N(heteroaryl)(aryl); OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-aryl; O-heteroaryl; O—C(═O)C$_{1-8}$ alkyl; O—C(═O)aryl; O—C(═O)heteroaryl; NH$_2$; NH—C$_{1-8}$ alkyl; N(C$_{1-8}$ alkyl)$_2$; NH—C(═O)C$_{1-8}$ alkyl; NH—C(═O)-aryl; NH—C(═O)-heteroaryl; SH; S—C$_{1-8}$ alkyl; SCF$_3$; S-benzyl; S-aryl; S-heteroaryl; S(═O)$_2$C$_{1-8}$ alkyl; S(═O)$_2$ aryl; S(═O)$_2$ heteroaryl; S(═O)$_2$OH; S(═O)$_2$ O—C$_{1-8}$ alkyl; S(═O)$_2$O-aryl; S(═O)$_2$O-heteroaryl; S(═O)$_2$—NH—C$_{1-8}$ alkyl; S(═O)$_2$—NH-aryl; and S(═O)$_2$—NH—C$_{1-8}$ heteroaryl.

Preferred "cycloalkyl$^1$" and "heterocyclyl$^1$" substituents are selected from the group of F; Cl; Br; I; NO$_2$; CF$_3$; CN; ═O; R$^0$; C(═O)(R$^0$ or H); C(═O)O(R$^0$ or H); C(═O)N(R$^0$ or H)$_2$; OH; OR$^0$; O—C(═O)—R$^0$; O—(C$_{1-8}$ alkyl)-OH; O—(C$_{1-8}$ alkyl)-O—C$_{1-8}$ alkyl; OCF$_3$; SH; SCF$_3$; SR$^0$; S(═O)$_2$R$^0$; S(═O)$_2$O(R$^0$ or H) and S(═O)$_2$—N(R$^0$ or H)$_2$.

Particularly preferred "cycloalkyl$^1$" and "heterocyclyl$^1$" substituents are selected from the group consisting of F; Cl; Br; I; NO$_2$; CF$_3$; CN; ═O; C$_{1-8}$ alkyl; aryl; heteroaryl; C$_{3-10}$ cycloalkyl; heterocyclyl; aryl, heteroaryl, C$_{3-10}$ cycloalkyl or heterocyclyl bridged via C$_{1-8}$ alkyl; CHO; C(═O)C$_{1-8}$ alkyl; C(═O)aryl; C(═O)heteroaryl; CO$_2$H; C(═O)O—C$_{1-8}$ alkyl; C(═O)O-aryl; C(═O)O-heteroaryl; CONH$_2$; C(═O)NH—C$_{1-8}$ alkyl; C(═O)N(C$_{1-8}$ alkyl)$_2$; C(═O)NH-aryl; C(═O)N(aryl)$_2$; C(═O)NH-heteroaryl; C(═O)N(heteroaryl)$_2$; C(═O)N(C$_{1-8}$ alkyl)(aryl); C(═O)N(C$_{1-8}$ alkyl)(heteroaryl); C(═O)N(heteroaryl)(aryl); OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-aryl; O-heteroaryl; O—C(═O)C$_{1-8}$ alkyl; O—C(═O)aryl; O—C(═O)heteroaryl; SH; S—C$_{1-8}$ alkyl; SCF$_3$; S-benzyl; S-aryl; S-heteroaryl; S(═O)$_2$C$_{1-8}$ alkyl; S(═O)$_2$aryl; S(═O)$_2$ heteroaryl; S(═O)$_2$OH; S(═O)$_2$O—C$_{1-8}$ alkyl; S(═O)$_2$O-aryl; S(═O)$_2$O-heteroaryl; S(═O)$_2$—NH—C$_{1-8}$ alkyl; S(═O)$_2$—NH-aryl; and S(═O)$_2$—NH—C$_{1-8}$ heteroaryl.

In relation to "aryl" and "heteroaryl", the term "mono- or polysubstituted" refers in the sense of this invention to the single or multiple, for example double, triple or quadruple, substitution of one or more hydrogen atoms of the ring system each independently of one another by substituents selected from the group of F; Cl; Br; I; NO$_2$; CN; CF$_3$; CF$_2$H; CFH$_2$; CF$_2$Cl; CFCl$_2$; R$^0$; C(═O)H; C(═O)R$^0$; CO$_2$H; C(═O) OR$^0$; CONH$_2$; C(═O)NHR$^0$; C(═O)N(R$^0$)$_2$; OH; OCF$_3$;

$OCF_2H$; $OCFH_2$; $OCF_2Cl$; $OCFCl_2$; $OR^0$; $O—C(=O)—R^0$; $O—C(=O)—O—R^0$; $O—(C=O)—NH—R^0$; $O—C(=O)—N(R)_2$; $O—S(=O)_2—R^0$; $O—S(=O)_2OH$; $O—S(=O)_2OR^0$; $O—S(=O)_2NH_2$; $O—S(=O)_2NHR^0$; $O—S(=O)_2N(R^0)_2$; $NH_2$; $NH—R^0$; $N(R^0)_2$; $NH—C(=O)—R^0$; $NH—C(=O)—O—R^0$; $NH—C(=O)—NH_2$; $NH—C(=O)—NH—R^0$; $NH—C(=O)—N(R^0)_2$; $NR^0—C(=O)—R^0$; $NR^0—C(=O)—O—R^0$; $NR^0—C(=O)—NH_2$; $NR^0—C(=O)—NH—R^0$; $NR^0—C(=O)—N(R^0)_2$; $NH—S(=O)_2OH$; $NH—S(=O)_2R^0$; $NH—S(=O)_2OR^0$; $NH—S(=O)_2NH_2$; $NH—S(=O)_2NHR^0$; $NH—S(=O)_2N(R^0)_2$; $NR^0—S(=O)_2OH$; $NR^0—S(=O)_2R^0$; $NR^0—S(=O)_2OR^0$; $NR^0—S(=O)_2NH_2$; $NR^0—S(=O)_2NHR^0$; $NR^0—S(=O)_2N(R^0)_2$; SH; $SCF_3$; $SCF_2H$; $SCFH_2$; $SCF_2Cl$; $SCFCl_2$; $SR^0$; $S(=O)R^0$; $S(=O)_2R^0$; $S(=O)_2OH$; $S(=O)_2OR^0$; $S(=O)_2NH_2$; $S(=O)_2NHR^0$; or $S(=O)_2N(R^0)_2$, on one or if appropriate different atoms, wherein a substituent can if appropriate for its part in turn be mono- or polysubstituted. The multiple substitution is carried out using the same or using different substituents.

In a particular preferred embodiment "aryl" substituents are ≠CN.

Preferred "aryl" and "heteroaryl" substituents are F; Cl; Br; I; $NO_2$; $CF_3$; CN; $R^0$; $C(=O)(R^0$ or H); $C(=O)O(R^0$ or H); $C(=O)N(R^0$ or H)$_2$; OH; $OR^0$; $O—C(=O)—R^0$; $O—(C_{1-8}$ alkyl)-$O—C_{1-8}$ alkyl; $OCF_3$; $N(R^0$ or H)$_2$; $N(R^0$ or H)$—C(=O)—R^0$; $N(R^0$ or H)$—C(=O)—N(R^0$ or H)$_2$; SH; $SCF_3$; $SR^0$; $S(=O)_2R^0$; $S(=O)_2O(R^0$ or H); $S(=O)_2—N(R^0$ or H)$_2$.

Particularly preferred "aryl" and "heteroaryl" substituents are selected from the group consisting of F; Cl; Br; I; $NO_2$; $CF_3$; CN; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; $C(=O)C_{1-8}$ alkyl; C(=O)aryl; C(=O)heteroaryl; $CO_2H$; $C(=O)O—C_{1-8}$ alkyl; C(=O)O-aryl; C(=O)O-heteroaryl; $CONH_2$; $C(=O)NH—C_{1-8}$ alkyl; $C(=O)N(C_{1-8}$ alkyl)$_2$; C(=O)NH-aryl; $C(=O)N(aryl)_2$; C(=O)NH-heteroaryl; $C(=O)N(heteroaryl)_2$; $C(=O)N(C_{1-8}$ alkyl)(aryl); $C(=O)N(C_{1-8}$ alkyl)(heteroaryl); C(=O)N(heteroaryl)(aryl); OH; $O—C_{1-8}$ alkyl; $OCF_3$; $O—(C_{1-8}$ alkyl)-OH; $O—(C_{1-8}$ alkyl)-$O—C_{1-8}$ alkyl; O-benzyl; O-aryl; O-heteroaryl; $O—C(=O)C_{1-8}$ alkyl; O—C(=O)aryl; O—C(=O)heteroaryl; $NH_2$; $NH—C_{1-8}$ alkyl; $N(C_{1-8}$ alkyl)$_2$; $NH—C(=O)C_{1-8}$ alkyl; NH—C(=O)-aryl; NH—C(=O)-heteroaryl; SH; $S—C_{1-8}$ alkyl; $SCF_3$; S-benzyl; S-aryl; S-heteroaryl; $S(=O)_2C_{1-8}$ alkyl; $S(=O)_2$aryl; $S(=O)_2$ heteroaryl; $S(=O)_2OH$; $S(=O)_2O—C_{1-8}$ alkyl; $S(=O)_2$O-aryl; $S(=O)_2$O-heteroaryl; $S(=O)_2—NH—C_{1-8}$ alkyl; $S(=O)_2—NH$-aryl; $S(=O)_2—NH—C_{1-8}$ heteroaryl.

The compounds according to the invention are defined by substituents, for example by $R^1$, $R^2$ and $R^3$ (1$^{st}$ generation substituents) which are for their part if appropriate substituted (2$^{nd}$ generation substituents). Depending on the definition, these substituents of the substituents can for their part be resubstituted (3$^{rd}$ generation substituents). If, for example, $R^1$=aryl (1$^{st}$ generation substituent), then aryl can for its part be substituted, for example with $C_{1-8}$ alkyl (2$^{nd}$ generation substituent). This produces the functional group aryl-$C_{1-8}$ alkyl. $C_{1-8}$ alkyl can then for its part be resubstituted, for example with Cl (3$^{rd}$ generation substituent). Overall, this then produces the functional group aryl-$C_{1-8}$ alkyl-Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^{10}$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, respectively unsubstituted or mono- or polysubstituted. Both these aryl or heteroaryl residues and the aromatic ring systems formed in this way can if appropriate be condensed with $C_{3-10}$ cycloalkyl or heterocyclyl, respectively saturated or unsaturated, or with aryl or heteroaryl, i.e. with a $C_{3-10}$ cycloalkyl such as cyclopentyl or a heterocyclyl such as morpholinyl, or an aryl such as phenyl or a heteroaryl such as pyridyl, wherein the $C_{3-10}$ cycloalkyl or heterocyclyl residues, aryl or heteroaryl residues condensed in this way can for their part be respectively unsubstituted or mono- or polysubstituted.

In some cases, the compounds according to the invention are defined by substituents which are or carry a $C_{3-10}$ cycloalkyl or heterocyclyl residue, respectively unsubstituted or mono- or polysubstituted, or which form together with the carbon atom(s) or heteroatom(s) connecting them, as the ring member or as the ring members, a ring, for example a $C_{3-10}$ cycloalkyl or heterocyclyl, respectively unsubstituted or mono- or polysubstituted. Both these $C_{3-10}$ cycloalkyl or heterocyclyl residues and the aliphatic ring systems formed can if appropriate be condensed with aryl or heteroaryl or with $C_{3-10}$ cycloalkyl or heterocyclyl, i.e. with an aryl such as phenyl or a heteroaryl such as pyridyl or a $C_{3-10}$ cycloalkyl such as cyclohexyl or a heterocyclyl such as morpholinyl, wherein the aryl or heteroaryl residues or $C_{3-10}$ cycloalkyl or heterocyclyl residues condensed in this way can for their part be respectively unsubstituted or mono- or polysubstituted.

Within the scope of the present invention, the symbol

used in the formulae denotes a link of a corresponding residue to the respective superordinate general structure.

The term "($R^0$ or H)" within a residue means that $R^0$ and H can occur within this residue in any possible combination. Thus, for example, the residue "N($R^0$ or H)$_2$" can represent "$NH_2$", "$NHR^0$" and "$N(R^0)_2$". If, as in the case of "$N(R^0)_2$", $R^0$ occurs multiply within a residue, then $R^0$ can respectively have the same or different meanings: in the present example of "$N(R^0)_2$", $R^0$ can for example represent aryl twice, thus producing the functional group "$N(aryl)_2$", or $R^0$ can represent once aryl and once $C_{1-10}$ alkyl, thus producing the functional group "$N(aryl)(C_{1-10}$ alkyl)".

If a residue occurs multiply within a molecule, such as for example the residue $R^0$, then this residue can have respectively different meanings for various substituents: if, for example, both $R^1$=$R^0$ and $R^2$=$R^0$, then $R^0$ can represent $R^1$=aryl and $R^0$ can represent $R^2$=$C_{1-10}$ alkyl.

The term "salt formed with a physiologically compatible acid" refers in the sense of this invention to salts of the respective active ingredient with inorganic or organic acids which are physiologically compatible—in particular when used in human beings and/or other mammals. Hydrochloride is particularly preferred. Examples of physiologically compatible acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

Physiologically compatible salts with cations or bases are salts of the respective compound—as an anion with at least one, preferably inorganic, cation—which are physiologically compatible—in particular when used in human beings and/or other mammals. Particularly preferred are the salts of the alkali and alkaline earth metals but also ammonium salts $[NH_xR_{4-x}]^+$, in which x=0, 1, 2, 3 or 4 and R represents a branched or unbranched $C_{1-4}$ alkyl residue, in particular (mono-) or (di)sodium, (mono-) or (di)potassium, magnesium or calcium salts.

In preferred embodiments of the compounds according to the invention of general formula (I), n represents 1, 2, 3 or 4, preferably 1, 2 or 3, particularly preferably 1 or 2, most particularly preferably 1.

Further preferred embodiments of the compounds according to the invention of general formula (I) have general formula (Ia), (Ib), (Ic) or (Id):

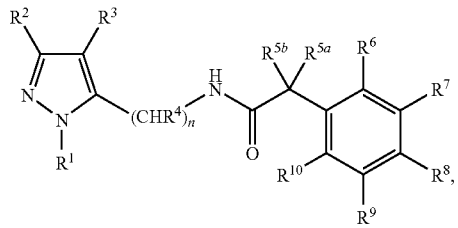
(Ia)

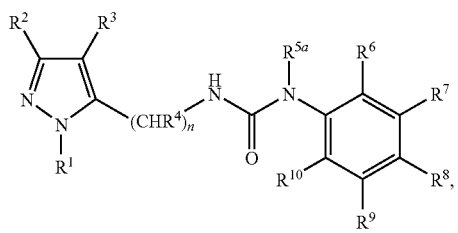
(Ib)

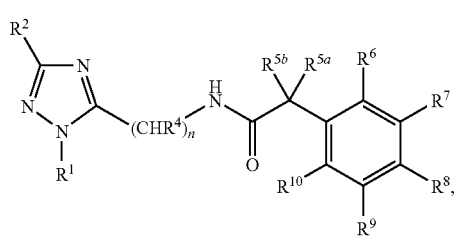
(Ic)

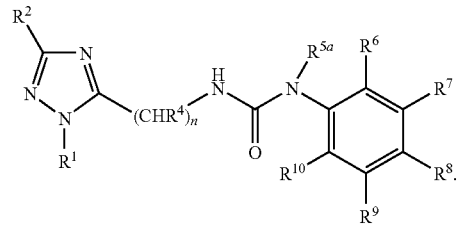
(Id)

Compounds of general formulae (Ia) and (Ib) are most particularly preferred.

In a particular preferred embodiment of the present invention $R^1$ is ≠H.

In a further preferred embodiment of the compounds according to the invention of general formula (I), the residue $R^1$ represents H; $C_{1-10}$ alkyl, C(=O)—$C_{1-10}$ alkyl, C(=O)—NH—$C_{1-10}$ alkyl, C(=O)—N($C_{1-10}$ alkyl)$_2$, O—$C_{1-10}$ alkyl, S—$C_{1-10}$ alkyl, NH($C_{1-10}$ alkyl), N($C_{1-10}$ alkyl)$_2$, NH—C(=O)—$C_{1-10}$ alkyl, NH—S(=O)$_2$—$C_{1-10}$ alkyl, N($C_{1-10}$ alkyl)-S(=O)$_2$—$C_{1-10}$ alkyl, S(=O)$_2$—$C_{1-10}$ alkyl, S(=O)$_2$—NH—$C_{1-10}$ alkyl, S(=O)$_2$—N($C_{1-10}$ alkyl)$_2$, in which $C_{1-10}$ alkyl can be respectively saturated or unsaturated, branched or unbranched, unsubstituted or mono- or polysubstituted with one or more substituents each selected independently of one another from the group consisting of F, Cl, Br, I, NO$_2$, CN, OH, =O, O—$C_{1-4}$ alkyl, OCF$_3$, CF$_3$, NH$_2$, NH($C_{1-4}$ alkyl), N($C_{1-4}$ alkyl)$_2$, SH, S—$C_{1-4}$ alkyl, SCF$_3$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—$C_{1-4}$ alkyl, OCF$_3$, $C_{1-4}$ alkyl, C(=O)—OH, CF$_3$, NH$_2$, NH($C_{1-4}$ alkyl), N($C_{1-4}$ alkyl)$_2$, SH, S—$C_{1-4}$ alkyl, SCF$_3$ and S(=O)$_2$OH;

or $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, NO$_2$, CN, OH, =O, O—$C_{1-4}$ alkyl, OCF$_3$, CF$_3$, SH, S—$C_{1-4}$ alkyl, SCF$_3$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—$C_{1-4}$ alkyl, OCF$_3$, $C_{1-4}$ alkyl, C(=O)—OH, CF$_3$, NH$_2$, NH($C_{1-4}$ alkyl), N($C_{1-4}$ alkyl)$_2$, SH, S—$C_{1-4}$ alkyl, SCF$_3$ and S(=O)$_2$OH;

or $C_{3-10}$ cycloalkyl$^1$ or heterocyclyl$^1$ bridged via $C_{1-8}$ alkyl, respectively saturated or unsaturated, unsubstituted or mono- or polysubstituted with one or more substituents each selected independently of one another from the group consisting of F, Cl, Br, I, NO$_2$, CN, OH, =O, O—$C_{1-4}$ alkyl, OCF$_3$, CF$_3$, SH, S—$C_{1-4}$ alkyl, SCF$_3$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—$C_{1-4}$ alkyl, OCF$_3$, $C_{1-4}$ alkyl, C(=O)—OH, CF$_3$, NH$_2$, NH($C_{1-4}$ alkyl), N($C_{1-4}$ alkyl)$_2$, SH, S—$C_{1-4}$ alkyl, SCF$_3$ and S(=O)$_2$OH; wherein the alkyl chain can be respectively branched or unbranched, saturated or unsaturated, unsubstituted, mono- or polysubstituted with one or more substituents each selected independently of one another from the group consisting of F, Cl, Br; I, OH and O—$C_{1-4}$ alkyl;

or C(=O)—$C_{3-10}$ cycloalkyl, O—$C_{3-10}$ cycloalkyl, S—$C_{3-10}$ cycloalkyl, respectively saturated or unsaturated, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH;

or aryl, heteroaryl, C(=O)-aryl, C(=O)-heteroaryl, O-aryl, O-heteroaryl, NH(aryl), N(aryl)$_2$, NH(heteroaryl), N(heteroaryl)$_2$, NH—C(=O)-aryl, NH—C(=O)-heteroaryl, NH—S(=O)$_2$-aryl, NH—S(=O)$_2$-heteroaryl, S(=O)$_2$-aryl, S(=O)$_2$-heteroaryl or aryl or heteroaryl bridged via $C_{1-8}$ alkyl, can be respectively unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, S(=O)$_2$OH and NH—S(=O)$_2$—$C_{1-4}$ alkyl, and wherein if appropriate the alkyl chain can be respectively branched or unbranched, saturated or unsaturated, unsubstituted, mono- or polysubstituted with one or more substituents each selected independently of one another from the group consisting of F, Cl, Br, I, OH and O—$C_{1-4}$ alkyl.

In another preferred embodiment of the compounds according to the invention of general formula (I), the residue $R^1$ represents substructure (T1)

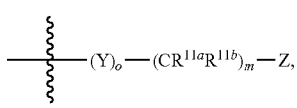

(T1)

in which

Y represents C(=O), O, S, S(=O)$_2$, NH—C(=O) or $NR^{12}$, wherein $R^{12}$ represents H; $C_{1-8}$ alkyl or S(=O)$_2$—$C_{1-8}$ alkyl, in which $C_{1-8}$ alkyl can be respectively saturated or unsaturated, branched or unbranched, unsubstituted or mono- or polysubstituted with one or more substituents each selected independently of one another from the group consisting of F, Cl, Br, I, OH, O—$C_{1-4}$ alkyl, $OCF_3$, $NH_2$, NH—$C_{1-4}$ alkyl and N($C_{1-4}$ alkyl)$_2$;

o represents 0 or 1, $R^{11a}$ and $R^{11b}$ each independently of one another represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, N($C_{1-4}$ alkyl)$_2$, in which $C_{1-4}$ alkyl can be respectively saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$;

on the condition that if $R^{11a}$ and $R^{11b}$ are bound to the same carbon atom, only one of the substituents $R^{11a}$ and $R^{11b}$ can represent OH, $OCF_3$, $NH_2$, O—$C_{1-4}$ alkyl, NH—$C_{1-4}$ alkyl or N($C_{1-4}$ alkyl)$_2$;

m represents 0, 1, 2, 3 or 4;

Z represents $C_{1-4}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, SH, S—$C_{1-4}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH.

If m≠0, then the residues $R^{11a}$ and $R^{11b}$ can, taking account of the foregoing condition, both on the same carbon atom and on different carbon atoms, each independently of one another represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, N($C_{1-4}$ alkyl)$_2$, in which $C_{1-4}$ alkyl can be respectively saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$.

Preferably, the residue $R^1$ represents substructure (T1) in which

Y represents C(=O), O, S, S(=O)$_2$, NH—C(=O) or $NR^{12}$, wherein $R^{12}$ represents H; methyl; ethyl; n-propyl; isopropyl; n-butyl; sec.-butyl; tert.-butyl; S(=O)$_2$-methyl; S(=O)$_2$-ethyl;

o represents 0 or 1;

$R^{11a}$ and $R^{11b}$ each independently of one another represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—($CH_2$)$_2$—O—$CH_3$; O—($CH_2$)$_2$—OH; $OCF_3$; $NH_2$; NH-methyl; N(methyl)$_2$; NH-ethyl; N(ethyl)$_2$; or N(methyl)(ethyl);

on the condition that if $R^{11a}$ and $R^{11b}$ are bound to the same carbon atom, only one of the substituents $R^{11a}$ and $R^{11b}$ can represent OH; $OCF_3$; O-methyl; O-ethyl; O—($CH_2$)$_2$—O—$CH_3$; O—($CH_2$)$_2$—OH; $NH_2$; NH-methyl; N(methyl)$_2$; NH-ethyl; N(ethyl)$_2$; or N(methyl)(ethyl);

m represents 0, 1 or 2;

Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, =O, O—$C_{1-4}$ alkyl, $OCF_3$, C(=O)—OH and $CF_3$; phenyl, naphthyl, furyl, pyridyl or thienyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-8}$ alkyl, $SCF_3$, benzyl and phenyl, wherein benzyl and phenyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-4}$ alkyl and $SCF_3$; $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, benzyl, phenyl and pyridyl, wherein benzyl, phenyl and pyridyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-4}$ alkyl and $SCF_3$.

If m≠0, then the residues $R^{11a}$ and $R^{11b}$ can, taking account of the foregoing condition, both on the same carbon atom and on different carbon atoms, each independently of one another represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; $N(methyl)_2$; NH-ethyl; $N(ethyl)_2$; or N(methyl)(ethyl).

Particularly preferably, the residue
$R^1$ represents substructure (T1) in which
Y represents C(=O), O, S, S(=O)$_2$, NH—C(=O) or $NR^{12}$,
    wherein $R^{12}$ represents H; methyl; ethyl; n-propyl; isopropyl; n-butyl; sec.-butyl; tert.-butyl; S(=O)$_2$-methyl; S(=O)$_2$-ethyl;
o represents 0 or 1;
$R^{11a}$ and $R^{11b}$ each independently of one another represent H; F; Cl; Br; I; methyl; ethyl; n-propyl; isopropyl; n-butyl; sec.-butyl; tert.-butyl; OH; O-methyl; O-ethyl;
    on the condition that if $R^{11a}$ and $R^{11b}$ are bound to the same carbon atom, only one of the substituents $R^{11a}$ and $R^{11b}$ can represent OH; O-methyl; O-ethyl;
m represents 0, 1 or 2;
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, O—$C_{1-4}$ alkyl, $OCF_3$, and $CF_3$; $C_{3-10}$ cycloalkyl$^1$, saturated or unsaturated, unsubstituted or mono- or polysubstituted independently of one another from the group consisting of F, Cl, Br, I, OH, O—$C_{1-4}$ alkyl, $OCF_3$, $C_{1-4}$ alkyl, $CF_3$, benzyl and phenyl, wherein benzyl and phenyl can be respectively unsubstituted or mono- or polysubstituted with one or more substituents selected independently of one another from the group consisting of F, Cl, Br, I, OH, O—$C_{1-4}$ alkyl, $OCF_3$, $C_{1-4}$ alkyl, $CF_3$, and $SCF_3$; morpholinyl, thiomorpholinyl, piperidinyl, pyrrolidinyl, 4-methylpiperazinyl, piperazinyl, respectively unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, benzyl and phenyl, wherein benzyl and phenyl can be respectively unsubstituted or mono- or polysubstituted with one or more substituents selected independently of one another from the group consisting of F, Cl, Br, I, OH, O—$C_{1-4}$ alkyl, $OCF_3$, $C_{1-4}$ alkyl, $CF_3$ and $SCF_3$; phenyl, naphthyl, pyridyl or thienyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$, benzyl and phenyl, wherein benzyl and phenyl can be respectively unsubstituted or mono- or polysubstituted with one or more substituents selected independently of one another from the group consisting of F, Cl, Br, I, OH, O—$C_{1-4}$ alkyl, $OCF_3$, $C_{1-4}$ alkyl, $CF_3$ and $SCF_3$.

If m≠0, then the residues $R^{11a}$ and $R^{11b}$ can, taking account of the foregoing condition, both on the same carbon atom and on different carbon atoms, each independently of one another represent H; F; Cl; Br; I; methyl; ethyl; n-propyl; isopropyl; n-butyl; sec.-butyl; tert.-butyl; OH; O-methyl; O-ethyl.

Most particularly preferably, the residue
$R^1$ represents substructure (T1) in which
Y represents C(=O), O, S, S(=O)$_2$, NH—C(=O) or $NR^{12}$,
    wherein $R^{12}$ represents H; methyl; ethyl; n-propyl; isopropyl; n-butyl; sec.-butyl; tert.-butyl; S(=O)$_2$-methyl;
o represents 0 or 1;
$R^{11a}$ and $R^{11b}$ each independently of one another represent H; methyl; ethyl; n-propyl; isopropyl; n-butyl; sec.-butyl; tert.-butyl;
m represents 0, 1 or 2;
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, O—$C_{1-4}$ alkyl; $C_{3-10}$ cycloalkyl$^1$, saturated or unsaturated, morpholinyl, piperidinyl, 4-methylpiperazinyl, piperazinyl, respectively unsubstituted or mono- or polysubstituted with one or more substituents each selected independently of one another from the group consisting of F, Cl, Br, I, OH, O—$C_{1-4}$ alkyl and $C_{1-4}$ alkyl; phenyl or pyridyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$.

If m≠0, then the residues $R^{11a}$ and $R^{11b}$ can, both on the same carbon atom and on different carbon atoms, each independently of one another represent H; methyl; ethyl; n-propyl; isopropyl; n-butyl; sec.-butyl; tert.-butyl.

In a particular preferred embodiment of the present invention $R^2$ is ≠Br and ≠Cl.

In a further preferred embodiment of the compounds according to the invention of general formula (I), the residue $R^2$ represents H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and S(=O)$_2$OH; $C_{3-10}$ cycloalkyl or heterocyclyl, respectively saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$, C(=O)—OH and $CF_3$; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br, I, OH, =O, $C_{1-4}$ alkyl, O—$C_{1-4}$ alkyl, $OCF_3$, C(=O)—OH and $CF_3$, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl.

Preferably, the residue $R^2$ represents H; F; Cl; Br; I; CN; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently of one another from the group consisting of F, Cl, Br, I, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$; $C_{3-10}$ cycloalkyl, saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$ and $CF_3$; or $C_{3-10}$ cycloalkyl bridged via $C_{1-8}$ alkyl, saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$ and $CF_3$, wherein the alkyl chain can be respectively branched or unbranched, saturated or unsaturated, unsubstituted; aryl or heteroaryl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-8}$ alkyl, $SCF_3$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; or aryl or heteroaryl bridged via $C_{1-8}$ alkyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-8}$ alkyl, $SCF_3$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$ OH, wherein the alkyl chain can be respectively branched or unbranched, saturated or unsaturated, unsubstituted.

Particularly preferably, $R^2$ represents H; F; Cl; Br; I; CN; $C_{1-10}$ alkyl, saturated or unsaturated, branched or unbranched, unsubstituted or mono- or polysubstituted with one or more substituents selected independently of one another from the group consisting of F, Cl, Br, I and OH; $C_{3-10}$ cycloalkyl, saturated or unsaturated, unsubstituted; or $C_{3-10}$ cycloalkyl bridged via $C_{1-4}$ alkyl, saturated or unsaturated, unsubstituted, wherein the alkyl chain can be branched or unbranched, saturated or unsaturated, unsubstituted; or phenyl, pyridyl, thienyl, respectively unsubstituted or mono- or polysubstituted with one or more substituents selected independently of one another from the group consisting of $C_{1-4}$ alkyl, O—$C_{1-4}$ alkyl, F, Cl, Br, I, $CF_3$, $OCF_3$, OH, SH and $SCF_3$; or phenyl, pyridyl or thienyl bridged via $C_{1-4}$ alkyl, respectively unsubstituted or mono- or polysubstituted with one or more substituents selected independently of one another from the group consisting of $C_{1-4}$ alkyl, O—$C_{1-4}$ alkyl, F, Cl, Br, I, $CF_3$, $OCF_3$, OH, SH and $SCF_3$, wherein the alkyl chain can be branched or unbranched, saturated or unsaturated, unsubstituted.

Most particularly preferably, the substituent $R^2$ is selected from the group consisting of H; F; Cl; Br; I; CN; cyclopropyl; cyclobutyl; $C_{1-10}$ alkyl, saturated or unsaturated, branched or unbranched, unsubstituted, or mono- or polysubstituted with one or more substituents selected independently of one another from the group consisting of F, Cl, Br; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$.

Particularly preferably, the substituent $R^2$ represents H; F; Cl; Br; I; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$;

Especially particularly preferably, $R^2$ represents tert.-butyl or $CF_3$.

In a further preferred embodiment of the compounds according to the invention of general formula (I), X represents $CR^3$ or N, preferably $CR^3$,
wherein $R^3$ represents H; $C_{1-10}$ alkyl, saturated or unsaturated, branched or unbranched, unsubstituted, mono- or polysubstituted with one or more substituents each selected independently of one another from the group consisting of F, Cl, Br, I and OH;

Preferably,

X represents $CR^3$ or N, preferably $CR^3$,
wherein $R^3$ represents H; $C_{1-10}$ alkyl, saturated or unsaturated, branched or unbranched, unsubstituted; or $CF_3$.

Particularly preferably,

X represents $CR^3$ or N, preferably $CR^3$,
wherein $R^3$ represents H; methyl; ethyl; n-propyl; isopropyl; n-butyl; sec.-butyl; tert.-butyl; or $CF_3$.

Most particularly preferably,

X represents $CR^3$ or N, preferably $CR^3$,
wherein $R^3$ represents H or $CH_3$, most preferred H.

In a further preferred embodiment of the compounds according to the invention of general formula (I), the residue $R^4$ represents H; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

A represents N or $CR^{5b}$;

$R^{5a}$ represents H; OH; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl; $C_{3-10}$ cycloalkyl or heterocyclyl, respectively saturated or unsaturated, unsubstituted or mono- or polysubstituted with one or more substituents each selected independently of one another from the group consisting of F, Cl, Br; I, OH, =O and O—$C_{1-4}$ alkyl; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br; I, OH, =O and O—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br; I, OH, =O and O—$C_{1-4}$ alkyl; or aryl, heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$, $S(=O)_2OH$ and NH—S(=O)$_2$—$C_{1-4}$ alkyl; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$, $S(=O)_2OH$ and NH—S(=O)$_2$—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br; I, OH, =O and O—$C_{1-4}$ alkyl;

or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently of one another from the group consisting of F, Cl, Br; I, OH, =O and O—$C_{1-4}$ alkyl.

Preferably, the residue $R^4$ represents H; or $C_{1-10}$ alkyl, saturated or unsaturated, branched or unbranched, unsubstituted;

A represents N or $CR^{5b}$;

$R^{5a}$ represents H; or $C_{1-10}$ alkyl, saturated or unsaturated, branched or unbranched, unsubstituted;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br, I, OH and O—$C_{1-4}$ alkyl; $C_{3-10}$ cycloalkyl, saturated or unsaturated, unsubstituted or mono- or polysubstituted with one or more substituents each selected independently of one another from the group consisting of F, Cl, Br, I and $C_{1-4}$ alkyl; or $C_{3-10}$ cycloalkyl bridged via $C_{1-4}$ alkyl, saturated or unsaturated, unsubstituted or mono- or polysubstituted with one or more substituents each selected independently of one another from the group consisting of F, Cl, Br, I and $C_{1-4}$ alkyl, wherein the alkyl chain can be respectively branched or unbranched, saturated or unsaturated, unsubstituted; or phenyl or pyridyl, respectively unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-4}$ alkyl, $SCF_3$ and NH—S(=O)$_2$—$C_{1-4}$ alkyl; or phenyl or pyridyl bridged via $C_{1-4}$ alkyl, respectively unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-4}$ alkyl, $SCF_3$ and NH—S(=O)$_2$—$C_{1-4}$ alkyl, wherein the alkyl chain can be respectively branched or unbranched, saturated or unsaturated, unsubstituted, or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently of one another from the group consisting of F, Cl, Br; I, OH, =O and O—$C_{1-4}$ alkyl.

Particularly preferably, the residue $R^4$ represents H; methyl; ethyl; n-propyl; or isopropyl;

A represents N or $CR^{5b}$;

$R^{5a}$ represents H or $CH_3$, preferably H, if A represents N;

or $R^{5a}$ represents H or $CH_3$, preferably H, if A represents $CR^{5b}$,
wherein $R^{5b}$ represents H; or $C_{1-4}$ alkyl, saturated or unsaturated, branched or unbranched, unsubstituted; $C_{3-10}$ cycloalkyl, saturated or unsaturated, unsubstituted; or phenyl or benzyl, in each case unsubstituted or mono- or polysubstituted with one or more substituents each selected independently of one another from the group consisting of F, Cl, Br, I, $CF_3$, O—$C_{1-4}$ alkyl, $OCF_3$ and $C_{1-4}$ alkyl, or $R^{5a}$ and $R^{5b}$ form together with the carbon atom connecting them a $C_{3-10}$ cycloalkyl, saturated or unsaturated, preferably saturated, unsubstituted or mono- or polysubstituted with one or more substituents each selected independently of one another from the group consisting of F, Cl, Br; I, OH, =O and O—$C_{1-4}$ alkyl, preferably unsubstituted.

Most particularly preferably, the residue
A represents N or $CR^{5b}$;
$R^4$ represents H;
$R^{5a}$ represents H;
$R^{5b}$ represents H; or $C_{1-4}$ alkyl, saturated or unsaturated, branched or unbranched, unsubstituted; cyclohexyl, unsubstituted; or phenyl or benzyl, in each case unsubstituted or mono- or polysubstituted with one or more substituents each selected independently of one another from the group consisting of F, Cl, Br, I, O—$C_{1-4}$ alkyl, $CF_3$, $OCF_3$ and $C_{1-4}$ alkyl,
or $R^{5a}$ and $R^{5b}$ form together with the carbon atom connecting them a $C_{3-10}$ cycloalkyl, saturated or unsaturated, unsubstituted.

In a further preferred embodiment of the compounds according to the invention of general formula (I), the residues $R^6$, $R^7$, $R^8$, $R^9$ and $R^{10}$ are each selected independently of one another from the group consisting of H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $NH_2$; C(=O)—$NH_2$; $C_{1-10}$ alkyl, $C_{1-10}$ alkyl-O—$C_{1-10}$ alkyl, C(=O)—NH—$C_{1-10}$ alkyl, O—$C_{1-10}$ alkyl, NH($C_{1-10}$ alkyl), N($C_{1-10}$ alkyl)$_2$, NH—C(=O)—$C_{1-10}$ alkyl, N($C_{1-10}$ alkyl)-C(=O)—$C_{1-10}$ alkyl, NH—S(=O)$_2$—$C_{1-10}$ alkyl, S—$C_{1-10}$ alkyl, $SO_2$—$C_{1-10}$ alkyl, $SO_2$—NH($C_{1-10}$ alkyl), $SO_2$—N($C_{1-10}$ alkyl)$_2$, in which $C_{1-10}$ alkyl can be respectively saturated or unsaturated, branched or unbranched, unsubstituted or mono- or polysubstituted with one or more substituents selected independently of one another from the group consisting of F, Cl, Br, I, $NO_2$, CN, OH, O—$C_{1-4}$ alkyl, $OCF_3$, $CF_3$, $NH_2$, NH($C_{1-4}$ alkyl), N($C_{1-4}$ alkyl)$_2$, NH—S(=O)$_2$—$C_{1-4}$ alkyl, N($C_{1-4}$ alkyl)-S(=O)$_2$—$C_{1-4}$ alkyl, SH, S—$C_{1-4}$ alkyl, S(=O)$_2$—$C_{1-4}$ alkyl and $SCF_3$;
$C_{3-10}$ cycloalkyl, heterocyclyl or $C_{3-10}$ cycloalkyl or heterocyclyl bridged via $C_{1-8}$ alkyl, respectively saturated or unsaturated, unsubstituted or mono- or polysubstituted with one or more substituents selected independently of one another from the group consisting of F, Cl, Br, I, $NO_2$, CN, OH, O—$C_{1-4}$ alkyl, $OCF_3$, $CF_3$, $C_{1-4}$ alkyl, $NH_2$, NH($C_{1-4}$ alkyl), N($C_{1-4}$ alkyl)$_2$, NH—S(=O)$_2$—$C_{1-4}$ alkyl, N($C_{1-4}$ alkyl)-S(=O)$_2$—$C_{1-4}$ alkyl, SH, S—$C_{1-4}$ alkyl, S(=O)$_2$—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—$C_{1-4}$ alkyl;
aryl, heteroaryl, C(=O)—NH-aryl, C(=O)—NH-heteroaryl, NH—C(=O)-aryl, NH(C=O)-heteroaryl, NH(aryl), NH(heteroaryl), N(aryl)$_2$, N(heteroaryl)$_2$ or aryl or heteroaryl bridged via $C_{1-8}$ alkyl, respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—$C_{1-4}$ alkyl.

In another preferred embodiment of the compounds according to the invention of general formula (I), the residues $R^6$ and $R^{10}$ each represent H.

In a further preferred embodiment of the compounds according to the invention of general formula (I), the residues $R^6$ and $R^{10}$ are each selected independently of one another from the group consisting of H; F; Cl; Br; I; CN; $CF_3$; OH; $OCF_3$; SH; $SCF_3$; $C_{1-4}$ alkyl, O—$C_{1-4}$ alkyl and NH—S(=O)$_2$—$C_{1-4}$ alkyl, in which $C_{1-4}$ alkyl can be respectively saturated or unsaturated, branched or unbranched, unsubstituted;
and the residues $R^7$, $R^8$ and $R^9$ are each selected independently of one another from the group consisting of H; F; Cl; Br; I; CN; $NO_2$; $CF_3$; OH; $OCF_3$; SH; $SCF_3$; $NH_2$; C(=O)—$NH_2$; $C_{1-4}$ alkyl, $C_{1-4}$ alkyl-O—$C_{1-4}$ alkyl, C(=O)—NH—$C_{1-4}$ alkyl, O—$C_{1-4}$ alkyl, NH($C_{1-4}$ alkyl), N($C_{1-4}$ alkyl)$_2$, NH—C(=O)—$C_{1-4}$ alkyl, NH—S(=O)$_2$—$C_{1-4}$ alkyl, S—$C_{1-4}$ alkyl, $SO_2$—$C_{1-4}$ alkyl, $SO_2$—NH($C_{1-4}$ alkyl), $SO_2$—N($C_{1-4}$ alkyl)$_2$, in which $C_{1-4}$ alkyl can be respectively saturated or unsaturated, branched or unbranched, unsubstituted or mono- or polysubstituted with one or more substituents selected independently of one another from the group consisting of F, Cl, Br, I, OH, O—$C_{1-4}$ alkyl, $OCF_3$, $CF_3$, NH—S(=O)$_2$—$C_{1-4}$ alkyl, SH, S—$C_{1-4}$ alkyl, S(=O)$_2$—$C_{1-4}$ alkyl and $SCF_3$; $C_{3-10}$ cycloalkyl, heterocyclyl or $C_{3-10}$ cycloalkyl or heterocyclyl bridged via $C_{1-8}$ alkyl, respectively saturated or unsaturated, unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, NH—S(=O)$_2$—$C_{1-4}$ alkyl, N($C_{1-4}$ alkyl)-S(=O)$_2$—$C_{1-4}$ alkyl, SH, S—$C_{1-4}$ alkyl, S(=O)$_2$—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—$C_{1-4}$ alkyl; phenyl, pyridyl, furyl, thienyl, C(=O)—NH-phenyl, NH—C(=O)-phenyl, NH(phenyl), C(=O)—NH-pyridyl, NH—C(=O)-pyridyl, NH(pyridyl) or phenyl or pyridyl bridged via $C_{1-8}$ alkyl, wherein phenyl, pyridyl, furyl or thienyl are respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—$C_{1-4}$ alkyl.

Preferably,
$R^6$, $R^7$, $R^9$ and $R^{10}$ are each selected independently of one another from the group consisting of H; F; Cl; Br; I; $CF_3$; $OCF_3$; $SCF_3$; $C_{1-4}$ alkyl, O—$C_{1-4}$ alkyl and NH—S(=O)$_2$—$C_{1-4}$ alkyl, in which $C_{1-4}$ alkyl can be respectively saturated or unsaturated, branched or unbranched, unsubstituted;
and $R^8$ is selected from the group consisting of H; F; Cl; Br; I; CN; $NO_2$; $CF_3$; OH; $OCF_3$; SH; $SCF_3$; $NH_2$; C(=O)—$NH_2$; $C_{1-4}$ alkyl, $C_{1-4}$ alkyl-O—$C_{1-4}$ alkyl, C(=O)—NH—$C_{1-4}$ alkyl, O—$C_{1-4}$ alkyl, NH($C_{1-4}$ alkyl), N($C_{1-4}$ alkyl)$_2$, NH—C(=O)—$C_{1-4}$ alkyl, NH—S(=O)$_2$—$C_{1-4}$ alkyl, S—$C_{1-4}$ alkyl, $SO_2$—$C_{1-4}$ alkyl, $SO_2$—NH($C_{1-4}$ alkyl), $SO_2$—N($C_{1-4}$ alkyl)$_2$, in which $C_{1-4}$ alkyl can be respectively saturated or unsaturated, branched or unbranched, unsubstituted or mono- or polysubstituted with one or more substituents selected independently of one another from the group consisting of F, Cl, Br, I, OH, O—$C_{1-4}$ alkyl, $OCF_3$, $CF_3$, NH—S(=O)$_2$—$C_{1-4}$ alkyl, SH, S—$C_{1-4}$ alkyl, S(=O)$_2$—$C_{1-4}$ alkyl and $SCF_3$; $C_{3-10}$ cycloalkyl, heterocyclyl or $C_{3-10}$ cycloalkyl or heterocyclyl bridged via 8 alkyl, respectively saturated or unsaturated, unsubstituted or mono- or polysubstituted with one or more substituents selected independently of one another from the group consisting of F, Cl, Br, I, NO₂, CN, OH, O—C₁₋₄ alkyl, OCF₃, C₁₋₄ alkyl, CF₃, NH₂, NH(C₁₋₄ alkyl), N(C₁₋₄ alkyl)₂, NH—S(=O)₂—C₁₋₄ alkyl, N(C₁₋₄ alkyl)-S(=O)₂—C₁₋₄ alkyl, SH, S—C₁₋₄ alkyl, S(=O)₂—C₁₋₄ alkyl and SCF₃, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—C₁₋₄ alkyl; phenyl, pyridyl, furyl, thienyl, C(=O)—NH-phenyl, NH—C(=O)-phenyl, NH(phenyl), C(=O)—NH-pyridyl, NH—C(=O)-pyridyl, NH(pyridyl) or phenyl or pyridyl bridged via C₁₋₈ alkyl, wherein phenyl, pyridyl, furyl or thienyl are respectively unsubstituted or mono- or polysubstituted with one or more substituents selected independently of one another from the group consisting of F, Cl, Br, I, CN, OH, O—C₁₋₄ alkyl, OCF₃, C₁₋₄ alkyl, CF₃, SH, S—C₁₋₄ alkyl and SCF₃, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—C₁₋₄ alkyl.

Particularly preferably,

R⁶ and R¹⁰ each represent H;

R⁷ and R⁹ each independently of one another represent H; F; Cl; Br; I; C₁₋₄ alkyl, O—C₁₋₄ alkyl;

R⁸ represents H; F; Cl; Br; I; CN; NO₂; CF₃; OH; OCF₃; SH; SCF₃; NH₂; C(=O)—NH₂; C(=O)—NH(methyl); C(=O)—NH(ethyl); C(=O)—N (methyl)₂; C(=O)—N (ethyl)₂; C₁₋₄ alkyl, saturated or unsaturated, branched or unbranched, unsubstituted or mono- or disubstituted with OH; NH—O(=O)-methyl; NH—O(=O)-ethyl; CH₂—NH—S(=O)₂-methyl; CH₂—NH—S(=O)₂-ethyl; NH—S(=O)₂-methyl; NH—S(=O)₂-ethyl; S-methyl; S-ethyl; S(=O)₂-methyl; S(=O)₂-ethyl; S(=O)₂—NH-methyl; S(=O)₂—NH-ethyl; S(=O)₂—N(methyl)₂; S(=O)₂—N(ethyl)₂; CH₂—S(=O)₂-(methyl); CH₂—S(=O)₂-ethyl); OC₁₋₄ alkyl, saturated or unsaturated, branched or unbranched, unsubstituted; C₁₋₄ alkyl-O—C₁₋₄ alkyl-O—C₁₋₄ alkyl, C₃₋₁₀ cycloalkyl or C₃₋₁₀ cycloalkyl bridged via C₁₋₈ alkyl, respectively saturated or unsaturated, and wherein if appropriate the alkyl chain can be respectively branched or unbranched, saturated or unsaturated, unsubstituted; piperidinyl; piperazinyl; 4-methylpiperazinyl; morpholinyl; dioxidoisothiazolidinyl; phenyl, pyridyl, furyl, thienyl, C(=O)—NH-phenyl, NH—O(=O)-phenyl, NH(phenyl), C(=O)—NH-pyridyl, NH—O(=O)-pyridyl, NH(pyridyl), wherein phenyl, pyridyl, thienyl or furyl are respectively unsubstituted or mono- or polysubstituted with one or more substituents selected independently of one another from the group consisting of F, Cl, Br, I, CN, OH, O—C₁₋₄ alkyl, OCF₃, C₁₋₄ alkyl, CF₃, SH, S—C₁₋₄ alkyl and SCF₃.

In a further, particularly preferred embodiment, the compounds according to the invention of general formula (I) have general formula (If)

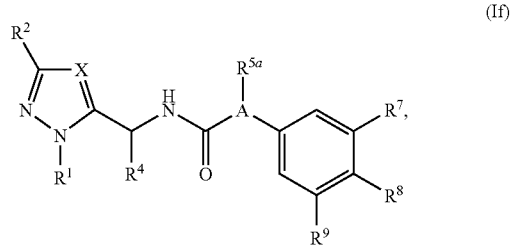

(If)

in which

X represents CR³ or N,
wherein R³ represents H; methyl; ethyl; n-propyl; isopropyl; n-butyl; sec.-butyl; tert.-butyl; or CF₃;

A represents N or CR⁵ᵇ;

R¹ represents substructure (T1)

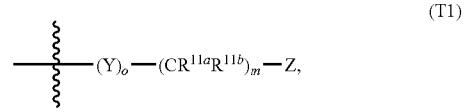

(T1)

in which

Y represents C(=O), O, S, S(=O)₂, NH—C(=O) or NR¹²,
wherein R¹² represents H; methyl; ethyl; n-propyl; isopropyl; n-butyl; sec.-butyl; tert.-butyl; S(=O)₂-methyl;

o represents 0 or 1;

R¹¹ᵃ and R¹¹ᵇ each independently of one another represent H; methyl; ethyl; n-propyl; isopropyl; n-butyl; sec.-butyl; tert.-butyl;

m represents 0, 1 or 2;

Z represents C₁₋₄ alkyl, saturated or unsaturated, branched or unbranched, unsubstituted or mono- or polysubstituted with one or more substituents each selected independently of one another from the group consisting of F, Cl, Br, I, OH, O—C₁₋₄ alkyl; C₃₋₁₀ cycloalkyl¹, saturated or unsaturated, morpholinyl, tetrahydropyranyl, piperidinyl, 4-methylpiperazinyl, piperazinyl, respectively unsubstituted or mono- or polysubstituted with one or more substituents each selected independently of one another from the group consisting of F, Cl, Br, I, OH, O—C₁₋₄ alkyl and C₁₋₄ alkyl; phenyl or pyridyl, respectively unsubstituted or mono- or polysubstituted with one or more substituents each selected independently of one another from the group consisting of F, Cl, Br, I, CN, OH, O—C₁₋₄ alkyl, OCF₃, C₁₋₄ alkyl, CF₃, SH, S—C₁₋₄ alkyl, SCF₃;

R² represents H; F; Cl; Br; I; CF₃; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of C₁₋₄ alkyl, O—C₁₋₄ alkyl, F, Cl, Br, I, CF₃ and OCF₃;

R⁴ represents H; methyl; ethyl; n-propyl; or isopropyl;

R⁵ᵃ represents H or CH₃ if A represents N; or represents H; methyl; ethyl; n-propyl; isopropyl if A represents CR⁵ᵇ;

R⁵ᵇ represents H; methyl; ethyl; n-propyl; isopropyl; cyclopentyl; cyclohexyl; or phenyl or benzyl, in each case unsubstituted or mono-, di- or trisubstituted with one, two or three substituents each selected independently of one another from the group consisting of $C_{1-4}$ alkyl, $O-C_{1-4}$ alkyl, F, Cl, Br, I, $CF_3$ and $OCF_3$;

or $R^{5a}$ and $R^{5b}$ form together with the carbon atom connecting them a $C_{3-10}$ cycloalkyl, saturated or unsaturated, unsubstituted, $R^7$ and $R^9$ each independently of one another represent H; F; Cl; Br; I; $C_{1-4}$ alkyl, $O-C_{1-4}$ alkyl; F; Cl; Br; I;

$R^8$ represents H; F; Cl; Br; I; CN; $NO_2$; $CF_3$; OH; $OCF_3$; SH; $SCF_3$; $NH_2$; $C(=O)-NH_2$; $C(=O)-NH$(methyl); $C(=O)-NH$(ethyl); $C(=O)-N$ (methyl)$_2$; $C(=O)-N$ (ethyl)$_2$; $C_{1-4}$ alkyl, saturated or unsaturated, branched or unbranched, unsubstituted or mono- or disubstituted with OH; $NH-C(=O)$-methyl; $NH-C(=O)$-ethyl; $CH_2-NH-S(=O)_2$-methyl; $CH_2-NH-S(=O)_2$-ethyl; $NH-S(=O)_2$-methyl; $NH-S(=O)_2$-ethyl; S-methyl; S-ethyl; $S(=O)_2$-methyl; $S(=O)_2$-ethyl; $S(=O)_2-NH$-methyl; $S(=O)_2-NH$-ethyl; $S(=O)_2-N$(methyl)$_2$; $S(=O)_2-N$(ethyl)$_2$; $CH_2-S(=O)_2$-methyl; $CH_2-S(=O)_2$-ethyl; $OC_{1-4}$ alkyl, saturated or unsaturated, branched or unbranched, unsubstituted; $C_{1-4}$ alkyl-$O-C_{1-4}$ alkyl, $C_{3-10}$ cycloalkyl, or $C_{3-10}$ cycloalkyl bridged via $C_{1-8}$ alkyl, respectively saturated or unsaturated, unsubstituted, and wherein if appropriate the alkyl chain can be respectively branched or unbranched, saturated or unsaturated, unsubstituted; piperidinyl; piperazinyl; 4-methylpiperazinyl; morpholinyl; dioxidoisothiazolidinyl; phenyl, pyridyl, furyl, thienyl, $C(=O)-NH$-phenyl, $NH-C(=O)$-phenyl, NH(phenyl), $C(=O)-NH$-pyridyl, $NH-C(=O)$-pyridyl, NH(pyridyl), wherein phenyl, pyridyl, thienyl or furyl are respectively unsubstituted or mono- or polysubstituted with one or more substituents selected independently of one another from the group consisting of F, Cl, Br, I, CN, OH, $O-C_{1-4}$ alkyl, $OCF_3$, $C_{1-4}$ alkyl, $CF_3$, SH, $S-C_{1-4}$ alkyl and $SCF_3$.

Particularly preferred are compounds according to the invention from the group

1  N-((3-tert-butyl-1H-pyrazol-5-yl)methyl)-2-(3-fluoro-4-(methylsulphonamido)phenyl)propanamide;
2  (S)—N-((3-tert-butyl-1H-pyrazol-5-yl)methyl)-2-(3-fluoro-4-(methylsulphonamido)phenyl)propanamide;
3  N-((3-tert-butyl-1-methyl-1H-pyrazol-5-yl)methyl)-2-(3-fluoro-4-(methylsulphonamido)phenyl)propanamide;
4  (S)—N-((3-tert-butyl-1-methyl-1H-pyrazol-5-yl)methyl)-2-(3-fluoro-4-(methylsulphonamido)phenyl)propanamide;
5  N-((3-tert-butyl-1-hexyl-1H-pyrazol-5-yl)methyl)-2-(3-fluoro-4-(methylsulphonamido)phenyl)propanamide;
6  (S)—N-((3-tert-butyl-1-hexyl-1H-pyrazol-5-yl)methyl)-2-(3-fluoro-4-(methylsulphonamido)phenyl)propanamide;
7  N-((3-tert-butyl-1-cyclohexyl-1H-pyrazol-5-yl)methyl)-2-(3-fluoro-4-(methylsulphonamido)phenyl)propanamide;
8  (S)—N-((3-tert-butyl-1-cyclohexenyl-1H-pyrazol-5-yl)methyl)-2-(3-fluoro-4-(methylsulphonamido)phenyl)propanamide;
9  2-(3-fluoro-4-(methylsulphonamido)phenyl)-N-((3-methyl-1-phenyl-1H-pyrazol-5-yl)methyl)propanamide;
10  N-((3-chloro-1-phenyl-1H-pyrazol-5-yl)methyl)-2-(3-fluoro-4-(methylsulphonamido)phenyl)propanamide;
11  2-(3-fluoro-4-(methylsulphonamido)phenyl)-N-((3-(4-fluorophenyl)-1-phenyl-1H-pyrazol-5-yl)methyl)propanamide;
12  N-((3-tert-butyl-1-p-tolyl-1H-pyrazol-5-yl)methyl)-2-(3-fluoro-4-(methylsulphonamido)phenyl)propanamide;
13  N-((3-tert-butyl-1-(4-tert-butylphenyl)-1H-pyrazol-5-yl)methyl)-2-(3-fluoro-4-(methylsulphonamido)phenyl)propanamide;
14  N-((3-tert-butyl-1-(4-chlorophenyl)-1H-pyrazol-5-yl)methyl)-2-(3-fluoro-4-(methylsulphonamido)phenyl)propanamide;
15  (S)—N-((3-tert-butyl-1-(4-chlorophenyl)-1H-pyrazol-5-yl)methyl)-2-(3-fluoro-4-(methylsulphonamido)phenyl)propanamide;
16  N-((3-tert-butyl-1-(3-chlorophenyl)-1H-pyrazol-5-yl)methyl)-2-(3-fluoro-4-(methylsulphonamido)phenyl)propanamide;
17  (S)—N-((3-tert-butyl-1-(3-chlorophenyl)-1H-pyrazol-5-yl)methyl)-2-(3-fluoro-4-(methylsulphonamido)phenyl)propanamide;
18  N-((3-tert-butyl-1-(3-chloro-4-fluorophenyl)-1H-pyrazol-5-yl)methyl)-2-(3-fluoro-4-(methylsulphonamido)phenyl)propanamide;
19  (E)-N-((3-tert-butyl-1-(4-methylstyryl)-1H-pyrazol-5-yl)methyl)-2-(3-fluoro-4-(methylsulphonamido)phenyl)propanamide;
20  N-((3-tert-butyl-1-(4-methoxyphenyl)-1H-pyrazol-5-yl)methyl)-2-(3-fluoro-4-(methylsulphonamido)phenyl)propanamide;
21  N-((1-(4-chlorophenyl)-3-(trifluoromethyl)-1H-pyrazol-5-yl)methyl)-2-(3-fluoro-4-(methylsulphonamido)phenyl)propanamide;
22  (R)—N-((1-(4-chlorophenyl)-3-(trifluoromethyl)-1H-pyrazol-5-yl)methyl)-2-(3-fluoro-4-(methylsulphonamido)phenyl)propanamide;
23  (S)—N-((1-(4-chlorophenyl)-3-(trifluoromethyl)-1H-pyrazol-5-yl)methyl)-2-(3-fluoro-4-(methylsulphonamido)phenyl)propanamide;
24  N-((1-(3-chlorophenyl)-3-(trifluoromethyl)-1H-pyrazol-5-yl)methyl)-2-(3-fluoro-4-(methylsulphonamido)phenyl)propanamide;
25  (R)—N-((1-(3-chlorophenyl)-3-(trifluoromethyl)-1H-pyrazol-5-yl)methyl)-2-(3-fluoro-4-(methylsulphonamido)phenyl)propanamide;
26  (S)—N-((1-(3-chlorophenyl)-3-(trifluoromethyl)-1H-pyrazol-5-yl)methyl)-2-(3-fluoro-4-(methylsulphonamido)phenyl)propanamide;
27  N-((3-tert-butyl-1-(3-chlorophenyl)-1H-pyrazol-5-yl)methyl)-2-(3-methoxy-4-(methylsulphonamido)phenyl)propanamide;
28  N-((1-(3-chlorophenyl)-3-(trifluoromethyl)-1H-pyrazol-5-yl)methyl)-2-(3-methoxy-4-(methylsulphonamido)phenyl)propanamide;
29  N-((3-tert-butyl-1-(3-chlorophenyl)-1H-pyrazol-5-yl)methyl)-2-(3,5-difluoro-4-(methylsulphonamido)phenyl)propanamide;
30  N-((1-(3-chlorophenyl)-3-(trifluoromethyl)-1H-pyrazol-5-yl)methyl)-2-(3,5-difluorophenyl)propanamide;
31  2-(4-bromo-3-fluorophenyl)-N-((1-(3-chlorophenyl)-3-(trifluoromethyl)-1H-pyrazol-5-yl)methyl)propanamide;
32  N-((3-tert-butyl-1-(3-chlorophenyl)-1H-pyrazol-5-yl)methyl)-2-(4-isobutylphenyl)propanamide;
33  N-((3-tert-butyl-1-(3-chlorophenyl)-1H-pyrazol-5-yl)methyl)-2-(3-fluoro-4-(methylsulphonamidomethyl)phenyl)propanamide;
34  N-((1-(3-chlorophenyl)-3-(trifluoromethyl)-1H-pyrazol-5-yl)methyl)-2-(3-fluoro-4-(furan-3-yl)phenyl)propanamide;
35  N-((3-tert-butyl-1-(3-chlorophenyl)-1H-pyrazol-5-yl)methyl)-2-(2-fluorobiphenyl-4-yl)propanamide;
36  N-((1-(3-chlorophenyl)-3-(trifluoromethyl)-1H-pyrazol-5-yl)methyl)-2-(4-(1,2-dihydroxyethyl)-3-fluorophenyl)propanamide;

37  4-(1-((1-(3-chlorophenyl)-3-(trifluoromethyl)-1H-pyrazol-5-yl)methylamino)-1-oxopropan-2-yl)-2-fluorobenzamide;
38  4-(1-((1-(3-chlorophenyl)-3-(trifluoromethyl)-1H-pyrazol-5-yl)methylamino)-1-oxopropan-2-yl)-N-ethylbenzamide;
39  4-(1-((1-(3-chlorophenyl)-3-(trifluoromethyl)-1H-pyrazol-5-yl)methylamino)-1-oxopropan-2-yl)-2-fluoro-N-phenylbenzamide;
40  4-(1-((1-(3-chlorophenyl)-3-(trifluoromethyl)-1H-pyrazol-5-yl)methylamino)-1-oxopropan-2-yl)-N-(4-fluorophenyl)benzamide;
41  4-(1-((1-(3-chlorophenyl)-3-(trifluoromethyl)-1H-pyrazol-5-yl)methylamino)-1-oxopropan-2-yl)-N-(4-(trifluoromethyl)phenyl)benzamide;
42  4-(1-((1-(3-chlorophenyl)-3-(trifluoromethyl)-1H-pyrazol-5-yl)methylamino)-1-oxopropan-2-yl)-N-(pyridin-4-yl)benzamide;
43  N-((1-(3-chlorophenyl)-3-(trifluoromethyl)-1H-pyrazol-5-yl)methyl)-2-(4-(trifluormethoxy)phenyl)propanamide;
44  N-((1-(3-chlorophenyl)-3-(trifluoromethyl)-1H-pyrazol-5-yl)methyl)-2-(3,5-dibromo-4-hydroxyphenyl)acetamide;
45  N-((1-(3-chlorophenyl)-3-(trifluoromethyl)-1H-pyrazol-5-yl)methyl)-2-(3,5-dibromo-4-hydroxyphenyl)propanamide;
46  N-((3-tert-butyl-1-(3-chlorophenyl)-1H-pyrazol-5-yl)methyl)-2-(3,5-difluoro-4-hydroxyphenyl)propanamide;
47  N-((1-(3-chlorophenyl)-3-(trifluoromethyl)-1H-pyrazol-5-yl)methyl)-2-(3,5-difluoro-4-methoxyphenyl)propanamide;
48  N-((3-tert-butyl-1-(3-chlorophenyl)-1H-pyrazol-5-yl)methyl)-2-(4-methoxy-3,5-dimethylphenyl)acetamide;
49  N-((3-tert-butyl-1-(3-chlorophenyl)-1H-pyrazol-5-yl)methyl)-2-(4-(N,N-dimethylsulphamoyl)-3-fluorophenyl)propanamide;
50  N-((1-(3-chlorophenyl)-3-(trifluoromethyl)-1H-pyrazol-5-yl)methyl)-2-(4-(4-chlorophenylamino)phenyl)propanamide;
51  N-((1-(3-chlorophenyl)-3-(trifluoromethyl)-1H-pyrazol-5-yl)methyl)-2-(4-(4-methoxyphenylamino)phenyl)propanamide;
52  2-(4-amino-3,5-difluorophenyl)-N-((1-(3-chlorophenyl)-3-(trifluoromethyl)-1H-pyrazol-5-yl)methyl)propanamide;
53  2-(4-acetamido-3-fluorophenyl)-N-((1-(3-chlorophenyl)-3-(trifluoromethyl)-1H-pyrazol-5-yl)methyl)propanamide;
54  N-(4-(1-((1-(3-chlorophenyl)-3-(trifluoromethyl)-1H-pyrazol-5-yl)methylamino)-1-oxopropan-2-yl)-2-fluorophenyl)benzamide;
55  N-((3-tert-butyl-1-(3-chlorophenyl)-1H-pyrazol-5-yl)methyl)-2-[4-(1,1-dioxidoisothiazolidin-2-yl)-3-fluorophenyl]propanamide;
56  N-((3-tert-butyl-1-(3-chlorophenyl)-1H-pyrazol-5-yl)methyl)-2-(4-(N,N-dimethylsulphamoyl)-3-fluorophenyl)propanamide;
57  1-((3-tert-butyl-1-(3-chlorophenyl)-1H-pyrazol-5-yl)methyl)-3-(3,5-difluorophenyl)urea;
58  1-(4-bromo-3-fluorophenyl)-3-((3-tert-butyl-1-(3-chlorophenyl)-1H-pyrazol-5-yl)methyl)urea;
59  1-((3-tert-butyl-1-(3-chlorophenyl)-1H-pyrazol-5-yl)methyl)-3-(4-(trifluoromethyl)phenyl)urea;
60  1-((3-tert-butyl-1-(3-chlorophenyl)-1H-pyrazol-5-yl)methyl)-3-(4-(difluormethoxy)phenyl)urea;
61  1-((3-tert-butyl-1-(3-chlorophenyl)-1H-pyrazol-5-yl)methyl)-3-(3,5-difluoro-4-methoxyphenyl)urea;
62  1-((3-tert-butyl-1-(3-chlorophenyl)-1H-pyrazol-5-yl)methyl)-3-(4-methoxy-3,5-dimethylphenyl)urea;
63  1-((3-tert-butyl-1-(3-chlorophenyl)-1H-pyrazol-5-yl)methyl)-3-(3-fluoro-4-(methylsulphonyl)phenyl)urea;
64  1-((3-tert-butyl-1-(3-chlorophenyl)-1H-pyrazol-5-yl)methyl)-3-(4-(phenylamino)phenyl)urea;
65  4-(3-((3-tert-butyl-1-(3-chlorophenyl)-1H-pyrazol-5-yl)methyl)ureido)-N-(4-fluorophenyl)benzamide;
66  N-((3-tert-butyl-1-(3-chlorophenyl)-1H-pyrazol-5-yl)methyl)-2-(3-fluoro-4-(methylsulphonamido)phenyl)-2-(3-fluorophenyl)acetamide;
67  N-((3-tert-butyl-1-(3-chlorophenyl)-1H-pyrazol-5-yl)methyl)-2-cyclohexyl-2-(3-fluoro-4-(methylsulphonamido)phenyl)acetamide;
68  N-((3-tert-butyl-1-(3-chlorophenyl)-1H-pyrazol-5-yl)methyl)-2-(3-fluoro-4-(methylsulphonamido)phenyl)-2-p-tolylacetamide;
69  N-((3-tert-butyl-1-(3-chlorophenyl)-1H-pyrazol-5-yl)methyl)-2-(3-chloro-4-(methylthio)phenyl)propanamide;
70  N-((3-tert-butyl-1-(3-chlorophenyl)-1H-pyrazol-5-yl)methyl)-2-(3-chloro-4-(methylsulphonyl)phenyl)propanamide;
71  N-((3-tert-butyl-1-(3-chlorophenyl)-1H-pyrazol-5-yl)methyl)-2-(3-fluoro-4-(methylthio)phenyl)propanamide;
72  N-((3-tert-butyl-1-(3-chlorophenyl)-1H-pyrazol-5-yl)methyl)-2-(3-fluoro-4-(methylsulphonyl)phenyl)propanamide;
73  N-((3-tert-butyl-1-(3-chlorophenyl)-1H-pyrazol-5-yl)methyl)-2-(3-fluorophenyl)acetamide;
74  N-((1-(3-chlorophenyl)-3-(trifluoromethyl)-1H-pyrazol-5-yl)methyl)-2-(3-fluorophenyl)acetamide;
75  N-[[5-tert-butyl-2-(3-chlorophenyl)-2H-[1,2,4]triazol-3-yl]methyl]-2-[3-fluoro-4-(methanesulphonamido)phenyl]propionamide;
76  N-[[2-(3-chlorophenyl)-5-(trifluoromethyl)-2H-[1,2,4]triazol-3-yl]-methyl]-2-[3-fluoro-4-(methanesulphonamido)phenyl]propionamide;
77  N-[(5-tert-butyl-2-cyclohexyl-2H-[1,2,4]triazol-3-yl)-methyl]-2-[3-fluoro-4-(methanesulphonamido)phenyl]propionamide;
78  N-[[2-cyclohexyl-5-(trifluoromethyl)-2H-[1,2,4]triazol-3-yl]methyl]-2-[3-fluoro-4-(methanesulphonamido)phenyl]propionamide;
79  N-[(5-tert-butyl-2-pyridin-3-yl-2H-[1,2,4]triazol-3-yl)-methyl]-2-[3-fluoro-4-(methanesulphonamido)phenyl]propionamide;
80  2-[3-fluoro-4-(methanesulphonamido)phenyl]-N-[[2-pyridin-3-yl-5-(trifluoromethyl)-2H-[1,2,4]triazol-3-yl]methyl]propionamide;
81  N-[[5-tert-butyl-2-(6-chloropyridin-2-yl)-2H-pyrazol-3-yl]-methyl]-2-[3-fluoro-4-(methanesulphonamido)phenyl]propionamide;
82  N-[[5-tert-butyl-2-(3,3-difluorocyclobutanecarbonyl)-2H-pyrazol-3-yl]-methyl]-2-[3-fluoro-4-(methanesulphonamido)phenyl]propionamide;
83  N-[[2-(3-chlorophenyl)-4-methyl-5-(trifluoromethyl)-2H-pyrazol-3-yl]-methyl]-2-[3-fluoro-4-(methanesulphonamido)phenyl]propionamide;
84  N-[[2-(dipropylamino)-5-(trifluoromethyl)-2H-pyrazol-3-yl]methyl]-2-[4-(methanesulphonamido)-3-methoxyphenyl]propionamide;
85  N-[[2-(dipropylamino)-5-(trifluoromethyl)-2H-pyrazol-3-yl]-methyl]-2-[3-fluoro-4-(hydroxymethyl)phenyl]propionamide;
86  N-[[2-(dipropylamino)-5-(trifluoromethyl)-2H-pyrazol-3-yl]methyl]-2-[3-fluoro-4-(methanesulphonamido)phenyl]propionamide;

87 N-[[2-(dipropylamino)-5-(trifluoromethyl)-2H-pyrazol-3-yl]-methyl]-2-(3-fluorophenyl)acetamide;
88 4-[1-[[2-(dipropylamino)-5-(trifluoromethyl)-2H-pyrazol-3-yl]methylcarbamoyl]ethyl]-2-fluorobenzamide;
89 4-[1-[[2-(dipropylamino)-5-(trifluoromethyl)-2H-pyrazol-3-yl]methylcarbamoyl]ethyl]-N-pyridin-2-yl-benzamide;
90 2-[3-fluoro-4-(hydroxymethyl)phenyl]-N-[[2-piperidin-1-yl-5-(trifluoromethyl)-2H-pyrazol-3-yl]-methyl]propionamide;
91 2-[3-fluoro-4-(2-hydroxyethyl)phenyl]-N-[[2-piperidin-1-yl-5-(trifluoromethyl)-2H-pyrazol-3-yl]-methyl]propionamide;
92 2-[3-fluoro-4-(methanesulphonamido)phenyl]-N-[[2-piperidin-1-yl-5-(trifluoromethyl)-2H-pyrazol-3-yl]-methyl]propionamide;
93 2-[4-(methanesulphonamido)-3-methoxyphenyl]-N-[[2-piperidin-1-yl-5-(trifluoromethyl)-2H-pyrazol-3-yl]-methyl]propionamide;
94 2-[4-(1,2-dihydroxyethyl)-3-fluorophenyl]-N-[[2-piperidin-1-yl-5-(trifluoromethyl)-2H-pyrazol-3-yl]-methyl]propionamide;
95 2-(3-fluorophenyl)-N-[[2-piperidin-1-yl-5-(trifluoromethyl)-2H-pyrazol-3-yl]-methyl]acetamide;
96 2-fluoro-4-[1-[[2-piperidin-1-yl-5-(trifluoromethyl)-2H-pyrazol-3-yl]-methylcarbamoyl]ethyl]benzamide;
97 2-[3-fluoro-4-(methanesulphonamido)phenyl]-N-[[2-[(4-fluorophenyl)methylmethylamino]-5-(trifluoromethyl)-2H-pyrazol-3-yl]-methyl]propionamide;
98 N-[[5-tert-butyl-2-(2,2,2-trifluoroethylamino)-2H-pyrazol-3-yl]-methyl]-2-[3-fluoro-4-(methanesulphonamido)phenyl]propionamide;
99 N-[[2-butoxy-5-(trifluoromethyl)-2H-pyrazol-3-yl]-methyl]-2-[3-fluoro-4-(hydroxymethyl)phenyl]propionamide;
100 N-[[2-butoxy-5-(trifluoromethyl)-2H-pyrazol-3-yl]-methyl]-2-[3-fluoro-4-(methanesulphonamido)phenyl]propionamide;
101 N-[[2-butoxy-5-(trifluoromethyl)-2H-pyrazol-3-yl]-methyl]-2-[4-(methanesulphonamido)-3-methoxyphenyl]propionamide;
102 N-[(2-butoxy-5-tert-butyl-2H-pyrazol-3-yl)-methyl]-2-(3-fluorophenyl)acetamide;
103 N-[[2-cyclopentyloxy-5-(trifluoromethyl)-2H-pyrazol-3-yl]-methyl]-2-[3-fluoro-4-(methanesulphonamido)phenyl]propionamide;
104 N-[[2-cyclopentyloxy-5-(trifluoromethyl)-2H-pyrazol-3-yl]-methyl]-2-[4-(methanesulphonamido)-3-methoxyphenyl]propionamide;
105 2-(3-fluorophenyl)-N-[[2-[(4-methoxyphenyl)methoxy]-5-(trifluoromethyl)-2H-pyrazol-3-yl]methyl]acetamide;
106 N-[[5-tert-butyl-2-(3-cyano-5-fluorophenoxy)-2H-pyrazol-3-yl]-methyl]-2-(3-fluorophenyl)acetamide;
107 N-[[2-(cyclohexylsulphanyl)-5-(trifluoromethyl)-2H-pyrazol-3-yl]methyl]-2-[3-fluoro-4-(methanesulphonamido)phenyl]propionamide;
108 N-[[2-(benzenesulphonyl)-5-tert-butyl-2H-pyrazol-3-yl]-methyl]-2-(3-fluorophenyl)acetamide;
109 N-[[2-cyclohexyl-5-(trifluoromethyl)-2H-[1,2,4]triazol-3-yl]methyl]-2-[4-(methanesulphonamido)-3-methoxyphenyl]propionamide;
110 N-[[2-cyclohexyl-5-(trifluoromethyl)-2H-[1,2,4]triazol-3-yl]methyl]-2-(3-fluorophenyl)acetamide;
111 4-[1-[[2-cyclohexyl-5-(trifluoromethyl)-2H-[1,2,4]triazol-3-yl]methylcarbamoyl]ethyl]-2-fluorobenzamide;
112 2-[3-fluoro-4-(hydroxymethyl)phenyl]-N-[[2-hexyl-5-(trifluoromethyl)-2H-[1,2,4]triazol-3-yl]-methyl]propionamide;
113 4-[1-[[2-cyclobutyl-5-(trifluoromethyl)-2H-[1,2,4]triazol-3-yl]methylcarbamoyl]ethyl]-2-fluorobenzamide;
114 N-[[5-tert-butyl-2-(3,3-difluorocyclobutanecarbonyl)-2H-[1,2,4]triazol-3-yl]methyl]-2-[3-fluoro-4-(methanesulphonamido)phenyl]propionamide;
115 N-[[5-tert-butyl-2-(3-cyano-5-fluorophenoxy)-2H-[1,2,4]triazol-3-yl]methyl]-2-(3-fluorophenyl)acetamide;
116 N-[[2-(benzenesulphonyl)-5-tert-butyl-2H-[1,2,4]triazol-3-yl]methyl]-2-(3-fluorophenyl)acetamide;
117 N-((1-(3-chlorophenyl)-3-(trifluoromethyl)-1H-pyrazol-5-yl)methyl)-2-(3-fluorophenyl)-2-methylpropanamide;
118 N-((3-tert-butyl-1-(3-chlorophenyl)-1H-pyrazol-5-yl)methyl)-1-(3-fluorophenyl)cyclopropancarboxamide;
119 N-((1-(3-chlorophenyl)-3-(trifluoromethyl)-1H-pyrazol-5-yl)methyl)-1-(3-fluorophenyl)cyclobutancarboxamide;
120 N-((1-(3-chlorophenyl)-3-(trifluoromethyl)-1H-pyrazol-5-yl)methyl)-1-(3-fluorophenyl)cyclopentancarboxamide;
121 N-((1-(3-chlorophenyl)-3-(trifluoromethyl)-1H-pyrazol-5-yl)methyl)-1-(3-fluorophenyl)cyclohexancarboxamide;
122 1-((3-tert-butyl-1-(4-fluorophenyl)-1H-pyrazol-5-yl)methyl)-3-(3-fluorophenyl)urea
123 3-((1-(3-chlorophenyl)-3-(trifluoromethyl)-1H-pyrazol-5-yl)methyl)-1-(3-fluorophenyl)-1-methylurea;
124 N-((1-(3-chloro-4-fluorophenyl)-3-(trifluoromethyl)-1H-pyrazol-5-yl)methyl)-2-(3-fluoro-4-(methylsulfonylmethyl)phenyl)propanamide;
125 N-((3-tert-butyl-1-(3-chlorophenyl)-1H-pyrazol-5-yl)methyl)-2-(4-cyclopropyl-3-fluorophenyl)propanamide;
126 1-((1-(3-chlorophenyl)-3-(trifluoromethyl)-1H-pyrazol-5-yl)methyl)-3-(4-cyclopropyl-3-fluorophenyl)urea;
127 N-((3-tert-butyl-1-(pyridin-2-yl)-1H-pyrazol-5-yl)methyl)-2-(3-fluoro-4-(methylsulfonamidmethyl)phenyl)propanamide;
128 N-((1-(3-chlorophenyl)-3-cyclopropyl-1H-pyrazol-5-yl)methyl)-2-(3-fluoro-4-(methylsulfonylmethyl)phenyl)propanamide;
129 2-(3-fluoro-4-(methylsulfonamidmethyl)phenyl)-N-((1-(pyridin-2-ylmethylamino)-3-(trifluoromethyl)-1H-pyrazol-5-yl)methyl)propanamide;
130 N-((1-(3-chlorophenyl)-4-methyl-3-(trifluoromethyl)-1H-pyrazol-5-yl)methyl)-2-(3-fluorophenyl)acetamide;
131 2-(3-fluorophenyl)-N-((1-pentyl-3-(trifluoromethyl)-1H-pyrazol-5-yl)methyl)acetamide;
132 2-(3-fluorophenyl)-N-((1-(4-methoxybenzyl)-3-(trifluoromethyl)-1H-pyrazol-5-yl)methyl)acetamide;
133 N-((3-tert-butyl-1-(2,2,2-trifluoroethylamino)-1H-pyrazol-5-yl)methyl)-2-(3-fluorophenyl)acetamide;
134 N-((1-(3-chlorophenyl)-4-methyl-3-(trifluoromethyl)-1H-pyrazol-5-yl)methyl)-2-(3-fluoro-4-(methylsulfonamidmethyl)phenyl)propanamide;
135 N-((3-tert-butyl-1-(3-chlorophenyl)-1H-1,2,4-triazol-5-yl)methyl)-2-(3-fluorophenyl)acetamide;
136 2-(3-fluorophenyl)-N-((1-(pyridin-3-yl)-3-(trifluoromethyl)-1H-pyrazol-5-yl)methyl)acetamide;
137 N-((1-cyclohexyl-3-(trifluoromethyl)-1H-pyrazol-5-yl)methyl)-2-(3-fluoro-4-(methylsulfonamidmethyl)phenyl)propanamide;
138 2-(3-fluoro-4-(methylsulfonamidmethyl)phenyl)-N-((1-(tetrahydro-2H-pyran-4-yl)-3-(trifluoromethyl)-1H-pyrazol-5-yl)methyl)propanamide;

139  1-((1-(3-chlorophenyl)-3-(trifluoromethyl)-1H-pyrazol-5-yl)methyl)-3-(4-(cyclopropylethynyl)-3-fluorophenyl)urea;
140  N-((1-(3-chlorophenyl)-3-(trifluoromethyl)-1H-pyrazol-5-yl)methyl)-2-(3-fluoro-4-(trifluoromethyl)phenyl)acetamide;
141  N-((1-(3-chlorophenyl)-3-(trifluoromethyl)-1H-pyrazol-5-yl)methyl)-2-(3-fluoro-4-(trifluoromethyl)phenyl)propanamide;
142  N-((3-tert-butyl-1-(3-chlorophenyl)-1H-pyrazol-5-yl)methyl)-2-(3-fluoro-4-((2-methoxyethoxy)methyl)phenyl)propanamide;
143  4-(1-((1-(3-chlorophenyl)-3-(trifluoromethyl)-1H-pyrazol-5-yl)methylamino)-1-oxopropan-2-yl)-N-phenylbenzamide;
144  1-((3-tert-butyl-1-(3-chlorophenyl)-1H-pyrazol-5-yl)methyl)-3-(3-fluoro-4-morpholinphenyl)urea;
145  N-((1-(3-chlorophenyl)-3-(trifluoromethyl)-1H-pyrazol-5-yl)methyl)-2-(3-fluoro-4-(methylsulfonamid)phenyl)-3-phenylpropanamide;
146  N-(5-((2-(3-fluorophenyl)acetamide)methyl)-3-(trifluoromethyl)-1H-pyrazol-1-yl)benzamide;
147  N-((1-(3-chlorophenyl)-3-(trifluoromethyl)-1H-pyrazol-5-yl)methyl)-2-(3,5-difluoro-4-hydroxyphenyl)acetamide;

respectively in the form of the free compounds; the racemate; the enantiomers, diastereomers, mixtures of the enantiomers or diastereomers or of an individual enantiomer or diastereomer; or in the form of the salts of physiologically compatible acids or bases; or in the form of solvates.

Furthermore, preference may be given to compounds according to the invention of general formula (I) that cause a 50 percent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The present invention further relates to a process for preparing compounds of the above-indicated general formula (I), according to which at least one compound of general formula (II), (II)

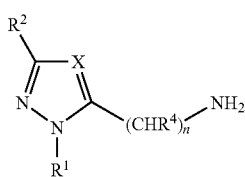

in which X, $R^1$, $R^2$, $R^4$ and n have one of the foregoing meanings, is reacted in a reaction medium, if appropriate in the presence of at least one suitable coupling reagent, if appropriate in the presence of at least one base, with a compound of general formula (III) or (IV), (III)

(IV)

in which Hal represents a halogen, preferably Cl or Br, and $R^{5a}$, $R^{5b}$, $R^6$, $R^7$, $R^8$, $R^9$ and $R^{10}$ each have one of the foregoing meanings, in a reaction medium, if appropriate in the presence of at least one suitable coupling reagent, if appropriate in the presence of at least one base, to form a compound of general formula (I), (I)

in which A represents $CR^{5b}$ and X, $R^1$, $R^2$, $R^4$, $R^{5a}$, $R^{5b}$, $R^6$, $R^7$, $R^8$, $R^9$, $R^{10}$ and n have one of the foregoing meanings; or in that at least one compound of general formula (II), (II)

in which X, $R^1$, $R^2$, $R^4$ and n have one of the foregoing meanings, is reacted to form a compound of general formula (V)

(V)

in which X, $R^1$, $R^2$, $R^4$ and n have one of the foregoing meanings, in a reaction medium, in the presence of phenyl chloroformate, if appropriate in the presence of at least one base and/or a coupling reagent, and said compound is if appropriate purified and/or isolated, and a compound of general formula (V) is reacted with a compound of general formula (VI),

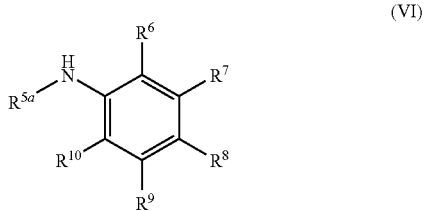

in which $R^6$, $R^7$, $R^8$, $R^9$ and $R^{10}$ have one of the foregoing meanings, in a reaction medium, if appropriate in the presence of at least one suitable coupling reagent, if appropriate in the presence of at least one base, to form a compound of general formula (I),

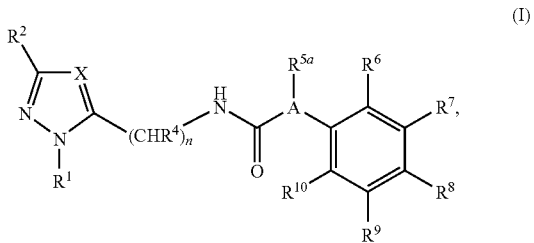

in which A represents N and X, $R^1$, $R^2$, $R^4$, $R^{5a}$, $R^6$, $R^7$, $R^8$, $R^9$ and $R^{10}$ and n have one of the foregoing meanings.

The reaction of compounds of the above-indicated general formulae (II) and (VI) with carboxylic acids of the above-indicated general formula (III) to form compounds of the above-indicated general formula (I) is carried out preferably in a reaction medium selected from the group consisting of diethyl ether, tetrahydrofuran, acetonitrile, methanol, ethanol, (1,2)-dichloroethane, dimethylformamide, dichloromethane and corresponding mixtures, if appropriate in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N-[dimethylamino)-1H-1, 2,3-triazolo[4,5-b]pyridino-1-yl-methylene]N-methyl-methanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N, N',N'-tetramethyluronium tetrafluoroborate (TBTU), N-hydroxybenzotriazole (HOBt) and 1-hydroxy-7-azabenzotriazole (HOAt), if appropriate in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the above-indicated general formulae (II) and (VI) with carboxylic acid halides of the above-indicated general formula (IV), in which Hal represents a halogen as the leaving group, preferably a chlorine or bromine atom, to form compounds of the above-indicated general formula (I) is carried out in a reaction medium preferably selected from the group consisting of diethyl ether, tetrahydrofuran, acetonitrile, methanol, ethanol, dimethylformamide, dichloromethane and corresponding mixtures, if appropriate in the presence of an organic or inorganic base, preferably selected from the group consisting of triethylamine, dimethylaminopyridine, pyridine and diisopropylamine, at temperatures of from −70° C. to 100° C.

The compounds of the above-indicated formulae (II), (III), (IV), (V) and (VI) are each commercially available and/or can be prepared using conventional processes known to the person skilled in the art.

The reactions described hereinbefore can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described hereinbefore, as well as the respective purification and/or isolation of intermediate or end products, can be carried out partly or completely under an inert gas atmosphere, preferably under a nitrogen atmosphere.

The substituted compounds according to the invention of the aforementioned general formula (I) and also corresponding stereoisomers can be isolated both in the form of their free bases, their free acids and also in the form of corresponding salts, in particular physiologically compatible salts.

The free bases of the respective substituted compounds according to the invention of the aforementioned general formula (I) and also of corresponding stereoisomers can be converted into the corresponding salts, preferably physiologically compatible salts, for example by reaction with an inorganic or organic acid, preferably with hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulphame.

Accordingly, the free acids of the substituted compounds of the aforementioned general formula (I) and of corresponding stereoisomers can be converted into the corresponding physiologically compatible salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds according to the invention of the aforementioned general formula (I) and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the prophylaxis and/or treatment of disorders or diseases which are mediated, at least in some cases, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of the above-indicated formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or prophylaxis of one or more disorders selected from the group consisting of pain selected from the group consisting of acute pain, chronic pain, neuropathic pain and visceral pain; joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or prophylaxis of pain, preferably of pain selected from the group consisting of acute pain, chronic pain, neuropathic pain and visceral pain, and/or urinary incontinence.

The present invention further relates to the use of at least one compound according to the invention and also if appropriate of one or more pharmaceutically compatible auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to the use of at least one substituted compound according to the invention and also if appropriate of one or more pharmaceutically compatible auxiliaries for the preparation of a pharmaceutical composition for the prophylaxis and/or treatment of disorders or diseases which are mediated, at least in some cases, by vanilloid receptors 1.

Particular preference is given to the use of at least one compound according to the invention and also if appropriate of one or more pharmaceutically compatible auxiliaries for the preparation of a pharmaceutical composition for the treatment and/or prophylaxis of one or more disorders selected from the group consisting of pain, preferably of pain selected from the group consisting of acute pain, chronic pain, neuropathic pain and visceral pain and joint pain.

Particular preference is given to the use of at least one compound according to the invention and also if appropriate of one or more pharmaceutically compatible auxiliaries for the preparation of a pharmaceutical composition for the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to the use of at least one substituted compound according to the invention and also if appropriate of one or more pharmaceutically compatible auxiliaries for the preparation of a pharmaceutical composition for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to the use of at least one substituted compound according to the invention and also if appropriate of one or more pharmaceutically compatible auxiliaries for the preparation of a pharmaceutical composition for the treatment and/or prophylaxis of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for the prophylaxis and/or treatment of disorders or diseases which are mediated, at least in some cases, by vanilloid receptors 1.

Particular preference is given to at least one compound according to the invention and also if appropriate to one or more pharmaceutically compatible auxiliaries for the treatment and/or prophylaxis of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for the treatment and/or prophylaxis of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for use in vanilloid receptor 1-(VR1/TRPV1) regulation, preferably for use in vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for use in the prophylaxis and/or treatment of disorders or diseases which are mediated, at least in some cases, by vanilloid receptors 1.

Particular preference is given to at least one compound according to the invention and also if appropriate to one or more pharmaceutically compatible auxiliaries for use in the treatment and/or prophylaxis of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for use in the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for use in the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for use in the treatment and/or prophylaxis of pain, preferably selected from the group consisting of acute pain, chronic pain, neuropathic pain and visceral pain, and/or urinary incontinence.

Pharmacological Methods

I. Functional Testing Carried Out on the Vanilloid Receptor 1 (VR1/TRPV1 Receptor)

The agonistic or antagonistic effect of the substances to be tested on the rat-species vanilloid receptor 1 (VR1/TRPV1) can be determined using the following assay. In this assay, the influx of $Ca^{2+}$ through the receptor channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Complete medium: 50 ml HAMS F12 nutrient mixture (Gibco Invitrogen GmbH, Karlsruhe, Germany) with
10% by volume of FCS (foetal calf serum, Gibco Invitrogen GmbH, Karlsruhe, Germany, heat-inactivated);
2 mM L-glutamine (Sigma, Munich, Germany);
1% by weight of AA solution (antibiotic/antimyotic solution, PAA, Pasching, Austria)
and 25 ng/ml NGF medium (2.5 S, Gibco Invitrogen GmbH, Karlsruhe, Germany)

Cell culture plate: Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 µg/ml. Aliquots having a laminin concentration of 100 µg/ml are removed and stored at −20° C. The aliquots are diluted with PBS in a ratio of 1:10 to 10 µg/ml of laminin and respectively 50 µL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:

The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 µL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 µL of complete medium are added to each of the remaining DRG. The DRG are respectively suspended several times, drawn through cannulae No. 1, No. 12 and No. 16 using a syringe and transferred to a 50 ml Falcon tube which is filled up to 15 ml with complete medium. The contents of each Falcon tube are respectively filtered through a 70 µm Falcon filter element and centrifuged for 10 minutes at 1,200 rpm and RT. The resulting pellet is respectively taken up in 250 µL of complete medium and the cell count is determined.

The number of cells in the suspension is set to $3 \times 10^5$ per ml and 150 µL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 µM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at RT used for $Ca^{2+}$ measurement in a FLIPR assay. The $Ca^{2+}$-dependent fluorescence is in this case measured before and after the addition of substances ($\lambda ex=488$ nm, $\lambda em=540$ nm). Quantification is carried out by measuring the highest fluorescence intensity (FC, fluorescence counts) over time.

FLIPR Assay:

The FLIPR protocol consists of 2 substance additions. First the compounds to be tested (10 µM) are pipetted onto the cells and the $Ca^{2+}$ influx is compared with the control (capsaicin 10 µM). This provides the result in % activation based on the $Ca^{2+}$ signal after the addition of 10 µM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 µM of capsaicin.

Triple analyses (n=3) are carried out and repeated in at least 3 independent experiments (N=4).

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

II. Functional Tests Carried Out on the Vanilloid Receptor (VR1)

The agonistic or antagonistic effect of the substances to be tested on the vanilloid receptor 1 (VR1) can also be determined using the following assay. In this assay, the influx of $Ca^{2+}$ through the channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Chinese hamster ovary cells (CHO K1 cells, European Collection of Cell Cultures (ECACC) United Kingdom) are stably transfected with the VR1 gene. For functional testing, these cells are plated out on poly-D-lysine-coated black 96-well plates having a clear base (BD Biosciences, Heidelberg, Germany) at a density of 25,000 cells/well. The cells are incubated overnight at 37° C. and 5% $CO_2$ in a culture medium (Ham's F12 nutrient mixture, 10% by volume of FCS (foetal calf serum), 18 µg/ml of L-proline). The next day the cells are incubated with Fluo-4 (Fluo-4 2 µM, 0.01% by volume of Pluronic F127, Molecular Probes in HBSS (Hank's buffered saline solution), Gibco Invitrogen GmbH, Karlsruhe, Germany) for 30 minutes at 37° C. Subsequently, the plates are washed three times with HBSS buffer and after further incubation for 15 minutes at RT used for $Ca^{2+}$ measurement in a FLIPR assay. The $Ca^{2+}$-dependent fluorescence is measured before and after the addition of the substances to be tested ($\lambda$ex wavelength=488 nm, $\lambda$em=540 nm). Quantification is carried out by measuring the highest fluorescence intensity (FC, fluorescence counts) over time.

FLIPR Assay:

The FLIPR protocol consists of 2 substance additions. First the compounds to be tested (10 µM) are pipetted onto the cells and the $Ca^{2+}$ influx is compared with the control (capsaicin 10 µM) (% activation based on the $Ca^{2+}$ signal after the addition of 10 µM of capsaicin). After 5 minutes' incubation, 100 nM of capsaicin are applied and the $Ca^{2+}$ influx is also determined.

Desensitising agonists and antagonists led to suppression of the $Ca^{2+}$ influx. The % inhibition is calculated compared to the maximum achievable inhibition with 10 µM of capsaicin.

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

III. Formalin Test Carried Out on Mice

In the formalin test, the testing to determine the antinociceptive effect of the compounds according to the invention is carried out on male mice (NMRI, 20 to 30 g body weight, Iffa, Credo, Belgium).

In the formalin test as described by D. Dubuisson et al., Pain 1977, 4, 161-174, a distinction is drawn between the first (early) phase (0 to 15 minutes after the injection of formalin) and the second (late) phase (15 to 60 minutes after the injection of formalin). The early phase, as an immediate reaction to the injection of formalin, is a model of acute pain, whereas the late phase is regarded as a model of persistent (chronic) pain (T. J. Coderre et al., Pain 1993, 52, 259-285). The corresponding descriptions in the literature are introduced herewith by way of reference and form part of the disclosure.

The compounds according to the invention are tested in the second phase of the formalin test to obtain information about the effects of substances on chronic/inflammatory pain.

The moment at which the compounds according to the invention are applied before the injection of formalin is selected as a function of the type of application of the compounds according to the invention. 10 mg of the test substances/kg of body weight are applied intravenously 5 minutes before the injection of formalin which is carried out by a single subcutaneous injection of formalin (20 µL, 1% aqueous solution) into the dorsal side of the right hind paw, thus inducing in free moving test animals a nociceptive reaction which manifests itself in marked licking and biting of the paw in question.

Subsequently, the nociceptive behaviour is continuously detected by observing the animals over a test period of three minutes in the second (late) phase of the formalin test (21 to 24 minutes after the injection of formalin). The pain behaviour is quantified by adding up the seconds over which the animals display licking and biting of the paw in question during the test period.

The comparison is carried out respectively with control animals which are given vehicles (0.9% aqueous sodium chloride solution) instead of the compounds according to the invention before the administration of formalin. Based on the quantification of the pain behaviour, the effect of the substance is determined in the formalin test as a percentage change relative to the corresponding control.

After the injection of substances having an antinociceptive effect in the formalin test, the described behaviour of the animals, i.e. licking and biting, is reduced or eliminated.

IV. Testing of Analgesic Efficacy in the Writhing Test

The testing of analgesic efficacy in the compounds according to the invention of general formula I was carried out by phenylquinone-induced writhing in mice (modified in accordance with I. C. Hendershot and J. Forsaith (1959), J. Pharmacol. Exp. Ther. 125, 237-240). The corresponding description in the literature is introduced herewith by way of reference and forms part of the disclosure.

Male NMRI mice weighing from 25 to 30 g were used for this purpose. 10 minutes after intravenous administration of the compounds to be tested, groups of 10 animals per compound dose received 0.3 ml/mouse of a 0.02% aqueous solution of phenylquinone (phenylbenzoquinone, Sigma, Deisenhofen, Germany; solution prepared by adding 5% by weight of ethanol and storage in a water bath at 45° C.) applied intraperitoneally. The animals were placed individually into observation cages. A pushbutton counter was used to record the number of pain-induced stretching movements (what are known as writhing reactions=straightening of the torso with stretching of the rear extremities) for 5 to 20 minutes after the administration of phenylquinone. The control was provided by animals which had received only physiological saline solution. All the compounds were tested at the standard dosage of 10 mg/kg.

V. Hypothermia Assay Carried Out on Mice

Description of the Method:

The hypothermia assay is carried out on male NMRI mice (weight 25-35 grams, breeder IFFA CREDO, Brussels, Belgium). The animals were kept under standardised conditions: light/dark rhythm (from 6:00 to 18:00 light phase; from 18:00 to 6:00 dark phase), RT 19-22° C., relative humidity 35-70%, 15 room air changes per hour, air movement<0.2 m/sec. The animals received standard feed (ssniff R/M–Haltung, ssniff Spezialdiäten GmbH, Soest, Germany) and tap water. Water and feed were withdrawn during the experiment. All the animals were used only once during the experiment. The animals had an acclimatisation period of at least 5 days.

Acute application of capsaicin (VR-1 agonist) leads to a drop in the core temperature of the body in rats and mice due to stimulation of heat sensors. Only specifically effective VR-1 receptor antagonists can antagonise the capsaicin-induced hypothermia. By contrast, hypothermia induced by morphine is not antagonised by VR-1 antagonists. This model is therefore suitable for identifying substances with VR-1 antagonistic properties via their effect on body temperature.

Measurement of the core temperature was carried out using a digital thermometer (Thermalert TH-5, physitemp, Clifton N.J., USA). The sensing element is in this case inserted into the rectum of the animals.

To give an individual basic value for each animal, the body temperature is measured twice at an interval of approx. half an hour. One group of animals (n=6 to 10) then receives an intraperitoneal (i.p.) application of capsaicin 3 mg/kg and vehicle (control group). Another group of animals receives the substance to be tested (i.v. or p.o.) and additionally capsaicin (3 mg/kg) i.p. The test substance is applied i.v. 10 min, or p.o 15 minutes, prior to capsaicin. The body temperature is then measured 7.5/15 and 30 min following capsaicin (i.v.+i.p.) or 15/30/60/90/120 min (p.o.+i.p.) following capsaicin. In addition, one group of animals is treated with the test substance only and one group with vehicle only. The evaluation or representation of the measured values as the mean+/−SEM of the absolute values is carried out as a graphical representation. The antagonistic effect is calculated as the percentage reduction of the capsaicin-induced hypothermia.

VI. Neuropathic Pain in Mice

Efficacy in neurotic pain was tested using the Bennett model (chronic constriction injury; Bennett and Xie, 1988, Pain 33: 87-107).

Three loose ligatures are tied around the right ischiadic nerve of Ketavet/Rompun-anaesthetised NMRI mice weighing 16-18 g. The animals develop hypersensitivity of the innervated paw caused by the damaged nerve, which hypersensitivity is quantified, following a recovery phase of one week, over a period of approximately three weeks by means of a cold metal plate (temperature 4° C.) (cold allodynia). The animals are observed on this plate over a period of 2 min and the withdrawal reactions of the damaged paw are counted. Based on the pre-value prior to the application of the substance, the substance's effect over a certain period of time is determined at various points in time (for example 15, 30, 45, or 60 min following application) and the resultant area under the curve (AUC) and/or the inhibition of cold allodynia at the individual measuring points is/are expressed as a percentage effect relative to the vehicle control (AUC) or to the starting value (individual measuring points). The group size is n=10, the significance of an antiallodynic effect (*=p<0.05) is determined with the aid of an analysis of variance with repeated measures and Bonferroni post hoc analysis.

The invention will be described hereinafter with the aid of a few examples. This description is intended merely by way of example and does not limit the general idea of the invention.

EXAMPLES

The indication "equivalents" ("eq.") means molar equivalents, "RT" means room temperature, "M" and "N" are indications of concentration in mol/l, "aq." means aqueous, "sat." means saturated, "sol." means solution, "conc." means concentrated.

Further Abbreviations:

| | |
|---|---|
| AcOH | acetic acid |
| d | days |
| BOP | 1-benzotriazolyloxy-tris-(dimethylamino) phosphonium hexafluorophosphate |
| brine | saturated sodium chloride solution (NaCl sol.) |
| bipy | 2,2'-bipyridine/2,2'-bipyridyl |
| Boc | tert-butyloxycarbonyl |
| DCC | N,N'-dicyclohexylcarbodiimide |
| DCM | dichloromethane |
| DIPEA | N,N-diisopropylethylamine |
| DMF | N,N-dimethylformamide |
| DMAP | 4-dimethylaminopyridine |
| EDC | N-(3-dimethylaminopropyl)-N'-ethylcarbodiimide |
| EDCl | N-ethyl-N'-(3-dimethylaminopropyl) carbodiimide hydrochloride |
| EE | ethyl acetate |
| ether | diethyl ether |
| EtOH | ethanol |
| sat. | saturated |
| h | hour(s) |
| $H_2O$ | water |
| HOBt | N-hydroxybenzotriazole |
| LAH | lithium aluminium hydride |
| LG | leaving group |
| m/z | mass-to-charge ratio |
| MeOH | methanol |
| min | minutes |
| MS | mass spectrometry |
| NA | not available |
| $NEt_3$ | triethylamine |
| $R_f$ | retention factor |
| SC | silica gel column chromatography |
| THF | tetrahydrofuran |
| TFA | trifluoroacetic acid |
| TLC | thin layer chromatography |
| vv | volume ratio |

The yields of the compounds prepared were not optimised.

All temperatures are uncorrected.

All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US, for example) or the synthesis thereof has already been described precisely in the specialist literature (experimental guidelines can be looked up in the Reaxys® Database of Elsevier, Amsterdam, NL, for example) or can be prepared using the conventional methods known to the person skilled in the art.

The stationary phase used for the column chromatography was silica gel 60 (0.0-0-0.063 mm) from E. Merck, Darmstadt. The thin-layer chromatographic tests were carried out using HPTLC precoated plates, silica gel 60 F 254, from E. Merck, Darmstadt.

The mixing ratios of solvents, mobile solvents or for chromatographic tests are respectively specified in volume/volume.

All the intermediate products and exemplary compounds were analytically characterised by means of $^1$H-NMR spectroscopy. In addition, mass spectrometry tests (MS, m/z indication for [M+H]$^+$) were carried out for all the exemplary compounds and selected intermediate products.

General reaction scheme (scheme 1a):
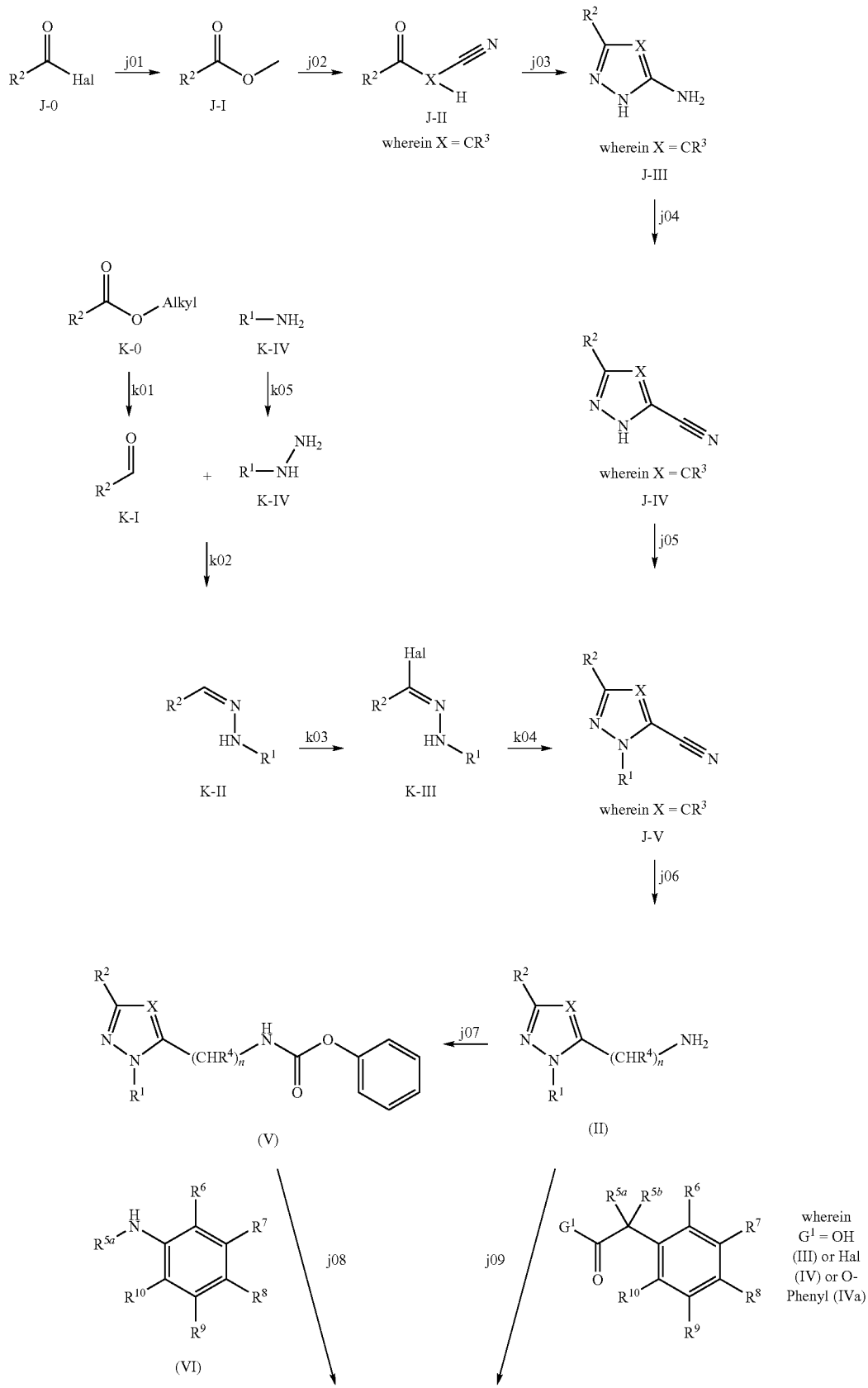

-continued

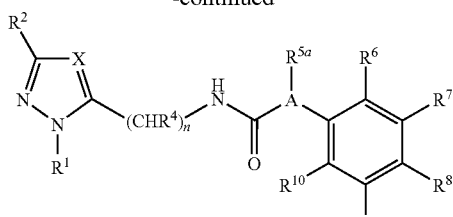

(I)

In step j01 an acid halide J-0, in which Hal preferably represents Cl or Br, can be esterified using methanol to form the compound J-I by means of methods with which the person skilled in the art is familiar.

In step j02 the methyl pivalate J-I can be converted into an oxoalkylnitrile J-II, wherein X=$CR^3$, by means of methods known to the person skilled in the art, such as for example using an alkyl nitrile $R^3CH_2$—CN, if appropriate in the presence of a base.

In step j03 the compound J-II can be converted into an amino-substituted pyrazolyl derivative J-III, wherein X=$CR^3$, by means of methods known to the person skilled in the art, such as for example using hydrazine hydrate, with cyclisation.

In step j04 the amino compound J-III can first be converted into a diazonium salt by means of methods known to the person skilled in the art, such as for example using nitrite, and the diazonium salt can be converted into a cyano-substituted pyrazolyl derivative J-IV, wherein X=$CR^3$, with elimination of nitrogen using a cyanide, if appropriate in the presence of a coupling reagent.

In step j05 the compound J-IV can be substituted in the N position by means of methods known to the person skilled in the art, for example using a halide $R^1$—Hal, if appropriate in the presence of a base and/or a coupling reagent, wherein Hal is preferably Cl, Br or I, or using a boronic acid $B(OH)_2R^1$ or a corresponding boronic acid ester, if appropriate in the presence of a coupling reagent and/or a base and the compound J-V, wherein X=$CR^3$, can in this way be obtained. If $R^1$ is linked to general formula (I) via a heteroatom (if $R^1$ represents substructure (T-1), for example, in which o represents 1 and Y can represent inter alia O, S, S(=O)$_2$, NH—C(=O) or $NR^{12}$), then the substitution can be carried out using methods known to the person skilled in the art, for example with the aid of hydroxylamine-O-sulphonic acid and subsequent conversion into secondary or tertiary amines, wherein Y=$NR^{13}$. In the case of Y=O, the substitution can be carried out using methods known to the person skilled in the art, for example with the aid of peroxy reagents and subsequent conversion into ether. In the case of Y=S(=O)$_2$, the substitution can be carried out by sulphonylation with sulphonyl chlorides, for example. In the case of Y=S, the preparation can for example be carried out by reaction with disulphides or else with sulphenyl chlorides or sulphene amides, or else by transformation into the mercaptan by means of methods known to the person skilled in the art and subsequent conversion into the thioether.

Alternatively, a second synthesis pathway, in which in step k01 an ester K-0 is first reduced to form the aldehyde K-I by means of methods known to the person skilled in the art, for example using suitable hydrogenation reagents such as metal hydrides, is suitable for preparing the compound J-V, wherein X=$CR^3$.

In step k02 the aldehyde K-I can then be reacted with a hydrazine K-V, which can be obtained in step k05, starting from the primary amine K-IV, by means of methods known to the person skilled in the art, to form the hydrazine K-II by means of methods known to the person skilled in the art with elimination of water.

In step k03 the hydrazine K-II can be halogenated, preferably chlorinated, by means of methods known to the person skilled in the art with the double bond intact, such as for example using a chlorination reagent such as NCS, and the compound K-III can in this way be obtained.

In step k04 the hydrazonoyl halide K-III can be converted into a cyano-substituted compound J-V, wherein X=$CR^3$, by means of methods known to the person skilled in the art, such as for example using a halogen-substituted nitrile, with cyclisation.

In step j06 the compound J-V can be hydrogenated by means of methods known to the person skilled in the art, for example using a suitable catalyst such as palladium/activated carbon or using suitable hydrogenation reagents, and the compound (II) can in this way be obtained.

In step j07 the compound (II) can be converted into the compound (V) by means of methods known to the person skilled in the art, such as for example using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j08 the amine (VI) can be converted into the urea compound (I) (wherein A=N). This can be achieved by reaction with (V) by means of methods with which the person skilled in the art is familiar, if appropriate in the presence of a base.

In step j09 the amine (II) can be converted into the amide (I) (wherein A=C—$R^{5b}$). This can for example be achieved by reaction with an acid halide, preferably a chloride of formula (IV) by means of methods with which the person skilled in the art is familiar, if appropriate in the presence of a base or by reaction with an acid of formula (III), if appropriate in the presence of a suitable coupling reagent, for example HATU or CDI, if appropriate with the addition of a base. Further, the amine (II) may be converted into the amide (I) (wherein A=C—$R^{5b}$) by reaction of a compound (IVa) by means of methods with which the person skilled in the art is familiar, if appropriate in the presence of a base.

For preparing compounds (II), wherein X=N, it is necessary to take a third synthesis route according to the general reaction scheme 1b. The compounds (II) which are then obtained, wherein X=N, can subsequently be further reacted in accordance with the above-described steps j07-j09.

General reaction scheme (scheme 1b):

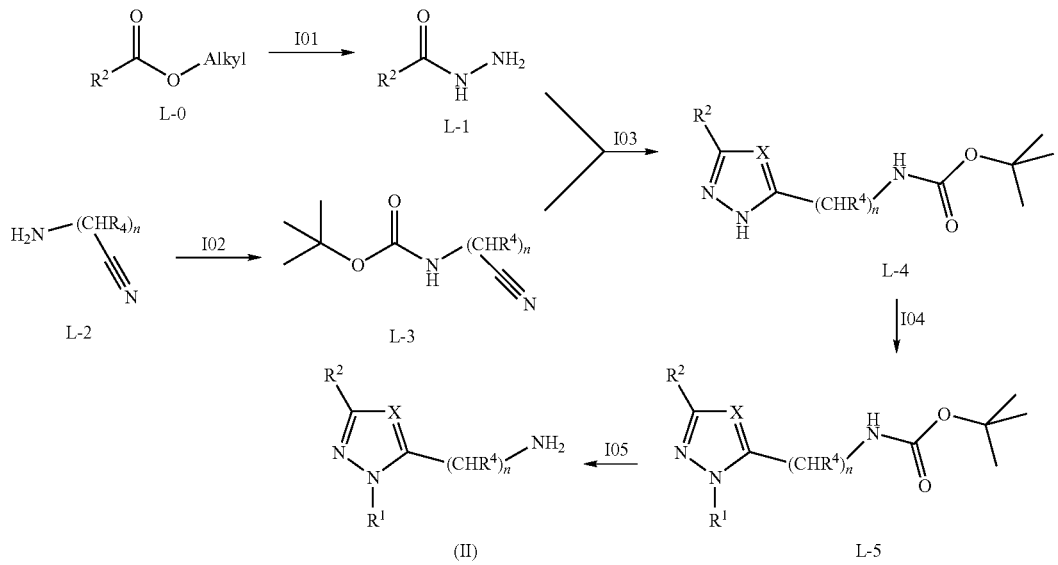

In step I01 a carboxylic acid alkyl ester L-0, preferably a methyl or ethyl ester, can be reacted with hydrazine hydrate to form the hydrazide L-1 by means of methods with which the person skilled in the art is familiar.

In step I02 the amino-substituted nitrile L-2 or the salts thereof can be reacted with boc anhydride to form the urethane L-3 by means of methods with which the person skilled in the art is familiar.

In step I03 L-1 and L-3 can be condensed in the presence of a base, preferably an alkali alcoholate, particularly preferably sodium methanolate, to form the triazole L-4, wherein X=N, by means of methods with which the person skilled in the art is familiar.

In step I04 the compound L-4, wherein X=N, can be substituted in the N position by means of methods known to the person skilled in the art, in a manner similar to the step j05 according to general reaction scheme 1a by means of the methods described hereinbefore, and compound L-5, wherein X=N, can in this way be obtained.

In step I05 the ester group in L-4 can be eliminated in the presence of an acid, preferably trifluoroacetic acid or hydrochloric acid, by means of methods known to the person skilled in the art, and the amine (II) can in this way be obtained.

The compounds according to general formula (I), wherein A=N, may be further prepared by a reaction sequence according to general reaction scheme 1c.

General reaction scheme (scheme 1c)

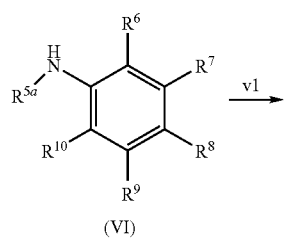

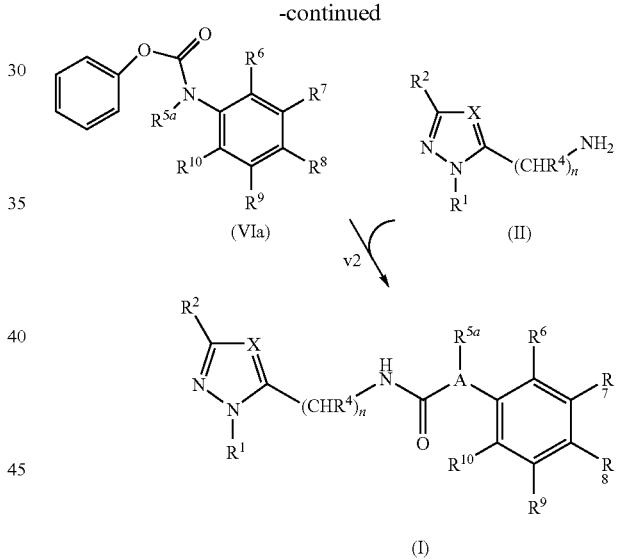

In step v1 the compound (VI) can be converted into the compound (VIa) by means of methods known to the person skilled in the art, such as for example using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (II) can be converted into the urea compound (I) (wherein A=N). This can be achieved by reaction with (VIa) by means of methods with which the person skilled in the art is familiar, if appropriate in the presence of a base.

The methods with which the person skilled in the art is familiar for carrying out the reaction steps j01 to j09 and also k01 to k05 and l01 to l05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

Synthesis of Intermediate Products

1. Synthesis of 3-tert-butyl-1-methyl-1H-pyrazol-5-yl-methanamine (steps j01-j06)

Step j01: Pivaloyl chloride (J-0) (1 eq., 60 g) was added dropwise to a solution of MeOH (120 ml) within 30 min at 0° C. and the mixture was stirred for 1 h at room temperature. After the addition of water (120 ml), the separated organic phase was washed with water (120 ml), dried over sodium sulphate and codistilled with dichloromethane (150 ml). The liquid product J-I was able to be obtained at 98.6% purity (57 g).

Step j02: NaH (50% in paraffin oil) (1.2 eq., 4.6 g) was dissolved in 1,4-dioxane (120 ml) and the mixture was stirred for a few minutes. Acetonitrile (1.2 eq., 4.2 g) was added dropwise within 15 min and the mixture was stirred for a further 30 min. The methyl pivalate (J-I) (1 eq., 10 g) was added dropwise within 15 min and the reaction mixture was refluxed for 3 h. After complete reaction, the reaction mixture was placed in iced water (200 g), acidified to pH 4.5 and extracted with dichloromethane (12×250 ml). The combined organic phases were dried over sodium sulphate, distilled and after recrystallisation from hexane (100 ml) 5 g of the product (J-II) (51% yield) was able to be obtained as a solid brown substance.

Step j03: At room temperature 4,4-dimethyl-3-oxopentanenitrile (J-II) (1 eq., 5 g) was taken up in EtOH (100 ml), mixed with hydrazine hydrate (2 eq., 4.42 g) and refluxed for 3 h. The residue obtained after removal of the EtOH by distillation was taken up in water (100 ml) and extracted with EE (300 ml). The combined organic phases were dried over sodium sulphate, the solvent was removed under vacuum and the product (J-III) (5 g, 89% yield) was obtained as a light red solid after recrystallisation from hexane (200 ml).

Step j04: 3-Tert-butyl-1H-pyrazol-5-amine (J-III) (1 eq., 40 g) was dissolved in dilute HCl (120 ml of HCl in 120 ml of water) and mixed dropwise with $NaNO_2$ (1.03 eq., 25 g in 100 ml) at 0-5° C. over a period of 30 min. After stirring for 30 minutes, the reaction mixture was neutralised with $Na_2CO_3$. A diazonium salt obtained by reaction of KCN (2.4 eq., 48 g), water (120 ml) and CuCN (1.12 eq., 31 g) was added dropwise to the reaction mixture within 30 min and the mixture was stirred for a further 30 min at 75° C. After complete reaction, the reaction mixture was extracted with EE (3×500 ml), the combined organic phases were dried over sodium sulphate and the solvent was removed under vacuum. The purification ($SiO_2$, 20% EE/hexane) of the residue by column chromatography produced a white solid (J-IV) (6.5 g, 15.1% yield).

Step J05 (Method 1):
3-tert.-butyl-1H-pyrazol-5-carbonitrile (J-IV) (10 mmol) was added to a suspension of NaH (60%) (12.5 mmol) in DMF (20 ml) at room temperature while stirring. After stirring for 15 minutes, methyl iodide (37.5 mmol) was added dropwise to this reaction mixture at room temperature. After stirring for 30 min at 100° C., the reaction mixture was mixed with water (150 ml) and extracted with dichloromethane (3×75 ml). The combined organic extracts were washed with water (100 ml) and sat. NaCl solution (100 ml) and dried over magnesium sulphate. After removal of the solvent under vacuum, the residue was purified by column chromatography ($SiO_2$, various mixtures of EE and cyclohexane as the mobile solvent) and the product J-V was obtained.

Step j06:
Method 1:
J-V was dissolved together with palladium on carbon (10%, 500 mg) and concentrated HCl (3 ml) in MeOH (30 ml) and exposed to a hydrogen atmosphere for 6 hours at room temperature. The reaction mixture was filtered over celite and the filtrate was concentrated under vacuum. The residue was purified by means of flash chromatography ($SiO_2$, EE) and the product (II) was in this way obtained.

Method 2:
J-V was dissolved in THF (10 ml) and $BH_3.S(CH_3)_2$ (2.0 M in THF, 3 ml, 3 equivalent) was added thereto. The reaction mixture was heated to reflux for 8 hours, aq. 2 N HCl (2 N) was added thereto and the reaction mixture was refluxed for a further 30 minutes. The reaction mixture was mixed with aq. NaOH solution (2N) and washed with EE. The combined organic phases were washed with sat. aq. NaCl solution and dried over magnesium sulphate. The solvent is removed under vacuum and the residue is purified by column chromatography ($SiO_2$, various mixtures of dichloromethane and methanol as the mobile solvent) and the product (II) (3-tert-butyl-1-methyl-1H-pyrazol-5-yl)methanamine) is in this way obtained.

2. The Following Further Intermediate Products were Synthesised in a Similar Manner Using The Process Described Hereinbefore Under 1

3-tert-butyl-1-hexyl-1H-pyrazol-5-yl-methanamine

3. Alternatively, Step J05 can Also be Carried Out as Follows (Method 2)

Step j05 (method 2):
A mixture of 3-tert-butyl-1H-pyrazol-5-carbonitrile (J-IV) (10 mmol), a boronic acid $B(OH)_2R^1$ or a corresponding boronic acid ester (20 mmol) and copper (II) acetate (15 mmol) is placed in dichloromethane (200 ml), mixed with pyridine (20 mmol) while stirring at room temperature and the mixture is stirred for 16 h. After removal of the solvent under vacuum, the residue obtained is purified by column chromatography ($SiO_2$, various mixtures of EE and cyclohexane as the mobile solvent) and the product J-V is in this way obtained.

The following further intermediate products were prepared in this way (steps j01-j06):
(3-tert-butyl-1-cyclohexenyl-1H-pyrazol-5-yl)methanamine
(3-tert-butyl-1-phenyl-1H-pyrazol-5-yl)methanamine
(3-tert-butyl-1-p-tolyl-1H-pyrazol-5-yl)methanamine
(3-tert-butyl-1-(4-tert-butylphenyl)-1H-pyrazol-5-yl)methanamine
(3-tert-butyl-1-(4-chlorophenyl)-1H-pyrazol-5-yl)methanamine
(3-tert-butyl-1-(3-chlorophenyl)-1H-pyrazol-5-yl)methanamine
(3-tert-butyl-1-(3-chloro-4-fluorophenyl)-1H-pyrazol-5-yl)methanamine (3-tert-butyl-1-(4-methoxyphenyl)-1H-pyrazol-5-yl)methanamine (E)-(3-tert-butyl-1-(4-methylstyryl)-1H-pyrazol-5-yl)methanamine 4. Synthesis of 1-(3-chlorophenyl)-3-(trifluoromethyl)-1H-pyrazol-5-yl-methanamine (steps k01-k05 and j06)

Step k01: LAIH (lithium aluminium hydride) (0.25 eq., 0.7 g) was dissolved in dry diethyl ether (30 ml) under a protective gas atmosphere and stirred for 2 h at room temperature. The suspension obtained was taken up in diethyl ether (20 ml). Ethyl-2,2,2-trifluoroacetate (K-0) (1 eq., 10 g) was taken up in dry diethyl ether (20 ml) and added dropwise to the suspension at −78° C. over a period of 1 h. The mixture was then the stirred for a further 2 h at −78° C. EtOH (95%) (2.5 ml) was then added dropwise, the reaction mixture was heated to room temperature and placed on iced water (30 ml) with concentrated $H_2SO_4$ (7.5 ml). The organic phase was separated and concentrated under vacuum and the reaction product K-I was immediately introduced into the next reaction step k02.

Step k05: 3-chloroaniline (K-IV) (1 eq., 50 g) was dissolved at −5 to 0° C. in concentrated HCl (300 ml) and stirred for 10 min. A mixture of $NaNO_2$ (1.2 eq., 32.4 g), water (30 ml), $SnCl_2.2H_2O$ (2.2 eq., 70.6 g) and concentrated HCl (100 ml) was added dropwise over a period of 3 h while maintaining the temperature. After stirring for a further 2 h at −5 to 0° C., the reaction mixture was set to pH 9 using NaOH solution and extracted with EE (250 ml). The combined organic phases were dried over magnesium sulphate and the solvent was removed under vacuum. The purification by column chromatography ($SiO_2$, 8% EE/hexane) produced 40 g (72% yield) of (3-chlorophenyl)hydrazine (K-IV) as a brown oil.

Step k02: The aldehyde (K−1) (2 eq., 300 ml) obtained from k01 and (3-chlorophenyl)hydrazine (K-IV) (1 eq., 20 g) were placed in EtOH (200 ml) and refluxed for 5 h. The solvent was removed under vacuum, the residue was purified by column chromatography ($SiO_2$, hexane) and the product (25 g, 72% yield) K-II was obtained as a brown oil.

Step k03: The hydrazine K-II (1 eq., 25 g) was dissolved in DMF (125 ml). N-chlorosuccinimide (1.3 eq., 19.5 g) was added portionwise at room temperature within 15 min and the mixture was stirred for 3 h. The DMF was removed by distillation and the residue was taken up in EE. The EE was removed under vacuum, the residue obtained was purified by column chromatography ($SiO_2$, hexane) and the product K-III (26.5 g, 92% yield) was obtained as a pink-coloured oil.

Step k04: At room temperature the hydrazonoyl chloride K-III (1 eq., 10 g) was taken up in toluene (150 ml) and mixed with 2-chloroacrylonitrile (2 eq., 6.1 ml) and TEA (2 eq., 10.7 ml). This reaction mixture was stirred for 20 h at 80° C. The mixture was then diluted with water (200 ml) and the phases were separated. The organic phase was dried over magnesium sulphate and the solvent was removed under vacuum. The residue was purified by means of column chromatography ($SiO_2$, 5% EE/hexane) and the product (5.5 g, 52% yield) was obtained as a white solid J-V.

Step J06 (Method 3):

The carbonitrile J-V (1 eq., 1 g) was dissolved in methanolic ammonia solution (150 ml, 1:1) and hydrogenated in an H-cube (10 bar, 80° C., 1 ml/min, 0.25 mol/L). After removal of the solvent under vacuum, (1-(3-chlorophenyl)-3-(trifluoromethyl)-1H-pyrazol-5-yl)methanamine (II) was able to be obtained as a white solid (0.92 g, 91% yield).

5. The Following Further Intermediate Products were Synthesised in a Similar Manner Using the Process Described Hereinbefore Under 4.:

(1-(4-chlorophenyl)-3-(trifluoromethyl)-1H-pyrazol-5-yl)methanamine (1-(3-chloro-4-fluorophenyl)-3-(trifluoromethyl)-1H-pyrazol-5-yl)methanamine 6. Preparation of Selected Acids of General Formula (III)

6.1 Synthesis of 2-(4-(N,N-dimethylsulphamoyl)-3-fluorophenyl)propanoic acid

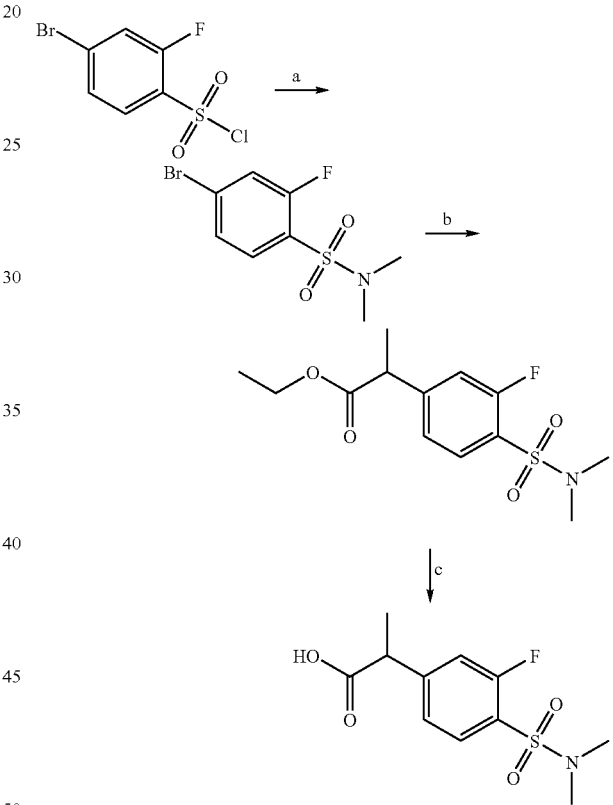

Step a: 4-bromo-2-fluorobenzene sulphonyl chloride (9.15 mmol, 2.5 g) was dissolved in dichloromethane (75 ml) at room temperature, mixed with dimethylamine (2 mol/l in MeOH) (18.3 mmol, 9.15 ml) and stirred for 2 h at room temperature after addition of the pyridine (32 mmol, 2.58 ml). The reaction mixture was mixed with water (75 ml) and the organic phase was separated off. The aqueous phase was extracted with EE (2×75 ml), the organic phases were combined and dried over magnesium sulphate. After removal of the solvent under vacuum, 2.51 g (97% yield) of the product could be obtained.

Step b: step-a-product (8.9 mmol, 2.5 g) and ethyl-2-chloropropionate (11.5 mmol, 1.57 g) were dissolved in DMF (15 ml) at room temperature under a protective gas atmosphere. Subsequently, manganese (17.7 mmol, 0.974 g), (2,2'-bipyridine) nickel (II) dibromide (0.62 mmol, 0.231 g) and TFA (0.23 mmol, 18 μL) were added and stirred for 48 h at 50° C. After cooling of the reaction mixture to room temperature, the mixture was hydrolysed with 1 N HCl (25 ml) and the mix was extracted with diethyl ether (3×25 ml). The combined organic phases were washed with water (25 ml) and aq. sat. NaCl solution (25 ml) and dried over magnesium sulphate. The solvent was removed under vacuum and the residue was purified by means of column chromatography ($SiO_2$, dichloromethane/MeOH=15:1) and the product was in this way obtained.

Step c: Step-b-product (5.9 mmol, 1.8 g) was dissolved in a THF-water mix (15 ml, 2:1), LiOH (17.8 mmol, 0.414 g) was added and refluxed for 10 h. The reaction mixture was extracted with diethyl ether (25 ml), the aqueous phase was acidified to pH 2 using 1 N HCl and extracted with EE (3×25 ml). The combined organic phases were dried over magnesium sulphate and the solvent was concentrated to dryness under vacuum. 2-(4-(N,N-dimethylsulphamoyl)-3-fluorophenyl)propanoic acid (C) could be obtained at a 48% yield (0.78 g).

6.2 Synthesis of 2-(4-methoxy-3,5-dimethylphenyl)acetic acid

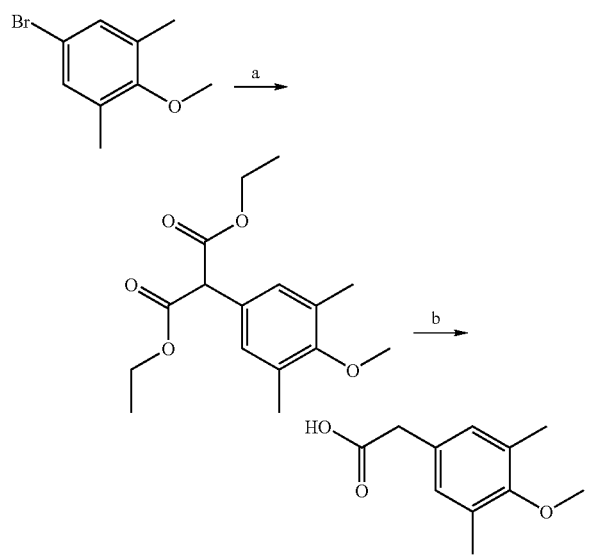

Step a: Bromo-2,6-dimethylanisol (23.2 mmol, 5 g), CuBr (46.5 mmol, 6.67 g) and diethyl malonate (46.5 mmol, 7.09 ml) were dissolved in 1,4-dioxane (30 ml). NaH (60% in mineral oil) (51.1 mmol, 1.225 g) was added slowly at room temperature while stirring and the mixture was stirred for 10 h at 100° C. After cooling of the reaction mixture, a brown solid was removed by filtration and the filtrate was concentrated under vacuum. The purification by column chromatography ($SiO_2$, EE/cyclohexane, 1:2) produces 0.87 g (13% yield) of the malonic acid diethyl ester.

Step b: The malonic acid diethyl ester (0.34 mmol, 0.1 g) obtained was then dissolved in 2 N $NaOH/THF:H_2O$ (1:1) (350 μL) and refluxed for 3 h. After acidifying the reaction mixture to pH 1 using conc. HCl, the mixture was stirred for a further hour at room temperature. The solution was then set to pH 13 using 1 N NaOH and extracted with diethyl ether (20 ml). The aqueous phase was set to pH 5 using 1 N HCl and extracted with EE (3×20 ml). The combined organic phases were washed with sat. NaCl solution, dried over magnesium sulphate and filtered. After removal of the solvent under vacuum, 0.021 g (32% yield) of the desired 2-(4-methoxy-3,5-dimethylphenyl)acetic acid could be obtained.

6.3 Synthesis of 2-(3,5-difluoro-4-hydroxyphenyl)acetic acid (employed for the synthesis of example compound no. 147)

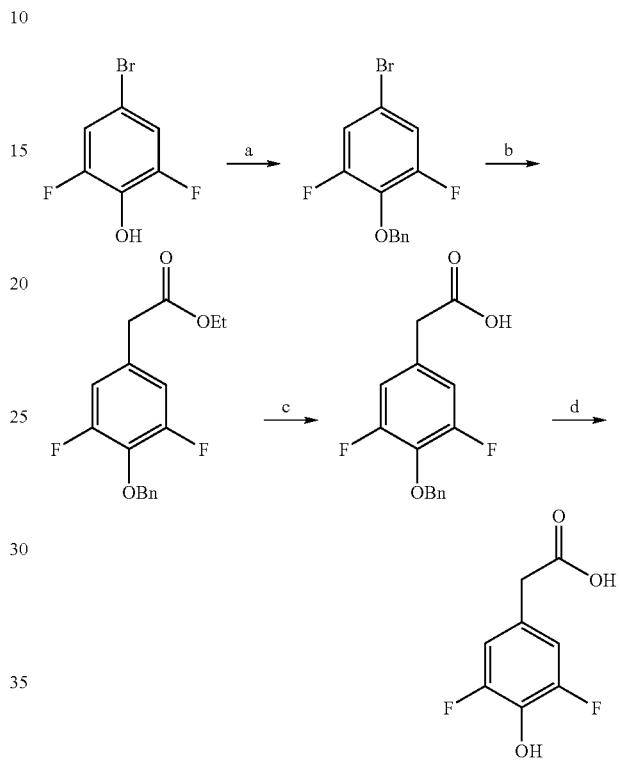

Step a: 4-bromo-2,6-difluorophenol (5 g, 23.92 mmol) was dissolved in dimethylformamide (50 mL) in 250 ml round bottom flask equipped with argon atmosphere. Potassium carbonate (5 g, 35.55 mmol) was added and stirred for 10 minutes, followed by addition of benzyl bromide (4.5 g, 26.31 mmol) and stirred at ambient temperature for 4 h. TLC showed (hexane, $R_f$: 0.8) complete conversion of starting material. The reaction mixture was diluted with water (500 mL) and extracted with ethyl acetate (3×100 mL). The combined organic part was dried over anhydrous magnesium sulfate and concentrated under reduced pressure to afford crude material, which was purified by column chromatography (silica gel: 100-200 mesh, eluent: 5% ethyl acetate in hexane) to afford the pure compound (7 g, 95.8%).

Step b: In a 50 mL two necked round bottom flask step-a product (2 g, 6.68 mmol), ethyl chloroacetate (1.06 g, 8.69 mmol), and dimethylformamide (14 mL) were charged. The system was degassed and refilled with argon followed by addition of Mn (735 mg, 13.36 mmol) and $NiBr_2$.bipy (202 mg, 0.53 mmol). Finally trifluoroacetic acid (14 μL) was added and the reaction mixture was degassed and refilled with argon. Then it was heated to 65° C. for one and half hour. TLC showed (10% ethyl acetate in hexane, $R_f$: 0.4) complete conversion of starting material. The reaction mixture was diluted with water (50 mL) and HCl (4N, 0.5 mL) and extracted with ethyl acetate (3×50 mL). The combined organic part was dried over anhydrous magnesium sulfate and concentrated under reduced pressure to afford crude material which was purified by column chromatography (silica gel: 100-200 mesh, eluent: 10% ethyl acetate in hexane) to afford 700 mg product. ¹H NMR (DMSO-d₆, 400 MHz): δ 7.54 (t, 1H), 7.15 (d, 2H), 4.16 (q, 2H), 3.64 (s, 2H), 1.26 (t, 3H).

Step c: Step-b product (700 mg, 2.6 mmol) was dissolved in THF (4 mL). LiOH (4 mL, 1M, 4 mmol) was added to it. The reaction mixture was stirred at ambient temperature for 2 h. TLC showed (60% ethyl acetate in hexane, R$_f$: 0.2) complete conversion of starting material. The reaction mixture was diluted with water (30 mL) and washed with ethyl acetate (2×30 mL). The aqueous part was acidified with 4N HCl (pH ~2) and extracted with in ethyl acetate (3×40 mL). The combined organic layer was washed with water (50 mL) and brine (50 mL). It was dried over anhydrous magnesium sulfate and concentrated under reduced pressure to afford 500 mg pure compound. ¹H NMR (DMSO-d₆, 400 MHz): δ 12.45 (s, 1H), 7.32-7.42 (m, 5H), 7.03 (d, 2H), 5.13 (s, 2H), 3.56 (s, 2H)

Step d: Step-c product (1.4 g, 5 mmol) was dissolved in EtOH (14 mL). Palladium on carbon (140 mg, 10% Pd) was added to it under argon atmosphere. The reaction mixture was hydrogenated at 50 psi hydrogen pressure for 16 h. TLC showed (in ethyl acetate, R$_f$: 0.1) complete conversion of starting material. The reaction mixture was filtered over celite bed and washed with ethyl acetate and concentrated under reduced pressure to afford desired product (800 mg, 84.5%). ¹H NMR (DMSO-d₆, 400 MHz): δ 12.38 (bs, 1H), 10.03 (bs, 1H), 6.92 (d, 2H), 3.49 (s, 2H); LCMS [M−H]: 187.

6.4 Synthesis of
2-(3,5-difluoro-4-hydroxyphenyl)propanoic acid
(employed for the synthesis of example compound
no. 46)

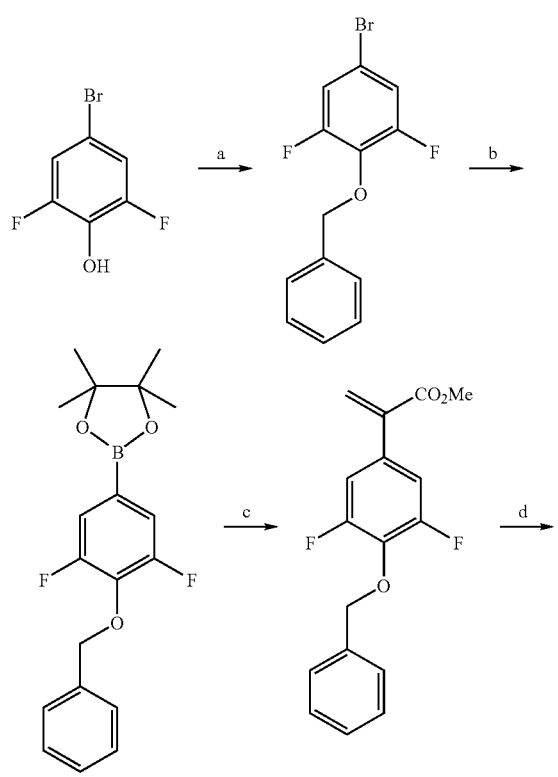

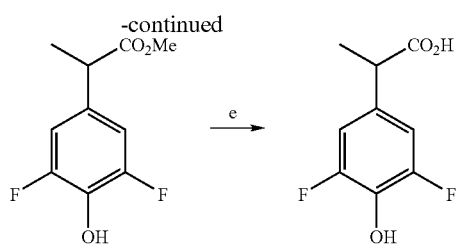

Step a: To a stirred solution of 4-bromo-2,6-difluorophenol (8 g, 38.27 mmol) in dimethyl formamide (80 mL), potassium carbonate (7.9 g, 57.41 mmol) was added and stirred for 15 minutes at ambient temperature. Then benzyl bromide (7.85 g, 45.93 mmol) was added dropwise for 10 minutes. It was allowed to stir at ambient temperature for 10 h. Water (800 mL) was added to it and extracted with ethyl acetate (3×100 mL). The combined organic layer was dried over magnesium sulfate and concentrated to afford crude, which was purified through column chromatography (silica gel: 100-200 mesh; eluent: 5% ethyl acetate in hexane) to afford compound (10.2 g, 87.8%).

Step b: To a stirred solution of step-a product (5 g, 16.72 mmol) in toluene (120 mL), bis(pinacolato)diboron (5 g, 19.68 mmol) was added and deoxygenated twice. Potassium phenoxide (3.3 g, 24.61 mmol), PdCl₂(PPh₃)₂ (0.35 g, 0.49 mmol) and PPh₃ (0.26 g, 0.98 mmol) were added simultaneously to it and again deoxygenated with argon. The reaction was heated at 60° C. and maintained the same temperature for 12 h. The reaction mixture was filtered through celite bed and the filtrate was taken in ethyl acetate (200 mL) and was washed with water (2×100 mL). The final organic layer was dried over anhydrous magnesium sulfate and concentrated to afford the crude compound, which was purified through column chromatography (silica: 100-200 mesh, eluent: 3% ethyl acetate in hexane) to afford compound (3.0 g, 51.9%). ¹H NMR (DMSO-d₆, 400 MHz): δ 7.35-7.42 (m, 6H), 7.24 (d, 2H), 5.2 (s, 2H), 1.27 (s, 12H).

Step c: To a stirred solution of step-b product (2.5 g, 7.22 mmol) in a mixture of toluene and EtOH (1:1, 20 mL) compound 4 (2.53 g, 10.83 mmol) was added and deoxygenated twice. PdCl₂ (dppf) (264 mg, 0.36 mmol) and 2M sodium carbonate solution (7.2 mL) was added simultaneously and finally heated at 90° C. for 3 h. The reaction mixture was diluted with water (100 mL) and was extracted with ethyl acetate (2×50 mL). The combined organic layer was dried over anhydrous magnesium sulfate and concentrated to afford crude compound, which was purified through column chromatography (silica: 100-200 mesh, eluent: 2% ethyl acetate in hexane) to obtain pure compound (1.2 g, 54.5%). ¹H NMR (DMSO-d₆, 400 MHz): δ 7.35-7.44 (m, 5H), 7.27 (d, 2H), 6.2 (s, 1H), 6.14 (s, 1H), 5.19 (s, 2H), 3.7 (s, 3H).

Step d: Step-c product (2.5 g, 8.21 mmol) was dissolved in ethyl acetate (25 mL) and was taken in Parr hydrogenation bottle followed by palladium on charcoal (300 mg, 10% Pd) and was hydrogenated at 50 psi for 10 h. The reaction mixture was filtered through celite bed and was concentrated to obtain the crude compound (1.6 g, 90%). ¹H NMR (DMSO-d₆, 400 MHz): δ 10.08 (s, 1H), 6.93 (d, 2H), 3.70-3.76 (q, 1H), 3.58 (s, 3H), 1.34 (d, 3H).

Step e: To a stirred solution of step-d product (2.0 g, 9.25 mmol) in THF (19 mL), aqueous LiOH solution (1M, 19 mL) was added. The reaction mixture was stirred at ambient temperature for 10 h. TLC showed complete conversion of starting material. The organic solvent was concentrated and water (50 mL) was added to the residue. This aqueous part was washed with ethyl acetate (30 mL). The aqueous layer was acidified with 1N HCl up to pH 2 and extracted with ethyl acetate (3×25 mL). The combined organic layer was dried over anhydrous magnesium sulfate and concentrated to afford desired product (1.7 g, 91%). $^1$H NMR (DMSO-d$_6$, 400 MHz): δ 12.3 (bs0, 1H), 10.03 (bs, 1H), 6.94 (d, 2H), 3.58-3.61 (q, 1H), 1.30 (d, 3H); GCMS (m/z)[M−H]: 201.

6.5 Synthesis of 2-(3-fluoro-4-(trifluoromethyl)phenyl)acetic acid (employed for the synthesis of example compound no. 140)

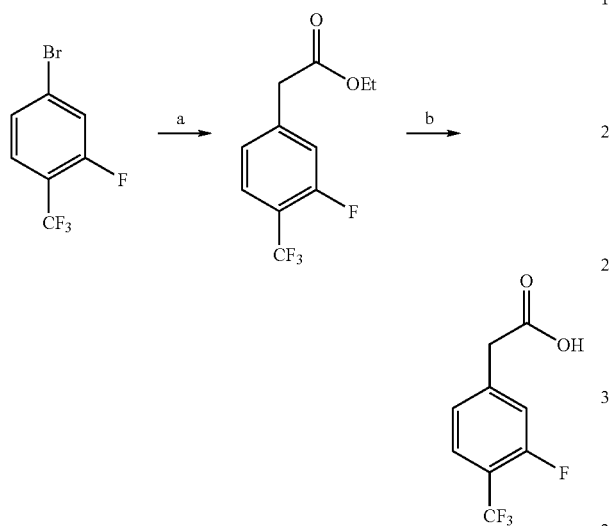

Step a: In a 50 mL two necked round bottom flask 4-bromo-2-fluoro-1-(trifluoromethyl)benzene (0.5 g, 2.05 mmol), ethyl chloroacetate (328 mg, 2.67 mmol), and dimethylformamide (4 mL) were charged. The system was degassed and re filled with argon followed by addition of Mn (225 mg, 4.1 mmol) and NiBr$_2$.bipy (62 mg, 0.16 mmol). Finally TFA (4.1 μL) was added and the reaction mixture was degasified and refilled with argon. Then it was heated to 65° C. for one hour. TLC showed (10% ethyl acetate in hexane, R$_f$: 0.2) complete conversion of starting material. The reaction mixture was diluted with water (50 mL) and HCl (4N, 0.5 mL) and extracted with ethyl acetate (3×40 mL). The combined organic part was dried over anhydrous magnesium sulfate and concentrated under reduced pressure to afford crude material which was purified by column chromatography (silica gel: 100-200 mesh, eluent: 10% ethyl acetate in hexane) to afford the pure compound (490 mg, 27%). $^1$H NMR (DMSO-d$_6$, 400 MHz): δ 7.54 (t, 1H), 7.15 (d, 2H), 4.16 (q, 2H), 3.64 (s, 2H), 1.26 (t, 3H).

Step b: Step-a product (1.48 g, 6 mmol) was dissolved in THF (9 mL). LiOH (9 mL, 1M, 9 mmol) was added to it. The reaction mixture was stirred at ambient temperature for 2 h. TLC showed (60% ethyl acetate in hexane, R$_f$: 0.2) complete conversion of starting material. The reaction mixture was diluted with water (50 mL) and washed with ethyl acetate (2×40 mL). The aqueous part was acidified with 4N HCl (pH~2) and extracted with in ethyl acetate (3×50 mL). The combined organic layer was washed with water (50 mL) and brine (50 mL). The combined organic part was dried over anhydrous magnesium sulfate and concentrated under reduced pressure to afford desired product (1.2 g, 94%). $^1$H NMR (DMSO-d$_6$, 400 MHz): δ 12.58 (s, 1H), 7.72 (t, 1H), 7.43 (d, 1H), 7.32 (d, 1H), 3.74 (s, 2H); LCMS [M−H—CO$_2$]: 177.

6.6 Synthesis of 2-(3-fluoro-4-(trifluoromethyl)phenyl)propanoic acid (employed for the synthesis of example compound no. 141)

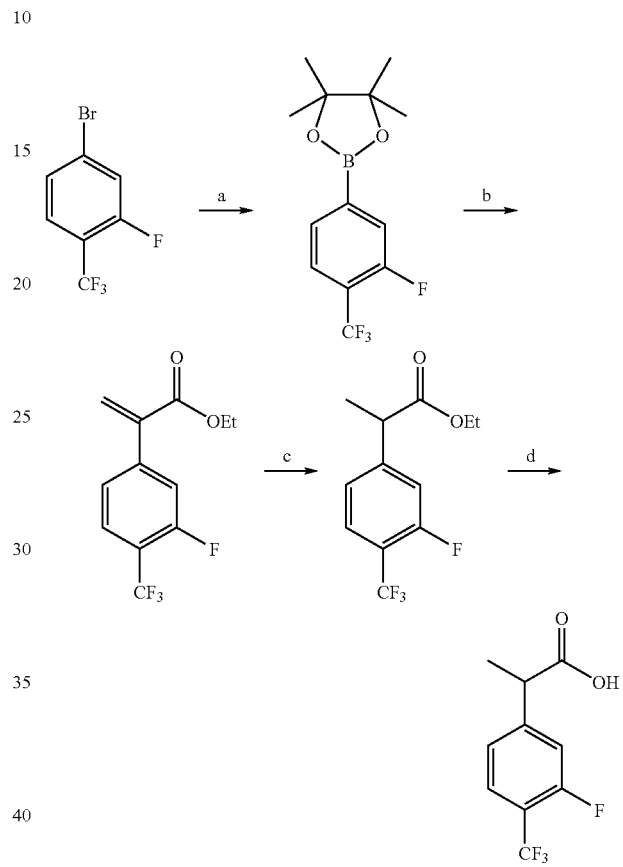

Step a: To a stirred solution of 4-bromo-2-fluoro-1-(trifluoromethyl)benzene (5 g, 20.57 mmol) in 1,4-dioxane (400 mL), bis(pinacolato)diboron (5.2 g, 20.57 mmol) was added and deoxygenated twice. Potassium acetate (6.05 g, 61.72 mmol), PdCl$_2$(PPh$_3$)$_2$ (0.43 g, 0.61 mmol) were added to it and again deoxygenated. The reaction was heated to 100° C. for 12 h. The reaction mixture was filtered through celite bed and evaporated to dryness. It was taken in ethyl acetate (200 mL) and was washed with water (2×100 mL). The final organic layer was dried over anhydrous magnesium sulfate and evaporated to dryness to afford crude compound, which was purified through column chromatography (silica: 100-20 mesh, eluent: 5% ethyl acetate in hexane) to afford compound (4 g, 67%).

Step b: To a stirred solution of step-a product (4 g, 13.78 mmol) in toluene (50 mL) ethyl 2-(trifluoromethylsulfonyloxy)acrylate (4.1 g, 17.92 mmol) was added and deoxygenated twice. Pd(PPh$_3$)$_4$ (0.8 g, 0.68 mmol) was added and again deoxygenated. 2M sodium carbonate solution (16 mL) was added and heated at 60° C. for 10 h. The reaction mixture was diluted with water (100 mL) and was extracted with ethyl acetate (2×100 mL). The combined organic layer was dried over anhydrous magnesium sulfate and evaporated to dryness to afford crude compound, which was purified through column chromatography (silica: 100-200 mesh, eluent: 2% ethyl acetate in hexane) to obtained 1.8 g pure compound (52.6%). $^1$H NMR (DMSO-$d_6$, 400 MHz): δ 7.78 (t, 1H), 7.63 (d, 1H), 7.48 (d, 1H), 6.45 (s, 1H), 6.25 (s, 1H), 3.77 (s, 3H).

Step c: Step-b product (1.8 g, 7.62 mmol) in (20 mL) was dissolved in ethyl acetate and was taken in Parr hydrogenation bottle followed by palladium on charcoal (180 mg, 10% Pd) and was hydrogenated at 50 psi for 10 h. The reaction mixture was filtered through celite bed and was concentrated to obtain 1.7 g of the crude compound (94%). $^1$H NMR (DMSO-$d_6$, 400 MHz): δ 7.73 (t, 1H), 7.47 (d, 1H), 7.34 (d, 1H), 3.99 (q, 1H), 3.61 (s, 3H), 1.42 (d, 3H).

Step d: To a stirred solution of step-c product (1.7 g, 6.79 mmol) in THF (12 mL), 1M LiOH (12 mL) was added. The reaction mixture was stirred at ambient temperature for 30 minutes. TLC showed complete conversion of starting material. The organic solvent was concentrated and water (50 mL) was added to the residue. This aqueous part was washed with ethyl acetate (30 mL). The aqueous layer was acidified with 1N HCl up to pH 2 and extracted with ethyl acetate (3×25 mL). The combined organic layer was dried over anhydrous magnesium sulfate and evaporated to dryness to obtained compound (1.3 g, 81%). $^1$H NMR (DMSO-$d_6$, 400 MHz): δ 12.59 (bs, 1H), 7.73 (t, 1H), 7.45 (d, 1H), 7.34 (d, 1H), 3.86 (q, 1H), 1.40 (d, 3H); GCMS (m/z): 236.

6.7 Synthesis of 2-(4-cyclopropyl-3-fluorophenyl)propanoic acid (employed for the synthesis of example compound no. 125)

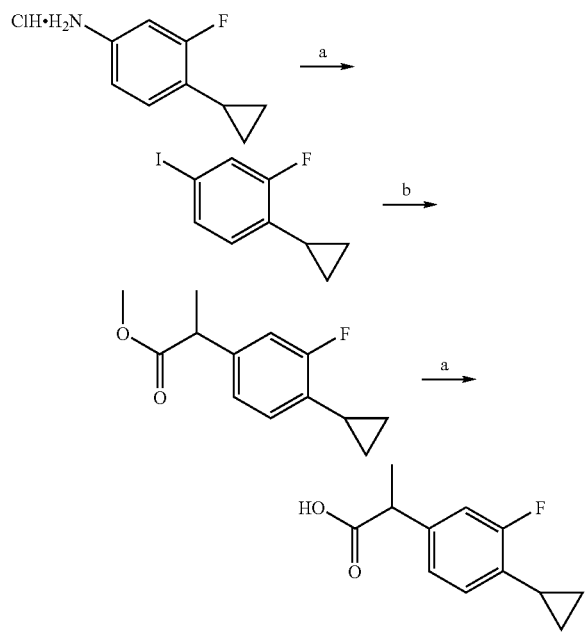

Step a: To a suspension of potassium iodide (9 g, 94.42 mmol) and isoamyl nitrite (4.89 mL, 36.34 mmol) in acetonitrile (30 mL), a solution of 4-cyclopropyl-3-fluoroaniline hydrochloride (3.4 g, 18.18 mmol) in acetonitrile (20 mL) was added at 0° C. After addition reaction mixture was stirred at room temperature for 30 h. Acetonitrile was evaporated; the obtained residue was diluted with ethyl acetate (250 mL), washed with water (2×100 mL), brine solution (50 mL), dried (Na$_2$SO$_4$) and concentrated. The obtained crude compound was purified by column chromatography (100-200 mesh Silica gel) using petroleum ether as eluent to afford a yellow liquid (4.1 g, 57.6%).

Step b: A solution of step-a product (1.9 g, 7.25 mmol) and methyl-2-bromopropanate (2.22 mL, 18.12 mmol) in dimethylformamide (20 mL) was degassed with Argon, added 2,2'-bipyridyl (0.113 g, 0.723 mmol), NiBr$_2$ (158 mg, 0.723 mmol), Mn powder (796 mg, 14.49 mmol), TFA (cat) at room temperature and the reaction mixture was stirred at 75° C. for 24 h. The reaction mixture was cooled to room temperature, diluted with ether (200 mL), washed with water (100 mL), brine solution (30 mL), dried (Na$_2$SO$_4$), filtered and concentrated. The obtained crude compound was purified by column chromatography (100-200 mesh Silica gel) using 5% ethyl acetate in petroleum ether as eluent to afford product as pale yellow liquid (520 mg, 32%).

Step c: To a solution of step-b product (1.2 g, 5.4 mmol) in MeOH (3 mL), THF (6 mL), H$_2$O (6 mL), LiOH.H$_2$O (900 mg, 21.61 mmol) was added at room temperature and the reaction mixture stirred at room temperature for 3 h. The reaction mixture was concentrated under reduced pressure and residual aqueous layer was diluted with water (75 mL), washed with ethyl acetate (50 mL) to remove the impurities. The aqueous layer was acidified (pH-4) using 1N aq. HCl (5 mL) and extracted with ethyl acetate (2×50 mL). The combined organic layer washed with brine solution (15 ml), dried (Na$_2$SO$_4$), filtered and concentrated. The obtained crude compound was purified by column chromatography (100-200 mesh Silica gel) using 5% ethyl acetate in petroleum ether as eluent to afford compound title compound as pale yellow liquid (650 mg, 58%).

6.8 Synthesis of 2-(3-fluoro-4((2-methoxyethoxy)methyl)phenyl)propanoic acid (employed for the synthesis of example compound no. 142)

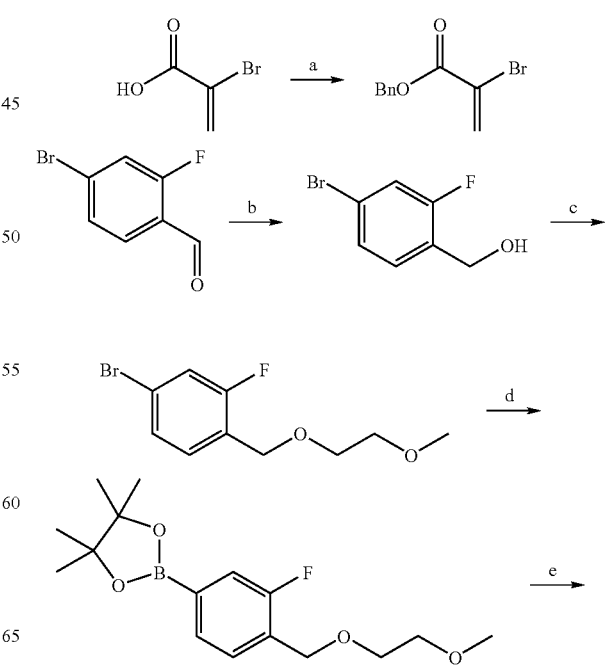

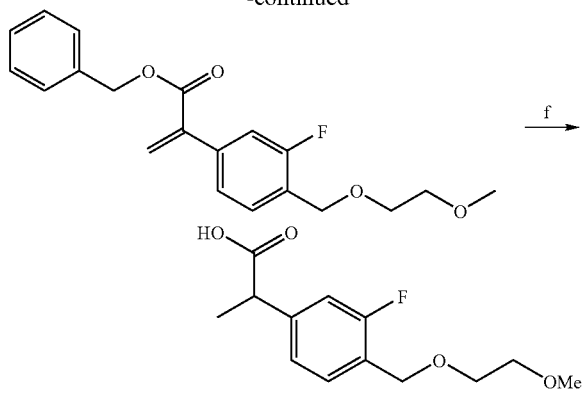

Step a: A suspension of 2-bromoacrylic acid (10 g, 66.66 mmol), BnBr (9 mL, 73.72 mmol) and potassium carbonate (18 g, 133.3 mmol). in acetonitrile (100 ml) was stirred at 80° C. for 3 h until complete consumption. The reaction mixture was filtered and concentrated. The obtained crude compound was purified by column chromatography (100-200 mesh silica gel) using 5% ethyl acetate in petroleum ether as eluent to afford a yellow liquid (10 g, 62.8%).

Step b: To a stirred solution of 4-bromo-2-fluoro benzaldehyde (15 g, 79.36 mmol) in MeOH (100 mL) at 0° C. to −5° C., added $NaBH_4$ (6.0 g, 158.73 mmol) in equal portions and stirred at room temperature. The reaction mixture was diluted with ice cold water (100 mL) and concentrated under reduced pressure. The obtained aqueous residue was extracted with ethyl acetate (2×200 mL); the ethyl acetate layer was washed with brine solution (50 mL), dried over anhydrous $NaSO_4$, filtered and concentrated to afford a colorless oil (15 g, 99%).

Step c: To a stirred solution of step-b product (10 g, 49.02 mmol) in THF (250 ml) at 0° C., added 60% NaH (2.93 g, 73.53 mmol) slowly in portions. After addition, the suspension was heated to 50° C. for 30 minutes, cooled to room temperature, added 1-bromo-2-methoxy ethane (5 ml, 53.92 mmol) and stirred at room temperature for 20 h. The reaction mixture was diluted with ice cold water (100 mL) and concentrated under reduced pressure. The obtained aqueous residue was extracted with ethyl acetate (2×150 mL); the combined ethyl acetate layer was washed with brine solution (50 mL), dried over anhydrous $NaSO_4$, filtered and concentrated. The obtained crude compound was purified by column chromatography (100-200 mesh silica gel) using 5% ethyl acetate in petroleum ether as eluent to afford product as yellow liquid (6 g, 47%).

Step d: A stirred suspension of step-c product (6 g, 22.8 mmol), bis(pinacolato)diboron (5.8 g, 22.8 mmol), potassium acetate (6.7 g, 68.4 mmol) in THF (50 ml) was deoxygenated by purging with a stream of Argon for 30 minutes, and added $Pd(PPh_3)_2Cl_2$ (36.5 mg, 0.228 mmol), purging was continued for further 10 minutes. The reaction mixture was stirred at 100° C. for 1 h. The reaction mixture was concentrated and the obtained crude compound was purified by column chromatography (100-200 mesh silica gel) using 10% ethyl acetate in petroleum ether as eluent to afford product as a pale yellow oil (5 g, 61.7%).

Step e: A suspension of step-d product (5 g, 16.129 mmol), caesium carbonate (15.7 g, 48.38 mmol) in dimethylformamide (50 ml) was deoxygenated by purging Argon for 30 minutes at room temperature. $Pd(dppf)Cl_2$ (657 mg, 0.806 mmol) was added and purging was continued. After 10 minutes, step-a product (4.6 g, 19.35 mmol) was added and stirred at 100° C. for 1 h. The reaction mixture was diluted with ethyl acetate (200 mL), filtered through a celite pad, washed with ethyl acetate (2×25 mL). The filtrate was washed with water (2×100 mL), brine (50 mL), dried over anhydrous $NaSO_4$, filtered and concentrated. The obtained crude compound was purified by column chromatography (100-200 mesh silica gel) using 10% ethyl acetate in petroleum ether as eluent to afford product as pale brown oil (1.4 g, 25%).

Step f: A suspension of step-e product (2.8 g, 8.139 mmol), 10% Pd/C (300 mg) in MeOH (20 ml) was hydrogenated (balloon pressure) at room temperature for 1 h. The reaction mixture was filtered through celite pad, washed with MeOH (2×15 mL). The combined filtrate was concentrated and the obtained crude compound was purified by column chromatography (100-200 mesh silica gel) using 30% ethyl acetate in petroleum ether as eluent to afford title compound as colorless oil (1.2 g, 57.7%).

6.9 Synthesis of 2-(4-(phenylcarbamoyl)phenyl)propanoic acid (employed for the synthesis of example compound no. 143)

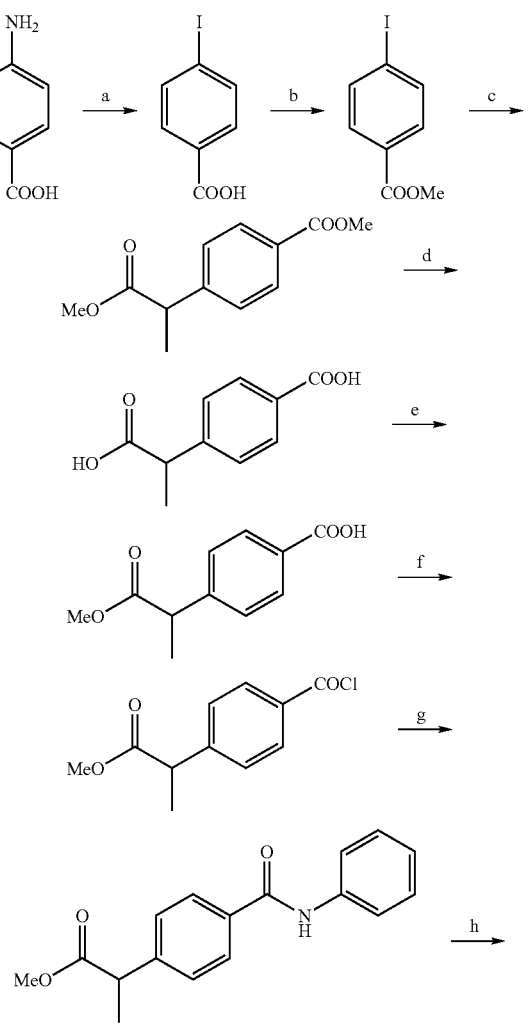

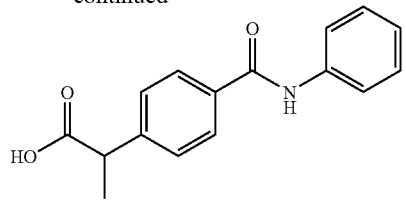

Step a: A solution of sulfuric acid (118 ml) in water (500 ml) was added to 4-aminobenzoic acid (150 g, 1094 mmol) and stirred the contents for 10 minutes at 0° C. Then a solution of sodium nitrite (98.1 g, 1420 mmol, 1.3 eq) in water (500 ml) was added dropwise for 2 h at 0° C. and stirred the contents for 1 hr at the same temperature.

In another round-bottom flask, a solution of sulfuric acid (118 ml) in water (500 ml) was added to potassium iodide (253.3 g, 1520 mmol, 1.4 eq) and the stirred the contents for 15 minutes at 0° C. Above prepared diazonium solution was added dropwise at 0° C. for 2 h. Overall reaction mixture was allowed to stir for 1 hr at 0° C. and later for another 1 hr at 40° C. Progress of the reaction was monitored by TLC (50% ethyl acetate-hexane, $R_f$~0.1). On completion of the reaction, ice cold water (500 ml) was added and filtered the contents. Residue was washed with sodiumthio sulfate solution (2×100 ml) and dried to obtain the crude product as dark brown colored solid (125 g, crude).

Step b: To a solution of the crude step-a product (125 g) in acetone (800 ml), potassium carbonate (103 g, 750 mmol, 1.5 eq) and stirred for some time at room temperature. DMS (76.2 g, 600 mmol, 1.2 eq) taken in acetone (500 ml) was added dropwise for 30 minutes and the reaction mixture was allowed to stir for 8 h at room temperature. Progress of the reaction was monitored by TLC (50% ethyl acetate-hexane, $R_f$~0.6). On completion of the reaction, reaction contents were filtered over a celite bed and washed with acetone (100 ml). Filtrate was concentrated under reduced pressure, residue was taken in dichloromethane (250 ml) and washed with cold water (2×100 ml). Combined organic layer was dried over sodium sulfate, concentrated under reduced pressure and the crude obtained was purified by column chromatography (silica gel, 5% ethyl acetate-hexane) to yield the required product as a white solid (60 g, 45%).

Step c: To a solution of step-b product (10 g, 39 mmol) in dimethylformamide (DMF) (150 ml, 15 times), 2-chloropropionate (14 g, 110 mmol, 3 eq) was added and stirred the contents for 30 minutes while nitrogen gas is being bubbled. Manganese (4.2 g, 70 mmol, 2 eq) was added and stirred the contents for 30 minutes under $N_2$ atmosphere. $NiBr_2$.bypridine (1.42 g, 2.6 mmol, 0.07 eq) was added and stirred for 30 minutes under $N_2$ atmosphere. Then a 15-20 drops of TFA was added stirred the contents for 1 hr. Progress of the reaction was monitored by TLC (10% ethyl acetate-hexane, $R_f$~0.4). On completion of the reaction, water (30 ml) was added and stirred the contents for 30 minutes. Then the contents were filtered and the bed was washed with hexane (2×50 ml). Filtrate was extracted with hexane (4×100 ml) and the obtained aqueous layer was extracted with hexane (2×50 ml). Combined extract was dried over sodium sulfate, concentrated under reduced pressure and the crude obtained was purified by column chromatography (silica gel, 3% ethyl acetate-hexane) to yield the required product as a red colored liquid (6 g, 70%).

Step d: To a stirred solution of step-c product (6 g, 27 mmol) in MeOH (60 ml, 10 times), a solution of sodium hydroxide (2.7 g, 67 mmol, 2.5 eq) in water (60 ml, 10 times) was added dropwise at room temperature. Overall reaction mixture was allowed to stir for 3 h at room temperature. Progress of the reaction was monitored by TLC (50% ethyl acetate-hexane, $R_f$~0.1). As the reaction not moved completely, reaction contents were allowed to stir for another 5 h. Again TLC was checked and confirmed that the starting material was disappeared. Methanol was distilled off completely and the residue was cooled to 0° C. Then the contents were acidified at a pH~2 with 6N HCl solution and solid thrown out was filtered. Solid obtained was dissolved in ethyl acetate (100 ml), dried over sodium sulfate and concentrated under reduced pressure to yield the required product as an off white solid (4.5 g, 86%).

Step d: To a stirred solution of step-d product (2.5 g, 12 mmol) in dry MeOH (25 ml, 10 times), TMS Chloride (1.39 g (1.64 ml), 12 mmol, 1 eq) was added dropwise and the reaction mixture was allowed to stir for 2 h at room temperature. Progress of the reaction was monitored by TLC (50% ethyl acetate-hexane, $R_f$~0.4). On completion of the reaction, MeOH was distilled off completely under reduced pressure. Residue was taken in dichloromethane (50 ml) and washed with sodium bicarbonate solution (2×50 ml). Aqueous layer was washed with ethyl acetate (50 ml) followed by hexane (50 ml). Then the aqueous layer was cooled to 0° C., acidified with to a pH-2 6N HCl solution and the solid thrown out was filtered. Solid obtained was dissolved in ethyl acetate (100 ml), dried over sodium sulfate and concentrated under reduced pressure to yield the required product as an off white solid (1.54 g, 61%).

Step f-g: To a stirred solution of step-e product (2.3 g, 10 mmol) in dichloromethane (23 ml), oxalyl chloride (2.08 g (1.44 ml), 16 mmol, 1.5 eq) followed by catalytic amount of dimethylformamide were added at room temperature. Reaction contents were stirred for 20 minutes at room temperature. Progress of the reaction was monitored by TLC (5% ethyl acetate-hexane, $R_f$~0.7). As the reaction not moved completely, reaction contents were heated to 40° C. and stirred for 1 hr at the same temperature. Again TLC was checked and confirmed that the starting material was disappeared. Dichloromethane was distilled off completely under reduced pressure. In another round-bottom flask, TEA (triethylamine) (3.2 g (2.5 ml), 25 mmol, 2.5 eq) was added to a solution of aniline (0.83 g, 9 mmol) in dichloromethane (10 ml) and stirred the contents for 15 minutes at 0° C. Then the above prepared acid chloride was taken in dichloromethane (13 ml) and added dropwise at 0° C. and the overall reaction mixture was allowed to stir for 1 hr at 0° C. Progress of the reaction was monitored by TLC (5% ethyl acetate-hexane, $R_f$~0.3). On completion of the reaction, water (10 ml) was added and the layers formed were separated out. Organic layer was dried over sodium sulfate and concentrated under reduced pressure to yield the required product as an off white solid (3 g, 96%).

Step h: To a solution of step-g product (3 g, 10 mmol) in THF (30 ml, 10 times), water (30 ml, 10 times) was added and the reaction contents were stirred for 15 minutes at room temperature. Then LiOH (0.5 g, 21 mmol, 2 eq) was added and the overall reaction mixture was allowed to stir for 5 h at room temperature. Progress of the reaction was monitored by TLC (5% ethyl acetate-hexane, $R_f$~0.1). On completion of the reaction, THF was distilled off completely under reduced pressure. Aqueous layer was washed with ethyl acetate (50 ml) followed by hexane (50 ml). Then the aqueous layer was cooled to 0° C., acidified to a pH-2 with 6N HCl solution and the solid thrown out was filtered. Solid obtained was dissolved in ethyl acetate (100 ml), dried over sodium sulfate and concentrated under reduced pressure to yield the required product as an off white solid (2.15 g, 75%).

6.10 General scheme for the synthesis of 2-(4-sulphonamidophenyl)propanoic acids
Scheme 2:
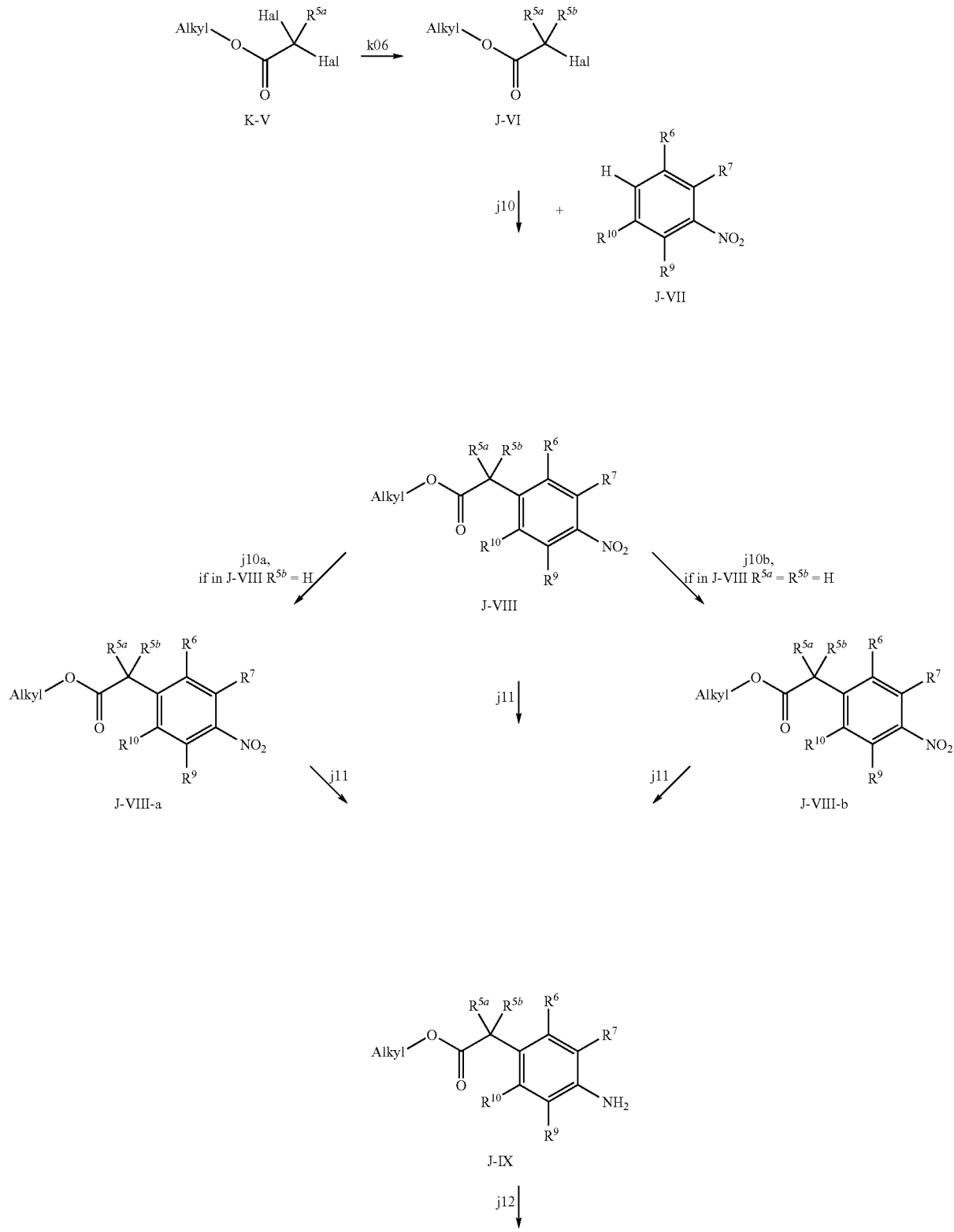

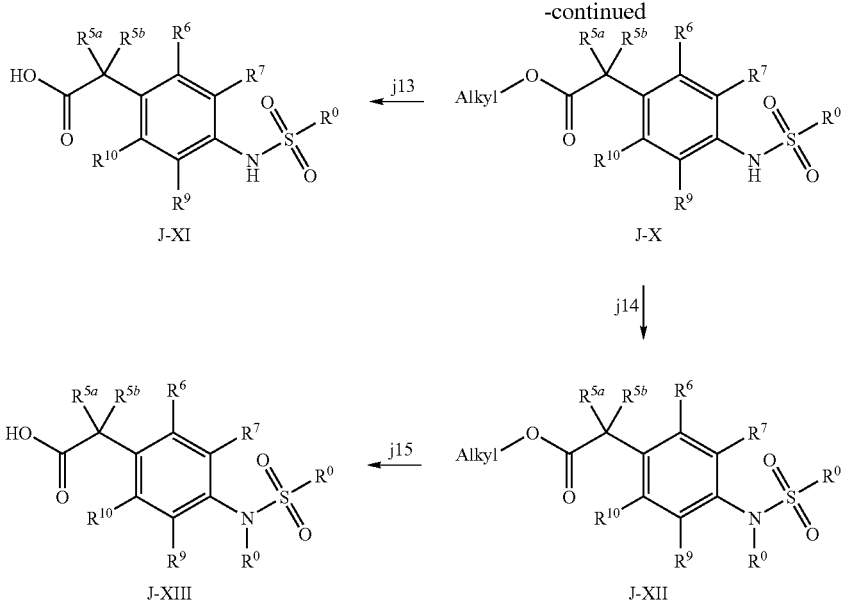

Hal = Halogen

In step j10 the nitro-substituted phenyl J-VII can be reacted to form the compound J-VIII by means of methods known to the person skilled in the art, for example in a substitution reaction using a singly halogenated, preferably singly chlorinated or brominated ester J-VI, if appropriate in the presence of a base.

If appropriate, the singly halogenated, preferably singly chlorinated ester J-VI, for which $R^{5b} \neq H$, can be prepared in a preceding step k06 from a dihalogen carboxylic acid ester K-V, wherein halogen is preferably Br or Cl, by means of methods known to the person skilled in the art, in order in this way to introduce the residue $R^{5b}$ ($R^{5b} \neq H$) into J-VI.

If, in step j10, use is made of compounds J-VI for which $R^{5a}$ and $R^{5b}$ are each H or for which the substituent is $R^{5b}$=H, then functional groups in the positions $R^{5a}$ and $R^{5b}$ or the position $R^{5b}$ can each be introduced in the synthesis sequence at a later point in time, for example after step j10 and before step j11. In this case, compounds J-VIII, in which $R^{5b}$=H, or compounds J-VIII, in which $R^{5a}$ and $R^{5b}$ each =H, are reacted in a further step j10a and j10b respectively, which are each carried out between the steps j10 and j11, to form compounds J-VIII-a, in which $R^{5b} \neq H$, or compounds J-VIII-b, in which $R^{5a}$ and $R^{5b}$ each $\neq H$. The compounds J-VIII-a and J-VIII-b can subsequently be reacted further in step j11.

In step j11 the nitro function of the compound J-VIII (or J-VIII-a or J-VIII-b) can be converted into an aniline derivative J-IX by means of methods known to the person skilled in the art, such as for example by hydrogenation with hydrogen or by reduction by acidic metal salt solutions.

In step j12 the aniline compound J-IX can be reacted to form the compound J-X by means of methods known to the person skilled in the art, for example using a halogenated, preferably chlorinated sulphonyl compound of formula $R^0$—S(=O)$_2$-Hal, preferably $R^0$—S(=O)$_2$—Cl, if appropriate in the presence of a base.

J-X can be reacted to form the compound J-XI immediately in step j13 using an ester cleavage known to the person skilled in the art, for example using a base or an acid. However, alternatively, the sulphonyl amino function of J-X can in step j14 first be N-substituted to form the compound J-XII by means of methods known to the person skilled in the art, for example using a halide $R^0$—Hal, preferably an iodide $R^0$—I, and the aforementioned ester cleavage to form J-XIII can then subsequently be carried out in step j15.

The methods with which the person skilled in the art is familiar for carrying out the reaction steps j10 to j15 and also k06 may be inferred from the standard works on Organic Chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007); team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

6.10.1 Synthesis of 2-(3-fluoro-4-(sulphonamido)phenyl)propanoic acids

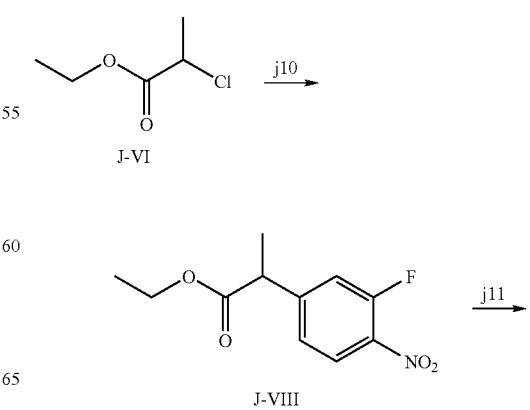

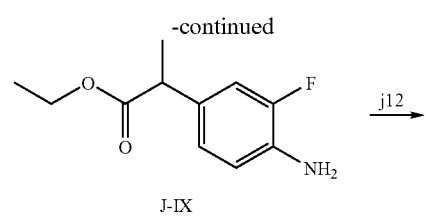

J-IX

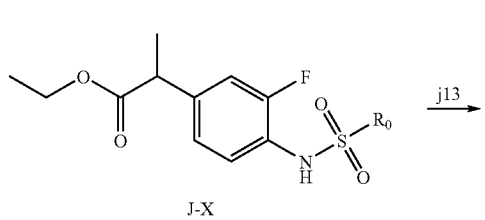

J-X

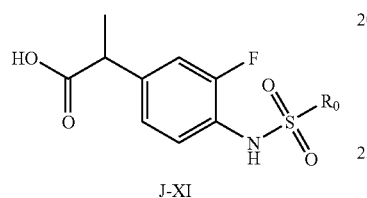

J-XI

Step j10: Under a nitrogen atmosphere, 3 equivalents of potassium tert.butyloxide are slurried in DMF and cooled to −40° C. A mixture of o-fluoronitrobenzene (J-VII) (1 equivalent) and ethyl-2-chloropropionate (J-VI) (1.2 equivalent) is then added while maintaining this temperature and the mixture is stirred for 10 minutes. The reaction mixture is diluted with acetic acid and with water at −40° C. The aqueous phase is then repeatedly extracted with 20% EE in hexane, the combined organic phases are washed with water and sat. aq. NaCl sol. and dried over magnesium sulphate. The concentrated organic phase is purified by column chromatography ($SiO_2$, 10% EE/hexane), as a result of which the product J-VIII is obtained.

Step j11: A suspension of J-VIII (1 equivalent) and palladium on activated carbon (10% Pd) in EtOH is hydrogenated for 1 h under a hydrogen atmosphere. The suspension is removed by filtration, concentrated under vacuum and purified by column chromatography ($SiO_2$, EE/hexane) and J-IX is in this way obtained.

Step j12: J-IX (1 equivalent) is placed in dichloromethane and pyridine and cooled to 0° C. Compounds of general formula Cl—S(=O)$_2$—R$^0$ (1.5 equivalents) are added dropwise at 0° C. and the reaction mixture is stirred for 2 h at room temperature. After recooling of the mixture to 0° C., the mixture is acidified to pH 3 using 4 N aq. HCl. The organic phase is repeatedly extracted with dichloromethane. The combined organic phases are washed with water and sat. aq. NaCl sol., dried over magnesium sulphate and concentrated to dryness. The purification ($SiO_2$, EE/hexane) by column chromatography produces the desired product J-X.

Step j13: 1 equivalent of J-X is dissolved in a 2:1 mix of THF/water and stirred for 15 minutes. 3 equivalents of LiOH, which is also dissolved in a 2:1 THF/water mix, are added to this solution and the suspension is stirred for 2 h at 45° C. While cooling, the aqueous phase is set to pH 1 using 4 N aq. HCl and repeatedly extracted with dichloromethane. The combined organic phases are dried over magnesium sulphate and concentrated under reduced pressure and the product J-XI is in this way obtained.

6.10.2 Synthesis of 2-(3,5-difluoro-4-(methylsulphonamido)phenyl)propanoic acid

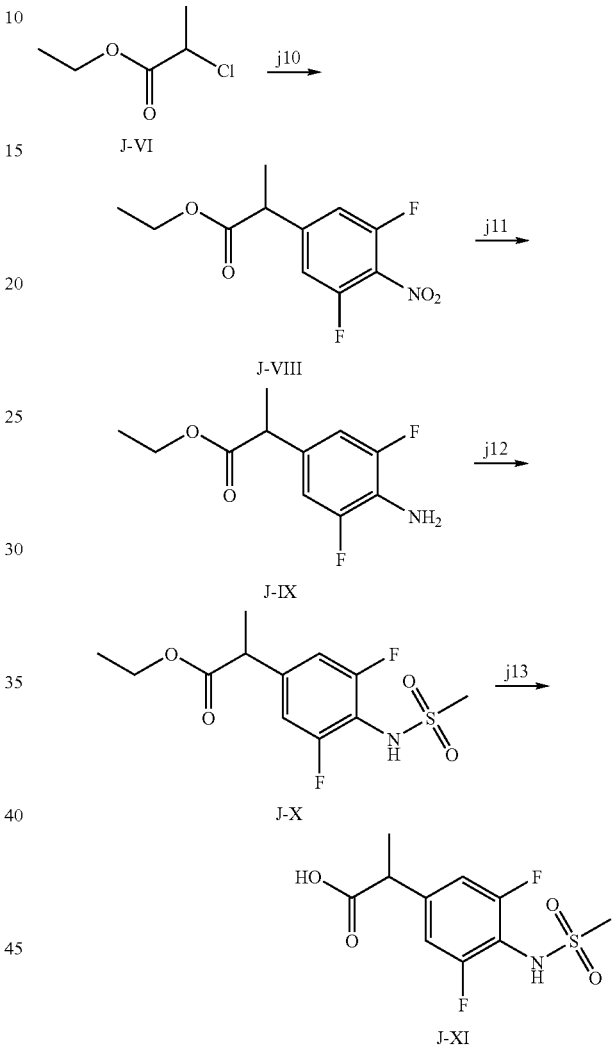

Step j10: KOtBu (31.85 mmol, 3.57 g) was dissolved in DMF (30 ml) and cooled to −45° C. A mix of ethyl-2-chloropropionate (15.9 mmol, 2 ml) and 1,3-difluoro-2-nitrobenzene (15.7 mmol, 2.5 g) was slowly added dropwise to the solution, which was kept at −40° C., and after addition the mixture was stirred for a further 1 h. For working up, the reaction mix was set to pH 4 using 16% HCl and diluted with water (150 ml). The mix was extracted with EE (3×50 ml), the combined organic phases were washed with water (50 ml) and sat. NaCl solution (2×50 ml) and dried over magnesium sulphate. After removal of the solvent under vacuum, the product was obtained as an oil (4.12 g, 99% yield).

Step j11: The difluoronitrophenylpropanoate (10 mmol, 2.59 g) was dissolved in EtOH/EE (200 ml, 1:1) and hydrogenated in an H-cube (1 bar, 25° C., 1 ml/min, 0.25 mol/L). After removal of the solvent under vacuum, the difluoroaminopropionate could be obtained as an oil (2.27 g, 99% yield).

Step j12: The difluoroaminophenylpropanoate (5 mmol, 1.15 g) was dissolved in pyridine (4 ml), cooled to 0° C. under a protective gas atmosphere and mixed dropwise with methanesulphonyl chloride (7.5 mmol, 582 µL). After stirring for one hour at 0° C., the reaction mixture was mixed with water (25 ml) while being cooled with ice, set to pH 1 using 16% HCl and extracted with dichloromethane (2×50 ml). The organic phases were combined, dried over magnesium sulphate and the solvent was removed under vacuum. The purification (SiO₂, cyclohexane/EE 2:1) of the residue by column chromatography produced 0.458 g of product (28% yield).

Step j13: The product of the mesylation (1.46 mmol, 0.45 g) was dissolved in THF/water (5 ml, 2:1), LiOH (4.39 mmol, 0.105 g) was added and the mixture was refluxed for 12 h. Water (25 ml) and diethyl ether (25 ml) were added to the reaction mix. After phase separation, the aqueous phase was acidified to pH 2 using HCl and extracted with dichloromethane (3×25 ml). The combined organic phases were dried over magnesium sulphate and the solvent was removed under vacuum. The product was obtained as a white solid (0.402 g, 98% yield).

6.10.3 Synthesis of 2-(3-fluoro-4(methysulphonylamino)phenyl)propanoic acid

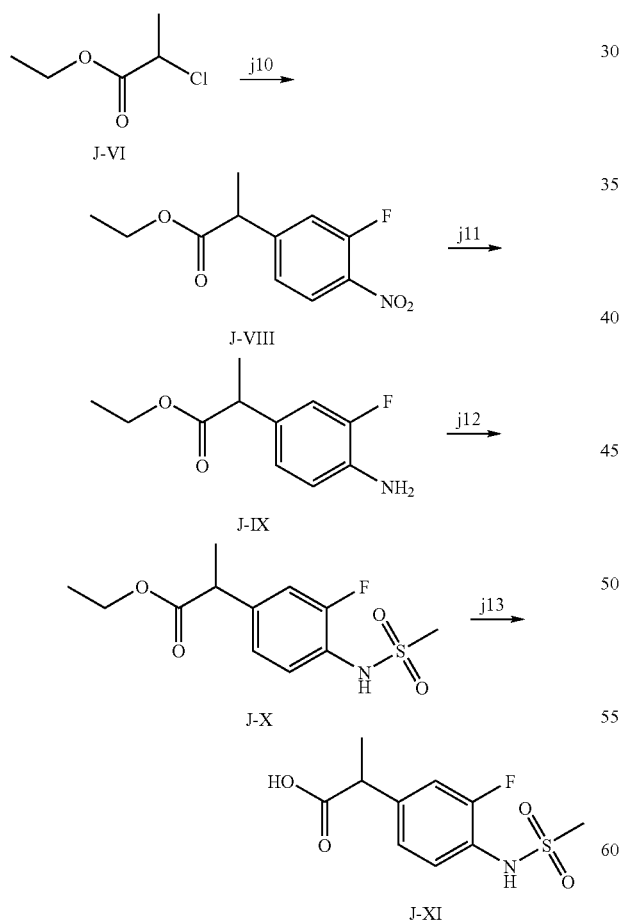

Step j10: Potassium tert.butyloxide (1,000 g, 8.93 mol) was placed under a nitrogen atmosphere and the slurry obtained after addition von 4 l of DMF was cooled to −40° C. A mixture of o-fluoronitrobenzene (420 g, 2.97 mol) and ethyl-2-chloropropionate (488 g, 3.57 mol) was added while maintaining this temperature and stirred for 10 minutes. The reaction mixture was quenched with HOAc at −40° C. and diluted with 30 l of water. The liquid phase was repeatedly extracted with 20% EE in hexane (3×15 l), the combined organic phases were washed with water (4×10 l) and sat. aq. NaCl (10 l) and dried over MgSO₄. The concentrated organic phase was purified by column chromatography (silica gel. 100-200 mesh, eluent: 10% EE in hexane) and produced 483 g of the nitro-ester (67.3%). $^1$H NMR (CDCl₃, 400 MHz): δ [ppm] 8.01 (t, 1H), 7.21-7.26 (m, 2H), 4.06-4.19 (m, 2H), 3.76 (q, 1H), 1.50 (d, 3H), 1.22 (t, 3H). HPLC: 97%.

Step j11: The nitroester (250 g, 0.248 mol) and MeOH (1.1 l), followed by palladium on activated carbon (10 g, 10% Pd), were introduced in a 2 l Parr hydrogenator under a nitrogen atmosphere, flushed with nitrogen and hydrogenated at 45 psi for 3 h at room temperature. The reaction mix was removed by filtration and washed with 1 l of MeOH. The brown liquid obtained after concentration of the organic phase was purified by column chromatography (silica gel: 100-200 mesh, eluent: 10% EE in hexane). 118.8 g of the amino ester (54.24%) were obtained. $^1$H NMR (DMSO-d₆, 400 MHz): δ [ppm] 6.88 (dd, 1H), 6.78 (dd, 1H), 6.69 (t, 1H), 3.96-4.06 (m, 2H), 3.55-3.60 (q, 1H), 1.29 (d, 3H), 1.15 (t, 3H). Qualitative HPLC: 99%.

Step j12: The amino ester (110 g, 0.52 mol) was placed in 900 ml of dichloromethane and pyridine (63 ml, 0.78 mol) and cooled to 0° C. Methanesulphonyl chloride (44.4 ml, 0.57 mol) was added dropwise at 0° C. and the reaction mixture was stirred for 2 h at room temperature. After recooling of the mixture to 0° C., the mixture was acidified to pH 3 using 4 N HCl. The organic phase was repeatedly extracted with dichloromethane (3×600 ml). The combined organic phases were washed with water (2×1 l) and sat. aq. NaCl sol. (1×1 l), dried over MgSO₄ and concentrated to dryness. The purification by column chromatography (silica gel: 100-200 mesh, eluent; 15% EE in hexane) produced 85.8 g of product (56.9%). $^1$H NMR (DMSO-d₆, 400 MHz): δ [ppm] 7.33 (t, 1H), 7.21 (d, 1H), 7.10 (dd, 1H), 4.01-4.10 (m, 2H), 3.80 (q, 1H), 3.01 (s, 3H), 1.37 (d, 3H), 1.13 (t, 3H). Qualitative HPLC: 99%.

Step j13 is carried out as described under 6.10.2.

6.10.4 Synthesis of N-methyl-2-(3-fluoro-(4-methysulphonylamino)phenyl)propanoic acid

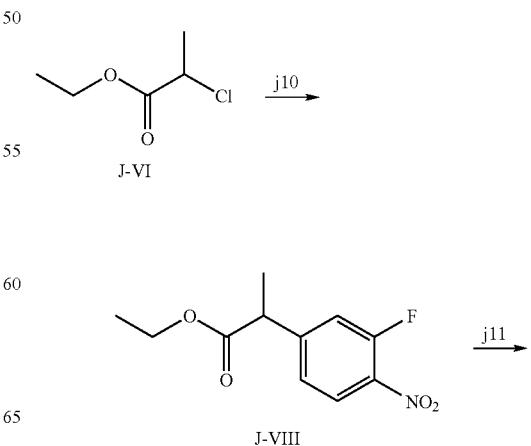

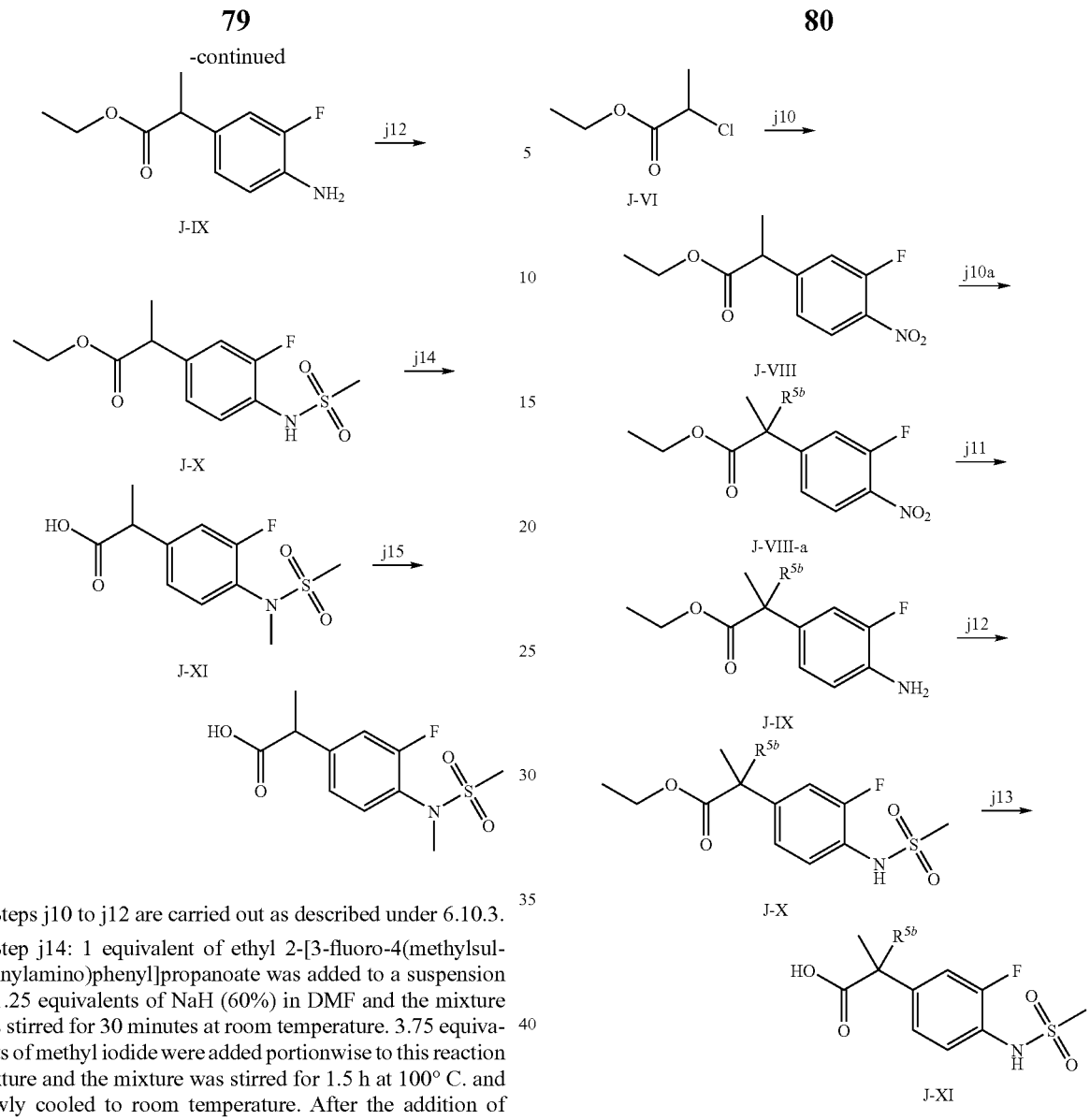

Steps j10 to j12 are carried out as described under 6.10.3.

Step j14: 1 equivalent of ethyl 2-[3-fluoro-4(methylsulphonylamino)phenyl]propanoate was added to a suspension of 1.25 equivalents of NaH (60%) in DMF and the mixture was stirred for 30 minutes at room temperature. 3.75 equivalents of methyl iodide were added portionwise to this reaction mixture and the mixture was stirred for 1.5 h at 100° C. and slowly cooled to room temperature. After the addition of water, the reaction mix was extracted twice with EE, the combined organic phases were repeatedly washed with sat. aq. NaCl sol., dried over MgSO$_4$ and concentrated. The crude product J-XI was further processed immediately in step j15.

Step j15: 1 equivalent of J-XI was dissolved in a 2:1 THF/water mix and stirred for 15 minutes. 3 equivalents of LiOH, which is also dissolved in a 2:1 THF/water mix, are added to this solution and the mixture is stirred for 2 h at 45° C. While cooling, the aqueous phase is set to pH 1 using 4 N HCl and repeatedly extracted with dichloromethane. The combined organic phases are dried over MgSO$_4$ and concentrated under reduced pressure.

6.11 Synthesis of further 2-(3-fluoro-(4-methylsulphonylamido)phenyl)-propanoic and acetic acids

6.11.1 Acids Wherein $R^{5b}$=$C_{1-10}$ Alkyl (Preferably $CH_3$, $CH_2$—$CH_3$, $CH_2$—$CH_2$—$CH_3$)

The substituent $R^{5b}$ is introduced in a reaction step j10a intervening between j10 and j11 as in scheme 2.

Steps j10 and also j11 to j13 are carried out as described above.

Step j10a: 0.75 equivalents of alkyl iodide ($R^{5b}$—I) are slowly added dropwise to a solution of J-VIII (1 equivalent) and NaH (0.6 equivalents) in DMF at 0° C. and the reaction batch is stirred for approx. 10 minutes. Afterwards the reaction mixture is quenched with 1 N HCl sol., diluted with water and repeatedly extracted with diethyl ether. The combined organic phases are washed with water and sat. aq. NaCl sol., dried over MgSO$_4$ and concentrated under vacuum. A further purification of the crude product can be carried out by column chromatography (silica gel: 100-200 mesh, eluent: 10-20% EE in hexane), as a result of which the product J-VIII-a is obtained.

6.11.2 Acids in which $R^{5a}$ and $R^{5b}$ Form Together with the Carbon Atom Connecting them a $C_{3-10}$ Cycloalkyl The substituents $R^{5a}$ and $R^{5b}$ are introduced in a reaction step j10b intervening between j10 and j11 as in scheme 2.

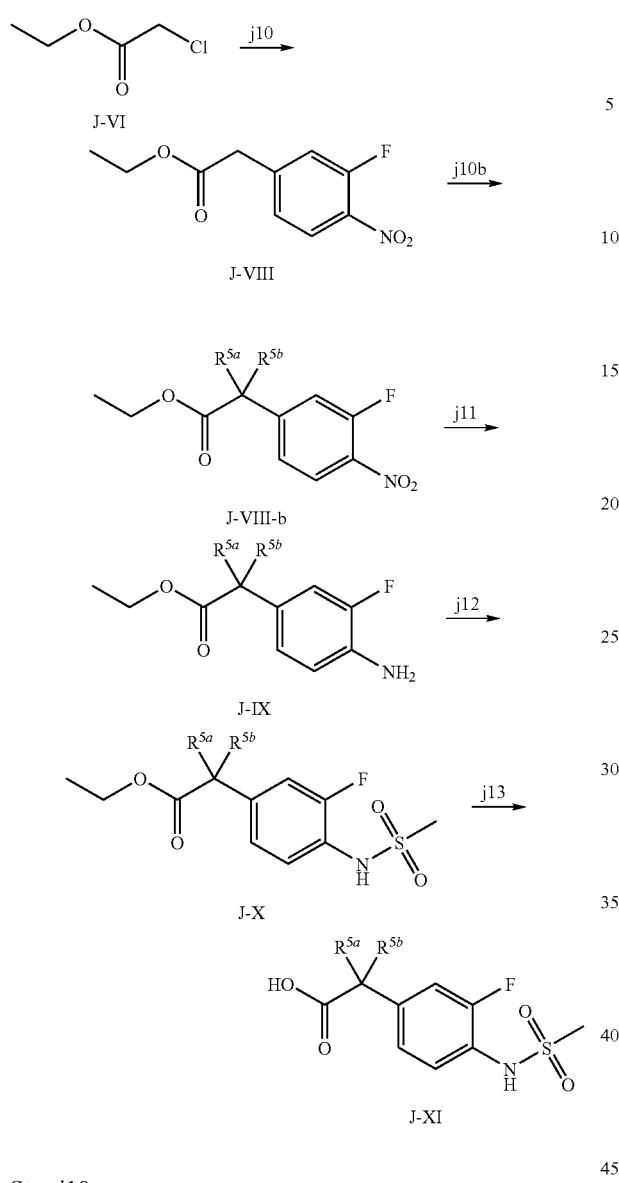

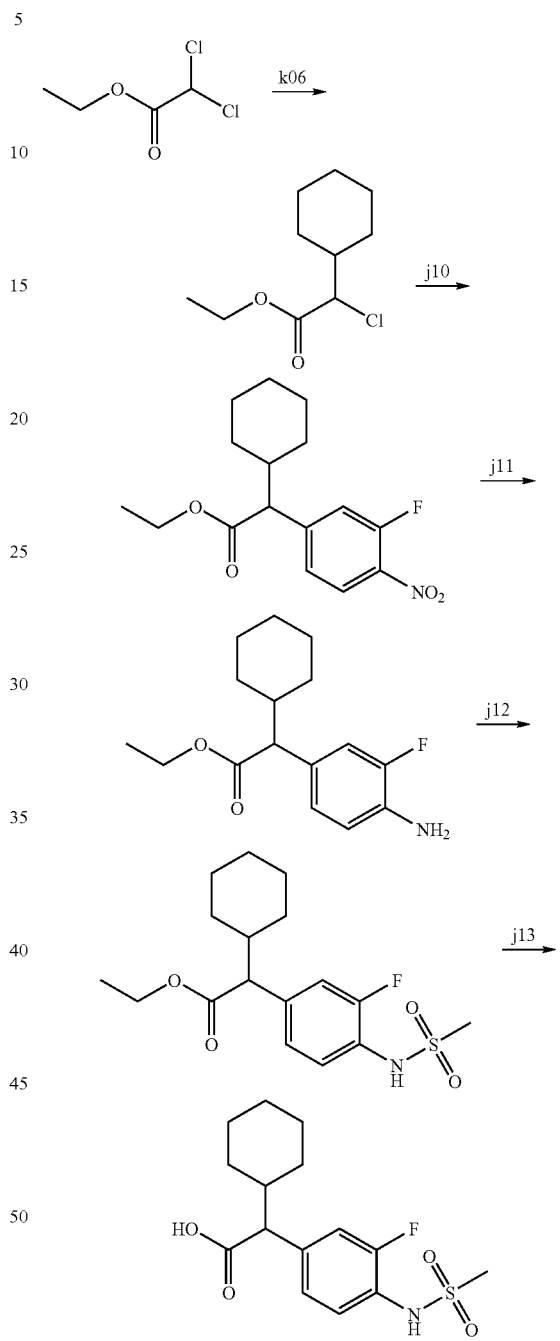

6.11.3 Synthesis of 2-cyclohexyl-2-(3-fluoro-4-(methylsulphonamido)phenyl)acetic acid Step j10:

At 0° C. a mixture of 3-fluorophenyl acetate (1 equivalent) and sulphuric acid (0.261 equivalents) is added dropwise to a solution of nitric acid (1 equivalent) and the mixture is stirred for 2 h. The reaction mix is diluted with iced water and repeatedly extracted with EE. The combined organic phases are washed with water, concentrated under vacuum and purified by column chromatography (eluent: EE/hexane) and J-VIII is in this way obtained.

Step j10b:

NaH (10 equivalents) is slowly added to the J-VIII (1 equivalent) dissolved in dry THF, the mixture is stirred for 10 minutes and the corresponding 1,1-dihalogenalkyl compound, preferably a dibromoalkyl compound (5 equivalents), is then added. Within 30 minutes the mixture is heated to room temperature heated and quenched with sat. aq. NH$_4$Cl sol. After aqueous working up, the crude product obtained is purified by flash chromatography (eluent: EE/hexane) and J-VIII-b is in this way obtained.

Steps j11 to j13 are carried out as described hereinbefore.

Step k06: Ethyl 2-chloro-2-cyclohexyl acetate 170 ml of dry THF were mixed with 100 ml of 1 M BH$_3$-THF complex (100 mmol) at room temperature under a nitrogen atmosphere. Within 5 minutes 12.3 ml of cis-1,5-cyclooctadiene (100 mmol) were added dropwise to this mix, wherein the temperature rose to 45° C. The reaction mix was boiled to reflux for 1.5 h, recooled to 45° C., mixed with 10.1 ml of cyclohexene (100 mmol) and stirred for a further 2 h at 45° C.

After cooling of the reaction batch in an ice bath, 12.2 ml of ethyl dichloroacetate (100 mmol) were added in 50 ml of tert.butanol, the mixture was stirred for 15 minutes and within a further 15 minutes 1 M potassium tert.butylate (100 mmol, 100 ml) was added dropwise. The reaction mix was stirred for a further 15 minutes, mixed with 33 ml of 3 M sodium acetate sol. (100 mmol) and 22.5 ml of 30% $H_2O_2$ (750 mmol) were carefully added dropwise. The mix was stirred for 30 minutes at room temperature and subsequently salted out with NaCl; the organic phase was dried over $MgSO_4$ and the solvent was removed under reduced pressure. After washing of the solid residue with tert. BME, cyclohexane tert. BME (9:1), tert. BME and EE, 7.6 g (37.4%) of product could be obtained.

Step j10: Ethyl 2-cyclohexyl-2-(3-fluoro-4-nitrophenyl)acetate 8.2 g of potassium tert.butylate were dissolved in 70 ml of DMF and cooled to −45° C. For this purpose, a mix of ethyl 2-chloro-2-cyclohexylacetate (36.6 mmol, 7.5 g) and 1-fluoro-2-nitrobenzene (36.6 mmol, 3.9 ml) was carefully added dropwise and stirred for a further 20 minutes. The reaction mix was set to pH 4 using 16% HCl, diluted with 25 ml of water and extracted with EE (3×50 ml). Once combined, the organic phases were washed with water and sat. aq. NaCl sol., dried over $MgSO_4$ and concentrated under vacuum. The residue obtained was purified by column chromatography (silica gel: mesh 100-200, eluent: 10% EE in cyclohexane) and produced 5.5 g (49%) of product.

Step j11: Ethyl 2-(4-amino-3-fluorophenyl)-2-cyclohexylacetate

The ethyl 2-cyclohexyl-2-(3-fluoro-4-nitrophenyl)acetate was dissolved in a 1:1 mix of EtOH and EE (420 ml) and hydrogenated in an H-cube (1 bar, 25° C., 1 ml/min and 0.25 mol/L). After removal of the solvent and drying, 5 g (quantitative turnover) of product could be obtained.

Step j12: Ethyl 2-cyclohexyl-2-(3-fluoro-4-(methylsulphonamido)phenyl)acetate The amine compound (5 g, 17.9 mmol) was dissolved in 15 ml of pyridine, cooled to 0° C. under a nitrogen atmosphere and mixed with 2 ml of methanesulphonyl chloride (26.8 mmol) and stirred for a further 1 h at 0° C. The reaction mix was mixed with 15 ml of water while being cooled with ice and set to pH 1 using 16% HCl. After extraction of the mix with dichloromethane (3×50 ml), the organic phases were combined, dried over $MgSO_4$ and concentrated under vacuum. The crude product was purified by column chromatography (silica gel: 100-200 mesh, eluent: 50% EE in cyclohexane), producing 5.4 g (85.4%) of product.

Step j13: 2-cyclohexyl-2-(3-fluoro-4-(methylsulphonamido)phenyl)acetic acid

The phenylacetate (15.2 mmol, 5.4 g) was dissolved in a mix of 30 ml of THF and 15 ml of water, mixed with 1.09 g of LiOH (45.7 mmol) and boiled to reflux for 6 h and stirred for a further 12 h at room temperature. 15 ml of water were added to the reaction mix and the phases were separated. The aqueous phase was acidified using HCl and repeatedly extracted with dichloromethane (3×50 ml). The combined organic phases were dried over $MgSO_4$, concentrated and the residue obtained was purified by means of column chromatography (silica gel: 100-200 mesh, eluent: 50% EE in cyclohexane). Yield 1.05 g (21%).

6.11.4 Synthesis of 2-(3-fluoro-4-(methylsulphonamido)phenyl)-2-phenylacetic acid:

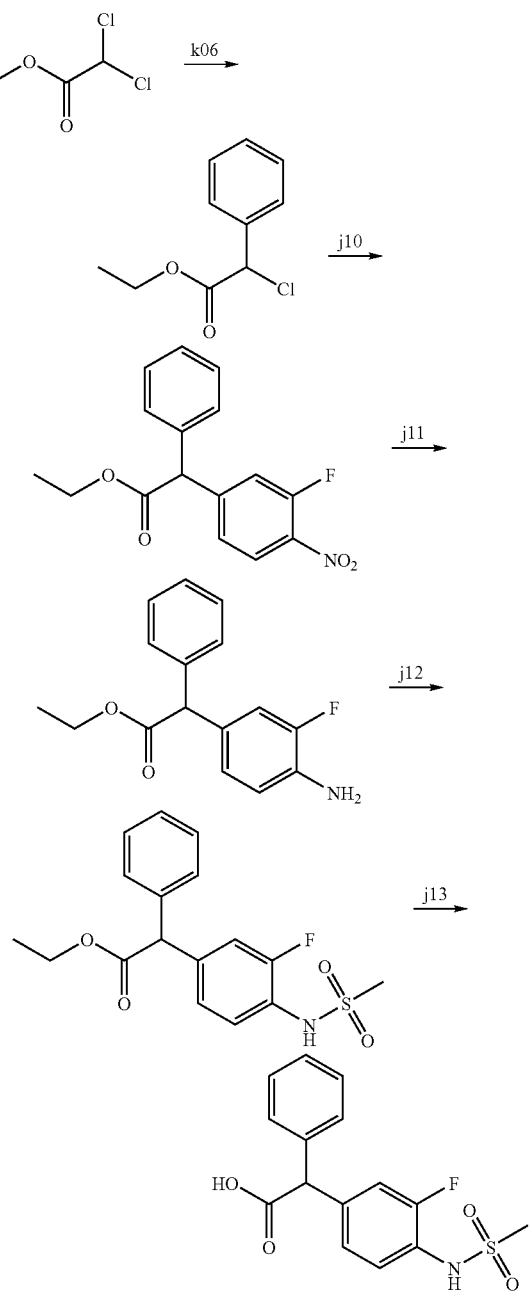

Step k06: Ethyl 2-chloro-2-phenylacetate

Chlorophenyl acetyl chloride (53 mmol, 7.6 ml) was added dropwise to a solution of triethylamine (63.5 mmol, 8.7 ml) in methanol at 0° C. and the mixture was subsequently stirred for 3.5 h at room temperature. The reaction mix was then placed in 100 ml of water and repeatedly extracted with EE (3×100 ml). Once combined, the organic phases were dried over MgSO4, concentrated under vacuum and 8.76 g (83.4%) of product was obtained.

Step j10: Ethyl 2-(3-fluoro-4-nitrophenyl)-2-phenylacetate 9.8 g of potassium tert.butylate were dissolved in 90 ml of DMF and cooled to −45° C. For this purpose, a mix of ethyl 2-chloro-2-phenylacetate (43.8 mmol, 8.7 g) and 1-fluoro-2-nitrobenzene (43.8 mmol, 4.6 ml) was carefully added dropwise and the mixture was stirred for a further 20 minutes. The reaction mix was set to pH 4 using 16% HCl, diluted with 25 ml of water and extracted with EE (3×50 ml). Once combined, the organic phases were washed with water and sat. aq. NaCl sol., dried over $MgSO_4$ and concentrated under vacuum. The residue obtained was purified by column chromatography (silica gel: mesh 100-200, eluent: 10% EE in cyclohexane) and produced 5.9 g (44.9%) of product.

Step j11: Ethyl 2-(4-amino-3-fluorophenyl)-2-phenylacetate

The ethyl 2-phenyl-2-(3-fluoro-4-nitrophenyl)acetate was dissolved in a 1:1 mix of EtOH and EE (465 ml) and hydrogenated in an H-cube (1 bar, 25° C., 1 ml/min and 0.25 mol/L). After removal of the solvent and drying, 5.2 g (97.5%) of product could be obtained.

Step j12: Ethyl 2-phenyl-2-(3-fluoro-4-(methylsulphonamido)phenyl)acetate

The amine compound (5.2 g, 19 mmol) was dissolved in 15 ml of pyridine, cooled to 0° C. under a nitrogen atmosphere and mixed with 2.2 ml of methanesulphonyl chloride (28.5 mmol) and stirred for a further 1 h at 0° C. The reaction mix was mixed with 15 ml of water while being cooled with ice and set to pH 1 using 16% HCl. After extraction of the mix with dichloromethane (3×50 ml), the organic phases were combined, dried over $MgSO_4$ and concentrated under vacuum. The crude product was purified by column chromatography (silica gel: 100-200 mesh, eluent: 50% EE in cyclohexane), producing 5.8 g (87%) of product.

Step j13: 2-phenyl-2-(3-fluoro-4-(methylsulphonamido)phenyl)acetic acid

The phenylacetate (16.5 mmol, 5.8 g) was dissolved in a mix of 32 ml of THF and 16 ml of water, mixed with 1.18 g of LiOH (49.5 mmol) and boiled to reflux for 15 h. 15 ml of water were added to the reaction mix and the phases were separated. The aqueous phase was acidified using HCl and repeatedly extracted with dichloromethane (3×50 ml). The combined organic phases were dried over $MgSO_4$, concentrated and the residue obtained was purified by means of column chromatography (silica gel: 100-200 mesh, eluent: 50% EE in cyclohexane). Yield 3.3 g (61.3%).

6.11.5 Synthesis of 2-(3-fluoro-4-(methylsulfonamido)phenyl)-2-(3-fluorophenyl)acetic acid (employed for the synthesis of example compound no. 66):

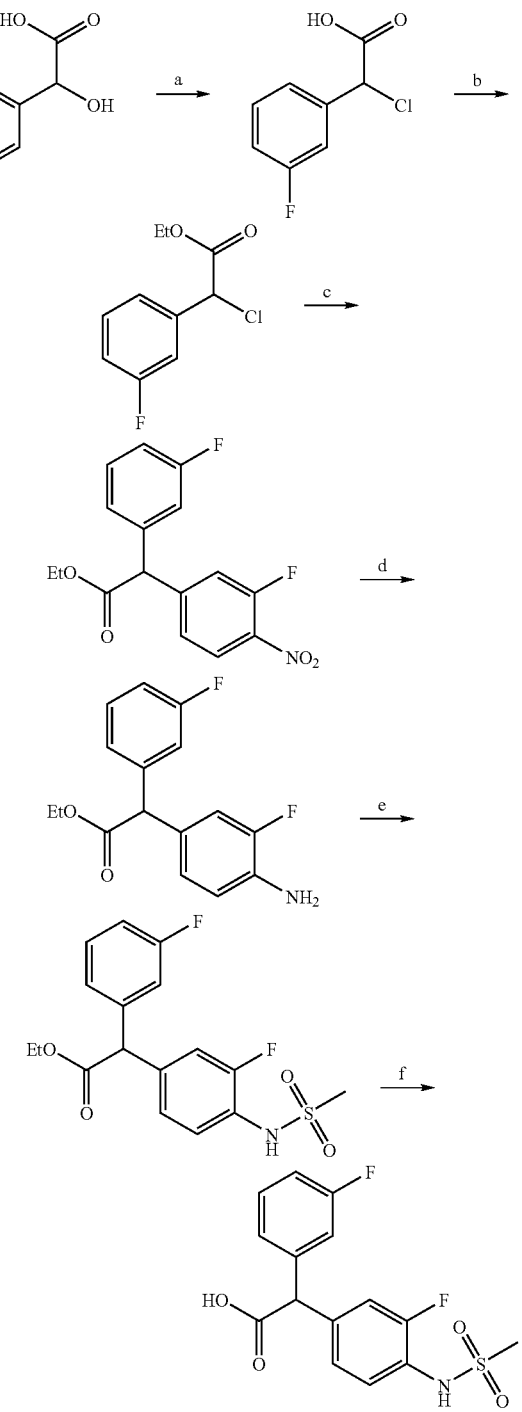

Step a: 2-(3-fluorophenyl)-2-hydroxyacetic acid (12 g, 70.5 mmol), was dissolved in THF (120 mL). Thionyl chloride (10 g, 84.6 mmol) was added to it. Catalytic amount of dimethylformamide (1 mL) was added to the reaction mixture. The reaction mixture was stirred at ambient temperature for overnight. The organic solvent was removed under reduced pressure; the residue was diluted with water (200 mL) and extracted with dichloromethane (2×200 mL). The combined organic layer was dried over anhydrous magnesium sulfate and concentrated under reduced pressure to afford 12 g crude compound.

Step b: The crude step-a product (12 g) was dissolved in benzene (240 mL). EtOH (120 mL) and sulphuric acid (2 mL) was added to it. The reaction mixture was refluxed for 4 h using Dean stark apparatus. TLC (5% ethyl acetate-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound (8.2 g, 59.5%).

Step c: To a stirred suspension of potassium tertiary butoxide (8.5 g, 75.75 mmol) in dimethylformamide (50 mL), a mixture of step-b product (8.2 g, 38 mmol) and 1-fluoro-2-nitrobenzene (5.34 g, 38 mmol) in dimethylformamide (30 mL) was added at −30° C. The reaction mixture was stirred for 30 minutes at the same temperature. TLC (10% ethyl acetate-Hexane, $R_f$=0.6) showed complete consumption of starting material. Reaction mixture was diluted with water (800 mL) and extracted with 20% ethyl acetate in hexane (3×200 mL). Then the organic layer was dried over anhydrous magnesium sulfate. The removal of organic solvent under reduced pressure afforded a brown liquid compound, which was purified by column chromatography (silica gel: 100-200 mesh, eluent: 2% ethyl acetate in hexane) to afford a light brown liquid compound (3.2 g, 26%)

Step d: In a 250 mL round-bottom flask step-c product (3.2 g, 10 mmol) was dissolved in ethyl acetate (50 mL). Palladium on charcoal (150 mg, 10% Pd) was added under nitrogen atmosphere. It was stirred under atmospheric hydrogen pressure for 12 h. TLC (20% ethyl acetate in hexane, $R_f$=0.3) showed complete conversion of starting material. The reaction mixture was filtered over celite bed and the bed was washed with ethyl acetate (3×50 mL). The organic layer was concentrated to afford a yellow residue, which was purified through column chromatography (silica gel: 100-200 mesh, eluent: 10% ethyl acetate in hexane) to afford the pure amine compound (2.3 g, 79%).

Step e: Step-d product (2.3 g, 7.8 mmol) was dissolved in dichloromethane (35 mL). Pyridine (1.9 mL, 23.4 mmol) was added to it. Methanesulphonyl chloride (1.1 g, 9.4 mmol) was added dropwise to the reaction mixture at 0° C. and stirred for 16 h at ambient temperature. TLC (20% ethyl acetate in hexane, $R_f$=0.2) showed complete consumption of starting material. The reaction mixture was diluted with dichloromethane (100 mL) and washed with water (3×50 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound (2.8 g, 96%). $^1$H NMR (CDCl$_3$, 400 MHz): δ 7.55 (t, 1H), 7.30-7.35 (q, 1H), 6.98-7.18 (m, 5H), 6.50 (s, 1H), 4.21-4.27 (q, 2H), 3.04 (s, 3H), 1.28 (t, 3H).

Step f: Step-e product (2.8 g, 7.5 mmol), was dissolved in THF (30 mL). Aqueous LiOH solution (1M, 23 mL, 23 mmol) was added dropwise at 0° C. to it. The reaction mixture was then stirred at ambient temperature for 16 h. TLC (30% ethyl acetate-Hexane, $R_f$=0.05) showed complete consumption of starting material. The solvent was removed under reduced pressure and residue was diluted with water (70 mL). The aqueous layer was washed with ethyl acetate (70 mL) and aqueous part was acidified with 2N HCl up to pH=3-4. The acidified aqueous part was then extracted with ethyl acetate (3×150 mL). The combine organic part was dried over anhydrous magnesium sulfate and concentrated under reduced pressure to afford a white solid compound. (1.8 g, 70%). $^1$H NMR (DMSO-d$_6$, 400 MHz): δ 12.99 (bs, 1H), 9.58 (s, 1H), 7.08-7.41 (m, 7H), 5.16 (s, 1H), 3.01 (s, 3H); Mass (M+1): 342.

6.11.6 Synthesis of 2-(3-fluoro-4-(methylsulfonamido)phenyl)-2-p-tolylacetic acid (employed for the synthesis of example compound no. 68):

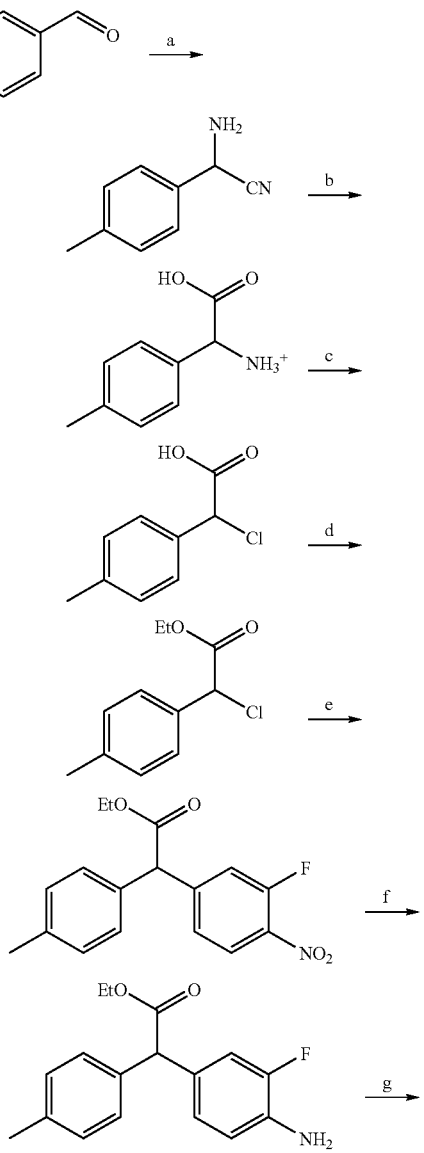

-continued

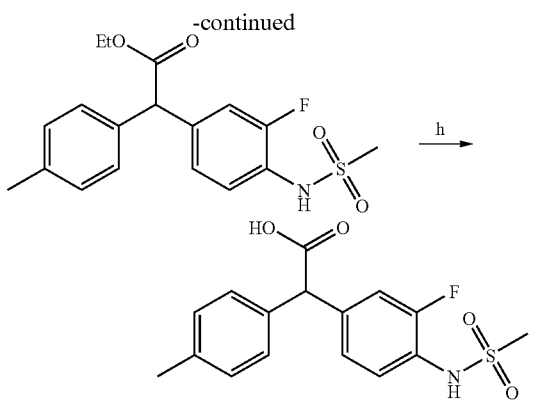

Step a: Sodium cyanide (7.3 g, 149.8 mmol) was dissolved in water (30 mL) and ammonium chloride (13.3 g, 249.6 mmol) was added to it. 4-Methylbenzaldehyde (15 g, 124.8 mmol) in MeOH (25 mL) was added to the reaction mixture and stirred it at ambient temperature for two days. TLC (5% ethyl acetate-Hexane, $R_f$=0.4) showed complete consumption of starting material. Water (100 mL) and benzene (100 mL) was added to the reaction mixture and stirred for 10 minutes. The separated organic layer was dried over anhydrous magnesium sulfate and concentrated under reduced pressure to afford a yellow liquid compound (17 g, crude).

Step b: The crude step-a product (17 g) was dissolved 6N HCl (136 mL) and refluxed for 20 h. HCl was removed under reduced pressure. The residue was diluted with EtOH (2×200 mL) and concentrated under reduced pressure. Finally ethyl acetate (250 mL) was added and stirred at 70° C. for 1 hour. A solid came out upon cooling and it was filtered through glass-sintered funnel to afford yellow crystalline solid compound (15 g, crude).

Step c: Step-b product (15 g, 74.4 mmol) was dissolved in HCl (300 mL) and it was cooled to −5° C. Sodium nitrite solution (9.75 g, 141.3 mmol) in water (45 mL) was added dropwise over the period of 30 minutes. After complete addition, reaction mixture was stirred at ambient temperature for 3 h. TLC (in ethyl acetate $R_f$=0.3) showed complete consumption of starting material. The aqueous part was extracted in ethyl acetate (3×250 mL). The organic layer was washed with water (2×200 mL) and finally with brine (200 mL). The washed organic layer was dried over anhydrous magnesium sulfate and concentrated under reduced pressure to afford a yellow solid (12.5 g, crude).

Step d: Step-c product (10 g, 54 mmol) was dissolved in benzene (200 mL). EtOH (100 mL) and sulphuric acid (2 mL) was added to it. The reaction mixture was refluxed for 4 h. TLC (in 5% ethyl acetate-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound (10 g, 87%).

Step e: To a stirred suspension of potassium tertiary butoxide (10.6 g, 94 mmol) in dimethylformamide (60 mL), a mixture of step-d product (10 g, 47 mmol) and 1-fluoro-2-nitrobenzene (6.6 g, 47 mmol) in dimethylformamide (40 mL) was added at −30° C. The reaction mixture was stirred for 30 minutes at the same temperature. TLC (10% ethyl acetate-Hexane, $R_f$=0.6) showed complete consumption of starting material. Reaction mixture was diluted with water (1 L) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a yellow liquid compound (10.4 g, 68%). $^1$H NMR (CDCl$_3$, 400 MHz): δ 8.12 (t, 1H), 7.55 (dd, 1H), 7.37 (dd, 1H), 7.16-7.23 (m, 4H), 5.38 (s, 1H), 4.13-4.18 (m, 2H), 2.27 (s, 3H), 1.16 (t, 3H).

Step f: In a 500 mL round-bottom flask step-e product (10.4 g, 33 mmol) was dissolved in ethyl acetate (150 mL). Palladium on charcoal (520 mg, 10% Pd) was added under nitrogen atmosphere. It was stirred under atmospheric hydrogen pressure for 12 h. TLC (20% ethyl acetate in hexane, $R_f$=0.3) showed complete conversion of starting material. The reaction mixture was filtered over celite bed and the bed was washed with ethyl acetate (3×100 mL). The organic layer was concentrated to afford a yellow residue, which was purified through column chromatography (silica gel: 100-200 mesh, eluent: 10% ethyl acetate in hexane) to afford the pure amine compound (8 g, 85%). $^1$H NMR (CDCl$_3$, 400 MHz): δ 7.10-7.15 (m, 4H), 6.89 (dd, 1H), 6.80 (dd, 1H), 6.68 (t, 1H), 5.09 (s, 1H), 4.92 (s, 1H), 4.07-4.12 (m, 2H), 2.25 (s, 3H), 1.15 (t, 3H).

Step g: Step-f product (8 g, 27.8 mmol) was dissolved in dichloromethane (120 mL). Pyridine (6.7 mL, 83.5 mmol) was added to it. Methanesulphonylchloride (3.8 g, 33.4 mmol) was added dropwise to the reaction mixture at 0° C. and stirred for 16 h at ambient temperature. TLC (20% ethyl acetate in hexane, $R_f$=0.2) showed complete conversion of starting material. The reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound (8.8 g, 78.6%). $^1$H NMR (CDCl$_3$, 400 MHz): δ 9.57 (s, 1H), 7.32 (t, 1H), 7.12-7.21 (m, 6H), 5.16 (s, 1H), 4.10-4.16 (m, 2H), 3.00 (s, 3H), 2.26 (s, 3H), 1.16 (t, 3H).

Step h: Step-g product (4 g, 10.9 mmol), was dissolved in THF (60 mL). Aqueous LiOH solution (1M, 33 mL, 33 mmol) was added dropwise at 0° C. to it. The reaction mixture was then stirred at ambient temperature for 16 h. TLC (30% ethyl acetate-Hexane, $R_f$=0.05) showed complete consumption of starting material. The solvent was removed under reduced pressure and residue was diluted with water (70 mL). The aqueous layer was washed with ethyl acetate (50 mL) and aqueous part was acidified with 2N HCl up to pH=3-4. The acidified aqueous part was then extracted with ethyl acetate (3×50 mL). The combine organic part was dried over anhydrous magnesium sulfate and concentrated under reduced pressure to afford a white solid compound (3.1 g, 84%). $^1$H NMR (CDCl₃, 400 MHz): δ 9.57 (s, 1H), 7.32 (t, 1H), 7.12-7.21 (m, 6H), 5.16 (s, 1H), 3.00 (s, 3H), 2.26 (s, 3H).

6.11.7 Synthesis of 2-(3-fluoro-4-(methylsulfonamido)phenyl)-3-phenylpropanoic acid (employed for the synthesis of example compound no. 145):

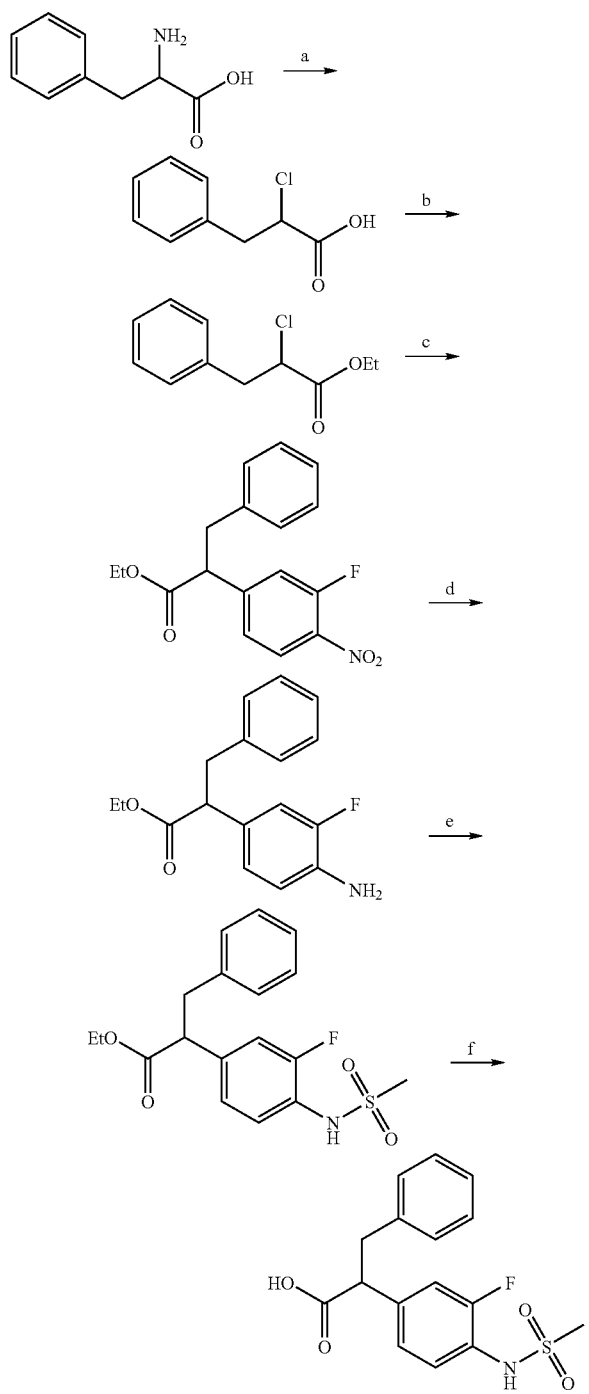

Step a: 2-amino-3-phenylpropanoic acid (10 g, 60.5 mmol) was dissolved in concentrated HCl (200 mL) and was cooled to −5° C. Sodium nitrite solution (7.9 g, 115 mmol) in water (30 mL) was added dropwise over the period of 30 minutes. After complete addition reaction mixture was stirred at ambient temperature for 2 h. TLC (in 50% ethyl acetate-Hexane, R$_f$=0.4) showed complete consumption of starting material. The aqueous part was extracted in ethyl acetate (3×200 mL). The overall organic layer was washed with water (2×200 mL) and finally with brine (200 mL). The washed organic layer was dried over anhydrous magnesium sulfate and concentrated under reduced pressure to afford a yellow liquid (12 g, crude).

Step b: Step-a product (12 g, 65 mmol) dissolved in benzene (240 mL). EtOH (120 mL) and sulphuric acid (2 mL) was added to it. The reaction mixture was refluxed for 4 h using Deanstark apparatus. TLC (20% ethyl acetate in hexane, R$_f$=0.6) showed complete consumption of starting material. The organic solvent was concentrated under reduced pressure and the residue was diluted with water (200 mL). The aqueous layer was extracted with 30% ethyl acetate in hexane (3×200 mL). The overall organic layer was dried over anhydrous magnesium sulfate and concentrated under reduced pressure to get a yellowish residue, which was purified by column chromatography (silica gel: 100-200 mesh; eluent: 2% ethyl acetate in hexane) to afford a light yellow liquid compound. (10 g, 87%). ¹H NMR (CDCl₃, 400 MHz): δ 7.23-7.35 (m, 5H), 4.81 (q, 1H), 4.11 (q, 2H), 3.10-3.34 (m, 2H), 1.14 (t, 3H).

Step c: To a stirred suspension of potassium tert-butoxide (14.3 g, 127 mmol) in dimethylformamide (90 mL), a mixture of step-b product (13.5 g, 63.5 mmol) and 1-fluoro 2-nitrobenzene (7.12 g, 63.5 mmol) in dimethylformamide (50 mL) was added at −30° C. The reaction mixture was stirred for 30 minutes at the same temperature. TLC (10% ethyl acetate-Hexane, R$_f$=0.4) showed complete consumption of starting material. Reaction mixture was diluted with water (1.5 L) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a light brown solid (14.5 g, 72%). ¹H NMR (CDCl₃, 400 MHz): δ 6.64-7.24 (m, 8H), 3.96 (q, 2H), 3.77 (t, 1H), 3.18 (q, 1H), 2.90 (q, 1H), 1.02 (t, 3H).

Step d: In a 500 mL round-bottom flask step-c product (14.5 g, 45.7 mmol) was dissolved in ethyl acetate (300 mL). Palladium on charcoal (0.700 mg, 10% Pd) was added under nitrogen atmosphere. It was stirred under atmospheric hydrogen pressure for 12 h. TLC (20% ethyl acetate in hexane, R$_f$=0.4) showed complete conversion of starting material. Reaction mixture was filtered over celite bed and washed with ethyl acetate (3×150 mL). The organic layer was concentrated to afford a yellowish residue, which was purified through column chromatography (silica gel: 100-200 mesh, eluent: 10% ethyl acetate in hexane) to afford the pure amine compound (12.5 g, 95%). ¹H NMR (CDCl₃, 400 MHz): δ 6.64-7.24 (m, 8H), 5.06 (s, 2H), 3.96 (q, 2H), 3.77 (t, 1H), 3.18 (q, 1H), 2.90 (q, 1H), 1.02 (t, 3H).

Step e: Step-d product (12.5 g, 43.5 mmol) was dissolved in dichloromethane (190 mL). Pyridine (10.5 mL, 130.5 mmol) was added to it. Methanesulphonylchloride (6 g, 47.85 mmol) was added dropwise to the reaction mixture at 0-5° C. and stirred for 16 h at ambient temperature. TLC (20% ethyl acetate in hexane, R$_f$=0.2) showed complete conversion of starting material. Reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 20% ethyl acetate in hexane) to afford the pure compound (13.5 g, 85%). ¹H NMR (CDCl₃, 400 MHz): δ 9.57 (s, 1H), 7.14-7.34 (m, 8H), 3.94-4.04 (m, 3H), 3.25 (q, 1H), 2.97-3.02 (m, 4H), 1.03 (t, 3H).

Step f: Step-e product (4 g, 11 mmol), was dissolved in THF (60 mL). LiOH solution (1M, 33 mL, 33 mmol) was added dropwise at 10-15° C. to it. The reaction mixture was then stirred at ambient temperature for 16 h. TLC (in 30% ethyl acetate-Hexane, R$_f$=0.05) showed complete consumption of starting material. The solvent was removed under reduced pressure and residue was diluted with water (150 mL). The aqueous layer was washed with ethyl acetate (150 mL) and aqueous part was acidified with 2N aqueous HCl solution up to pH=3-4. The acidified aqueous part was then extracted with ethyl acetate (3×150 mL). The organic layer was dried over anhydrous magnesium sulfate and concentrated under reduced pressure afforded a white solid compound (3 g, 81%). ¹H NMR (CDCl₃, 400 MHz): δ 12.53 (s, 1H), 9.56 (s, 1H), 7.15-7.33 (m, 8H), 3.91 (t, 1H), 3.26 (q, 1H), 3.00 (s, 3H), 2.96 (t, 1H). MS m/z (M+1): 338.

7. Preparation of Selected Amines of General Formula (VI)

7.1 Synthesis of 4-cyclopropyl-3-fluoroaniline hydrochloride (employed for the synthesis of example compound no. 126)

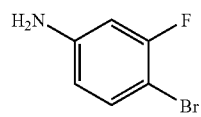

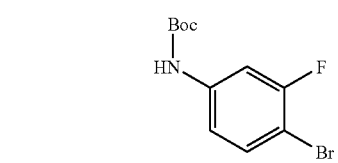

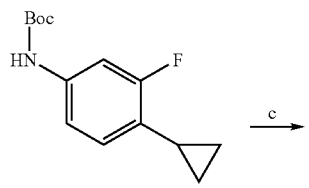

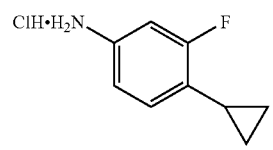

Step a: To a mixture of 4-bromo 3-fluoro aniline (5 g, 26.4 mmol) in water (40 mL), was added Boc-anhydride (6.4 g, 29.09 mmol) and stirred at room temperature for 16 h until complete consumption. To the clear solution water (50 mL) was added to obtain white precipitate, the solid filtered, washed with water (2×20 mL) and dried under reduced pressure to afford a white solid (5.82 g, 76%).

Step b: A suspension containing step-a product (1 g, 3.46 mmol), cyclopropyl boronic acid (0.74 mmol), tricyclohexyl phosphine (0.387 mg, 1.38 mmol), tripotassium phosphate (3.67 g, 17.38 mmol) in toluene (10 mL) and water (10 mL) was degassed by purging Ar for 30 minutes and Pd(OAc)₂ (155 mg, 0.69 mmol) was added. The mixture was stirred in a sealed tube at 110° C. for 20 h. The reaction mixture was cooled to room temperature, diluted with ethyl acetate (200 mL), washed with water (2×30 mL), brine solution (25 ml), dried (Na₂SO₄) and concentrated under reduced pressure to give a residue. Purification by column chromatography (silica gel; 100-200 mesh; eluent: 2% ethyl acetate-petroleum ether) afforded a white solid (600 mg, 69%).

Step c: To step-b product (2.65 g, 10.55 mmol), a solution of HCl in diethyl ether (60 ml) was added at 0° C. and the mixture was stirred at room temperature for 36 h. The solid was filtered, washed with ether (3×10 mL), pentane (3×10 mL) and dried to afford desired compound as white solid (810 mg, 43%).

7.2 Synthesis of 4-(cyclopropylethynyl)-3-fluoroaniline (employed for the synthesis of example compound no. 139)

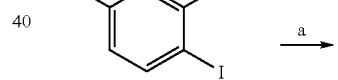

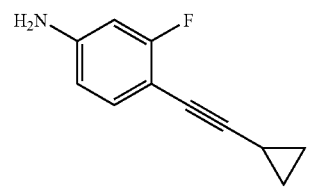

Step a: To a stirred solution of 4-iodo 3-fluoro aniline (2.25 g, 9.49 mmol) in THF (25 ml) at 0° C. to −5° C., CuI (90 mg, 0.47 mmol) and Et₃N (3.5 ml, 25.62 mmol) were added. The reaction mixture was deoxygenated by purging with a stream of Argon for 30 minutes at −5° C. Addition of Pd(dppf) Cl₂.CH₂Cl₂ (346 mg, 0.47 mmol) and purging was continued. After 10 minutes, cyclopropyl acetylene (0.72 ml, 8.54 mmol) was added at −5° C. and stirred at room temperature for 16 h. The reaction mixture was diluted with ether (200 mL), filtered through celite pad, washed with ether (2×25 mL). The filtrate was concentrated and the residue purified by column chromatography (100-200 mesh silica gel) using hexane as eluent to afford title compound as pale brown liquid (750 mg, 45%).

8. Preparation of Selected Carbamate Phenyl Esters of General Formula (VIA) or (V) and Phenyl Esters of General Formula (IVa)

8.1 Synthesis of methyl phenyl (3-tert-butyl-1-(3-chlorophenyl)-1H-pyrazol-5-yl)methylcarbamate (employed for the synthesis of example compounds no. 57-65, 122 and 144)

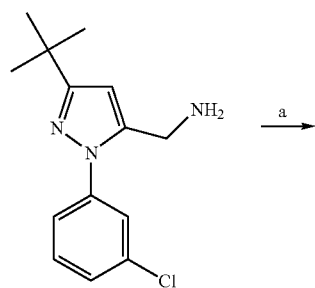

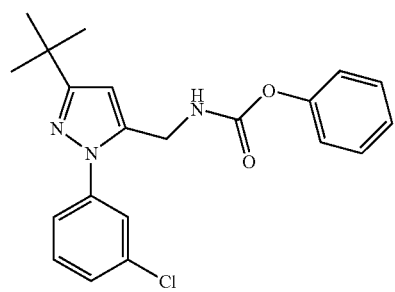

Step a: To a solution of (3-tert-butyl-1-(3-chlorophenyl)-1H-pyrazol-5-yl)methanamine (5 g, 18 mmol) in dimethylformamide (25 ml, 5 times), potassium carbonate (9.16 g, 66 mmol, 3.5 eq) was added and cooled the contents to 0° C. Then phenyl chloroformate (3.28 g (2.65 ml), 20 mmol, 1.1 eq) was added dropwise for 15 minutes and the overall reaction mixture was stirred for another 15 minutes at 0° C. Progress of the reaction was monitored by TLC (20% ethyl acetate-hexane, $R_f$~0.3). On completion of the reaction, reaction contents were filtered, filtrate was diluted with cold water (100 ml) and the product extracted with ethyl acetate (3×25 ml). Combined organic layer was washed with brine solution (100 ml), dried over sodium sulfate and concentrated under reduced pressure. Crude obtained was purified by column chromatography (silica gel, 10% ethyl acetate-hexane) to yield the required product as a white solid (3.2 g, 45%).

9. Preparation of Additional Selected Pyrazol Derivatives According to General Formula (II)

9.1 Synthesis of (1-(3-chlorophenyl)-4-methyl-3-(trifluoromethyl)-1H-pyrazol-5-yl)methanamine (employed for the synthesis of example compounds no. 84 and 134)

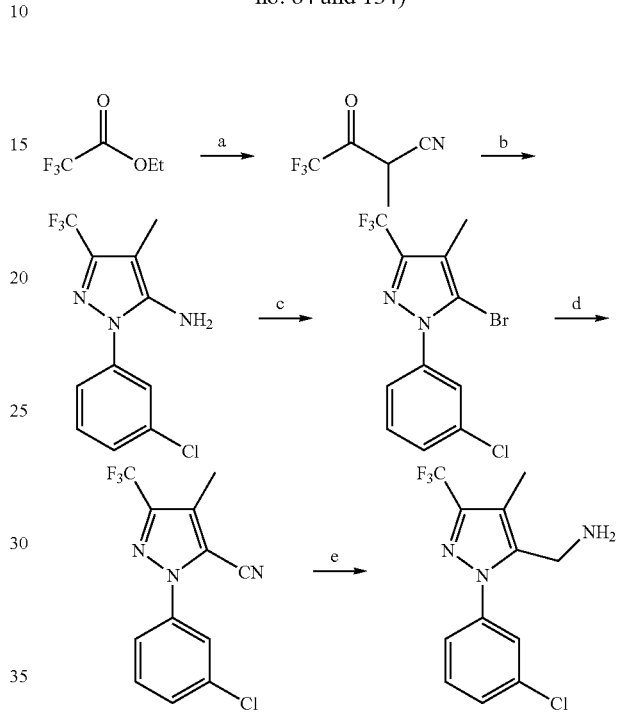

Step a: To a solution of diisopropylamine (40.8 g (57 ml), 0.404 mol, 2.3 eq) in THF (400 ml), n-BuLi (1.6 molar) (24.7 g (258.3 ml, 0.38 mol, 2.2 eq) was added drop wise for 2 hrs at −20° C. and stirred the contents for 30-45 min at 0° C. Cooled the contents to −75° C., a solution of ethyl 2,2,2-trifluoroacetate (25 g, 0.17 mol) in THF (200 ml) was added drop wise for 2 hrs. The reaction mixture was stirred initially for 1 hr at −75° C. and later for another 1 hr at rt. Progress of the reaction was monitored by TLC (50% ethyl acetate/hexane, $R_f$~0.5). On completion of the reaction, quenched the reaction with ice water (700 ml) and the solvents were distilled off completely. Residue washed with DCM (3×300 ml), acidified the contents with 30% HCl solution and the product extracted with ether (3×400 ml). Combined organic layer was dried over sodium sulfate, concentrated under reduced pressure and the crude obtained was distilled under vacuum to yield the product at 35° C./0.1 mm as a colorless liquid (17 g, 64% yield).

Step b: A step-a product (10 g, 0.066 mol) was taken in ethanolic HCl (300 ml, 30 times) and 3-chlorophenyl hydrazine (9.43 g, 0.066 mol, 1 eq) was added. The reaction mixture was heated to reflux for 2 hrs. Progress of the reaction was monitored by TLC (20% ethyl acetate/hexane, $R_f$~0.3). On completion of the reaction, reaction contents were concentrated and the residue taken in water (200 ml). Basified the contents to a pH~12 with 1N NaOH solution and filtered the contents. Solid obtained was taken in ethyl acetate (200 ml), dried the contents over sodium sulfate and concentrated under reduced pressure to yield the required product as a red colored solid (12 g, 65% yield).

Step c: Cupric bromide (11.33 g, 0.0511 mol, 1.2 eq) was taken in acetonitrile (176 ml) and heated to 150° C. Then n-butyl nitrite (6.59 g (7.47 ml), 0.063 mol, 1.5 eq) was added followed by a solution of step-b product (11.75 g, 0.042 mol) in acetonitrile (176 ml) was added drop wise for 30 min at 150° C. and stirred for 15 min. Progress of the reaction was monitored by TLC (5% ethyl acetate/hexane, $R_f$~0.7). On completion of the reaction, acetonitrile was distilled off, residue was taken in ice cold water (300 ml) and the product extracted with ethyl acetate (5×100 ml). Combined extract was dried over sodium sulfate, concentrated under reduced pressure and the crude obtained was subjected to column chromatography (silica gel, pure hexane). Pure product was not isolated and a mixture was obtained as a red colored liquid (16 g, crude) and the same product used for the next step.

Step d: To a solution of step-c product (13 g, 0.038 mol) in NMP (130 ml, 10 times), copper cyanide (6.8 g, 0.076 mol, 2 eq), sodium iodide (100 mg, catalytic) were added. The reaction mixture was placed in a pre-heated oil bath at 180° C. and allowed to stir for 8 hr. Progress of the reaction was monitored by TLC (5% ethyl acetate/hexane, $R_f$~0.4). On completion of the reaction, diluted the reaction contents with water (200 ml) and the product extracted with ethyl acetate (5×100 ml). Combined extract was washed with cold water (5×50 ml), dried over sodium sulfate and concentrated under reduced pressure. The crude obtained was purified by column chromatography (silica gel, 2% ethyl acetate/hexane) to yield the required product as a pale yellow colored solid (8 g).

Step e: To a solution of step-d product (5 g, 0.017 mol) in dry THF (30 ml, 6 times), Boran-THF in THF (70 ml) was added drop wise for 30 min at 0-5° C. Reaction mixture was slowly heated to 50° C. and allowed to stir for 12 hrs. Progress of the reaction was monitored by TLC (75% ethyl acetate/hexane, $R_f$~0.2). On completion of the reaction, acidified the contents to 0-5° C. with conc. HCl at 0° C. and stirred the contents for 2 hrs at rt. Then basified the contents to a pH~12 with 10% NaOH solution and the product extracted with ethyl acetate (5×50 ml). Combined extract was dried over sodium sulfate and concentrated under reduced pressure. Solid obtained was washed with 10% ether/hexane and dried to yield the required product as a white colored solid (3 g, 59% yield, mp 82-86° C.).

9.2 Synthesis of (1-(3-chlorophenyl)-3-cyclopropyl-1H-pyrazol-5-yl)methanamine hydrochloride (employed for the synthesis of example compound no. 128)

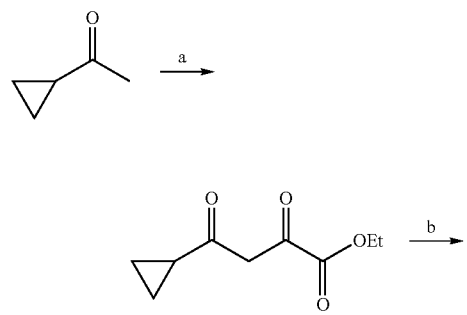

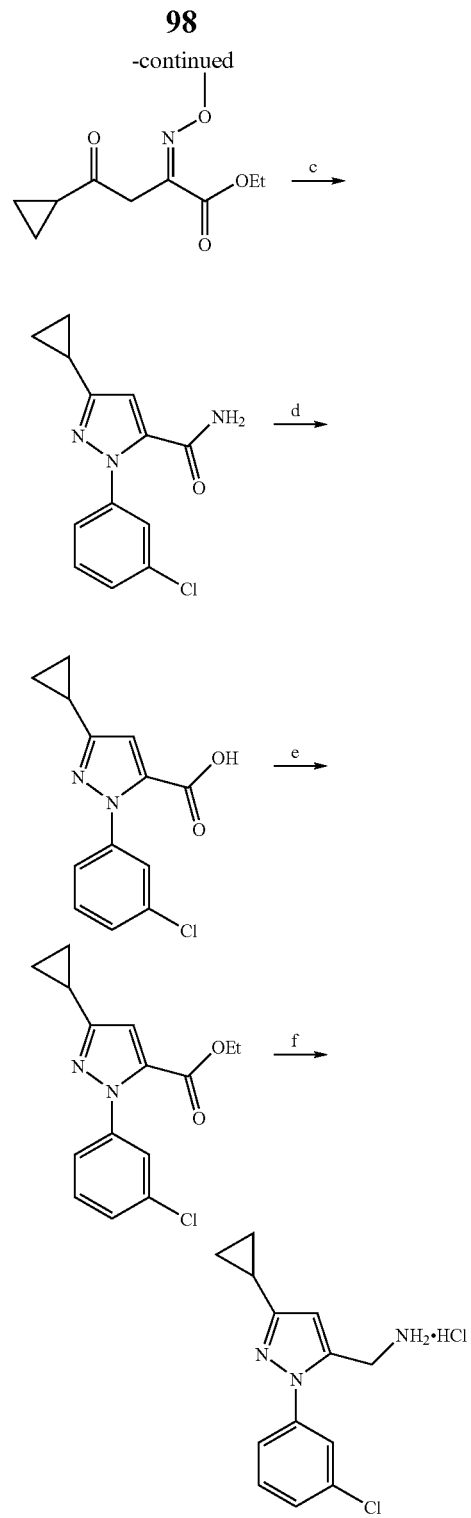

Step a: To a solution of sodium ethoxide (freshly prepared by dissolving sodium (1 g, 8.2 mmol, 1.2 eq) in EtOH (30 mL)), diethyl oxalate (0.92 mL, 6.85 mmol, 1 eq) was added at room temperature followed by addition of cyclopropyl methyl ketone (0.74 mL, 7.5 mmol, 1.1 eq) dropwise at 0° C. The reaction mixture was slowly warmed to room temperature and stirred for 3 h. Ice cold water (10 mL) was added and EtOH was evaporated under reduced pressure. The residual aqueous layer was diluted with 2 N aq. HCl (15 mL) and extracted with diethyl ether (2×25 mL). The organic layer was washed with brine solution and dried (Na$_2$SO$_4$), filtered and concentrated to give a pale brown liquid (400 mg, 31%).

Step b: To a solution of step-a product (200 mg, 0.543 mmol, 1 eq) in EtOH (8 mL), methoxylamine hydrochloride (30% solution in water, 0.4 mL, 0.651 mmol, 1.2 eq) was added at room temperature and the reaction mixture stirred for 1 h. EtOH was evaporated under reduced pressure and the residual aqueous layer was extracted with ethyl acetate (15 mL). The organic layer was washed with water (10 mL), brine solution (10 ml), dried (Na$_2$SO$_4$), filtered and concentrated under reduced pressure to give a pale yellow liquid (180 mg, 78%).

Step c: A mixture of step-b product (1.1 g, 5.164 mmol, 1 eq) and 3-chlorophenyl hydrazine hydrochloride (1.84 g, 10.27 mmol, 2 eq) was taken in acetic acid (20 mL), 2-methoxy EtOH (10 mL) and the reaction mixture was heated at 105° C. for 3 h. Solvent was evaporated and the residue was extracted with ethyl acetate (60 mL). The organic layer washed with water (10 mL), brine solution (10 ml), dried (Na$_2$SO$_4$), filtered and concentrated under reduced pressure to give a residue. Purification by column chromatography (silica gel: 100-200 mesh; eluent: ethyl acetate-petroleum ether (4:96)) afforded a pale brown semi solid (1.15 g, 77%).

Step d: To a solution of step-c product (2.5 g, 8.62 mmol, 1 eq) in THF (15 mL)—MeOH (9 mL)—water (3 mL), LiOH (1.08 g, 25.71 mmol, 3 eq) was added at 0° C. and the reaction mixture was stirred for 2 h at room temperature. Solvent was evaporated and pH of the residue was adjusted to ~3 sing 2 N aqueous HCl (1.2 mL). The acidic aqueous layer was extracted with ethyl acetate (2×60 mL); the combined organic layer washed with water (10 mL), brine solution (10 ml), dried (Na$_2$SO$_4$), filtered and concentrated under reduced pressure to give an off white solid (1.4 g, 62%).

Step e: To a solution of step-d product (1.4 g, 5.34 mmol, 1 eq) in 1,4-dioxane (30 mL), pyridine (0.25 mL, 3.2 mmol, 0.6 eq) and (Boc)$_2$O (1.4 mL, 6.37 mmol, 1.2 eq) were added at 0° C. and the resulting mixture was stirred for 30 minutes at the same temperature. Ammonium bicarbonate (0.84 g, 10.63 mmol, 2 eq) was added at 0° C. and the reaction mixture was stirred at room temperature overnight. The reaction mixture was diluted with water (10 mL) and the aqueous layer was extracted with ethyl acetate (2×30 mL). The organic layer was washed with 2N HCl (20 mL), water (10 mL), brine solution (10 ml), dried (Na$_2$SO$_4$), filtered and concentrated under reduced pressure to give a residue. Purification by column chromatography (silica gel: 100-200 mesh; eluent: ethyl acetate-petroleum ether (16:84)) gave a white solid (1 g, 72%).

Step f: To a solution of step-e product (2 g, 7.66 mmol, 1 eq) in THF (25 mL), BH$_3$. DMS (1.44 mL, 15.32 mmol, 2 eq) was added at 0° C. and the reaction mixture was heated at 70° C. for 3 h. The reaction mixture was cooled to 0° C. and MeOH (15 mL) was added and reaction mixture heated at reflux for 1 h. The reaction mixture was brought to room temperature and solvent was evaporated under reduced pressure. The residue was dissolved in ether (15 mL), cooled to 0° C. and a solution of HCl in 1,4-dioxane (3 mL) was added (pH of the reaction mixture ~4). The precipitated solid was filtered and washed with diethyl ether (5 mL, thrice) to give the hydrochloride salt compound as a white solid (600 mg, 28%).

9.3 Synthesis of (3-tert-butyl-1-(pyridin-2-yl)-1H-pyrazol-5-yl)methanamine (employed for the synthesis of example compound no. 127)

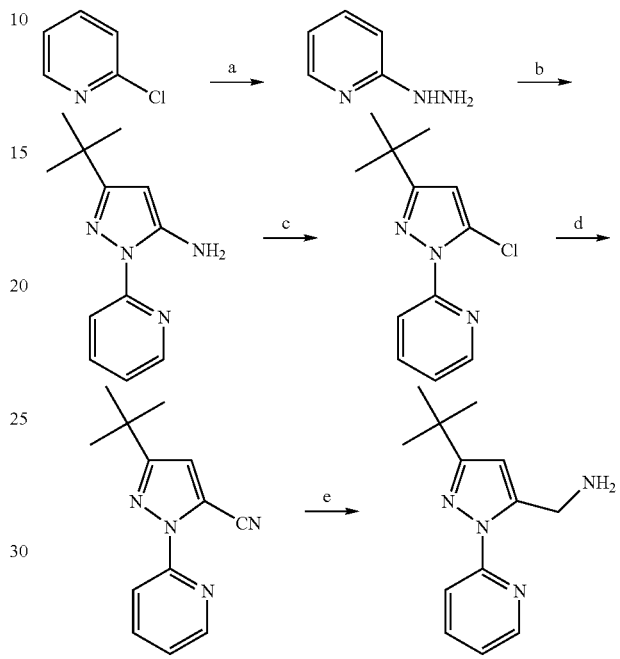

Step a: To a solution of 2-chloropyridine (20 g, 0.17 mol) in ethanol (100 ml, 5 times), hydrazine hydrate (132 ml, 6.6 times) was added and the reaction mixture was heated to reflux for 15 hrs. Progress of the reaction was monitored by TLC (40% ethyl acetate/hexane, R$_f$~0.1). As the reaction not completed, continued to reflux for another 15 hrs and monitored by TLC. On completion of the reaction, ethanolic hydrazine hydrochloride was distilled off completely at 100° C., residue was taken in DCM (500 ml) and washed the contents with saturated sodium carbonate solution (100 ml). Combined organic layer was dried over sodium sulfate and concentrated under reduced pressure to obtain the crude product as a low melting solid (11 g, crude). The crude obtained was directly used for the next step.

Step b: To a stirred solution of step-a product (11 g, crude) in ethanol (110 ml, 10 times), 4,4-dimethyl-3-oxopentanenitrile (11.3 g, 0.09 mol, 0.9 eq) was added portion wise followed by catalytic amount of HCl. The reaction mixture was heated to 100° C. and refluxed for 6 hrs. Progress of the reaction was monitored by TLC (20% ethyl acetate/hexane, R$_f$~0.7). On completion of the reaction, ethanol was distilled off, residue was taken in water (200 ml) and the product extracted with ethyl acetate (2×100 ml). Combined extract was dried over sodium sulfate, concentrated under reduced pressure and the crude obtained was purified by column chromatography (silica gel, 10% ethyl acetate/hexane) to yield the required product as an off white solid (18 g).

Step c: To a solution of step-b product (4 g, 0.01 mol) in acetonitrile (80 ml), cupric chloride (12.3 g, 0.09 mol, 5 eq) was added. A solution of tert-butyl nitrite (2.8 (3.3 ml), 0.023 mol, 1.5 eq) in acetonitrile (40 ml (total 120 ml, 30 times)) was added drop wise for 10 min and the overall reaction mass was stirred for 5 hrs at rt. Progress of the reaction was monitored by TLC (10% ethyl acetate/hexane, $R_f$~0.3). On completion of the reaction, acetonitrile was distilled off, residue was taken in water (100 ml) and the product extracted with ethyl acetate (2×200 ml). Combined extract was dried over sodium sulfate, concentrated under reduced pressure and the crude was purified by column chromatography (silica gel, 4% ethyl acetate/hexane) to yield the required product as a pale yellow colored liquid (2.1 g, 48% yield).

Step d: To a stirred solution of step-c product (2.1 g, 0.008 mol) in NMP (21 ml, 1 time), copper cyanide (1.56 g, 0.017 mol, 2 eq) was added portion wise followed by a catalytic amount of sodium iodide was added. The reaction mixture was heated to 180° C. and maintained at that temperature for 4 hrs. Progress of the reaction was monitored by TLC (10% ethyl acetate/hexane, $R_f$~0.5). On completion of the reaction, diluted the reaction contents with ethyl acetate, filtered the contents through celite bed and the filtrate washed with cold water (50 ml). Organic layer was dried over sodium sulfate, concentrated under reduced pressure and the crude was purified by column chromatography (silica gel, 6-8% ethyl acetate/hexane) to yield the required product as an off white solid (0.8 g, 40% yield).

Step e: To a solution of step-d product (1.5 g, 0.006 mol) in methanol (20 ml), catalytic amount of raney nickel. The reaction mixture was hydrogenated for 1 hr at 60 psi. Progress of the reaction was monitored by TLC (15% ethyl acetate/hexane, $R_f$~0.1). On disappearance of the starting material, filtered the contents on celite bed and washed with methanol. To the filtrate was purified by column chromatography (silica gel, 6% ethyl acetate/hexane) to yield the titled product as a cream colored oil (1.4 g, 97% yield).

9.4 Synthesis of (1-(pyridin-3-yl)-3-(trifluoromethyl)-1H-pyrazol-5-yl)methanamine hydrochloride (employed for the synthesis of example compound no. 136)

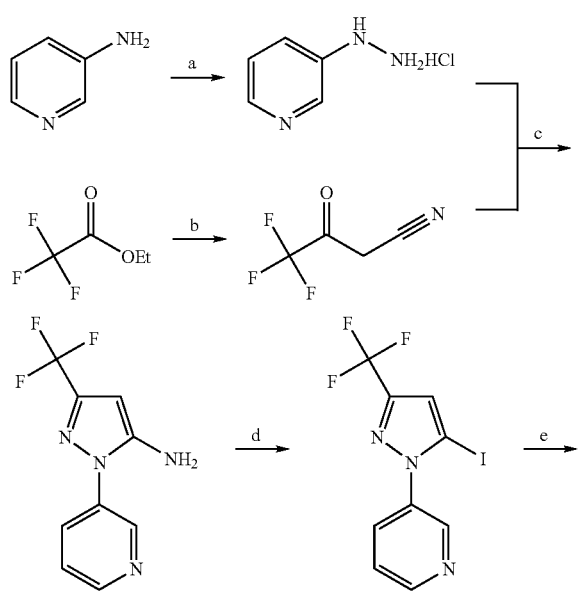

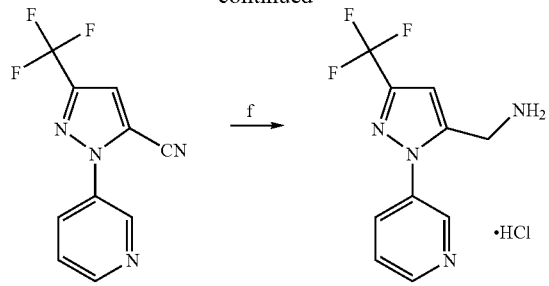

Step a: To a cold solution of pyridin-3-amine (40 g, 425.5 mmol) in conc. HCl (500 mL) at 0° C., a solution of NaNO₂ (35.23 g, 510.6 mmol) in water (40 mL) was added dropwise maintaining the temperature at 0° C. for 15 minutes. After addition the solution was stirred for 20 minutes. This solution was added to a solution of SnCl₂ (177.5 g, 936.3 mmol) in conc. HCl (100 mL) dropwise maintaining the temperature at 0° C. for 20 minutes and the resulting yellow solution was stirred at 0° C. for 30 minutes. The obtained yellow solid was filtered, washed with water (3×50 mL) and dried afford product (106.5 g, crude) as yellow solid.

Step b: To a cold suspension of NaH (60% dispersion in oil, 29.26 g, 731.7 mmol) in 1,4-dioxane (450 mL), acetonitrile (38.46 mL, 731.7 mmol) was added dropwise at 0° C. and stirred for 30 minutes. The reaction mixture was cooled to ~5° C., ethyl 2,2,2-trifluoroacetate (83.12 g, 585.36 mmol) was slowly added and the reaction mixture allowed to stir at room temperature for 16 h. The reaction mixture was cooled to 0° C., quenched with MeOH (150 mL), diluted with ethyl acetate (300 mL) and pH adjusted to ~4 using dilute aqueous HCl. The organic layer was separated and the aqueous layer was extracted with ethyl acetate (2×250 mL). The combined ethyl acetate layer was washed with water (250 mL), brine solution (200 mL), dried (Na₂SO₄), filtered and concentrated under reduced pressure to afford a brown liquid (57 g). The crude compound was used as such without further purification.

Step c: A solution of step-b product (57 g, crude; 416.05 mmol) and step-a product (60.5 g, 416.05 mmol) in EtOH (650 mL) was stirred at reflux for 3 h. The reaction mixture was concentrated; the obtained residue was diluted with ethyl acetate (2 L), washed with water (2×500 mL), brine solution (500 mL), dried (Na₂SO₄), filtered and concentrated under reduced pressure to give a residue. Purification by column chromatography (silica gel; 100-200 mesh; eluent: 30% ethyl acetate in petroleum ether) afforded a yellow solid (31.48 g).

Step d: To a cold suspension of potassium iodide (51.3 g, 309.21 mmol) and isoamyl nitrite (41.16 mL, 309.21 mmol) in dry acetonitrile (350 mL), a solution of step-c product (23.5 g, 103.07 mmol) in acetonitrile (100 mL) was added dropwise at 0° C. and the reaction mixture was stirred at 100° C. for 20 h. The reaction mixture was concentrated; the obtained residue was diluted with ethyl acetate (1 L), washed with water (2×400 mL), brine solution (200 mL), dried (Na₂SO₄), filtered and concentrated to give a residue. Purification by column chromatography (silica gel; 100-200 mesh; eluent: 30% ethyl acetate in petroleum ether) afforded a pale yellow solid (16.52 g, 37%).

Step e: To a solution of step-d product (16.5 g, 48.67 mmol) in dry NMP (150 mL), CuCN (6.53 g, 73.0 mmol) was added and the reaction mixture was stirred at 200° C. for 2 h. The reaction mixture was cooled to room temperature, quenched with ethylene diamine (50 mL) and diluted with ethyl acetate (800 mL). The obtained suspension was filtered through celite bed, washed with ethyl acetate (2×100 mL). The combine filtrate was washed with water (2×300 mL), brine solution (250 mL), dried (Na$_2$SO$_4$), filtered and concentrated under reduced pressure to give a residue. Purification by column chromatography (silica gel; 100-200 mesh; eluent: 20-30% ethyl acetate in petroleum ether) to afford a yellow solid (5.12 g, 44%).

Step f: To a solution of step-e product (4.5 g, 18.9 mmol) in saturated methanolic NH$_3$ (50 mL), Raney-Nickel (3 g, wet, washed with MeOH (4×5 mL)) was added and the mixture was hydrogenated in a Parr hydrogenator at 40 Psi pressure at room temperature for 4 h. The reaction mixture was filtered through celite and the filtrate was concentrated under reduced pressure. The obtained residue was stirred in sat. HCl in ether (50 mL) for 2 h. Ether was decanted, the obtained solid was washed with ether (3×10 mL), vacuum dried to afford product compound as light brown solid (1.2 g, 23%).

9.5 Synthesis of 5-(aminomethyl)-3-tert-butyl-N-(2,2,2-trifluoroethyl)-1H-pyrazol-1-amine (employed for the synthesis of example compound no. 98)

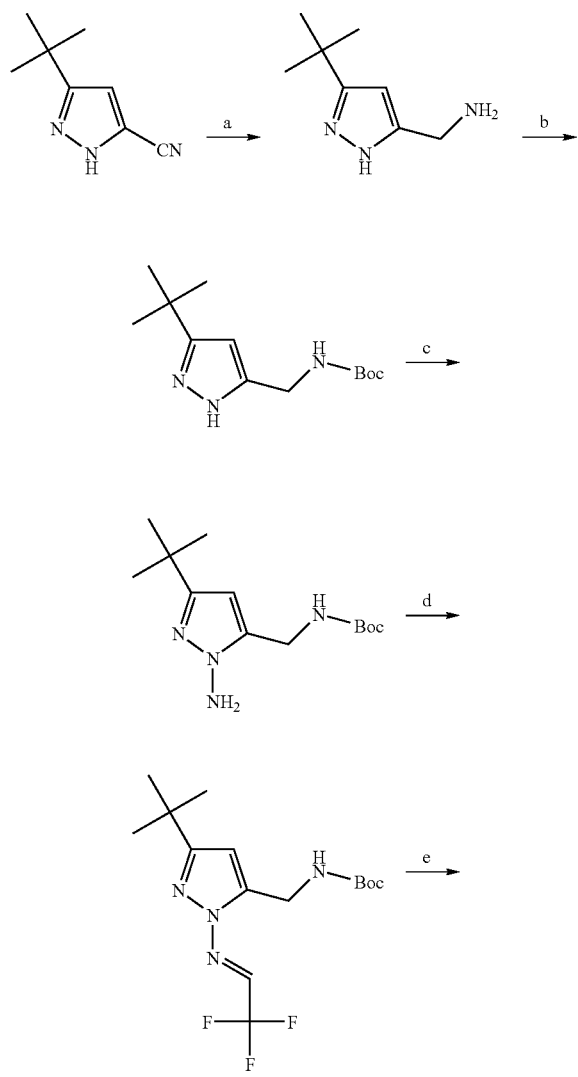

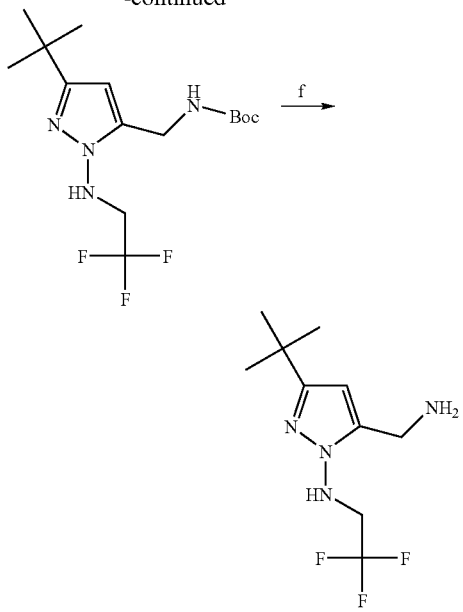

Step a: To a solution of tert-butyl-1H-pyrazole-5-carbonitrile (5 g, 0.033 mol) in methanol (100 ml, 20 times), Raney nickel (5 g, 1 times) was added and the reaction mixture was hydrogenated for 1-2 hrs 70 psi. Progress of the reaction was monitored by TLC (40% ethyl acetate/hexane, R$_f$~0.1). On completion of the reaction, filtered the reaction contents and the bed was washed with methanol (100 ml). Methanol was distilled off completely and the crude obtained as a pale yellow colored liquid (5 g., crude) was directly used for the next step.

Step b: To a stirred solution of step-a product (5 g, crude) in methanol (50 ml, 10 times), sodium carbonate (5.1 g, 0.04 mol, 1.5 eq) was added and stirred for 15 min. Cooled the contents to 0° C., Boc anhydride (6.97 g, 1.1 eq) was added drop wise for 10 min and the overall reaction mixture was stirred for 30 min at 0° C. Progress of the reaction was monitored by TLC (50% ethyl acetate/hexane, R$_f$~0.3). On completion of the reaction, methanol was distilled off completely, residue was taken in water (100 ml) and the product extracted with ethyl acetate (2×100 ml). Combined extract was dried over sodium sulfate, concentrated under reduced pressure and the crude was recrystalised from hexane to yield the required product as a white solid (4.5 g).

Step c: To a stirred solution of step-b product (5 g, 0.019 mol) in DMF (50 ml, 10 times), sodium hydroxide (7.9 g, 0.19 mol, 10 eq) was added. Cooled the contents to 0° C., Hydroxylamine-o-sulfonic acid (6.4 g, 0.057 mol, 3 eq) was added portion wise for 30 min and the reaction mixture was stirred for 2 hrs at 0° C. Progress of the reaction was monitored by TLC (30% ethyl acetate/hexane, R$_f$~0.4). On completion of the reaction, poured the reaction contents into crushed ice (200 g) and filtered the contents. Solid obtained was taken in hexane (100 ml), filtered and dried to yield the required product as a white solid (4 g, 75% yield).

Step d: To a stirred solution of step-c product (2 g, 0.001 mol) in ethanol (20 ml, 10 times), ether containing trifluoroacetaldehyde (1.41 g in 50 ml (0.014 mol, 2 eq)) was added. The reaction mixture was stirred for 12 hrs at rt. Progress of the reaction was monitored by TLC (10% ethyl acetate/hexane, R$_f$~0.7). On completion of the reaction, ethanol was distilled off completely and the crude obtained was purified by column chromatography (silica gel, hexane) to yield the required product as a white solid (2 g, 77% yield).

Step e: To a stirred solution of step-d product (1.7 g, 0.0048 mol) in methanol (170 ml), 10% Pd/C (0.5 g, catalytic) was added. The reaction mixture was stirred for 12 hrs under Hydrogen balloon pressure. Progress of the reaction was monitored by TLC (10% ethyl acetate/hexane, $R_f$~0.3). On completion of the reaction, filtered the contents over celite bed and the bed washed with methanol. Methanol distilled off from the filtrate and the crude obtained was purified by column chromatography (basic alumina, hexane) to yield the titled product as a white solid (1.02 g, 50% yield, mp 80-83° C.).

Step f: To a stirred solution of Boc-compound step e product (1.0 g), DCM (20 ml) was added at RT and stirred for about 20 min. This reaction mixture was cooled to 0-5° C. and pass the HCl gas for about 30 min. Progress of the reaction was monitored by TLC (10% ethyl acetate/hexane/50% ethyl acetate/hexane). On completion of the reaction, distill off DCM. Add water (20 ml) then extract the compound with 20% IPA/CHCl$_3$ and the layer were separated. The organic layer was distilled off under reduced pressure and dried under high vacuum. The crude was obtained by washing with heptane and drying under high vacuum. The compound was obtained light yellow colored viscous liquid (0.65 g, 91% yield).

9.6 Synthesis of (1-(4-methoxybenzyl)-3-(trifluoromethyl)-1H-pyrazol-5-yl)methanamine (employed for the synthesis of example compound no. 132)

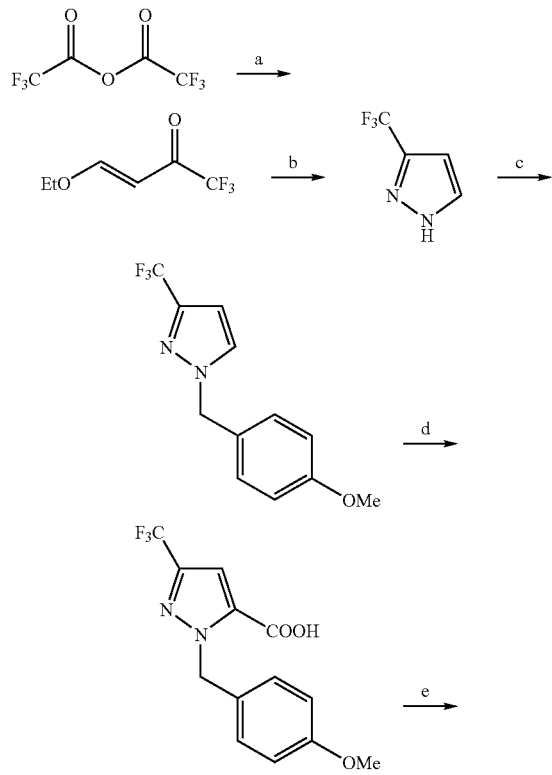

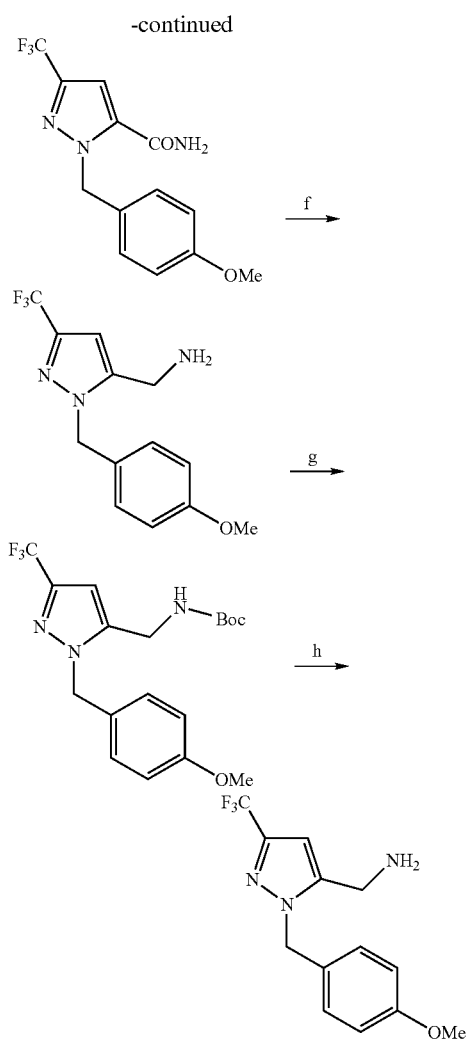

Step a: DMAP (4.25 g, 0.034 mol, 0.01 eq) was added to DCM (3 ltrs) and cooled the contents to −10° C. Trifluoroacetic anhydride (765 g (510 ml), 3.2 mol, 1.05 eq) was added followed by ethyl vinyl ether (250 g, 3.04 mol) was added drop wise for 45 min at −10° C. Then the overall reaction mixture was initially stirred for 8 hrs at 0° C. and later for overnight at RT. Progress of the reaction was monitored by TLC (10% ethyl acetate/hexane, $R_f$~0.7). On completion of the reaction, reaction contents were quenched with saturated NaHCO$_3$ solution (600 ml) and organic layer was separated. Aqueous layer was extracted with DCM (2×500 ml). Combined organic layer was washed with water (2×1 ltr), dried over sodium sulfate and concentrated under reduced pressure to obtain the crude product as a brown colored liquid (450 g, crude).

Step b: Hydrazine dihydrochloride (225 g, 2.14 mol, 1.6 eq) was taken in ethanol (1400 ml) and stirred well. TEA (135.4 g (185.4 ml), 1.34 mol, 1 eq) was added drop wise for 45 min at RT. Then step-a product (225 g, crude) was added drop wise at RT and the overall reaction mixture was refluxed for overnight. Progress of the reaction was monitored by TLC (20% ethyl acetate/hexane, $R_f$~0.4). On completion of the reaction, ethanol was distilled off completely, residue was taken in ice water (500 ml) and the product extracted with ethyl acetate (2×400 ml). Combined extract was washed with ice water (300 ml), dried over sodium sulfate and concentrated under reduced pressure to yield the required product as and off white solid (195 g).

Step c: NaH (33.08 g (19.85, 60%), 1.5 eq) was added to small quantity of hexane and stirred well for 10 min. Hexane was decanted, dry DMF (500 ml) was added drop wise under $N_2$ atmosphere and stirred well. A solution of step-b product (75 g, 0.55 mol) in DMF (125 ml) was added drop wise under $N_2$ atmosphere. Then a solution of 4-methoxyl benzoyl chloride (86.3 g, 0.55 mol, 1 eq) in DMF (125 ml) was added drop wise and the overall reaction mixture was allowed to stir for 12 hrs at RT. Progress of the reaction was monitored by TLC (10% ethyl acetate/hexane, $R_f$~0.4). On completion of the reaction, reaction contents were poured into ice water (500 ml) and the product extracted with ethyl acetate (2×400 ml). Then the contents were dried over sodium sulfate and concentrated under reduced pressure to yield the required product as a brown colored liquid (125 g, 88% yield).

Step d: Diisopropyl amine (28.4 (39.4 ml), 1.2 eq) was taken in THF (500 ml), stirred well and cooled the contents to 0° C. n-BuLi (234.4 ml, 1.5 eq) was added drop wise at 0° C. and cooled the contents to −78° C. A solution of step-c product (62 g, 0.24 mol) in THF (200 ml) was added drop wise for 30 min and stirred the contents for another 30 min at −78° C. Then dry $CO_2$ gas was bubbled through the reaction mixture for 1.5 hrs and the progress of the reaction was monitored by TLC (10% ethyl acetate/hexane, $R_f$~0.1). On completion of the reaction, reaction contents were poured into ice water (300 ml) and the aqueous layer was extracted with ethyl acetate (2×200 ml) in basic condition. Aqueous layer was acidified with 20% HCl solution and extracted with ethyl acetate (2×200 ml). Combined organic layer was dried over sodium sulfate and concentrated under reduced pressure to yield the required product as an off white solid (42 g, 58% yield).

Step e: To a solution of step-d product (50 g, 0.16 mol) in DCM (750 ml, 15 times), catalytic amount of DMF was added and cooled to 0° C. Thionyl chloride (99.3 g (61 ml), 0.83 mol, 5 eq) was added drop wise for 30 min at 0° C. Overall reaction mixture was slowly heated to a reflux temperature and allowed to reflux for 2 hrs. Progress of the reaction was monitored by TLC (10% ethyl acetate/hexane, $R_f$~0.4). On disappearance of the starting material, DCM was distilled off completely. Above prepared acid chloride was dissolved in DCM (500 ml) and added drop wise to aqueous ammonia solution (600-700 ml) at 0° C. Overall reaction mixture was allowed to stir for 1 hr and the progress of the reaction was monitored by TLC (10% ethyl acetate/hexane, $R_f$~0.7). On completion of the reaction, ice cold water (200 ml) was added and the product extracted with ethyl acetate (2×200 ml). Combined organic layer was dried over sodium sulfate and concentrated under reduced pressure to yield the required product as an off white solid (37 g, crude). Crude obtained was directly used for the next step.

Step f: LAH (4.7 g, 0.12 mol, 1 eq) was added to small quantity of hexane and stirred well for 10 min. Hexane was decanted and THF (250 ml) was added to LAH under cold condition. Then a solution of step-e product (37 g, 0.12 mol) in THF (120 ml) was added drop wise for 30 min at 0° C. and reaction mixture was heated to reflux for 5 hrs. Progress of the reaction was monitored by TLC (50% ethyl acetate/hexane, $R_f$~0.2). As the reaction moved completely, LAH (2.3 g) was added and refluxed for another 4 hrs. This time reaction was moved completely. Then the reaction contents were slowly added to saturated solution of sodium sulfate (1 ltr) and the product extracted with ethyl acetate (2×500 ml). Combined extract was dried over sodium sulfate and concentrated under reduced pressure to obtain the crude product as an off white solid (32.5 g). Crude obtained was directly used for the next step.

Step g: To a solution of step-f product ((80 g, 0.28 mol) in DCM (600 ml) cooled at 0° C., TEA (22.7 g (30.2 ml), 0.026 mol, 0.8 eq) was added drop wise for 10 min. Then Boc anhydride (61.2 g (62.5 ml), 0.28 mol, 1 eq) taken in DCM (200 ml) was added drop wise for 20-30 min at 0° C. Overall reaction mixture initially stirred for 30 min at 0° C. and alter for another 30 min at RT. Progress of the reaction was monitored by the TLC (20% ethyl acetate/hexane, $R_f$~0.6). On completion of the reaction, DCM was distilled off completely, residue was taken in ice water (500 ml) and the product extracted with ethyl acetate (2×300 ml). Combined extract was dried over sodium sulfate and concentrated under reduced pressure. Crude obtained was recrystalised from hexane (200 ml) to yield the required product as an off white solid (80 g, 74% yield).

Step h: Step-g (5 g, 0.012 mol) product was taken in DCM (30 ml, 6 times) and cooled to 0° C. HCl gas was bubbled through the reaction mixture for 45 min at 0° C. Progress of the reaction was monitored by TLC (30% ethyl acetate/hexane, $R_f$~0.2). On completion of the reaction, DCM was distilled off completely. Residue was taken in ice water (200 ml) and the product extracted with 20% ethyl acetate/hexane (2×100 ml). Aqueous layer was basified to a pH~10 with 2N NaOH solution and extracted with ethyl acetate (5×100 ml). Combined organic layer was washed with water (2×200 ml), dried over sodium sulfate and concentrated under reduced pressure to yield the required product as an yellow colored liquid (2.4 g, 64% yield).

9.7 Synthesis of N-(5-(aminomethyl)-3-(trifluoromethyl)-1H-pyrazol-1-yl)benzamide (employed for the synthesis of example compound no. 146)

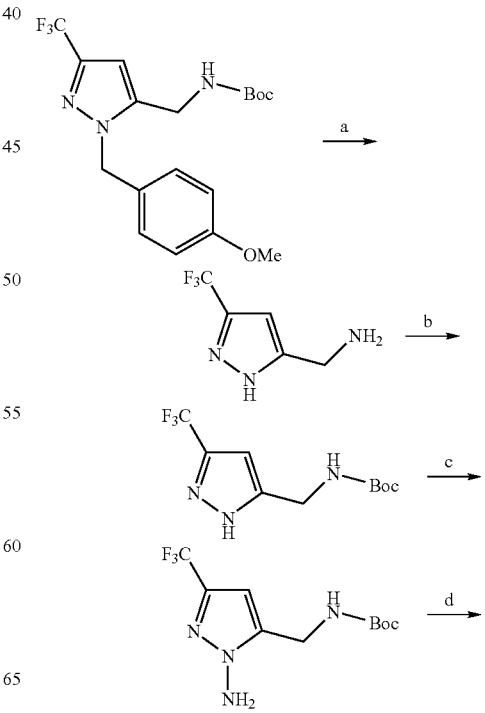

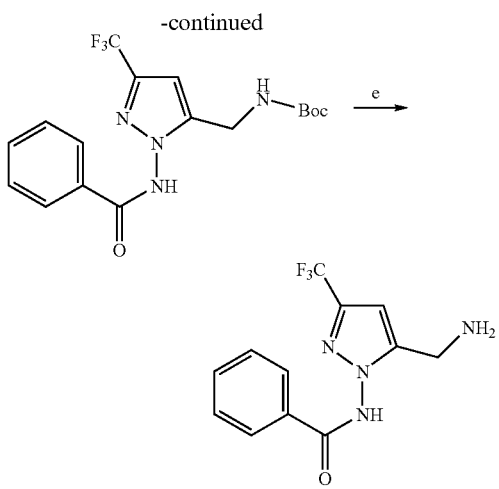

Step a: To a stirred solution of tert-butyl (1-(4-methoxy-benzyl)-3-(trifluoromethyl)-1H-pyrazol-5-yl)methylcarbamate (20 g, 0.052 mol) in toluene (300 ml, 15 times) cooled at 0° C., aluminum chloride (17.34 g, 0.129 mol, 2.5 eq) was added portion wise for 30 min. Reaction mixture was slowly heated to 50-60° C. and allowed stir for 2 hrs at the same temperature. Progress of the reaction was monitored by TLC (20% ethyl acetate/hexane, $R_f$~0.1). On completion of the reaction, reaction contents were quenched with dilute HCl, ice cold water (300 ml) was added and extracted with ethyl acetate (2×100 ml). Aqueous layer was basified with sodium hydroxide solution and extracted with ethyl acetate. Combined extract was dried over sodium sulfate and concentrated under reduced pressure to obtain the crude product as a brown colored solid (4.6 g). The crude obtained was directly used for the next step.

Step b: To a stirred solution of step-a product (5.7 g, 0.034 mol) in DCM (37 ml) cooled at 0° C., TEA (1.74 g (2.4 ml), 0.017 mol, 0.5 eq) was added drop wise for 10 min. Then Boc anhydride (3.76 g (3.9 ml), 0.017 mol, 0.5 eq) taken in DCM (20 ml) was added drop wise for 10-15 min at 0° C. Overall reaction mixture initially stirred for 30 min at 0° C. and alter for another 30 min at RT. Progress of the reaction was monitored by the TLC (20% ethyl acetate/hexane, $R_f$~0.6). As the reaction not moved completely, Boc anhydride (0.3 eq) was added and stirred for another 15 min at RT. Progress of the reaction was monitored by TLC and found that the reaction moved completely. DCM was distilled off completely, residue was taken in ice water (300 ml) and the product extracted with ethyl acetate (2×200 ml). Combined extract was dried over sodium sulfate and concentrated under reduced pressure to yield the required product as and off white solid (7 g, 76% yield).

Step c: A solution of step-b product (10 g, 0.037 mol) in DMF (50 ml) was added drop wise to a mixture of NaH (1.85 g, 0.077 mol, 1.2 eq) in DMF (50 ml) for 45 min at RT. Then 0.5M monochloro amine solution (322 ml) was added drop wise for 30 min and the overall reaction mixture was allowed to stir for 20 min at RT. Progress of the reaction was monitored by TLC (30% ethyl acetate/hexane, $R_f$~0.5). On completion of the reaction, reaction contents were quenched with saturate $Na_2S_2O_3$ solution in cold condition and the product was extracted with ethyl acetate (5×100 ml). Combined extract was dried over sodium sulfate, concentrated under reduced pressure and the crude obtained was purified by column chromatography (silica gel, 4% ethyl acetate/hexane) to yield the required product as an off white solid (4 g, 62% yield).

Step d: To a solution of step-c product (1.2 g, 0.0042 mol) in toluene (12 ml, 10 times), potassium carbonate (1.18 g, 2 eq), water (12 ml, 10 times) and TBAB (0.137 g, 0.0004 mol, 0.1 eq) were added. Then the contents were stirred for 15 min and cooled to 0° C. Benzoyl chloride (0.72 g, 0.005 mol, 1.2 eq) taken in toluene (6 ml) was added drop wise at 0° C. and the overall reaction mixture was stirred for 2 hrs at RT. Progress of the reaction was monitored by TLC (30% ethyl acetate/hexane, $R_f$~0.6). On completion of the reaction, ice water (100 ml) was added, organic layer separated and the aqueous layer extracted with ethyl acetate (5×75 ml). Combined organic layer was washed with water (2×100 ml) and dried over sodium sulfate. Then the contents were concentrated under reduced pressure and the crude obtained was purified by column chromatography (silica gel, 3% ethyl acetate/hexane) to yield the required product as a pale yellow colored liquid (1.1 g, 67% yield).

Step e: To a solution of step-d product (1.1 g, 0.0028 mol) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, $R_f$~0.2). On completion of the reaction, DCM was distilled off completely. Residue was taken in cold water (200 ml), basified with saturated $NaHCO_3$ solution and the product extracted with ethyl acetate (4×50 ml). Combined extract was washed with water (2×50 ml), dried over sodium sulfate and concentrated under reduced pressure. Crude obtained was purified by column chromatography (silica gel, 10% ethyl acetate/hexane) to yield the required product as a white solid (0.24 g, 30% yield).

9.8 Synthesis of 5-(aminomethyl)-N-(pyridin-2-ylmethyl)-3-(trifluoromethyl)-1H-pyrazol-1-amine (employed for the synthesis of example compound no. 129)

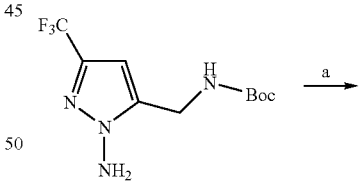

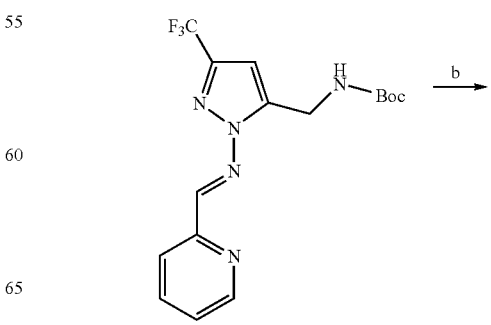

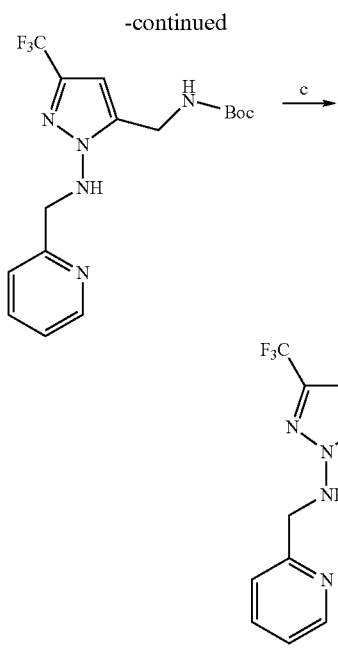

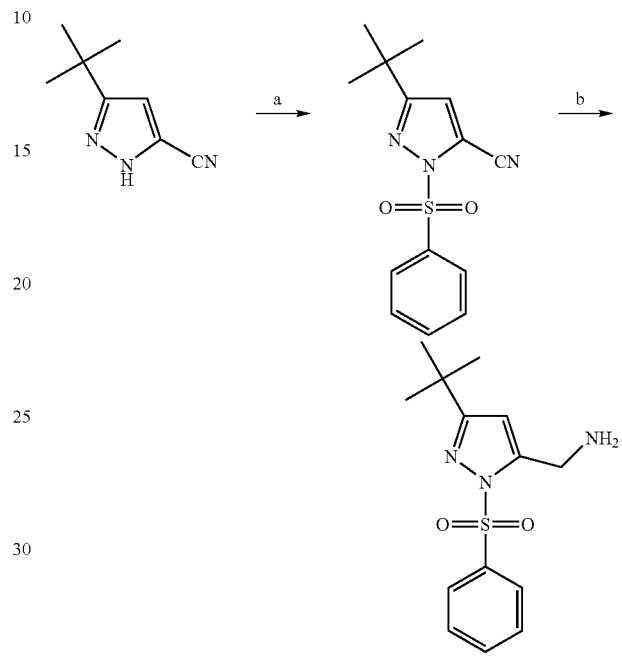

Step a: To a solution of tert-butyl (1-amino-3-(trifluoromethyl)-1H-pyrazol-5-yl)methylcarbamate (2 g, 0.0071 mol) in methanol (15 ml), picolinaldehyde (1.14 g (1 ml), 0.016 mol, 1.5 eq) taken in methanol (5 ml) was added. Then the reaction mixture was acidified with acetic acid (0.2 ml, catalytic) and heated to reflux for 24 hrs. Progress of the reaction was monitored by TLC (10% ethyl acetate/hexane, $R_f$~0.4). On completion of the reaction, methanol was distilled off completely. Residue was taken in ice water (200 ml) and the product extracted with ethyl acetate (4×50 ml). Combined extract was washed with water (2×50 ml), dried over sodium sulfate and the ethyl acetate was distilled off completely. Crude obtained was recrystalised from hexane (10 ml) to yield the required product as liquid (2 g, 76% yield).

Step b: To a solution of step-a product (2 g, 0.0054 mol) in methanol (20 ml, 10 times) cooled to at 0° C., NaBH$_4$ (0.2 g, 0.0054 mol, 1 eq) was added slowly. Overall reaction mixture was allowed to stir for 1 hr at RT. Progress of the reaction was monitored by TLC (20% ethyl acetate/hexane, $R_f$~0.2). On completion of the reaction, methanol was distilled off completely. Residue was taken in cold water (100 ml) and the product extracted with ethyl acetate (5×50 ml). Combined extract was washed with water (2×50 ml), dried over sodium sulfate and concentrated under reduced pressure. Crude obtained was purified by column chromatography (silica gel, 10% ethyl acetate/hexane) to yield the required product pale yellow colored solid (1.1 g, 57% yield).

Step c: To a solution of the Boc compound step b product (1.1 g) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, $R_f$~0.2). On completion of the reaction, DCM was distilled off completely. Residue was taken in cold water (200 ml), basified with saturated NaHCO$_3$ solution and the product extracted with ethyl acetate (4×50 ml). Combined extract was washed with water (2×50 ml), dried over sodium sulfate and concentrated under reduced pressure. Crude obtained was purified by column chromatography (silica gel, 10% ethyl acetate/hexane) to yield the required product as a white solid (0.425 g, 53% yield).

9.9 Synthesis (3-tert-butyl-1-(phenylsulfonyl)-1H-pyrazol-5-yl)methanamine (employed for the synthesis of example compound no. 108)

Step a: To a stirred solution of 3-tert-butyl-1H-pyrazole-5-carbonitrile (3 g, 20 mmol) in dichloromethane (30 ml, 10 times) TEA (2.44 g (3.36 ml), 24 mmol, 1.2 eq) was added at 0° C. Then phenylsulfonyl chloride (2.84 g (2 ml), 10 mmol, 0.8 eq) was added at 0° C. and the reaction mass was stirred for 12 h at room temperature. Progress of the reaction was monitored by TLC (20% ethyl acetate-hexane, $R_f$~0.6). On completion of the reaction, ice water (20 ml) was added to reaction mixture, organic layer was separated and washed with 1N HCl (2×20 ml followed by with water (2×15 ml), Dried the contents over sodium sulfate, concentrated under reduced pressure and the crude obtained was recrystallised from hexane to yield the required product as an off white solid (4 g, 68%).

Step b: To a solution of step-a product (2.3 g, 7 mmol) in THF (23 ml, 10 times) Boran-DMS (1.81 g (23.8 ml, 20 mmol, 3 eq) was added dropwise at 0-5° C. Then the reaction mixture was heated to 80° C. and stirred for 5 h. Progress of the reaction mixture was monitored by TLC (75% ethyl acetate-hexane, $R_f$~0.6). On completion of the reaction, quenched the reaction mixture with dilute HCl below 5° C. and stirred the contents for 12 h. Again TLC was monitored (75% ethyl acetate-hexane, $R_f$~0.4). Then the reaction contents were poured in ice water (100 ml) and the compound extracted with ethyl acetate (4×40 ml). Aqueous layer was basified with 2N NaOH solution at 0-5° C. and the compound extracted with ethyl acetate (5×20 ml). The combined extract was washed with water (2×50 ml), dried over sodium sulfate and concentrated under reduced pressure to obtain the crude product as pale yellow colored liquid (750 mg).

Synthesis of the Exemplary Compounds:
1. Preparation of Amides (A=CR$^{5b}$)

General directions for reacting amines of general formula (II) with carboxylic acids of general formula (III) or carboxylic acid derivatives of general formula (IV) to form compounds of general formula (I), wherein A=CR$^{5b}$ (amides), as in scheme 1a (step j09).

1.1 Method A:

The acid of general formula (III) (1 equivalent), the amine of general formula (II) (1.2 equivalents) and EDCI (1.2 equivalents) are stirred in DMF (10 mmol of acid/20 ml) for 12 hours at RT and water is subsequently added thereto. The reaction mixture is repeatedly extracted with EE, the aqueous phase is saturated with NaCl and subsequently reextracted with EE. The combined organic phases are washed with 1 N HCl and brine, dried over magnesium sulphate and the solvent is removed under vacuum. The residue is purified by means of flash chromatography (SiO$_2$, EE/hexane in different ratios such as 1:2) and the product (I) is in this way obtained.

1.2 Method B:

The acid of general formula (III) (1 equivalent) and the amine of general formulae (II) (1.1 equivalents) are dissolved in dichloromethane (1 mmol of acid in 6 ml) and mixed with EDCI (1.5 equivalents), HOBt (1.4 equivalents) and triethylamine (3 equivalents) at 0° C. The reaction mixture is stirred for 20 h at room temperature and the crude product is purified by means of column chromatography (SiO$_2$, n-hexane/EE in different ratios such as 2:1) and (I) is in this way obtained.

1.3 Method C:

The acid of general formula (III) (1 equivalent) is first mixed with a chlorinating agent, preferably with thionyl chloride and the mixture obtained in this way is boiled under reflux and the acid (III) is in this way converted into the corresponding acid chloride (IV). The amine of general formulae (II) (1.1 equivalents) is dissolved in dichloromethane (1 mmol of acid in 6 ml) and mixed with triethylamine (3 equivalents) at 0° C. The reaction mixture is stirred for 20 h at room temperature and the crude product is purified by means of column chromatography (SiO$_2$, n-hexane/EE in different ratios such as 2:1) and (I) is in this way obtained.

1.4 Method D:

The phenyl ester (IVa) obtained (1 equivalent) and the corresponding amine (II) (1.1 equivalents) are dissolved in THF (10 mmol of the reaction mixture in 120 ml) and stirred for 16 h at room temperature after addition of DBU (1.5 equivalents). After removal of the solvent under vacuum, the residue obtained is purified by means of flash chromatography (SiO$_2$, EE/hexane in different ratios such as 1:1) and (I) is in this way obtained.

The following exemplary compounds I-56, 66-80, 117-121, 124-125, 127-138, 140-143 and 145-147 were obtained using one of the methods described hereinbefore.

1 N-((3-tert-butyl-1H-pyrazol-5-yl)methyl)-2-(3-fluoro-4-(methylsulphonamido)phenyl)propanamide
2 (S)—N-((3-tert-butyl-1H-pyrazol-5-yl)methyl)-2-(3-fluoro-4-(methylsulphonamido)phenyl)propanamide
3 N-((3-tert-butyl-1-methyl-1H-pyrazol-5-yl)methyl)-2-(3-fluoro-4-(methylsulphonamido)phenyl)propanamide
4 (S)—N-((3-tert-butyl-1-methyl-1H-pyrazol-5-yl)methyl)-2-(3-fluoro-4-(methylsulphonamido)phenyl)propanamide
5 N-((3-tert-butyl-1-hexyl-1H-pyrazol-5-yl)methyl)-2-(3-fluoro-4-(methylsulphonamido)phenyl)propanamide
6 (S)—N-((3-tert-butyl-1-hexyl-1H-pyrazol-5-yl)methyl)-2-(3-fluoro-4-(methylsulphonamido)phenyl)propanamide
7 N-((3-tert-butyl-1-cyclohexyl-1H-pyrazol-5-yl)methyl)-2-(3-fluoro-4-(methylsulphonamido)phenyl)propanamide
8 (S)—N-((3-tert-butyl-1-cyclohexenyl-1H-pyrazol-5-yl)methyl)-2-(3-fluoro-4-(methylsulphonamido)phenyl)propanamide
9 2-(3-fluoro-4-(methylsulphonamido)phenyl)-N-((3-methyl-1-phenyl-1H-pyrazol-5-yl)methyl)propanamide
10 N-((3-chloro-1-phenyl-1H-pyrazol-5-yl)methyl)-2-(3-fluoro-4-(methylsulphonamido)phenyl)propanamide
11 2-(3-fluoro-4-(methylsulphonamido)phenyl)-N-((3-(4-fluorophenyl)-1-phenyl-1H-pyrazol-5-yl)methyl)propanamide
12 N-((3-tert-butyl-1-p-tolyl-1H-pyrazol-5-yl)methyl)-2-(3-fluoro-4-(methylsulphonamido)phenyl)propanamide
13 N-((3-tert-butyl-1-(4-tert-butylphenyl)-1H-pyrazol-5-yl)methyl)-2-(3-fluoro-4-(methylsulphonamido)phenyl)propanamide
14 N-((3-tert-butyl-1-(4-chlorophenyl)-1H-pyrazol-5-yl)methyl)-2-(3-fluoro-4-(methylsulphonamido)phenyl)propanamide
15 (S)—N-((3-tert-butyl-1-(4-chlorophenyl)-1H-pyrazol-5-yl)methyl)-2-(3-fluoro-4-(methylsulphonamido)phenyl)propanamide
16 N-((3-tert-butyl-1-(3-chlorophenyl)-1H-pyrazol-5-yl)methyl)-2-(3-fluoro-4-(methylsulphonamido)phenyl)propanamide
17 (S)—N-((3-tert-butyl-1-(3-chlorophenyl)-1H-pyrazol-5-yl)methyl)-2-(3-fluoro-4-(methylsulphonamido)phenyl)propanamide
18 N-((3-tert-butyl-1-(3-chloro-4-fluorophenyl)-1H-pyrazol-5-yl)methyl)-2-(3-fluoro-4-(methylsulphonamido)phenyl)propanamide
19 (E)-N-((3-tert-butyl-1-(4-methylstyryl)-1H-pyrazol-5-yl)methyl)-2-(3-fluoro-4-(methylsulphonamido)phenyl)propanamide
20 N-((3-tert-butyl-1-(4-methoxyphenyl)-1H-pyrazol-5-yl)methyl)-2-(3-fluoro-4-(methylsulphonamido)phenyl)propanamide
21 N-((1-(4-chlorophenyl)-3-(trifluoromethyl)-1H-pyrazol-5-yl)methyl)-2-(3-fluoro-4-(methylsulphonamido)phenyl)propanamide
22 (R)—N-((1-(4-chlorophenyl)-3-(trifluoromethyl)-1H-pyrazol-5-yl)methyl)-2-(3-fluoro-4-(methylsulphonamido)phenyl)propanamide
23 (S)—N-((1-(4-chlorophenyl)-3-(trifluoromethyl)-1H-pyrazol-5-yl)methyl)-2-(3-fluoro-4-(methylsulphonamido)phenyl)propanamide
24 N-((1-(3-chlorophenyl)-3-(trifluoromethyl)-1H-pyrazol-5-yl)methyl)-2-(3-fluoro-4-(methylsulphonamido)phenyl)propanamide
25 (R)—N-((1-(3-chlorophenyl)-3-(trifluoromethyl)-1H-pyrazol-5-yl)methyl)-2-(3-fluoro-4-(methylsulphonamido)phenyl)propanamide
26 (S)—N-((1-(3-chlorophenyl)-3-(trifluoromethyl)-1H-pyrazol-5-yl)methyl)-2-(3-fluoro-4-(methylsulphonamido)phenyl)propanamide
27 N-((3-tert-butyl-1-(3-chlorophenyl)-1H-pyrazol-5-yl)methyl)-2-(3-methoxy-4-(methylsulphonamido)phenyl)propanamide
28 N-((1-(3-chlorophenyl)-3-(trifluoromethyl)-1H-pyrazol-5-yl)methyl)-2-(3-methoxy-4-(methylsulphonamido)phenyl)propanamide
29 N-((3-tert-butyl-1-(3-chlorophenyl)-1H-pyrazol-5-yl)methyl)-2-(3,5-difluoro-4-(methylsulphonamido)phenyl)propanamide
30 N-((1-(3-chlorophenyl)-3-(trifluoromethyl)-1H-pyrazol-5-yl)methyl)-2-(3,5-difluorophenyl)propanamide
31 2-(4-bromo-3-fluorophenyl)-N-((1-(3-chlorophenyl)-3-(trifluoromethyl)-1H-pyrazol-5-yl)methyl)propanamide
32 N-((3-tert-butyl-1-(3-chlorophenyl)-1H-pyrazol-5-yl)methyl)-2-(4-isobutylphenyl)propanamide
33 N-((3-tert-butyl-1-(3-chlorophenyl)-1H-pyrazol-5-yl)methyl)-2-(3-fluoro-4-(methylsulphonamidomethyl)phenyl)propanamide
34 N-((1-(3-chlorophenyl)-3-(trifluoromethyl)-1H-pyrazol-5-yl)methyl)-2-(3-fluoro-4-(furan-3-yl)phenyl)propanamide
35 N-((3-tert-butyl-1-(3-chlorophenyl)-1H-pyrazol-5-yl)methyl)-2-(2-fluorobiphenyl-4-yl)propanamide
36 N-((1-(3-chlorophenyl)-3-(trifluoromethyl)-1H-pyrazol-5-yl)methyl)-2-(4-(1,2-dihydroxyethyl)-3-fluorophenyl)propanamide
37 4-(1-((1-(3-chlorophenyl)-3-(trifluoromethyl)-1H-pyrazol-5-yl)methylamino)-1-oxopropan-2-yl)-2-fluorobenzamide
38 4-(1-((1-(3-chlorophenyl)-3-(trifluoromethyl)-1H-pyrazol-5-yl)methylamino)-1-oxopropan-2-yl)-N-ethylbenzamide
39 4-(1-((1-(3-chlorophenyl)-3-(trifluoromethyl)-1H-pyrazol-5-yl)methylamino)-1-oxopropan-2-yl)-2-fluoro-N-phenylbenzamide
40 4-(1-((1-(3-chlorophenyl)-3-(trifluoromethyl)-1H-pyrazol-5-yl)methylamino)-1-oxopropan-2-yl)-N-(4-fluorophenyl)benzamide
41 4-(1-((1-(3-chlorophenyl)-3-(trifluoromethyl)-1H-pyrazol-5-yl)methylamino)-1-oxopropan-2-yl)-N-(4-(trifluoromethyl)phenyl)benzamide
42 4-(1-((1-(3-chlorophenyl)-3-(trifluoromethyl)-1H-pyrazol-5-yl)methylamino)-1-oxopropan-2-yl)-N-(pyridin-4-yl)benzamide

| | |
|---|---|
| 43 | N-((1-(3-chlorophenyl)-3-(trifluoromethyl)-1H-pyrazol-5-yl)methyl)-2-(4-(trifluormethoxy)phenyl)propanamide |
| 44 | N-((1-(3-chlorophenyl)-3-(trifluoromethyl)-1H-pyrazol-5-yl)methyl)-2-(3,5-dibromo-4-hydroxyphenyl)acetamide |
| 45 | N-((1-(3-chlorophenyl)-3-(trifluoromethyl)-1H-pyrazol-5-yl)methyl)-2-(3,5-dibromo-4-hydroxyphenyl)propanamide |
| 46 | N-((3-tert-butyl-1-(3-chlorophenyl)-1H-pyrazol-5-yl)methyl)-2-(3,5-difluoro-4-hydroxyphenyl)propanamide |
| 47 | N-((1-(3-chlorophenyl)-3-(trifluoromethyl)-1H-pyrazol-5-yl)methyl)-2-(3,5-difluoro-4-methoxyphenyl)propanamide |
| 48 | N-((3-tert-butyl-1-(3-chlorophenyl)-1H-pyrazol-5-yl)methyl)-2-(4-methoxy-3,5-dimethylphenyl)acetamide |
| 49 | N-((3-tert-butyl-1-(3-chlorophenyl)-1H-pyrazol-5-yl)methyl)-2-(4-(N,N-dimethylsulphamoyl)-3-fluorophenyl)propanamide |
| 50 | N-((1-(3-chlorophenyl)-3-(trifluoromethyl)-1H-pyrazol-5-yl)methyl)-2-(4-(4-chlorophenylamino)phenyl)propanamide |
| 51 | N-((1-(3-chlorophenyl)-3-(trifluoromethyl)-1H-pyrazol-5-yl)methyl)-2-(4-(4-methoxyphenylamino)phenyl)propanamide |
| 52 | 2-(4-amino-3,5-difluorophenyl)-N-((1-(3-chlorophenyl)-3-(trifluoromethyl)-1H-pyrazol-5-yl)methyl)propanamide |
| 53 | 2-(4-acetamido-3-fluorophenyl)-N-((1-(3-chlorophenyl)-3-(trifluoromethyl)-1H-pyrazol-5-yl)methyl)propanamide |
| 54 | N-(4-(1-((1-(3-chlorophenyl)-3-(trifluoromethyl)-1H-pyrazol-5-yl)methylamino)-1-oxopropan-2-yl)-2-fluorophenyl)benzamide |
| 55 | N-((3-tert-butyl-1-(3-chlorophenyl)-1H-pyrazol-5-yl)methyl)-2-[4-(1,1-dioxidoisothiazolidin-2-yl)-3-fluorophenyl]propanamide |
| 56 | N-((3-tert-butyl-1-(3-chlorophenyl)-1H-pyrazol-5-yl)methyl)-2-(4-(N,N-dimethylsulphamoyl)-3-fluorophenyl)propanamide |
| 66 | N-((3-tert-butyl-1-(3-chlorophenyl)-1H-pyrazol-5-yl)methyl)-2-(3-fluoro-4-(methylsulphonamido)phenyl)-2-(3-fluorophenyl)acetamide |
| 67 | N-((3-tert-butyl-1-(3-chlorophenyl)-1H-pyrazol-5-yl)methyl)-2-cyclohexyl-2-(3-fluoro-4-(methylsulphonamido)phenyl)acetamide |
| 68 | N-((3-tert-butyl-1-(3-chlorophenyl)-1H-pyrazol-5-yl)methyl)-2-(3-fluoro-4-(methylsulphonamido)phenyl)-2-p-tolylacetamide |
| 69 | N-((3-tert-butyl-1-(3-chlorophenyl)-1H-pyrazol-5-yl)methyl)-2-(3-chloro-4-(methylthio)phenyl)propanamide |
| 70 | N-((3-tert-butyl-1-(3-chlorophenyl)-1H-pyrazol-5-yl)methyl)-2-(3-chloro-4-(methylsulphonyl)phenyl)propanamide |
| 71 | N-((3-tert-butyl-1-(3-chlorophenyl)-1H-pyrazol-5-yl)methyl)-2-(3-fluoro-4-(methylthio)phenyl)propanamide |
| 72 | N-((3-tert-butyl-1-(3-chlorophenyl)-1H-pyrazol-5-yl)methyl)-2-(3-fluoro-4-(methylsulphonyl)phenyl)propanamide |
| 73 | N-((3-tert-butyl-1-(3-chlorophenyl)-1H-pyrazol-5-yl)methyl)-2-(3-fluorophenyl)acetamide |
| 74 | N-((1-(3-chlorophenyl)-3-(trifluoromethyl)-1H-pyrazol-5-yl)methyl)-2-(3-fluorophenyl)acetamide |
| 75 | N-[[5-tert-butyl-2-(3-chlorophenyl)-2H-[1,2,4]triazol-3-yl]-methyl]-2-[3-fluoro-4-(methanesulphonamido)phenyl]propionamide |
| 76 | N-[[2-(3-chlorophenyl)-5-(trifluoromethyl)-2H-[1,2,4]triazol-3-yl]-methyl]-2-[3-fluoro-4-(methanesulphonamido)phenyl]propionamide |
| 77 | N-[[5-tert-butyl-2-cyclohexyl-2H-[1,2,4]triazol-3-yl)-methyl]-2-[3-fluoro-4-(methanesulphonamido)phenyl]propionamide |
| 78 | N-[[2-cyclohexyl-5-(trifluoromethyl)-2H-[1,2,4]triazol-3-yl]-methyl]-2-[3-fluoro-4-(methanesulphonamido)phenyl]propionamide |
| 79 | N-[(5-tert-butyl-2-pyridin-3-yl-2H-[1,2,4]triazol-3-yl)-methyl]-2-[3-fluoro-4-(methanesulphonamido)phenyl]propionamide |
| 80 | 2-[3-fluoro-4-(methanesulphonamido)phenyl]-N-[[2-pyridin-3-yl-5-(trifluoromethyl)-2H-[1,2,4]triazol-3-yl]methyl]propionamide |
| 117 | N-((1-(3-chlorophenyl)-3-(trifluoromethyl)-1H-pyrazol-5-yl)methyl)-2-(3-fluorophenyl)-2-methylpropanamide |
| 118 | N-((3-tert-butyl-1-(3-chlorophenyl)-1H-pyrazol-5-yl)methyl)-1-(3-fluorophenyl)cyclopropancarboxamide |
| 119 | N-((1-(3-chlorophenyl)-3-(trifluoromethyl)-1H-pyrazol-5-yl)methyl)-1-(3-fluorophenyl)cyclobutancarboxamide |
| 120 | N-((1-(3-chlorophenyl)-3-(trifluoromethyl)-1H-pyrazol-5-yl)methyl)-1-(3-fluorophenyl)cyclopentancarboxamide |
| 121 | N-((1-(3-chlorophenyl)-3-(trifluoromethyl)-1H-pyrazol-5-yl)methyl)-1-(3-fluorophenyl)cyclohexancarboxamide |
| 124 | N-((1-(3-chloro-4-fluorophenyl)-3-(trifluoromethyl)-1H-pyrazol-5-yl)methyl)-2-(3-fluoro-4-(methylsulfonylmethyl)phenyl)propanamide |
| 125 | N-((3-tert-butyl-1-(3-chlorophenyl)-1H-pyrazol-5-yl)methyl)-2-(4-cyclopropyl-3-fluorophenyl)propanamide |
| 127 | N-((3-tert-butyl-1-(pyridin-2-yl)-1H-pyrazol-5-yl)methyl)-2-(3-fluoro-4-(methylsulfonamidmethyl)phenyl)propanamide |
| 128 | N-((1-(3-chlorophenyl)-3-cyclopropyl-1H-pyrazol-5-yl)methyl)-2-(3-fluoro-4-(methylsulfonylmethyl)phenyl)propanamide |
| 129 | 2-(3-fluoro-4-(methylsulfonamidmethyl)phenyl)-N-((1-(pyridin-2-ylmethylamino)-3-(trifluoromethyl)-1H-pyrazol-5-yl)methyl)propanamide |
| 130 | N-((1-(3-chlorophenyl)-4-methyl-3-(trifluoromethyl)-1H-pyrazol-5-yl)methyl)-2-(3-fluorophenyl)acetamide |
| 131 | 2-(3-fluorophenyl)-N-((1-pentyl-3-(trifluoromethyl)-1H-pyrazol-5-yl)methyl)acetamide |
| 132 | 2-(3-fluorophenyl)-N-((1-(4-methoxybenzyl)-3-(trifluoromethyl)-1H-pyrazol-5-yl)methyl)acetamide |
| 133 | N-((3-tert-butyl-1-(2,2,2-trifluoroethylamino)-1H-pyrazol-5-yl)methyl)-2-(3-fluorophenyl)acetamide |
| 134 | N-((1-(3-chlorophenyl)-4-methyl-3-(trifluoromethyl)-1H-pyrazol-5-yl)methyl)-2-(3-fluoro-4-(methylsulfonamid-methyl)phenyl)propanamide |
| 135 | N-((3-tert-butyl-1-(3-chlorophenyl)-1H-1,2,4-triazol-5-yl)methyl)-2-(3-fluorophenyl)acetamide |
| 136 | 2-(3-fluorophenyl)-N-((1-(pyridin-3-yl)-3-(trifluoromethyl)-1H-pyrazol-5-yl)methyl)acetamide |
| 137 | N-((1-cyclohexyl-3-(trifluoromethyl)-1H-pyrazol-5-yl)methyl)-2-(3-fluoro-4-(methylsulfonamidmethyl)phenyl)propanamide |
| 138 | 2-(3-fluoro-4-(methylsulfonamidmethyl)phenyl)-N-((1-(tetrahydro-2H-pyran-4-yl)-3-(trifluoromethyl)-1H-pyrazol-5-yl)methyl)propanamide |
| 140 | N-((1-(3-chlorophenyl)-3-(trifluoromethyl)-1H-pyrazol-5-yl)methyl)-2-(3-fluoro-4-(trifluoromethyl)phenyl)acetamide |
| 141 | N-((1-(3-chlorophenyl)-3-(trifluoromethyl)-1H-pyrazol-5-yl)methyl)-2-(3-fluoro-4-(trifluoromethyl)phenyl)propanamide |
| 142 | N-((3-tert-butyl-1-(3-chlorophenyl)-1H-pyrazol-5-yl)methyl)-2-(3-fluoro-4-((2-methoxyethoxy)methyl)phenyl)propanamide |
| 143 | 4-(1-((1-(3-chlorophenyl)-3-(trifluoromethyl)-1H-pyrazol-5-yl)methylamino)-1-oxopropan-2-yl)-N-phenylbenzamide |
| 145 | N-((1-(3-chlorophenyl)-3-(trifluoromethyl)-1H-pyrazol-5-yl)methyl)-2-(3-fluoro-4-(methylsulfonamid)phenyl)-3-phenylpropanamide |
| 146 | N-(5-((2-(3-fluorophenyl)acetamide)methyl)-3-(trifluoromethyl)-1H-pyrazol-1-yl)benzamide |
| 147 | N-((1-(3-chlorophenyl)-3-(trifluoromethyl)-1H-pyrazol-5-yl)methyl)-2-(3,5-difluoro-4-hydroxyphenyl)acetamide |

2. Preparation of Ureas (A=N)

General directions for reacting amines of general formula (II) or (VI) with phenyl chloroformate to form compounds of formula (V) or (VIa) (step j07 and step v1, respectively) and subsequent reaction of compounds of formula (V) with amines of general formula (VI) or of compounds of formula (VIa) with amines of general formula (II) to form compounds of general formula (I), wherein A=N, as in scheme 1a and 1c (step j08 and step v2, respectively):

Step j07/step v1: The amine of general formula (II) or (VI) (1 equivalent) is placed in dichloromethane (10 mmol of amine in 70 ml) and phenyl chloroformate (1.1 equivalents) is added thereto at room temperature and the mixture is stirred for 30 min. After removal of the solvent under vacuum, the residue is purified by means of flash chromatography ($SiO_2$, diethyl ether/hexane in different ratios such as 1:2) and (V) or (VIa) is in this way obtained.

Step j08/step v2: The carbamic acid phenyl ester (V) or (VIa) obtained (1 equivalent) and the corresponding amine (VI) or (II) (1.1 equivalents) are dissolved in THF (10 mmol of the reaction mixture in 120 ml) and stirred for 16 h at room temperature after addition of DBU (1.5 equivalents). After removal of the solvent under vacuum, the residue obtained is purified by means of flash chromatography ($SiO_2$, EE/hexane in different ratios such as 1:1) and (I) is in this way obtained.

The following exemplary compounds 57-65, 122-123, 126, 139 and 144 were obtained using one of the methods described hereinbefore.

| | |
|---|---|
| 57 | 1-((3-tert-butyl-1-(3-chlorophenyl)-1H-pyrazol-5-yl)methyl)-3-(3,5-difluorophenyl)urea |
| 58 | 1-(4-bromo-3-fluorophenyl)-3-((3-tert-butyl-1-(3-chlorophenyl)-1H-pyrazol-5-yl)methyl)urea |
| 59 | 1-((3-tert-butyl-1-(3-chlorophenyl)-1H-pyrazol-5-yl)methyl)-3-(4-(trifluoromethyl)phenyl)urea |
| 60 | 1-((3-tert-butyl-1-(3-chlorophenyl)-1H-pyrazol-5-yl)methyl)-3-(4-(difluormethoxy)phenyl)urea |
| 61 | 1-((3-tert-butyl-1-(3-chlorophenyl)-1H-pyrazol-5-yl)methyl)-3-(3,5-difluoro-4-methoxyphenyl)urea |
| 62 | 1-((3-tert-butyl-1-(3-chlorophenyl)-1H-pyrazol-5-yl)methyl)-3-(4-methoxy-3,5-dimethylphenyl)urea |
| 63 | 1-((3-tert-butyl-1-(3-chlorophenyl)-1H-pyrazol-5-yl)methyl)-3-(3-fluoro-4-(methylsulphonyl)phenyl)urea |
| 64 | 1-((3-tert-butyl-1-(3-chlorophenyl)-1H-pyrazol-5-yl)methyl)-3-(4-(phenylamino)phenyl)urea |
| 65 | 4-(3-((3-tert-butyl-1-(3-chlorophenyl)-1H-pyrazol-5-yl)methyl)-ureido)-N-(4-fluorophenyl)benzamide |
| 122 | 1-((3-tert-butyl-1-(4-fluorophenyl)-1H-pyrazol-5-yl)methyl)-3-(3-fluorophenyl)urea |
| 123 | 3-((1-(3-chlorophenyl)-3-(trifluoromethyl)-1H-pyrazol-5-yl)methyl)-1-(3-fluorophenyl)-1-methylurea |
| 126 | 1-((1-(3-chlorophenyl)-3-(trifluoromethyl)-1H-pyrazol-5-yl)methyl)-3-(4-cyclopropyl-3-fluorophenyl)urea |
| 139 | 1-((1-(3-chlorophenyl)-3-(trifluoromethyl)-1H-pyrazol-5-yl)methyl)-3-(4-(cyclopropylethynyl)-3-fluorophenyl)urea |
| 144 | 1-((3-tert-butyl-1-(3-chlorophenyl)-1H-pyrazol-5-yl)methyl)-3-(3-fluoro-4-morpholinphenyl)urea |

The methods illustrated hereinbefore for synthesising the compounds according to the invention enable a person skilled in the art also to synthesise the following exemplary compounds 81-116:

| | |
|---|---|
| 81 | N-[[5-tert-butyl-2-(6-chloropyridin-2-yl)-2H-pyrazol-3-yl]-methyl]-2-[3-fluoro-4-(methanesulphonamido)phenyl]propionamide |
| 82 | N-[[5-tert-butyl-2-(3,3-difluorocyclobutanecarbonyl)-2H-pyrazol-3-yl]-methyl]-2-[3-fluoro-4-(methanesulphonamido)phenyl]propionamide |
| 83 | N-[[2-(3-chlorophenyl)-4-methyl-5-(trifluoromethyl)-2H-pyrazol-3-yl]-methyl]-2-[3-fluoro-4-(methanesulphonamido)phenyl]propionamide |
| 84 | N-[[2-(dipropylamino)-5-(trifluoromethyl)-2H-pyrazol-3-yl]-methyl]-2-[4-(methanesulphonamido)-3-methoxyphenyl]propionamide |
| 85 | N-[[2-(dipropylamino)-5-(trifluoromethyl)-2H-pyrazol-3-yl]-methyl]-2-[3-fluoro-4-(hydroxymethyl)phenyl]propionamide |
| 86 | N-[[2-(dipropylamino)-5-(trifluoromethyl)-2H-pyrazol-3-yl]-methyl]-2-[3-fluoro-4-(methanesulphonamido)phenyl]propionamide |
| 87 | N-[[2-(dipropylamino)-5-(trifluoromethyl)-2H-pyrazol-3-yl]-methyl]-2-(3-fluorophenyl)acetamide |
| 88 | 4-[1-[[2-(dipropylamino)-5-(trifluoromethyl)-2H-pyrazol-3-yl]-methylcarbamoyl]ethyl]-2-fluorobenzamide |
| 89 | 4-[1-[[2-(dipropylamino)-5-(trifluoromethyl)-2H-pyrazol-3-yl]-methylcarbamoyl]ethyl]-N-pyridin-2-yl-benzamide |
| 90 | 2-[3-fluoro-4-(hydroxymethyl)phenyl]-N-[[2-piperidin-1-yl-5-(trifluoromethyl)-2H-pyrazol-3-yl]-methyl]propionamide |
| 91 | 2-[3-fluoro-4-(2-hydroxyethyl)phenyl]-N-[[2-piperidin-1-yl-5-(trifluoromethyl)-2H-pyrazol-3-yl]-methyl]propionamide |
| 92 | 2-[3-fluoro-4-(methanesulphonamido)phenyl]-N-[[2-piperidin-1-yl-5-(trifluoromethyl)-2H-pyrazol-3-yl]-methyl]propionamide |
| 93 | 2-[4-(methanesulphonamido)-3-methoxyphenyl]-N-[[2-piperidin-1-yl-5-(trifluoromethyl)-2H-pyrazol-3-yl]-methyl]propionamide |
| 94 | 2-[4-(1,2-dihydroxyethyl)-3-fluorophenyl]-N-[[2-piperidin-1-yl-5-(trifluoromethyl)-2H-pyrazol-3-yl]-methyl]propionamide |
| 95 | 2-(3-fluorophenyl)-N-[[2-piperidin-1-yl-5-(trifluoromethyl)-2H-pyrazol-3-yl]-methyl]acetamide |
| 96 | 2-fluoro-4-[1-[[2-piperidin-1-yl-5-(trifluoromethyl)-2H-pyrazol-3-yl]-methylcarbamoyl]ethyl]benzamide |
| 97 | 2-[3-fluoro-4-(methanesulphonamido)phenyl]-N-[[2-[(4-fluorophenyl)methylmethylamino]-5-(trifluoromethyl)-2H-pyrazol-3-yl]-methyl]propionamide |
| 98 | N-[[5-tert-butyl-2-(2,2,2-trifluoroethylamino)-2H-pyrazol-3-yl]-methyl]-2-[3-fluoro-4-(methanesulphonamido)phenyl]propionamide |
| 99 | N-[[2-butoxy-5-(trifluoromethyl)-2H-pyrazol-3-yl]-methyl]-2-[3-fluoro-4-(hydroxymethyl)phenyl]propionamide |
| 100 | N-[[2-butoxy-5-(trifluoromethyl)-2H-pyrazol-3-yl]-methyl]-2-[3-fluoro-4-(methanesulphonamido)phenyl]propionamide |
| 101 | N-[[2-butoxy-5-(trifluoromethyl)-2H-pyrazol-3-yl]-methyl]-2-[4-(methanesulphonamido)-3-methoxyphenyl]propionamide |
| 102 | N-[(2-butoxy-5-tert-butyl-2H-pyrazol-3-yl)-methyl]-2-(3-fluorophenyl)acetamide |
| 103 | N-[[2-cyclopentyloxy-5-(trifluoromethyl)-2H-pyrazol-3-yl]-methyl]-2-[3-fluoro-4-(methanesulphonamido)phenyl]propionamide |
| 104 | N-[[2-cyclopentyloxy-5-(trifluoromethyl)-2H-pyrazol-3-yl]-methyl]-2-[4-(methanesulphonamido)-3-methoxyphenyl]propionamide |
| 105 | 2-(3-fluorophenyl)-N-[[2-[(4-methoxyphenyl)methoxy]-5-(trifluoromethyl)-2H-pyrazol-3-yl]-methyl]acetamide |
| 106 | N-[[5-tert-butyl-2-(3-cyano-5-fluorophenoxy)-2H-pyrazol-3-yl]-methyl]-2-(3-fluorophenyl)acetamide |
| 107 | N-[[2-(cyclohexylsulphanyl)-5-(trifluoromethyl)-2H-pyrazol-3-yl]-methyl]-2-[3-fluoro-4-(methanesulphonamido)phenyl]propionamide; |
| 108 | N-[[2-(benzenesulphonyl)-5-tert-butyl-2H-pyrazol-3-yl]-methyl]-2-(3-fluorophenyl)acetamide |
| 109 | N-[[2-cyclohexyl-5-(trifluoromethyl)-2H-[1,2,4]triazol-3-yl]-methyl]-2-[4-(methanesulphonamido)-3-methoxyphenyl]propionamide |
| 110 | N-[[2-cyclohexyl-5-(trifluoromethyl)-2H-[1,2,4]triazol-3-yl]-methyl]-2-(3-fluorophenyl)acetamide |
| 111 | 4-[1-[[2-cyclohexyl-5-(trifluoromethyl)-2H-[1,2,4]triazol-3-yl]-methylcarbamoyl]ethyl]-2-fluorobenzamide |
| 112 | 2-[3-fluoro-4-(hydroxymethyl)phenyl]-N-[[2-hexyl-5-(trifluoromethyl)-2H-[1,2,4]triazol-3-yl]-methyl]propionamide |
| 113 | 4-[1-[[2-cyclobutyl-5-(trifluoromethyl)-2H-[1,2,4]triazol-3-yl]-methylcarbamoyl]ethyl]-2-fluorobenzamide |
| 114 | N-[[5-tert-butyl-2-(3,3-difluorocyclobutanecarbonyl)-2H-[1,2,4]triazol-3-yl]-methyl]-2-[3-fluoro-4-(methanesulphonamido)phenyl]propionamide |
| 115 | N-[[5-tert-butyl-2-(3-cyano-5-fluorophenoxy)-2H-[1,2,4]triazol-3-yl]-methyl]-2-(3-fluorophenyl)acetamide |
| 116 | N-[[2-(benzenesulphonyl)-5-tert-butyl-2H-[1,2,4]triazol-3-yl]-methyl]-2-(3-fluorophenyl)acetamide |

Mass spectrometric data are cited hereinafter by way of example for the following exemplary compounds:

| Exemplary compound | [M + H] |
|---|---|
| 1 | 397.2 |
| 2 | 397.2 |
| 3 | 411.2 |
| 4 | 411.2 |
| 5 | 481.1 |
| 6 | 481.1 |
| 7 | 479.3 |
| 8 | 477.1 |
| 12 | 478.2 |
| 13 | 529.3 |
| 14 | 507.0 |
| 15 | 507.0 |
| 16 | 507.2 |
| 17 | 507.0 |
| 18 | 525.2 |
| 19 | 513.2 |
| 20 | 503.2 |
| 21 | 518.9 |
| 22 | 518.9 |
| 23 | 518.9 |
| 24 | 518.9 |
| 25 | 518.9 |
| 26 | 518.9 |
| 27 | 519.3 |
| 28 | 531.2 |
| 29 | 525.3 |
| 30 | 444.0 |
| 33 | 521.3 |
| 39 | 545.4 |

| Exemplary compound | [M + H] |
|---|---|
| 40 | 545.0 |
| 41 | 595.3 |
| 47 | 474.3 |
| 49 | 521.3 |
| 55 | 533.3 |
| 56 | 521.3 |
| 61 | 449.3 |
| 74 | 412.1 |
| 117 | 440.2 |
| 118 | 426.3 |
| 119 | 452.2 |
| 120 | 466.3 |
| 122 | 385.1 |
| 123 | 427.0 |
| 125 | 454.0 |
| 126 | 452.9 |
| 127 | 488.2 |
| 128 | 504.9 |
| 129 | 529.3 |
| 130 | 426.3 |
| 131 | 372.1 |
| 132 | 422.1 |
| 133 | 387.3 |
| 134 | 546.9 |
| 135 | 401.3 |
| 137 | 505.0 |
| 139 | 477.2 |
| 141 | 493.9 |
| 142 | 502.0 |
| 143 | 527.0 |
| 144 | 486.1 |
| 147 | 446.0 |

Pharmacological data

The affinity of the compounds according to the invention for the vanilloid receptor 1 (VR1/TRPV1 receptor) was determined as described hereinbefore (pharmacological methods I and II respectively).

The compounds according to the invention of the above-indicated formula (I) display outstanding affinity to the VR1/TRPV1 receptor (Table 1.).

In Table 1 the abbreviations below have the following meanings:

Cap=capsaicin
AG=agonist
pAG=partial agonist
pH=after pH stimulus
NADA=N-arachidonoyl dopamine
NE=no effect
FTm=formalin test carried out on mice The value after the "@" symbol indicates the concentration at which the inhibition (as a percentage) was respectively determined.

TABLE 1

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm |
|---|---|---|---|---|---|---|---|
| 1 | 25% @ 5 µM | NE | NE | | | | |
| 2 | 25% @ 5 µM | NE | NE | | | | |
| 3 | 14% @ 5 µM | 12% @ 5 µM | NE | | | | |
| 4 | 20% @ 5 µM | 9% @ 5 µM | NE | | | | |
| 5 | 76% @ 1 µM | 50.2 | 36% @ 10 µM | | 4.99 | 282 | |
| 6 | 14.5 | 27.7 | 13% @ 10 µM | | | | |
| 7 | 0.35 | 21.6 | NE | | | | |
| 12 | 5.9 | 8 | 40% @ 10 µM | | | | |
| 13 | 25.9 (15) | 75.2 (49) | | | | | |
| 14 | 7.2 | 3.7 | 25% @ 10 µM | | | | |
| 15 | 2.5 | 2.1 | 14% @ 5 µM | | | | |
| 16 | 0.2 | 0.3 | NE | 0.03 | 0.04 | 35% @ 0.625 µM | |
| 17 | 0.1 | 0.1 | 37% @ 10 µM | | | | |
| 18 | | 0.5 | 31% @ 10 µM | | 0.22 | 7.0 | |
| 19 | 819 | 44% @ 1 µM | NE | | | | |
| 20 | 2834 | 55% @ 1 µM | NE | | | | |
| 21 | 1.2 | 0.3 | 179 | | 0.12 | 27.0 | |
| 22 | 42.7 | 31.7 | 42% @ 10 µM | | | | |
| 23 | 0.4 | 0.3 | 47.1 | | | 16.13 | |
| 24 | 0.4 | 0.3 | 39.2 | | | | |
| 25 | 5.1 | 26.5 | 2,585 | | | | |
| 26 | 0.1 | 0.1 | 8.0 | | 0.1 | 8.05 | |
| 27 | 1.2 | 2.2 | NE | | 0.12 | | |
| 28 | | 0.4 | 16 | | | 665 | |
| 29 | | 1.2 | 42% @ 10µM | | 0.08 | 34% @ 2 µM | |
| 30 | | 6.3 | | | | | |
| 33 | | 4.0 | | | | | |
| 39 | | 7.2 | | | | | |
| 40 | | 0.8 | | | | | |
| 41 | | 85 | | | | | |
| 47 | | 17 | | | | | |
| 49 | | AG | AG | | | AG | AG |
| 55 | | 114 | NE | | | | |
| 56 | | AG | AG | | | AG | AG |
| 61 | | AG | | | | | |
| 73 | | AG | | | | | |
| 74 | 85 | 51.8 | | | 49 | 12% @ 2.5 µM | 1 po FTm 13% |
| 117 | | 56 | | | | | |

TABLE 1-continued

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm |
|---|---|---|---|---|---|---|---|
| 118 | | AG | | | | | |
| 119 | | 107 | | | | | |
| 120 | | 6% @ 1 μM | | | | | |
| 122 | | AG | | | | | |
| 123 | | 44% @ 5 μM | | | | | |
| 125 | | AG | | | | | |
| 126 | | 31.4 | | | | | |
| 127 | | 58.1 | | | | | |
| 128 | | 16.3 | | | | | |
| 129 | | 63.6 | | | | | |
| 130 | | 112 | | | | | |
| 131 | | 58% @ 5 μM | | | | | |
| 132 | | 34% @ 5 μM | | | | | |
| 133 | | 12% @ 5 μM | | | | | |
| 134 | | 2.5 | | | | 546 | |
| 135 | | 24% @ 5 μM | | | | | |
| 137 | | 65.1 | | | | | |
| 139 | | AG | | | | | |
| 141 | 25.5 | 13.6 | | | | 28% @ 2.5 μM | |
| 142 | | AG | | | | | |
| 143 | | 56% @ 1 μM | | | | | |
| 144 | | AG | | | | | |
| 147 | | 26 | | | | | |

The invention claimed is:

1. Substituted compounds of general formula (I)

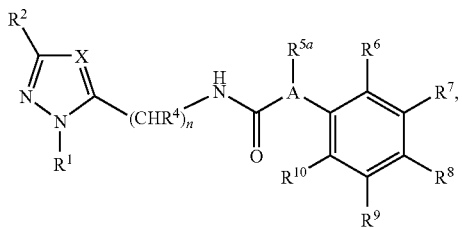

wherein

X represents $CR^3$ or N,
  wherein $R^3$ represents H; $C_{1-10}$ alkyl, saturated or unsaturated, branched or unbranched, unsubstituted or mono- or polysubstituted;

A represents N or $CR^{5b}$, n represents 1, 2, 3 or 4;

$R^0$ represents $C_{1-10}$ alkyl, saturated or unsaturated, branched or unbranched, unsubstituted or mono- or polysubstituted; $C_{3-10}$ cycloalkyl or heterocyclyl, respectively saturated or unsaturated, unsubstituted or mono- or polysubstituted; aryl or heteroaryl, respectively unsubstituted or mono- or polysubstituted; $C_{3-10}$ cycloalkyl or heterocyclyl bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted;

$R^1$ represents $C_{1-10}$ alkyl, saturated or unsaturated, branched or unbranched, unsubstituted or mono- or polysubstituted; $C_{3-10}$ cycloalkyl[1] or heterocyclyl[1], respectively saturated or unsaturated, unsubstituted or mono- or polysubstituted; aryl or heteroaryl, respectively unsubstituted or mono- or polysubstituted; $C_{3-10}$ cycloalkyl[1] or heterocyclyl[1] bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; $C(=O)-R^0$; $C(=O)-OH$; $C(=O)-OR^0$; $C(=O)-NHR^0$; $C(=O)-N(R^0)_2$; OH; $O-R^0$; SH; $S-R^0$; $S(=O)_2-R^0$; $S(=O)_2-OR^0$; $S(=O)_2-NHR^0$; $S(=O)_2-N(R^0)_2$; $NH_2$; $NHR^0$; $N(R^0)_2$; $NH-S(=O)_2-R^0$; $N(R^0)(S(=O)_2-R^0$; or $SCl_3$;

$R^2$ represents H; $R^0$; F; I; CN; $NO_2$; OH; SH; $CF_3$; $CF_2H$; $CFH_2$; $CF_2Cl$; $CFCl_2$; $CH_2CF_3$; $OCF_3$; $OCF_2H$; $OCFH_2$; $OCF_2Cl$; $OCFCl_2$; $SCF_3$; $SCF_2H$; $SCFH_2$; $SCF_2Cl$; $SCFCl_2$; $S(=O)_2-CF_3$; $S(=O)_2-CF_2H$; $S(=O)_2-CFH_2$; or $SF_5$;

$R^4$ represents H; F; Cl; Br; I; OH; $C_{1-10}$ alkyl, saturated or unsaturated, branched or unbranched, unsubstituted or mono- or polysubstituted;

$R^{5a}$ represents H; OH; $C_{1-10}$ alkyl, saturated or unsaturated, branched or unbranched, unsubstituted or mono- or polysubstituted;

$R^{5b}$ represents H or $R^0$;

or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted;

$R^6$, $R^7$, $R^9$ and $R^{10}$ each independently of one another represent H; F; Cl; Br; I; $NO_2$; CN; $CF_3$; $CF_2H$; $CFH_2$; $CF_2Cl$; $CFCl_2$; $R^0$; $C(=O)H$; $C(=O)R^0$; $CO_2H$; $C(=O)OR^0$; $CONH_2$; $C(=O)NHR^0$; $C(=O)N(R^0)_2$; OH; $OCF_3$; $OCF_2H$; $OCFH_2$; $OCF_2Cl$; $OCFCl_2$; $OR^0$; $O-C(=O)-R^0$; $O-C(=O)-O-R^0$;

O—C(=O)—NH—R⁰; O—C(=O)—N(R)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

$R^8$ represents H; F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂; wherein, if $R^8$ denotes R⁰ and R⁰ represents heteroaryl, said heteroaryl is selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl;

in which "substituted alkyl", "substituted heterocyclyl" and "substituted cycloalkyl" relate, with respect to the corresponding residues, to the substitution of one or more hydrogen atoms each independently of one another by F; Cl; Br; I; NO₂; CN; =O; =NH; =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted cycloalkyl¹" and "substituted heterocyclyl¹" relate, with respect to the corresponding residues, to the substitution of one or more hydrogen atoms each independently of one another by F; Cl; Br; I; NO₂; CN; =O; =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted aryl" relates, with respect to the corresponding residues, to the substitution of one or more hydrogen atoms each independently of one another by F; Cl; Br; I; NO₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted heteroaryl" relates, with respect to the corresponding residues, to the substitution of one or more hydrogen atoms each independently of one another by F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰;

$NR^0$—$S(=O)_2OR^0$; $NR^0$—$S(=O)_2NH_2$; $NR^0$—$S(=O)_2NHR^0$; $NR^0$—$S(=O)_2N(R^0)_2$; SH; $SCF_3$; $SCF_2H$; $SCFH_2$; $SCF_2Cl$; $SCFCl_2$; $SR^0$; $S(=O)R^0$; $S(=O)_2R^0$; $S(=O)_2OH$; $S(=O)_2OR^0$; $S(=O)_2NH_2$; $S(=O)_2NHR^0$; or $S(=O)_2N(R^0)_2$;

in the form of the free compounds; the tautomers; the N-oxides; the racemate; the enantiomers, diastereomers, mixtures of the enantiomers or diastereomers or of an individual enantiomer or diastereomer; or in the form of the salts of physiologically compatible acids or bases.

2. Substituted compounds according to claim 1, wherein $R^4$ represents H; $C_{1-10}$ alkyl, saturated or unsaturated, branched or unbranched, unsubstituted or mono- or polysubstituted with one or more substituents each selected independently of one another from the group consisting of F, Cl, Br, I, OH and O—$C_{1-4}$ alkyl;

A represents N or $CR^{5b}$;

$R^{5a}$ represents H; OH; $C_{1-10}$ alkyl, saturated or unsaturated, branched or unbranched, unsubstituted or mono- or polysubstituted with one or more substituents each selected independently of one another from the group consisting of F, Cl, Br, I, OH and O—$C_{1-4}$ alkyl;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br, I, OH and O—$C_{1-4}$ alkyl; $C_{3-10}$ cycloalkyl or heterocyclyl, respectively saturated or unsaturated, unsubstituted or mono- or polysubstituted with one or more substituents each selected independently of one another from the group consisting of F, Cl, Br, I, OH, =O and O—$C_{1-4}$ alkyl; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br; I, OH, =O and O—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; or aryl, heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$, $S(=O)_2$ OH and NH—$S(=O)_2$—$C_{1-4}$ alkyl; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$, $S(=O)_2OH$ and NH—$S(=O)_2$—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl;

or $R^{5a}$ and $R^{5b}$ form together with the carbon atom connecting them a $C_{3-10}$ cycloalkyl or a heterocyclyl, respectively saturated or unsaturated or mono- or polysubstituted with one or more substituents each selected independently of one another from the group consisting of F, Cl, Br, I, OH, =O and O—$C_{1-4}$ alkyl.

3. Substituted compounds according to claim 1, wherein $R^4$ represents H; methyl; ethyl; n-propyl; or isopropyl;

A represents N or $CR^{5b}$;

$R^{5a}$ represents H or $CH_3$, preferably H, if A represents N; or $R^{5a}$ represents H or $CH_3$, preferably H, if A represents $CR^{5b}$, wherein $R^{5b}$ represents H; or $C_{1-4}$ alkyl, saturated or unsaturated, branched or unbranched, unsubstituted; $C_{3-10}$ cycloalkyl, saturated or unsaturated, unsubstituted; or phenyl or benzyl, in each case unsubstituted or mono- or polysubstituted with one or more substituents each selected independently of one another from the group consisting of F, Cl, Br, I, $CF_3$, O—$C_{1-4}$ alkyl, $OCF_3$ and $C_{1-4}$ alkyl, or $R^{5a}$ and $R^{5b}$ form together with the carbon atom connecting them a $C_{3-10}$ cycloalkyl, saturated or unsaturated, unsubstituted or mono- or polysubstituted with one or more substituents each selected independently of one another from the group consisting of F, Cl, Br, I, OH, =O and O—$C_{1-4}$ alkyl.

4. Substituted compounds according to claim 1, wherein $R^1$ represents substructure (T1)

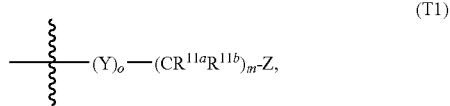

in which

Y represents C(=O), O, S, $S(=O)_2$, NH—C(=O) or $NR^{12}$, wherein $R^{12}$ represents H; $C_{1-8}$ alkyl or $S(=O)_2$—$C_{1-8}$ alkyl, in which $C_{1-8}$ alkyl can be respectively saturated or unsaturated, branched or unbranched, unsubstituted or mono- or polysubstituted with one or more substituents each selected independently of one another from the group consisting of F, Cl, Br, I, OH, O—$C_{1-4}$ alkyl, $OCF_3$, $NH_2$, NH—$C_{1-4}$ alkyl and $N(C_{1-4}$ alkyl)$_2$;

o represents 0 or 1, $R^{11a}$ and $R^{11b}$ each independently of one another represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, $N(C_{1-4}$ alkyl)$_2$, in which $C_{1-4}$ alkyl can be respectively saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$;

on the condition that if $R^{11a}$ and $R^{11b}$ are bound to the same carbon atom, only one of the substituents $R^{11a}$ and $R^{11b}$ can represent OH; $OCF_3$; $NH_2$; O—$C_{1-4}$ alkyl, NH—$C_{1-4}$ alkyl or $N(C_{1-4}$ alkyl)$_2$;

m represents 0, 1, 2, 3 or 4;

Z represents $C_{1-4}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and $S(=O)_2OH$; $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, SH, S—$C_{1-4}$ alkyl, $SCF_3$, $S(=O)_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2$OH; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, $S(=O)_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2$OH.

5. Substituted compounds according to claim 4, wherein
Y represents C(=O), O, S, $S(=O)_2$, NH—C(=O) or $NR^{12}$,
  wherein $R^{12}$ represents H; methyl; ethyl; n-propyl; isopropyl; n-butyl; sec.-butyl; tert.-butyl; $S(=O)_2$-methyl; $S(=O)_2$-ethyl;
o represents 0 or 1;
$R^{11a}$ and $R^{11b}$ each independently of one another represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; N(methyl$)_2$; NH-ethyl; N(ethyl$)_2$; or N(methyl)(ethyl);
  on the condition that if $R^{11a}$ and $R^{11b}$ are bound to the same carbon atom, only one of the substituents $R^{11a}$ and $R^{11b}$ can represent OH; $OCF_3$; O-methyl; O-ethyl; O—$(CH_2)_2$—O—$CH_3$; O—$(CH_2)_2$—OH; $NH_2$; NH-methyl; N(methyl$)_2$; NH-ethyl; N(ethyl$)_2$; or N(methyl)(ethyl);
m represents 0, 1 or 2;
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, =O, O—$C_{1-4}$ alkyl, $OCF_3$, C(=O)—OH and $CF_3$; phenyl, naphthyl, furyl, pyridyl or thienyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-8}$ alkyl, $SCF_3$, benzyl and phenyl, wherein benzyl and phenyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-4}$ alkyl and $SCF_3$; $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, benzyl, phenyl and pyridyl, wherein benzyl, phenyl and pyridyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-4}$ alkyl and $SCF_3$.

6. Substituted compounds according to claim 1, wherein
$R^2$ represents H; F; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ $S(=O)_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2$OH; $C_{3-10}$ cycloalkyl or heterocyclyl, respectively saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$, C(=O)—OH and $CF_3$; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br, I, OH, =O, $C_{1-4}$ alkyl, O—$C_{1-4}$ alkyl, $OCF_3$, C(=O)—OH and $CF_3$, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-8}$ alkyl, $SCF_3$, $S(=O)_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2$OH; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-8}$ alkyl, $SCF_3$, $S(=O)_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—

OH, CF₃, NH₂, NH(C₁₋₄ alkyl), N(C₁₋₄ alkyl)₂, SH, S—C₁₋₄ alkyl, SCF₃ and S(═O)₂OH, wherein the alkyl chain can be respectively branched or unbranched, saturated or unsaturated, unsubstituted, mono- or polysubstituted with one or more substituents each selected independently of one another from the group consisting of F, Cl, Br, I, OH, ═O and O—C₁₋₄ alkyl.

7. Substituted compounds according to claim 1, wherein R⁶ and R¹⁰ are each selected independently of one another from the group consisting of H; F; Cl; Br; I; CN; CF₃; OH; OCF₃; SH; SCF₃; C₁₋₄ alkyl, O—C₁₋₄ alkyl and NH—S(═O)₂—C₁₋₄ alkyl, in which C₁₋₄ alkyl can be respectively saturated or unsaturated, branched or unbranched, unsubstituted;

R⁷, R⁸ and R⁹ are each selected independently of one another from the group consisting of H; F; Cl; Br; I; CN; NO₂; CF₃; OH; OCF₃; SH; SCF₃; NH₂; C(═O)—NH₂; C₁₋₄ alkyl, C₁₋₄ alkyl-O—C₁₋₄ alkyl, C(═O)—NH—C₁₋₄ alkyl, O—C₁₋₄ alkyl, NH(C₁₋₄ alkyl), N(C₁₋₄ alkyl)₂, NH—C(═O)—C₁₋₄ alkyl, NH—S(═O)₂—C₁₋₄ alkyl, S—C₁₋₄ alkyl, SO₂—C₁₋₄ alkyl, SO₂—NH(C₁₋₄ alkyl), SO₂—N(C₁₋₄ alkyl)₂, in which C₁₋₄ alkyl can be respectively saturated or unsaturated, branched or unbranched, unsubstituted or mono- or polysubstituted with one or more substituents selected independently of one another from the group consisting of F, Cl, Br, I, OH, O—C₁₋₄ alkyl, OCF₃, CF₃, NH—S(═O)₂—C₁₋₄ alkyl, SH, S—C₁₋₄ alkyl, S(═O)₂—C₁₋₄ alkyl and SCF₃; C₃₋₁₀ cycloalkyl, heterocyclyl or C₃₋₁₀ cycloalkyl or heterocyclyl bridged via C₁₋₈ alkyl, respectively saturated or unsaturated, unsubstituted or mono- or polysubstituted with one or more substituents selected independently of one another from the group consisting of F, Cl, Br, I, NO₂, CN, OH, O—C₁₋₄ alkyl, OCF₃, O₁₋₄ alkyl, CF₃, NH₂, NH(C₁₋₄ alkyl), N(C₁₋₄ alkyl)₂, NH—S(═O)₂—C₁₋₄ alkyl, N(C₁₋₄ alkyl)-S(═O)₂—C₁₋₄ alkyl, SH, S—C₁₋₄ alkyl, S(═O)₂—C₁₋₄ alkyl and SCF₃, and wherein if appropriate the alkyl chain can be respectively branched or unbranched, saturated or unsaturated, mono- or polysubstituted with one or more substituents each selected independently of one another from the group consisting of F, Cl, Br; I, OH and O—C₁₋₄ alkyl; phenyl, pyridyl, furyl, thienyl, C(═O)—NH-phenyl, NH—C(═O)-phenyl, NH(phenyl), C(═O)—NH-pyridyl, NH—C(═O)-pyridyl, NH(pyridyl) or phenyl or pyridyl bridged via C₁₋₈ alkyl, wherein phenyl, pyridyl, furyl or thienyl are respectively unsubstituted or mono- or polysubstituted with one or more substituents selected independently of one another from the group consisting of F, Cl, Br, I, CN, OH, O—C₁₋₄ alkyl, OCF₃, C₁₋₄ alkyl, CF₃, SH, S—C₁₋₄ alkyl and SCF₃, and wherein if appropriate the alkyl chain can be respectively branched or unbranched, saturated or unsaturated, unsubstituted, mono- or polysubstituted with one or more substituents each selected independently of one another from the group consisting of F, Cl, Br; I, OH and O—C₁₋₄ alkyl.

8. Substituted compounds according to claim 7, wherein R⁶ and R¹⁰ represent H.

9. Substituted compounds according to claim 1, having general formula (If),

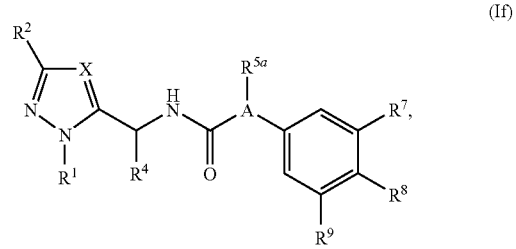

(If)

wherein
X represents CR³ or N,
wherein R³ represents H; methyl; ethyl; n-propyl; isopropyl; n-butyl; sec.-butyl; tert.-butyl; or CF₃;
A represents N or CR⁵ᵇ;
R¹ represents substructure (T1)

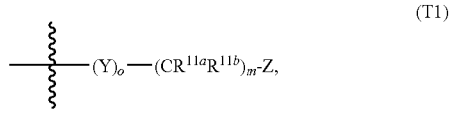

(T1)

in which
Y represents C(═O), O, S, S(═O)₂, NH—C(═O) or NR¹²,
wherein R¹² represents H; methyl; ethyl; n-propyl; isopropyl; n-butyl; sec.-butyl; tert.-butyl; S(═O)₂-methyl;
o represents 0 or 1;
R¹¹ᵃ and R¹¹ᵇ each independently of one another represent H; methyl; ethyl; n-propyl; isopropyl; n-butyl; sec.-butyl; tert.-butyl;
m represents 0, 1 or 2;
Z represents C₁₋₄ alkyl, saturated or unsaturated, branched or unbranched, unsubstituted or mono- or polysubstituted with one or more substituents each selected independently of one another from the group consisting of F, Cl, Br, I, OH, O—C₁₋₄ alkyl; C₃₋₁₀ cycloalkyl¹, saturated or unsaturated, morpholinyl, tetrahydropyranyl, piperidinyl, 4-methylpiperazinyl, piperazinyl, respectively unsubstituted or mono- or polysubstituted with one or more substituents each selected independently of one another from the group consisting of F, Cl, Br, I, OH, O—C₁₋₄ alkyl and C₁₋₄ alkyl; phenyl or pyridyl, respectively unsubstituted or mono- or polysubstituted with one or more substituents each selected independently of one another from the group consisting of F, Cl, Br, I, CN, OH, O—C₁₋₄ alkyl, OCF₃, C₁₋₄ alkyl, CF₃, SH, S—C₁₋₄ alkyl, SCF₃;
R² represents H; F; I; CF₃; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of C₁₋₄ alkyl, O—C₁₋₄ alkyl, F, Cl, Br, I, CF₃ and OCF₃;
R⁴ represents H; methyl; ethyl; n-propyl; or isopropyl;
R⁵ᵃ represents H or CH₃ if A represents N; or represents H; methyl; ethyl; n-propyl; isopropyl if A represents CR⁵ᵇ;
R⁵ᵇ represents H; methyl; ethyl; n-propyl; isopropyl; cyclopentyl; cylohexyl; or phenyl or benzyl, in each case unsubstituted or mono-, di- or trisubstituted with one, two or three substituents each selected independently of one another from the group consisting of $C_{1-4}$ alkyl, O—$C_{1-4}$ alkyl, F, Cl, Br, I, $CF_3$ and $OCF_3$;

or $R^{5a}$ and $R^{5b}$ form together with the carbon atom connecting them a $C_{3-10}$ cycloalkyl, saturated or unsaturated, unsubstituted, $R^7$ and $R^9$ each independently of one another represent H; F; Cl; Br; I; $C_{1-4}$ alkyl, O—$C_{1-4}$ alkyl; F; Cl; Br; I;

$R^8$ represents H; F; Cl; Br; I; CN; $NO_2$; $CF_3$; OH; $OCF_3$; SH; $SCF_3$; $NH_2$; C(=O)—$NH_2$; C(=O)—NH(methyl); C(=O)—NH(ethyl); C(=O)—N (methyl)$_2$; C(=O)—N(ethyl)$_2$; $C_{1-4}$ alkyl, saturated or unsaturated, branched or unbranched, unsubstituted or mono- or disubstituted with OH; NH—C(=O)-methyl; NH—C(=O)-ethyl; $CH_2$—NH—S(=O)$_2$-methyl; $CH_2$—NH—S(=O)$_2$-ethyl; NH—S(=O)$_2$-methyl; NH—S(=O)$_2$-ethyl; S-methyl; S-ethyl; S(=O)$_2$-methyl; S(=O)$_2$-ethyl; S(=O)$_2$—NH-methyl; S(=O)$_2$—NH-ethyl; S(=O)$_2$—N(methyl)$_2$; S(=O)$_2$—N(ethyl)$_2$; $CH_2$—S(=O)$_2$-methyl; $CH_2$—S(=O)$_2$-ethyl; O$C_{1-4}$ alkyl, saturated or unsaturated, branched or unbranched, unsubstituted; $C_{1-4}$ alkyl-O—$C_{1-4}$ alkyl-O—$C_{1-4}$ alkyl, $C_{3-10}$ cycloalkyl, or $C_{3-10}$ cycloalkyl bridged via $C_{1-8}$ alkyl, respectively saturated or unsaturated, unsubstituted, and wherein if appropriate the alkyl chain can be respectively branched or unbranched, saturated or unsaturated, unsubstituted; piperidinyl; piperazinyl; 4-methylpiperazinyl; morpholinyl; dioxidoisothiazolidinyl; phenyl, pyridyl, furyl, thienyl, C(=O)—NH-phenyl, NH—C(=O)-phenyl, NH(phenyl), C(=O)—NH-pyridyl, NH—C(=O)-pyridyl, NH(pyridyl), wherein phenyl, pyridyl, thienyl or furyl are respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl and $SCF_3$.

10. Substituted compounds according to claim 1, selected from the group consisting of 3 N-((3-tert-butyl-1-methyl-1H-pyrazol-5-yl)methyl)-2-(3-fluoro-4-(methylsulphonamido)phenyl)propanamide;

4 (S)—N-((3-tert-butyl-1-methyl-1H-pyrazol-5-yl)methyl)-2-(3-fluoro-4-(methylsulphonamido)phenyl)propanamide;

5 N-((3-tert-butyl-1-hexyl-1H-pyrazol-5-yl)methyl)-2-(3-fluoro-4-(methylsulphonamido)phenyl)propanamide;

6 (S)—N-((3-tert-butyl-1-hexyl-1H-pyrazol-5-yl)methyl)-2-(3-fluoro-4-(methylsulphonamido)phenyl)propanamide;

7 N-((3-tert-butyl-1-cyclohexyl-1H-pyrazol-5-yl)methyl)-2-(3-fluoro-4-(methylsulphonamido)phenyl)propanamide;

8 (S)—N-((3-tert-butyl-1-cyclohexenyl-1H-pyrazol-5-yl)methyl)-2-(3-fluoro-4-(methylsulphonamido)phenyl)propanamide;

9 2-(3-fluoro-4-(methylsulphonamido)phenyl)-N-((3-methyl-1-phenyl-1H-pyrazol-5-yl)methyl)propanamide;

11 2-(3-fluoro-4-(methylsulphonamido)phenyl)-N-((3-(4-fluorophenyl)-1-phenyl-1H-pyrazol-5-yl)methyl)propanamide;

12 N-((3-tert-butyl-1-p-tolyl-1H-pyrazol-5-yl)methyl)-2-(3-fluoro-4-(methylsulphonamido)phenyl)propanamide;

13 N-((3-tert-butyl-1-(4-tert-butylphenyl)-1H-pyrazol-5-yl)methyl)-2-(3-fluoro-4-(methylsulphonamido)phenyl)propanamide;

14 N-((3-tert-butyl-1-(4-chlorophenyl)-1H-pyrazol-5-yl)methyl)-2-(3-fluoro-4-(methylsulphonamido)phenyl)propanamide;

15 (S)—N-((3-tert-butyl-1-(4-chlorophenyl)-1H-pyrazol-5-yl)methyl)-2-(3-fluoro-4-(methylsulphonamido)phenyl)propanamide;

16 N-((3-tert-butyl-1-(3-chlorophenyl)-1H-pyrazol-5-yl)methyl)-2-(3-fluoro-4-(methylsulphonamido)phenyl)propanamide;

17 (S)—N-((3-tert-butyl-1-(3-chlorophenyl)-1H-pyrazol-5-yl)methyl)-2-(3-fluoro-4-(methylsulphonamido)phenyl)propanamide;

18 N-((3-tert-butyl-1-(3-chloro-4-fluorophenyl)-1H-pyrazol-5-yl)methyl)-2-(3-fluoro-4-(methylsulphonamido)phenyl)propanamide;

19 (E)-N-((3-tert-butyl-1-(4-methylstyryl)-1H-pyrazol-5-yl)methyl)-2-(3-fluoro-4-(methylsulphonamido)phenyl)propanamide;

20 N-((3-tert-butyl-1-(4-methoxyphenyl)-1H-pyrazol-5-yl)methyl)-2-(3-fluoro-4-(methylsulphonamido)phenyl)propanamide;

21 N-((1-(4-chlorophenyl)-3-(trifluoromethyl)-1H-pyrazol-5-yl)methyl)-2-(3-fluoro-4-(methylsulphonamido)phenyl)propanamide;

22 (R)—N-((1-(4-chlorophenyl)-3-(trifluoromethyl)-1H-pyrazol-5-yl)methyl)-2-(3-fluoro-4-(methylsulphonamido)phenyl)propanamide;

23 (S)—N-((1-(4-chlorophenyl)-3-(trifluoromethyl)-1H-pyrazol-5-yl)methyl)-2-(3-fluoro-4-(methylsulphonamido)phenyl)propanamide;

24 N-((1-(3-chlorophenyl)-3-(trifluoromethyl)-1H-pyrazol-5-yl)methyl)-2-(3-fluoro-4-(methylsulphonamido)phenyl)propanamide;

25 (R)—N-((1-(3-chlorophenyl)-3-(trifluoromethyl)-1H-pyrazol-5-yl)methyl)-2-(3-fluoro-4-(methylsulphonamido)phenyl)propanamide;

26 (S)—N-((1-(3-chlorophenyl)-3-(trifluoromethyl)-1H-pyrazol-5-yl)methyl)-2-(3-fluoro-4-(methylsulphonamido)phenyl)propanamide;

27 N-((3-tert-butyl-1-(3-chlorophenyl)-1H-pyrazol-5-yl)methyl)-2-(3-methoxy-4-(methylsulphonamido)phenyl)propanamide;

28 N-((1-(3-chlorophenyl)-3-(trifluoromethyl)-1H-pyrazol-5-yl)methyl)-2-(3-methoxy-4-(methylsulphonamido)phenyl)propanamide;

29 N-((3-tert-butyl-1-(3-chlorophenyl)-1H-pyrazol-5-yl)methyl)-2-(3,5-difluoro-4-(methylsulphonamido)phenyl)propanamide;

30 N-((1-(3-chlorophenyl)-3-(trifluoromethyl)-1H-pyrazol-5-yl)methyl)-2-(3,5-difluorophenyl)propanamide;

31 2-(4-bromo-3-fluorophenyl)-N-((1-(3-chlorophenyl)-3-(trifluoromethyl)-1H-pyrazol-5-yl)methyl)propanamide;

32 N-((3-tert-butyl-1-(3-chlorophenyl)-1H-pyrazol-5-yl)methyl)-2-(4-isobutylphenyl)propanamide;

33 N-((3-tert-butyl-1-(3-chlorophenyl)-1H-pyrazol-5-yl)methyl)-2-(3-fluoro-4-(methylsulphonamidomethyl)phenyl)propanamide;

34 N-((1-(3-chlorophenyl)-3-(trifluoromethyl)-1H-pyrazol-5-yl)methyl)-2-(3-fluoro-4-(furan-3-yl)phenyl)propanamide;

35 N-((3-tert-butyl-1-(3-chlorophenyl)-1H-pyrazol-5-yl)methyl)-2-(2-fluorobiphenyl-4-yl)propanamide;

36 N-((1-(3-chlorophenyl)-3-(trifluoromethyl)-1H-pyrazol-5-yl)methyl)-2-(4-(1,2-dihydroxyethyl)-3-fluorophenyl)propanamide;

37  4-(1-((1-(3-chlorophenyl)-3-(trifluoromethyl)-1H-pyrazol-5-yl)methylamino)-1-oxopropan-2-yl)-2-fluorobenzamide;
38  4-(1-((1-(3-chlorophenyl)-3-(trifluoromethyl)-1H-pyrazol-5-yl)methylamino)-1-oxopropan-2-yl)-N-ethylbenzamide;
39  4-(1-((1-(3-chlorophenyl)-3-(trifluoromethyl)-1H-pyrazol-5-yl)methylamino)-1-oxopropan-2-yl)-2-fluoro-N-phenylbenzamide;
40  4-(1-((1-(3-chlorophenyl)-3-(trifluoromethyl)-1H-pyrazol-5-yl)methylamino)-1-oxopropan-2-yl)-N-(4-fluorophenyl)benzamide;
41  4-(1-((1-(3-chlorophenyl)-3-(trifluoromethyl)-1H-pyrazol-5-yl)methylamino)-1-oxopropan-2-yl)-N-(4-(trifluoromethyl)phenyl)benzamide;
42  4-(1-((1-(3-chlorophenyl)-3-(trifluoromethyl)-1H-pyrazol-5-yl)methylamino)-1-oxopropan-2-yl)-N-(pyridin-4-yl)benzamide;
43  N-((1-(3-chlorophenyl)-3-(trifluoromethyl)-1H-pyrazol-5-yl)methyl)-2-(4-(trifluormethoxy)phenyl)propanamide;
44  N-((1-(3-chlorophenyl)-3-(trifluoromethyl)-1H-pyrazol-5-yl)methyl)-2-(3,5-dibromo-4-hydroxyphenyl)acetamide;
45  N-((1-(3-chlorophenyl)-3-(trifluoromethyl)-1H-pyrazol-5-yl)methyl)-2-(3,5-dibromo-4-hydroxyphenyl)propanamide;
46  N-((3-tert-butyl-1-(3-chlorophenyl)-1H-pyrazol-5-yl)methyl)-2-(3,5-difluoro-4-hydroxyphenyl)propanamide;
47  N-((1-(3-chlorophenyl)-3-(trifluoromethyl)-1H-pyrazol-5-yl)methyl)-2-(3,5-difluoro-4-methoxyphenyl)propanamide;
48  N-((3-tert-butyl-1-(3-chlorophenyl)-1H-pyrazol-5-yl)methyl)-2-(4-methoxy-3,5-dimethylphenyl)acetamide;
49  N-((3-tert-butyl-1-(3-chlorophenyl)-1H-pyrazol-5-yl)methyl)-2-(4-(N,N-dimethylsulphamoyl)-3-fluorophenyl)propanamide;
50  N-((1-(3-chlorophenyl)-3-(trifluoromethyl)-1H-pyrazol-5-yl)methyl)-2-(4-(4-chlorophenylamino)phenyl)propanamide;
51  N-((1-(3-chlorophenyl)-3-(trifluoromethyl)-1H-pyrazol-5-yl)methyl)-2-(4-(4-methoxyphenylamino)phenyl)propanamide;
52  2-(4-amino-3,5-difluorophenyl)-N-((1-(3-chlorophenyl)-3-(trifluoromethyl)-1H-pyrazol-5-yl)methyl)propanamide;
53  2-(4-acetamido-3-fluorophenyl)-N-((1-(3-chlorophenyl)-3-(trifluoromethyl)-1H-pyrazol-5-yl)methyl)propanamide;
54  N-(4-(1-((1-(3-chlorophenyl)-3-(trifluoromethyl)-1H-pyrazol-5-yl)methylamino)-1-oxopropan-2-yl)-2-fluorophenyl)benzamide;
55  N-((3-tert-butyl-1-(3-chlorophenyl)-1H-pyrazol-5-yl)methyl)-2-[4-(1,1-dioxidoisothiazolidin-2-yl)-3-fluorophenyl]propanamide;
56  N-((3-tert-butyl-1-(3-chlorophenyl)-1H-pyrazol-5-yl)methyl)-2-(4-(N,N-dimethylsulphamoyl)-3-fluorophenyl)propanamide;
57  1-((3-tert-butyl-1-(3-chlorophenyl)-1H-pyrazol-5-yl)methyl)-3-(3,5-difluorophenyl)urea;
58  1-(4-bromo-3-fluorophenyl)-3-((3-tert-butyl-1-(3-chlorophenyl)-1H-pyrazol-5-yl)methyl)urea;
59  1-((3-tert-butyl-1-(3-chlorophenyl)-1H-pyrazol-5-yl)methyl)-3-(4-(trifluoromethyl)phenyl)urea;
60  1-((3-tert-butyl-1-(3-chlorophenyl)-1H-pyrazol-5-yl)methyl)-3-(4-(difluormethoxy)phenyl)urea;
61  1-((3-tert-butyl-1-(3-chlorophenyl)-1H-pyrazol-5-yl)methyl)-3-(3,5-difluoro-4-methoxyphenyl)urea;
62  1-((3-tert-butyl-1-(3-chlorophenyl)-1H-pyrazol-5-yl)methyl)-3-(4-methoxy-3,5-dimethylphenyl)urea;
63  1-((3-tert-butyl-1-(3-chlorophenyl)-1H-pyrazol-5-yl)methyl)-3-(3-fluoro-4-(methylsulphonyl)phenyl)urea;
64  1-((3-tert-butyl-1-(3-chlorophenyl)-1H-pyrazol-5-yl)methyl)-3-(4-(phenylamino)phenyl)urea;
65  4-(3-((3-tert-butyl-1-(3-chlorophenyl)-1H-pyrazol-5-yl)methyl)ureido)-N-(4-fluorophenyl)benzamide;
66  N-((3-tert-butyl-1-(3-chlorophenyl)-1H-pyrazol-5-yl)methyl)-2-(3-fluoro-4-(methylsulphonamido)phenyl)-2-(3-fluorophenyl)acetamide;
67  N-((3-tert-butyl-1-(3-chlorophenyl)-1H-pyrazol-5-yl)methyl)-2-cyclohexyl-2-(3-fluoro-4-(methylsulphonamido)phenyl)acetamide;
68  N-((3-tert-butyl-1-(3-chlorophenyl)-1H-pyrazol-5-yl)methyl)-2-(3-fluoro-4-(methylsulphonamido)phenyl)-2-p-tolylacetamide;
69  N-((3-tert-butyl-1-(3-chlorophenyl)-1H-pyrazol-5-yl)methyl)-2-(3-chloro-4-(methylthio)phenyl)propanamide;
70  N-((3-tert-butyl-1-(3-chlorophenyl)-1H-pyrazol-5-yl)methyl)-2-(3-chloro-4-(methylsulphonyl)phenyl)propanamide;
71  N-((3-tert-butyl-1-(3-chlorophenyl)-1H-pyrazol-5-yl)methyl)-2-(3-fluoro-4-(methylthio)phenyl)propanamide;
72  N-((3-tert-butyl-1-(3-chlorophenyl)-1H-pyrazol-5-yl)methyl)-2-(3-fluoro-4-(methylsulphonyl)phenyl)propanamide;
73  N-((3-tert-butyl-1-(3-chlorophenyl)-1H-pyrazol-5-yl)methyl)-2-(3-fluorophenyl)acetamide;
74  N-((1-(3-chlorophenyl)-3-(trifluoromethyl)-1H-pyrazol-5-yl)methyl)-2-(3-fluorophenyl)acetamide;
75  N-[[5-tert-butyl-2-(3-chlorophenyl)-2H-[1,2,4]triazol-3-yl]-methyl]-2-[3-fluoro-4-(methanesulphonamido)phenyl]propionamide;
76  N-[[2-(3-chlorophenyl)-5-(trifluoromethyl)-2H-[1,2,4]triazol-3-yl]methyl]-2-[3-fluoro-4-(methanesulphonamido)phenyl]propionamide;
77  N-[(5-tert-butyl-2-cyclohexyl-2H-[1,2,4]thiazol-3-yl)-methyl]-2-[3-fluoro-4-(methanesulphonamido)phenyl]propionamide;
78  N-[[2-cyclohexyl-5-(trifluoromethyl)-2H-[1,2,4]triazol-3-yl]methyl]-2-[3-fluoro-4-(methanesulphonamido)phenyl]propionamide;
79  N-[(5-tert-butyl-2-pyridin-3-yl-2H-[1,2,4]triazol-3-yl)-methyl]-2-[3-fluoro-4-(methanesulphonamido)phenyl]propionamide;
80  2-[3-fluoro-4-(methanesulphonamido)phenyl]-N-[[2-pyridin-3-yl-5-(trifluoromethyl)-2H-[1,2,4]triazol-3-yl]methyl]propionamide;
81  N-[[5-tert-butyl-2-(6-chloropyridin-2-yl)-2H-pyrazol-3-yl]-methyl]-2-[3-fluoro-4-(methanesulphonamido)phenyl]propionamide;
82  N-[[5-tert-butyl-2-(3,3-difluorocyclobutanecarbonyl)-2H-pyrazol-3-yl]-methyl]-2-[3-fluoro-4-(methanesulphonamido)phenyl]propionamide;
83  N-[[2-(3-chlorophenyl)-4-methyl-5-(trifluoromethyl)-2H-pyrazol-3-yl]methyl]-2-[3-fluoro-4-(methanesulphonamido)phenyl]propionamide;
84  N-[[2-(dipropylamino)-5-(trifluoromethyl)-2H-pyrazol-3-yl]methyl]-2-[4-(methanesulphonamido)-3-methoxyphenyl]propionamide;

85  N-[[2-(dipropylamino)-5-(trifluoromethyl)-2H-pyrazol-3-yl]methyl]-2-[3-fluoro-4-(hydroxymethyl)phenyl]propionamide;
86  N-[[2-(dipropylamino)-5-(trifluoromethyl)-2H-pyrazol-3-yl]methyl]-2-[3-fluoro-4-(methanesulphonamido)phenyl]propionamide;
87  N-[[2-(dipropylamino)-5-(trifluoromethyl)-2H-pyrazol-3-yl]methyl]-2-(3-fluorophenyl)acetamide;
88  4-[1-[[2-(dipropylamino)-5-(trifluoromethyl)-2H-pyrazol-3-yl]-methylcarbamoyl]ethyl]-2-fluorobenzamide;
89  4-[1-[[2-(dipropylamino)-5-(trifluoromethyl)-2H-pyrazol-3-yl]-methylcarbamoyl]ethyl]-N-pyridin-2-ylbenzamide;
90  2-[3-fluoro-4-(hydroxymethyl)phenyl]-N-[[2-piperidin-1-yl-5-(trifluoromethyl)-2H-pyrazol-3-yl]-methyl]propionamide;
91  2-[3-fluoro-4-(2-hydroxyethyl)phenyl]-N-[[2-piperidin-1-yl-5-(trifluoromethyl)-2H-pyrazol-3-yl]-methyl]propionamide;
92  2-[3-fluoro-4-(methanesulphonamido)phenyl]-N-[[2-piperidin-1-yl-5-(trifluoromethyl)-2H-pyrazol-3-yl]methyl]propionamide;
93  2-[4-(methanesulphonamido)-3-methoxyphenyl]-N-[[2-piperidin-1-yl-5-(trifluoromethyl)-2H-pyrazol-3-yl]-methyl]propionamide;
94  2-[4-(1,2-dihydroxyethyl)-3-fluorophenyl]-N-[[2-piperidin-1-yl-5-(trifluoromethyl)-2H-pyrazol-3-yl]methyl]propionamide;
95  2-(3-fluorophenyl)-N-[[2-piperidin-1-yl-5-(trifluoromethyl)-2H-pyrazol-3-yl]-methyl]acetamide;
96  2-fluoro-4-[1-[[2-piperidin-1-yl-5-(trifluoromethyl)-2H-pyrazol-3-yl]-methylcarbamoyl]ethyl]benzamide;
97  2-[3-fluoro-4-(methanesulphonamido)phenyl]-N-[[2-[(4-fluorophenyl)methylmethylamino]-5-(trifluoromethyl)-2H-pyrazol-3-yl]-methyl]propionamide;
98  N-[[5-tert-butyl-2-(2,2,2-trifluoroethylamino)-2H-pyrazol-3-yl]-methyl]-2-[3-fluoro-4-(methanesulphonamido)phenyl]propionamide;
99  N-[[2-butoxy-5-(trifluoromethyl)-2H-pyrazol-3-yl]-methyl]-2-[3-fluoro-4-(hydroxymethyl)phenyl]propionamide;
100  N-[[2-butoxy-5-(trifluoromethyl)-2H-pyrazol-3-yl]-methyl]-2-[3-fluoro-4-(methanesulphonamido)phenyl]propionamide;
101  N-[[2-butoxy-5-(trifluoromethyl)-2H-pyrazol-3-yl]-methyl]-2-[4-(methanesulphonamido)-3-methoxyphenyl]propionamide;
102  N-[(2-butoxy-5-tert-butyl-2H-pyrazol-3-yl)-methyl]-2-(3-fluorophenyl)acetamide;
103  N-[[2-cyclopentyloxy-5-(trifluoromethyl)-2H-pyrazol-3-yl]-methyl]-2-[3-fluoro-4-(methanesulphonamido)phenyl]propionamide;
104  N-[[2-cyclopentyloxy-5-(trifluoromethyl)-2H-pyrazol-3-yl]-methyl]-2-[4-(methanesulphonamido)-3-methoxyphenyl]propionamide;
105  2-(3-fluorophenyl)-N-[[2-[(4-methoxyphenyl)methoxy]-5-(trifluoromethyl)-2H-pyrazol-3-yl]methyl]acetamide;
107  N-[[2-(cyclohexylsulphanyl)-5-(trifluoromethyl)-2H-pyrazol-3-yl]methyl]-2-[3-fluoro-4-(methanesulphonamido)phenyl]propionamide;
108  N-[[2-(benzenesulphonyl)-5-tert-butyl-2H-pyrazol-3-yl]-methyl]-2-(3-fluorophenyl)acetamide;
109  N-[[2-cyclohexyl-5-(trifluoromethyl)-2H-[1,2,4]triazol-3-yl]methyl]-2-[4-(methanesulphonamido)-3-methoxyphenyl]propionamide;
110  N-[[2-cyclohexyl-5-(trifluoromethyl)-2H-[1,2,4]triazol-3-yl]methyl]-2-(3-fluorophenyl)acetamide;
111  4-[1-[[2-cyclohexyl-5-(trifluoromethyl)-2H-[1,2,4]triazol-3-yl]-methylcarbamoyl]ethyl]-2-fluorobenzamide;
112  2-[3-fluoro-4-(hydroxymethyl)phenyl]-N-[[2-hexyl-5-(trifluoromethyl)-2H-[1,2,4]triazol-3-yl]methyl]propionamide;
113  4-[1-[[2-cyclobutyl-5-(trifluoromethyl)-2H-[1,2,4]triazol-3-yl]-methylcarbamoyl]ethyl]-2-fluorobenzamide;
114  N-[[5-tert-butyl-2-(3,3-difluorocyclobutanecarbonyl)-2H-[1,2,4]triazol-3-yl]-methyl]-2-[3-fluoro-4-(methanesulphonamido)phenyl]propionamide;
116  N-[[2-(benzenesulphonyl)-5-tert-butyl-2H-[1,2,4]triazol-3-yl]methyl]-2-(3-fluorophenyl)acetamide;
117  N-((1-(3-chlorophenyl)-3-(trifluoromethyl)-1H-pyrazol-5-yl)methyl)-2-(3-fluorophenyl)-2-methylpropanamide;
118  N-((3-tert-butyl-1-(3-chlorophenyl)-1H-pyrazol-5-yl)methyl)-1-(3-fluorophenyl)cyclopropancarboxamide;
119  N-((1-(3-chlorophenyl)-3-(trifluoromethyl)-1H-pyrazol-5-yl)methyl)-1-(3-fluorophenyl)cyclobutancarboxamide;
120  N-((1-(3-chlorophenyl)-3-(trifluoromethyl)-1H-pyrazol-5-yl)methyl)-1-(3-fluorophenyl)cyclopentancarboxamide;
121  N-((1-(3-chlorophenyl)-3-(trifluoromethyl)-1H-pyrazol-5-yl)methyl)-1-(3-fluorophenyl)cyclohexancarboxamide;
122  1-((3-tert-butyl-1-(4-fluorophenyl)-1H-pyrazol-5-yl)methyl)-3-(3-fluorophenyl)urea
123  3-((1-(3-chlorophenyl)-3-(trifluoromethyl)-1H-pyrazol-5-yl)methyl)-1-(3-fluorophenyl)-1-methylurea;
124  N-((1-(3-chloro-4-fluorophenyl)-3-(trifluoromethyl)-1H-pyrazol-5-yl)methyl)-2-(3-fluoro-4-(methylsulfonylmethyl)phenyl)propanamide;
125  N-((3-tert-butyl-1-(3-chlorophenyl)-1H-pyrazol-5-yl)methyl)-2-(4-cyclopropyl-3-fluorophenyl)propanamide;
126  1-((1-(3-chlorophenyl)-3-(trifluoromethyl)-1H-pyrazol-5-yl)methyl)-3-(4-cyclopropyl-3-fluorophenyl)urea;
127  N-((3-tert-butyl-1-(pyridin-2-yl)-1H-pyrazol-5-yl)methyl)-2-(3-fluoro-4-(methylsulfonamidmethyl)phenyl)propanamide;
128  N-((1-(3-chlorophenyl)-3-cyclopropyl-1H-pyrazol-5-yl)methyl)-2-(3-fluoro-4-(methylsulfonylmethyl)phenyl)propanamide;
129  2-(3-fluoro-4-(methylsulfonamidmethyl)phenyl)-N-((1-(pyridin-2-ylmethylamino)-3-(trifluoromethyl)-1H-pyrazol-5-yl)methyl)propanamide;
130  N-((1-(3-chlorophenyl)-4-methyl-3-(trifluoromethyl)-1H-pyrazol-5-yl)methyl)-2-(3-fluorophenyl)acetamide;
131  2-(3-fluorophenyl)-N-((1-pentyl-3-(trifluoromethyl)-1H-pyrazol-5-yl)methyl)acetamide;
132  2-(3-fluorophenyl)-N-((1-(4-methoxybenzyl)-3-(trifluoromethyl)-1H-pyrazol-5-yl)methyl)acetamide;
133  N-((3-tert-butyl-1-(2,2,2-trifluoroethylamino)-1H-pyrazol-5-yl)methyl)-2-(3-fluorophenyl)acetamide;
134  N-((1-(3-chlorophenyl)-4-methyl-3-(trifluoromethyl)-1H-pyrazol-5-yl)methyl)-2-(3-fluoro-4-(methylsulfonamidmethyl)phenyl)propanamide;
135  N-((3-tert-butyl-1-(3-chlorophenyl)-1H-1,2,4-triazol-5-yl)methyl)-2-(3-fluorophenyl)acetamide;

136 2-(3-fluorophenyl)-N-((1-(pyridin-3-yl)-3-(trifluoromethyl)-1H-pyrazol-5-yl)methyl)acetamide;
137 N-((1-cyclohexyl-3-(trifluoromethyl)-1H-pyrazol-5-yl)methyl)-2-(3-fluoro-4-(methylsulfonamidmethyl)phenyl)propanamide;
138 2-(3-fluoro-4-(methylsulfonamidmethyl)phenyl)-N-((1-(tetrahydro-2H-pyran-4-yl)-3-(trifluoromethyl)-1H-pyrazol-5-yl)methyl)propanamide;
139 1-((1-(3-chlorophenyl)-3-(trifluoromethyl)-1H-pyrazol-5-yl)methyl)-3-(4-(cyclopropylethynyl)-3-fluorophenyl)urea;
140 N-((1-(3-chlorophenyl)-3-(trifluoromethyl)-1H-pyrazol-5-yl)methyl)-2-(3-fluoro-4-(trifluoromethyl)phenyl)acetamide;
141 N-((1-(3-chlorophenyl)-3-(trifluoromethyl)-1H-pyrazol-5-yl)methyl)-2-(3-fluoro-4-(trifluoromethyl)phenyl)propanamide;
142 N-((3-tert-butyl-1-(3-chlorophenyl)-1H-pyrazol-5-yl)methyl)-2-(3-fluoro-4-((2-methoxyethoxy)methyl)phenyl)propanamide;
143 4-(1-((1-(3-chlorophenyl)-3-(trifluoromethyl)-1H-pyrazol-5-yl)methylamino)-1-oxopropan-2-yl)-N-phenylbenzamide;
144 1-((3-tert-butyl-1-(3-chlorophenyl)-1H-pyrazol-5-yl)methyl)-3-(3-fluoro-4-morpholinphenyl)urea;
145 N-((1-(3-chlorophenyl)-3-(trifluoromethyl)-1H-pyrazol-5-yl)methyl)-2-(3-fluoro-4-(methylsulfonamid)phenyl)-3-phenylpropanamide;
146 N-(5-((2-(3-fluorophenyl)acetamide)methyl)-3-(trifluoromethyl)-1H-pyrazol-1-yl)benzamide; and
147 N-((1-(3-chlorophenyl)-3-(trifluoromethyl)-1H-pyrazol-5-yl)methyl)-2-(3,5-difluoro-4-hydroxyphenyl)acetamide;

respectively in the form of the free compounds; the racemate; the enantiomers, diastereomers, mixtures of the enantiomers or diastereomers or of an individual enantiomer or diastereomer; or in the form of the salts of physiologically compatible acids or bases.

11. Pharmaceutical composition containing at least one substituted compound according to claim 1, in the form of an individual stereoisomer or the mixture thereof, the free compounds and/or their physiologically compatible salts, and also if appropriate suitable additives and/or auxiliaries and/or if appropriate further active ingredients.

\* \* \* \* \*